US012043836B2

(12) United States Patent
Verruto et al.

(10) Patent No.: US 12,043,836 B2
(45) **Date of Patent: *Jul. 23, 2024**

(54) RNA-GUIDED ENDONUCLEASE EXPRESSING ALGAL STRAIN FOR HIGH EFFICIENCY IN VIVO GENOME EDITING

(71) Applicant: Viridos, Inc., La Jolla, CA (US)

(72) Inventors: John Verruto, San Diego, CA (US); Eric Moellering, San Diego, CA (US)

(73) Assignee: Viridos, Inc., La Jolla, CA (US)

( * ) Notice: Subject to any disclaimer, the term of this patent is extended or adjusted under 35 U.S.C. 154(b) by 726 days.

This patent is subject to a terminal disclaimer.

(21) Appl. No.: 17/039,839

(22) Filed: Sep. 30, 2020

(65) Prior Publication Data

US 2021/0017530 A1 Jan. 21, 2021

Related U.S. Application Data

(63) Continuation of application No. 14/986,492, filed on Dec. 31, 2015, now Pat. No. 11,339,399.

(60) Provisional application No. 62/099,014, filed on Dec. 31, 2014.

(51) Int. Cl.

| | |
|---|---|
| ***C12N 15/82*** | (2006.01) |
| ***C12N 9/12*** | (2006.01) |
| ***C12N 9/22*** | (2006.01) |
| ***C12N 15/85*** | (2006.01) |
| ***C12N 15/90*** | (2006.01) |

(52) U.S. Cl.

CPC ....... *C12N 15/8213* (2013.01); *C12N 9/1241* (2013.01); *C12N 9/22* (2013.01); *C12N 15/8209* (2013.01); *C12N 15/8216* (2013.01); *C12N 15/85* (2013.01); *C12N 15/90* (2013.01); *C12N 15/905* (2013.01); *C12N 15/907* (2013.01); *C12Y 207/07* (2013.01)

(58) Field of Classification Search

CPC .... C12N 15/8213; C12N 9/1241; C12N 9/22; C12N 15/8209; C12N 15/8216; C12N 15/85; C12N 15/90; C12N 15/905; C12N 15/907; C12Y 207/07

See application file for complete search history.

(56) References Cited

U.S. PATENT DOCUMENTS

| | | | | |
|---|---|---|---|---|
| 2013/0247451 A1 | 9/2013 | Vanhercke et al. | | |
| 2014/0068797 A1 | 3/2014 | Doudna et al. | | |
| 2014/0170753 A1* | 6/2014 | Zhang | C12Q 1/68 | 435/320.1 |
| 2014/0179770 A1 | 6/2014 | Zhang et al. | | |
| 2014/0220638 A1 | 8/2014 | Bailey et al. | | |
| 2014/0357530 A1 | 12/2014 | Zhang et al. | | |
| 2016/0046961 A1* | 2/2016 | Jinek | C12N 15/102 | 435/91.53 |
| 2016/0201089 A1* | 7/2016 | Gersbach | C12N 9/96 | 435/320.1 |
| 2018/0186842 A1* | 7/2018 | Moellering | C12P 21/00 | |

FOREIGN PATENT DOCUMENTS

| | | |
|---|---|---|
| CN | 103668472 A | 3/2014 |
| WO | 2014/204724 A1 | 12/2014 |

OTHER PUBLICATIONS

Kabadi et al. "Multiplex CRISPR/Cas9-based genome engineering from a single lentiviral vector." Nucleic Acids Res . Oct. 29, 2014;42(19):e147. (Year: 2014).*

Kaczmarczyk, et al. "A single vector containing modified cre recombinase and LOX recombination sequences for inducible tissue-specific amplification of gene expression." Nucleic Acids Research, vol. 29, Issue 12, Jun. 15, 2001, p. e56, (Year: 2001).*

Doench et al. "Rational design of highly active sgRNAs for CRISPR-Cas9-mediated gene inactivation." Nat Biotechnol . Dec. 2014;32(12): 1262-7. (Year: 2014).*

Cong et al., "Multiplex Genome Engineering Using CRISPR/Cas Systems", Science, 339(6121): 819-823, Feb. 15, 2013.

Anonymous, "Add this page to bookmarks View Bookmarks You are here: HomeProductsGenome-CRISP(TM) human single guide RNA (sgRNA) libraries", Nov. 29, 2014, Retrieved from the Internet: URL:https://web.archive.org/web/20141129020453/http:// www.genecopoeia.com:80/product/sgrna_libraries/, Retrieved on May 3, 2018.

Anonymous, "Cas9 Stable Cells (293T)", Jan. 1, 2013, Retrieved from the Internet: URL:http://www.primcells.com/image/data/pdfs/Human-Cas9293T.pdf, Retrieved on May 2, 2018, p. 1.

Anonymous, "Cas9 Stable Cells (C2C12)", Jan. 1, 2013, United States, Retrieved from the Internet: URL:http://www.primce1ls.com/image/data/pdfs/Mouse-Cas9-C2C12.pdf, Retrieved on May 2, 2018, p. 1.

Anonymous, "CRISPR & TALEN Genome Editing tools from GeneCopoeia, Cas9 stable cell lines", Dec. 18, 2014, Retrieved from the Internet: URL: https://web.archive.org/web/20141218041909/http://www.genecopoeia.com:80/product/genome-editing/, Retrieved on May 3, 2018.

Anonymous, "Genome-CRISP(TM) human single guide RNA (sgRNA) libraries", Nov. 29, 2014, Retrieved from the Internet: URL: https://web.archive.org/web/20141129020453/http://www.genecopoeia.com:80/product/sgrna_libraries/, retrieved on May 3, 2018.

Extended European Search Report received for EP Patent Application No. 15876386.2, issued on May 17, 2018.

Gentarget, "A549/Cas9 (GFP-Puro) stable cell line", Available Online at <URL: http://www.gentarget.com/productla549-cas9-gfp-puro-stable-cell-line/>, 2013, 1 page.

Gentarget, "CRISPR gRNA lentivector cloning kits", Available Online at <URL: http://www.gentarget.com/product-categort/expressionknockdown-crisprlentivectors/grna-lentivector-cloning-kits/>, 2013, pp. 1-2.

(Continued)

*Primary Examiner* — Titilayo Moloye
(74) *Attorney, Agent, or Firm* — DLA Piper LLP (US)

(57) ABSTRACT

The present invention provides cell lines for high efficiency genome editing using cas/CRISPR systems, methods of generating such cells lines and methods of generating mutations in the genome of an organism using such cell lines.

18 Claims, 41 Drawing Sheets

Specification includes a Sequence Listing.

(56) References Cited

OTHER PUBLICATIONS

Gilbert et al., "CRISPR-Mediated Modular RNA-Guided Regulation of Transcription in Eukaryotes (includes Supplemental Information)", CELL, vol. 154, No. 2, Jul. 11, 2013, p. 442.
Gilbert et al., "Genome-Scale CRISPR-Mediated Control of Gene Repression and Activation", CELL, vol. 159, No. 3, Oct. 1, 2014, pp. 647-661.
International Preliminary Report on Patentability received for PCT Patent Application No. PCT/US2015/068356, mailed on Jul. 13, 2017, 11 pages.
International Search Report received for PCT Patent Application No. PCT/US2015/068356, issued on Jul. 8, 2016.
Jacobs et al., "Implementation of the CRISPR-Cas9 system in fission yeast", Nature Communications, vol. 5, Oct. 29, 2014, p. 5344.
Jiang et al., "Successful Transient Expression of Cas9 and Single Guide RNA Genes in Chlamydomonas reinhardtii", Eukaryotic Cell, vol. 13, No. 11, Nov. 1, 2014, pp. 1465-1469.
Li et al., "Optimization of Genome Engineering Approaches with the CRISPR/Cas9 System", Plos One, Aug. 2014, vol. 9, No. 8, 10 pages.
Meng et al., "Green fluorescent protein as a second selectable marker for selection of high producing clones from transfected CHO cells", Gene, vol. 242, No. 1-2, Jan. 1, 2000, pp. 201-207.
Munoz et al., "Improved Genome Editing in Human Cell Lines Using the CRISPR Method", Plos One, vol. 9, No. 10, Oct. 10, 2014, p. e109752.
Office Action received for Japanese Patent Application No. 2017-534947, issued on Nov. 21, 2019.
Ran et al., "Genome engineering using the CRISPR-Cas9 system", Nature Protocols, Nature Publishing Group, vol. 8, No. 11, Nov. 1, 2013, pp. 2281-2308.
Ronda et al., "Accelerating genome editing in CHO cells using CRISPR Cas9 and CRISPy, a web-based target finding tool", Biotechnology and Bioengineering, vol. 111, No. 8, Aug. 22, 2014, pp. 1604-1616.
Thermofisher Website, "GeneArt(R) CRISPR Nuclease Vector Kit", catalog, Life Technologies Japan Ltd., 2013, URL: https://www.thermofisher.com/content/dam/LifeTech/Documents/PDFs/ip/materials/geneartcrispr-nuclease-vector-kit.pdf. English Abstract, p. 10.
Wang et al., "Genetic Screens in Human Cells Using the CRISPR-Cas9 System", Science, vol. 343, No. 6166, Dec. 12, 2013, pp. 80-84.
Written Opinion received for PCT Patent Application No. PCT/US2015/068356, mailed on Jul. 8, 2016, 9 pages.
Yang et al., "CRISPR/Cas9-Directed Genome Editing of Cultured Cells: CRISPR/Cas9 Genome Editing", Current Protocols in Molecular Biology, Jul. 1, 2014, p. 31.1.1-31.1.17.
Zhang et al., "Establishment of stable high expression cell line with green fluorescent protein and resistance genes", Huazhong University of Science and Technology, Journal (Medical Sciences) = Huazhong Keji Daxue Xuebao (Yixue Yingdewen Ban), Huazhong Keji Daxue, Tongji Yixueyuan, CN, vol. 26, No. 3, Jan. 1, 2006, pp. 298-300.
Zhou et al., "High-throughput screening of a CRISPR/Cas9 library for functional genomics in human cells", Nature, vol. 509, No. 7501, Apr. 9, 2014, pp. 487-491.
JP Office Action in Japanese Application No. 2020-162773 , dated Sep. 27, 2021, 6 pages (with English translation).

* cited by examiner

| | Mean Fluorescence (GFP) | |
|---|---|---|
| | $NH_4$ | $NO_3$ |
| WE-SGI-E-03730 | 728 | 661 |
| pSGE06483-A11 | 1262 | 1180 |

pSGE06483-B11 pSGE06483-C12

| Mean Fluorescence (GFP) | | |
|---|---|---|
| | $NH_4$ | $NO_3$ |
| pSGE06483-B11 | 773 | 683 |
| pSGE06483-C12 | 807 | 667 |

| Mean Fluorescence (GFP) | | |
|---|---|---|
| | $NH_4$ | $NO_3$ |
| pSGE06483-D12 | 1266 | 1195 |
| pSGE06483-E12 | 1415 | 1248 |

| Mean Fluorescence (GFP) | $NH_4$ | $NO_3$ |
|---|---|---|
| pSGE06483-F12 | 1042 | 637 |

| pathway | Plasmid-line ID |
|---|---|
| ChytFAS | 6167-A |
| ChytFAS | 6167-B |
| DrFAS | 6200-33 |
| DrFAS | 6200-38 |
| DrFAS | 6200-43 |
| DrFAS | 6201-43 |
| DrFAS | 6201-48 |

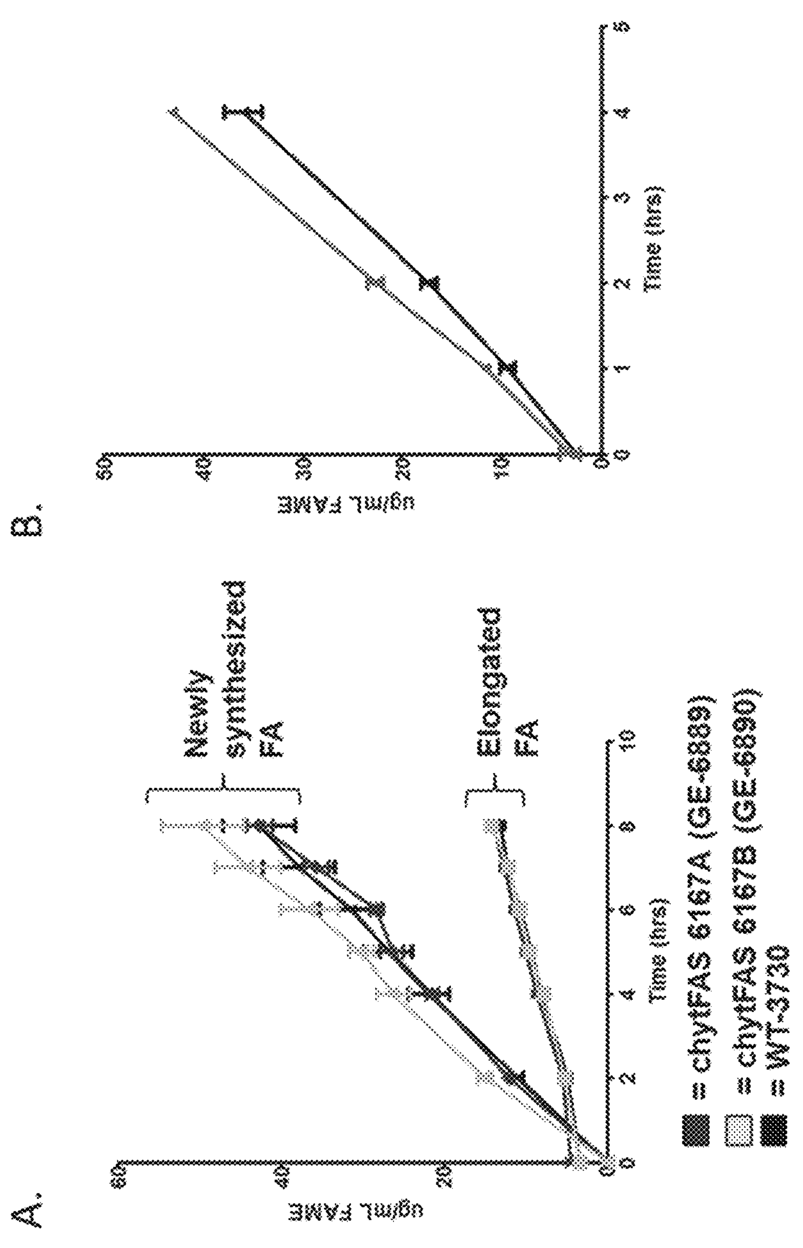
FIGS. 35A-B

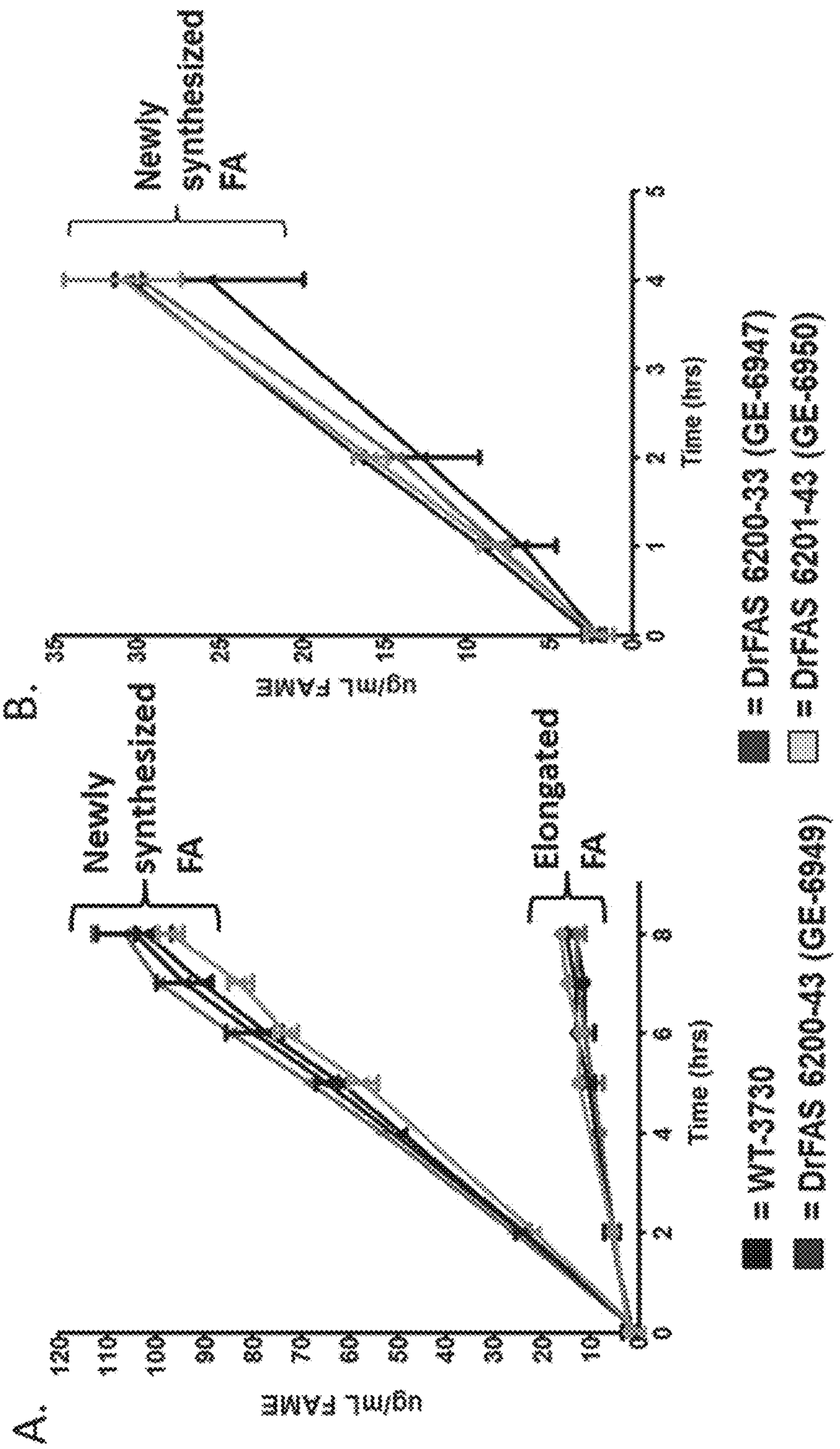
FIGS. 36A-B

SEQUENCE LISTING

```
<160> NUMBER OF SEQ ID NOS: 118

<210> SEQ ID NO 1
<211> LENGTH: 4101
<212> TYPE: DNA
<213> ORGANISM: Artificial Sequence
<220> FEATURE:
<223> OTHER INFORMATION: S. pyogenes
<220> FEATURE:
<221> NAME/KEY: misc_feature
<223> OTHER INFORMATION: CAS9 gene codon optimized for Nannochloropsis

<400> SEQUENCE: 1

gacaagaagt actccatcgg gctggacatc gggacgaact ccgtgggatg ggccgtgatc      60

acagacgaat acaaggtgcc ttccaagaag ttcaaggtgc tggggaacac ggacagacac     120

tccatcaaga agaacctcat cggggccttg ctcttcgact ccggagaaac cgccgaagca     180

acgcgattga aaagaaccgc cagaagacga tacacacgac ggaagaaccg catctgctac     240

ctccaggaga tcttcagcaa cgagatggcc aaggtggacg actcgttctt tcatcgcctg     300

gaggagagct tcctggtgga ggaagacaag aaacatgagc gccacccgat cttcgggaac     360

atcgtggacg aagtggccta ccacgagaaa taccccacga tctaccactt gcgcaagaaa     420

ctcgtggact ccacggacaa agcggacttg cggttgatct acttggcctt ggcccacatg     480

atcaaatttc ggggccactt cctgatcgag ggcgacttga atcccgacaa ttccgacgtg     540

gacaagctct tcatccagct ggtgcagacc tacaaccagc tcttcgagga gaaccccatc     600

aatgcctccg gagtggacgc caaagccatc ttgtccgccc gattgtccaa atccagacgc     660

ttggagaact tgatcgcaca acttcctggc gagaagaaga acggcctctt cggcaacttg     720

atcgcgctgt cgctgggatt gacgcctaac ttcaagtcca acttcgactt ggccgaggac     780

gccaagttgc aactgtccaa ggacacctac gacgacgacc tcgacaacct gctggcccaa     840

attggcgacc aatacgcgga cttgtttttg gcggccaaga acttgagcga cgccatcttg     900

ttgagcgaca tcttgcgcgt gaatacggag atcaccaaag ccccttttgtc cgcctctatg     960

atcaagcggt acgacgagca ccaccaagac ttgaccctgt tgaaagccct cgtgcggcaa    1020

caattgcccg agaagtacaa ggagatcttc ttcgaccagt ccaagaacgg gtacgccggc    1080

tacatcgacg gaggagcctc ccaagaagag ttctacaagt tcatcaagcc catcctggag    1140

aagatggacg gcaccgagga gttgctcgtg aagctgaacc gcgaagactt gttgcgaaaa    1200

cagcggacgt tcgacaatgg cagcatcccc caccaaatcc atttgggaga gttgcacgcc    1260
```

```
atcttgcgac ggcaagagga cttctacccg ttcctgaagg acaaccgcga gaaaatcgag   1320
aagatcctga cgttcagaat cccctactac gtgggaccct tggcccgagg caattcccgg   1380
tttgcatgga tgacgcgcaa aagcgaagag acgatcaccc cctggaactt cgaagaagtg   1440
gtcgacaaag gagcatccgc acagagcttc atcgagcgaa tgacgaactt cgacaagaac   1500
ctgcccaacg agaaggtgtt gcccaagcat tcgctgctgt acgagtactt cacggtgtac   1560
aacgagctga ccaaggtgaa gtacgtgacc gagggcatgc gcaaacccgc gttcctgtcg   1620
ggagagcaaa agaaggccat tgtggacctg ctgttcaaga ccaaccggaa ggtgaccgtg   1680
aaacagctga aagaggacta cttcaagaag atcgagtgct tcgactccgt ggagatctcc   1740
ggcgtggagg accgattcaa tgcctccttg ggaacctacc atgacctcct gaagatcatc   1800
aaggacaagg acttcctgga caacgaggag aacgaggaca tcctggagga catcgtgctg   1860
accctgaccc tgttcgagga ccgagagatg atcgaggaac ggttgaaaac gtacgcccac   1920
ttgttcgacg acaaggtgat gaagcagctg aaacgccgcc gctacaccgg atggggacga   1980
ttgagccgca aactgattaa tggaattcgc gacaagcaat ccggaaagac catcctggac   2040
ttcctgaagt ccgacgggtt cgccaaccgc aacttcatgc agctcatcca cgacgactcc   2100
ttgaccttca aggaggacat ccagaaggcc caagtgtccg gacaaggaga ctccttgcac   2160
gagcacatcg ccaatttggc cggatccccc gcaatcaaaa aaggcatctt gcaaaccgtg   2220
aaagtggtcg acgaactggt gaaggtgatg ggacggcaca agcccgagaa catcgtgatc   2280
gaaatggccc gcgagaacca aaccacccaa aaaggacaga agaactcccg agagcgcatg   2340
aagcggatcg aagagggcat caaggagttg ggctcccaga tcctgaagga gcatcccgtg   2400
gagaataccc aattgcaaaa cgagaagctc tacctctact acctccagaa cgggcgggac   2460
atgtacgtcg accaagagct ggacatcaac cgcctctccg actacgatgt ggatcatatt   2520
gtgccccaga gcttcctcaa ggacgacagc atcgacaaca aggtcctgac gcgcagcgac   2580
aagaaccggg gcaagtctga caatgtgcct tccgaagaag tcgtgaagaa gatgaagaac   2640
tactggcggc agctgctcaa cgccaagctc atcacccaac ggaagttcga caacctgacc   2700
aaggccgaga gaggaggatt gtccgagttg gacaaagccg gcttcattaa acgccaactc   2760
gtggagaccc gccagatcac gaagcacgtg gcccaaatct tggactcccg gatgaacacg   2820
aaatacgacg agaatgacaa gctgatccgc gaggtgaagg tgatcacgct gaagtccaag   2880
ctggtgagcg acttccggaa ggacttccag ttctacaagg tgcgggagat caacaactac   2940
catcacgccc atgacgccta cctgaacgcc gtggtcggaa ccgccctgat caagaaatac   3000
cccaagctgg agtccgaatt cgtgtacgga gattacaagg tctacgacgt gcggaagatg   3060
atcgcgaagt ccgagcagga gatcggcaaa gccaccgcca agtacttctt ttactccaac   3120
atcatgaact tcttcaagac cgagatcacg ctcgccaacg gcgagatccg caagcgcccc   3180
ctgatcgaga ccaacggcga gacgggagag attgtgtggg acaaaggaag agattttgcc   3240
acagtgcgca aggtgctgtc catgcctcag gtgaacatcg tgaagaagac cgaggtgcaa   3300
acaggagggt tttccaaaga gtccattttg cctaagagga attccgacaa gctcatcgcc   3360
cgcaagaagg actgggaccc caagaagtac gggggcttcg actcccccac ggtggcctac   3420
tccgtgttgg tggtggccaa agtggagaaa gggaagagca agaagctgaa atccgtgaag   3480
gagttgctcg gaatcacgat catggaacga tcgtcgttcg agaaaaaccc catcgacttc   3540
ctcgaagcca aagggtacaa agaggtgaag aaggacctga tcatcaagct gcccaagtac   3600
```

-continued

```
tccctgttcg agctggagaa cggccgcaag cggatgctgg cctccgccgg ggaactgcag   3660

aaagggaacg aattggcctt gccctccaaa tacgtgaact tcctctactt ggcctcccat   3720

tacgaaaagc tcaaaggatc ccctgaggac aatgagcaga agcaactctt cgtggaacaa   3780

cacaagcact acctggacga gatcatcgag cagatcagcg agttctccaa gcgcgtgatc   3840

ctcgccgacg ccaacctgga caaggtgctc tccgcctaca acaagcaccg cgacaagcct   3900

atccgcgagc aagccgagaa tatcattcac ctgtttaccc tgacgaattt gggagcccct   3960

gccgccttta aatactttga caccaccatc gaccgcaaaa gatacacctc caccaaggaa   4020

gtcttggacg ccaccctcat ccaccagtcc atcacgggcc tctacgagac gcgcatcgac   4080

ctctcccaat tgggcggcga c                                             4101


<210> SEQ ID NO 2
<211> LENGTH: 1367
<212> TYPE: PRT
<213> ORGANISM: Streptococcus pyogenes
<220> FEATURE:
<221> NAME/KEY: misc_feature
<223> OTHER INFORMATION: Cas9

<400> SEQUENCE: 2

Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270
```

-continued

```
Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685
```

-continued

```
Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                 1015                 1020

Ser Glu  Gln Glu Ile Gly Lys  Ala Thr Ala Lys Tyr  Phe Phe Tyr
    1025                 1030                 1035

Ser Asn  Ile Met Asn Phe Phe  Lys Thr Glu Ile Thr  Leu Ala Asn
    1040                 1045                 1050

Gly Glu  Ile Arg Lys Arg Pro  Leu Ile Glu Thr Asn  Gly Glu Thr
    1055                 1060                 1065

Gly Glu  Ile Val Trp Asp Lys  Gly Arg Asp Phe Ala  Thr Val Arg
    1070                 1075                 1080

Lys Val  Leu Ser Met Pro Gln  Val Asn Ile Val Lys  Lys Thr Glu
    1085                 1090                 1095

Val Gln  Thr Gly Gly Phe Ser  Lys Glu Ser Ile Leu  Pro Lys Arg
```

-continued

```
    1100                1105                1110

Asn Ser  Asp Lys Leu Ile Ala  Arg Lys Lys Asp Trp  Asp Pro Lys
    1115                1120                1125

Lys Tyr  Gly Gly Phe Asp Ser  Pro Thr Val Ala Tyr  Ser Val Leu
    1130                1135                1140

Val Val  Ala Lys Val Glu Lys  Gly Lys Ser Lys Lys  Leu Lys Ser
    1145                1150                1155

Val Lys  Glu Leu Leu Gly Ile  Thr Ile Met Glu Arg  Ser Ser Phe
    1160                1165                1170

Glu Lys  Asn Pro Ile Asp Phe  Leu Glu Ala Lys Gly  Tyr Lys Glu
    1175                1180                1185

Val Lys  Lys Asp Leu Ile Ile  Lys Leu Pro Lys Tyr  Ser Leu Phe
    1190                1195                1200

Glu Leu  Glu Asn Gly Arg Lys  Arg Met Leu Ala Ser  Ala Gly Glu
    1205                1210                1215

Leu Gln  Lys Gly Asn Glu Leu  Ala Leu Pro Ser Lys  Tyr Val Asn
    1220                1225                1230

Phe Leu  Tyr Leu Ala Ser His  Tyr Glu Lys Leu Lys  Gly Ser Pro
    1235                1240                1245

Glu Asp  Asn Glu Gln Lys Gln  Leu Phe Val Glu Gln  His Lys His
    1250                1255                1260

Tyr Leu  Asp Glu Ile Ile Glu  Gln Ile Ser Glu Phe  Ser Lys Arg
    1265                1270                1275

Val Ile  Leu Ala Asp Ala Asn  Leu Asp Lys Val Leu  Ser Ala Tyr
    1280                1285                1290

Asn Lys  His Arg Asp Lys Pro  Ile Arg Glu Gln Ala  Glu Asn Ile
    1295                1300                1305

Ile His  Leu Phe Thr Leu Thr  Asn Leu Gly Ala Pro  Ala Ala Phe
    1310                1315                1320

Lys Tyr  Phe Asp Thr Thr Ile  Asp Arg Lys Arg Tyr  Thr Ser Thr
    1325                1330                1335

Lys Glu  Val Leu Asp Ala Thr  Leu Ile His Gln Ser  Ile Thr Gly
    1340                1345                1350

Leu Tyr  Glu Thr Arg Ile Asp  Leu Ser Gln Leu Gly  Gly Asp
    1355                1360                1365


<210> SEQ ID NO 3
<211> LENGTH: 8
<212> TYPE: PRT
<213> ORGANISM: SV40 virus
<220> FEATURE:
<221> NAME/KEY: misc_feature
<223> OTHER INFORMATION: nuclear localization signal peptide

<400> SEQUENCE: 3

Pro Lys Lys Lys Arg Lys Val Gly
1               5


<210> SEQ ID NO 4
<211> LENGTH: 24
<212> TYPE: DNA
<213> ORGANISM: Artificial Sequence
<220> FEATURE:
<223> OTHER INFORMATION: encoding codon optimized SV40 nuclear
      localization sequence

<400> SEQUENCE: 4

cccaagaaaa agcggaaggt cggc                                         24
```

<210> SEQ ID NO 5
<211> LENGTH: 24
<212> TYPE: DNA
<213> ORGANISM: Artificial Sequence
<220> FEATURE:
<223> OTHER INFORMATION: Encoding FLAG tag

<400> SEQUENCE: 5
gactacaagg atgacgatga caag 24

<210> SEQ ID NO 6
<211> LENGTH: 8
<212> TYPE: PRT
<213> ORGANISM: Artificial Sequence
<220> FEATURE:
<223> OTHER INFORMATION: FLAG tag peptide

<400> SEQUENCE: 6

Asp Tyr Lys Asp Asp Asp Asp Lys
1 5

<210> SEQ ID NO 7
<211> LENGTH: 4158
<212> TYPE: DNA
<213> ORGANISM: Artificial Sequence
<220> FEATURE:
<223> OTHER INFORMATION: Engineered Cas9 gene encoding NLS-Cas9-C
terminal FLAG tag

<400> SEQUENCE: 7
atggctccca agaaaaagcg gaaggtcggc gacaagaagt actccatcgg gctggacatc 60
gggacgaact ccgtgggatg ggccgtgatc acagacgaat acaaggtgcc ttccaagaag 120
ttcaaggtgc tggggaacac ggacagacac tccatcaaga agaacctcat cggggccttg 180
ctcttcgact ccggagaaac cgccgaagca acgcgattga aaagaaccgc cagaagacga 240
tacacacgac ggaagaaccg catctgctac ctccaggaga tcttcagcaa cgagatggcc 300
aaggtggacg actcgttctt tcatcgcctg gaggagagct tcctggtgga ggaagacaag 360
aaacatgagc gccacccgat cttcgggaac atcgtggacg aagtggccta ccacgagaaa 420
taccccacga tctaccactt gcgcaagaaa ctcgtggact ccacggacaa agcggacttg 480
cggttgatct acttggcctt ggcccacatg atcaaatttc ggggccactt cctgatcgag 540
ggcgacttga atcccgacaa ttccgacgtg gacaagctct tcatccagct ggtgcagacc 600
tacaaccagc tcttcgagga gaaccccatc aatgcctccg gagtggacgc caaagccatc 660
ttgtccgccc gattgtccaa atccagacgc ttggagaact tgatcgcaca acttcctggc 720
gagaagaaga acggcctctt cggcaacttg atcgcgctgt cgctgggatt gacgcctaac 780
ttcaagtcca acttcgactt ggccgaggac gccaagttgc aactgtccaa ggacacctac 840
gacgacgacc tcgacaacct gctggcccaa attggcgacc aatacgcgga cttgtttttg 900
gcggccaaga acttgagcga cgccatcttg ttgagcgaca tcttgcgcgt gaatacggag 960
atcaccaaag cccctttgtc cgcctctatg atcaagcggt acgacgagca ccaccaagac 1020
ttgaccctgt tgaaagccct cgtgcggcaa caattgcccg agaagtacaa ggagatcttc 1080
ttcgaccagt ccaagaacgg gtacgccggc tacatcgacg gaggagcctc ccaagaagag 1140
ttctacaagt tcatcaagcc catcctggag aagatggacg gcaccgagga gttgctcgtg 1200
aagctgaacc gcgaagactt gttgcgaaaa cagcggacgt tcgacaatgg cagcatcccc 1260

-continued

```
caccaaatcc atttgggaga gttgcacgcc atcttgcgac ggcaagagga cttctacccg   1320
ttcctgaagg acaaccgcga gaaaatcgag aagatcctga cgttcagaat cccctactac   1380
gtgggaccct tggcccgagg caattcccgg tttgcatgga tgacgcgcaa aagcgaagag   1440
acgatcaccc cctggaactt cgaagaagtg gtcgacaaag gagcatccgc acagagcttc   1500
atcgagcgaa tgacgaactt cgacaagaac ctgcccaacg agaaggtgtt gcccaagcat   1560
tcgctgctgt acgagtactt cacggtgtac aacgagctga ccaaggtgaa gtacgtgacc   1620
gagggcatgc gcaaacccgc gttcctgtcg ggagagcaaa agaaggccat tgtggacctg   1680
ctgttcaaga ccaaccggaa ggtgaccgtg aaacagctga aagaggacta cttcaagaag   1740
atcgagtgct tcgactccgt ggagatctcc ggcgtggagg accgattcaa tgcctccttg   1800
ggaacctacc atgacctcct gaagatcatc aaggacaagg acttcctgga caacgaggag   1860
aacgaggaca tcctggagga catcgtgctg accctgaccc tgttcgagga ccgagagatg   1920
atcgaggaac ggttgaaaac gtacgcccac ttgttcgacg acaaggtgat gaagcagctg   1980
aaacgccgcc gctacaccgg atggggacga ttgagccgca aactgattaa tggaattcgc   2040
gacaagcaat ccggaaagac catcctggac ttcctgaagt ccgacgggtt cgccaaccgc   2100
aacttcatgc agctcatcca cgacgactcc ttgaccttca aggaggacat ccagaaggcc   2160
caagtgtccg gacaaggaga ctccttgcac gagcacatcg ccaatttggc cggatccccc   2220
gcaatcaaaa aaggcatctt gcaaaccgtg aaagtggtcg acgaactggt gaaggtgatg   2280
ggacggcaca agcccgagaa catcgtgatc gaaatggccc gcgagaacca aaccacccaa   2340
aaaggacaga agaactcccg agagcgcatg aagcggatcg aagagggcat caaggagttg   2400
ggctcccaga tcctgaagga gcatcccgtg gagaataccc aattgcaaaa cgagaagctc   2460
tacctctact acctccagaa cgggcgggac atgtacgtcg accaagagct ggacatcaac   2520
cgcctctccg actacgatgt ggatcatatt gtgccccaga gcttcctcaa ggacgacagc   2580
atcgacaaca aggtcctgac gcgcagcgac aagaaccggg gcaagtctga caatgtgcct   2640
tccgaagaag tcgtgaagaa gatgaagaac tactggcggc agctgctcaa cgccaagctc   2700
atcacccaac ggaagttcga caacctgacc aaggccgaga gaggaggatt gtccgagttg   2760
gacaaagccg gcttcattaa acgccaactc gtggagaccc gccagatcac gaagcacgtg   2820
gcccaaatct tggactcccg gatgaacacg aaatacgacg agaatgacaa gctgatccgc   2880
gaggtgaagg tgatcacgct gaagtccaag ctggtgagcg acttccggaa ggacttccag   2940
ttctacaagg tgcgggagat caacaactac catcacgccc atgacgccta cctgaacgcc   3000
gtggtcggaa ccgccctgat caagaaatac cccaagctgg agtccgaatt cgtgtacgga   3060
gattacaagg tctacgacgt gcggaagatg atcgcgaagt ccgagcagga gatcggcaaa   3120
gccaccgcca agtacttctt ttactccaac atcatgaact tcttcaagac cgagatcacg   3180
ctcgccaacg gcgagatccg caagcgcccc ctgatcgaga ccaacggcga gacgggagag   3240
attgtgtggg acaaaggaag agattttgcc acagtgcgca aggtgctgtc catgcctcag   3300
gtgaacatcg tgaagaagac cgaggtgcaa acaggagggt tttccaaaga gtccattttg   3360
cctaagagga attccgacaa gctcatcgcc cgcaagaagg actgggaccc caagaagtac   3420
gggggcttcg actcccccac ggtggcctac tccgtgttgg tggtggccaa agtggagaaa   3480
gggaagagca agaagctgaa atccgtgaag gagttgctcg gaatcacgat catggaacga   3540
tcgtcgttcg agaaaaaccc catcgacttc ctcgaagcca aagggtacaa agaggtgaag   3600
aaggacctga tcatcaagct gcccaagtac tccctgttcg agctggagaa cggccgcaag   3660
```

```
cggatgctgg cctccgccgg ggaactgcag aaagggaacg aattggcctt gccctccaaa   3720

tacgtgaact tcctctactt ggcctcccat tacgaaaagc tcaaaggatc ccctgaggac   3780

aatgagcaga agcaactctt cgtggaacaa cacaagcact acctggacga gatcatcgag   3840

cagatcagcg agttctccaa gcgcgtgatc ctcgccgacg ccaacctgga caaggtgctc   3900

tccgcctaca acaagcaccg cgacaagcct atccgcgagc aagccgagaa tatcattcac   3960

ctgtttaccc tgacgaattt gggagcccct gccgccttta aatactttga caccaccatc   4020

gaccgcaaaa gatacacctc caccaaggaa gtcttggacg ccaccctcat ccaccagtcc   4080

atcacgggcc tctacgagac gcgcatcgac ctctcccaat tgggcggcga cgactacaag   4140

gatgacgatg acaagtga                                                 4158
```

<210> SEQ ID NO 8
<211> LENGTH: 1385
<212> TYPE: PRT
<213> ORGANISM: Artificial Sequence
<220> FEATURE:
<223> OTHER INFORMATION: NLS-Cas9-C terminal FLAG tag

<400> SEQUENCE: 8

```
Met Ala Pro Lys Lys Lys Arg Lys Val Gly Asp Lys Lys Tyr Ser Ile
1               5                   10                  15

Gly Leu Asp Ile Gly Thr Asn Ser Val Gly Trp Ala Val Ile Thr Asp
            20                  25                  30

Glu Tyr Lys Val Pro Ser Lys Lys Phe Lys Val Leu Gly Asn Thr Asp
        35                  40                  45

Arg His Ser Ile Lys Lys Asn Leu Ile Gly Ala Leu Leu Phe Asp Ser
    50                  55                  60

Gly Glu Thr Ala Glu Ala Thr Arg Leu Lys Arg Thr Ala Arg Arg Arg
65                  70                  75                  80

Tyr Thr Arg Arg Lys Asn Arg Ile Cys Tyr Leu Gln Glu Ile Phe Ser
                85                  90                  95

Asn Glu Met Ala Lys Val Asp Asp Ser Phe Phe His Arg Leu Glu Glu
            100                 105                 110

Ser Phe Leu Val Glu Glu Asp Lys Lys His Glu Arg His Pro Ile Phe
        115                 120                 125

Gly Asn Ile Val Asp Glu Val Ala Tyr His Glu Lys Tyr Pro Thr Ile
    130                 135                 140

Tyr His Leu Arg Lys Lys Leu Val Asp Ser Thr Asp Lys Ala Asp Leu
145                 150                 155                 160

Arg Leu Ile Tyr Leu Ala Leu Ala His Met Ile Lys Phe Arg Gly His
                165                 170                 175

Phe Leu Ile Glu Gly Asp Leu Asn Pro Asp Asn Ser Asp Val Asp Lys
            180                 185                 190

Leu Phe Ile Gln Leu Val Gln Thr Tyr Asn Gln Leu Phe Glu Glu Asn
        195                 200                 205

Pro Ile Asn Ala Ser Gly Val Asp Ala Lys Ala Ile Leu Ser Ala Arg
    210                 215                 220

Leu Ser Lys Ser Arg Arg Leu Glu Asn Leu Ile Ala Gln Leu Pro Gly
225                 230                 235                 240

Glu Lys Lys Asn Gly Leu Phe Gly Asn Leu Ile Ala Leu Ser Leu Gly
                245                 250                 255

Leu Thr Pro Asn Phe Lys Ser Asn Phe Asp Leu Ala Glu Asp Ala Lys
            260                 265                 270
```

-continued

```
Leu Gln Leu Ser Lys Asp Thr Tyr Asp Asp Asp Leu Asp Asn Leu Leu
        275                 280                 285

Ala Gln Ile Gly Asp Gln Tyr Ala Asp Leu Phe Leu Ala Ala Lys Asn
    290                 295                 300

Leu Ser Asp Ala Ile Leu Leu Ser Asp Ile Leu Arg Val Asn Thr Glu
305                 310                 315                 320

Ile Thr Lys Ala Pro Leu Ser Ala Ser Met Ile Lys Arg Tyr Asp Glu
                325                 330                 335

His His Gln Asp Leu Thr Leu Leu Lys Ala Leu Val Arg Gln Gln Leu
            340                 345                 350

Pro Glu Lys Tyr Lys Glu Ile Phe Phe Asp Gln Ser Lys Asn Gly Tyr
        355                 360                 365

Ala Gly Tyr Ile Asp Gly Gly Ala Ser Gln Glu Glu Phe Tyr Lys Phe
    370                 375                 380

Ile Lys Pro Ile Leu Glu Lys Met Asp Gly Thr Glu Glu Leu Leu Val
385                 390                 395                 400

Lys Leu Asn Arg Glu Asp Leu Leu Arg Lys Gln Arg Thr Phe Asp Asn
                405                 410                 415

Gly Ser Ile Pro His Gln Ile His Leu Gly Glu Leu His Ala Ile Leu
            420                 425                 430

Arg Arg Gln Glu Asp Phe Tyr Pro Phe Leu Lys Asp Asn Arg Glu Lys
        435                 440                 445

Ile Glu Lys Ile Leu Thr Phe Arg Ile Pro Tyr Tyr Val Gly Pro Leu
    450                 455                 460

Ala Arg Gly Asn Ser Arg Phe Ala Trp Met Thr Arg Lys Ser Glu Glu
465                 470                 475                 480

Thr Ile Thr Pro Trp Asn Phe Glu Glu Val Val Asp Lys Gly Ala Ser
                485                 490                 495

Ala Gln Ser Phe Ile Glu Arg Met Thr Asn Phe Asp Lys Asn Leu Pro
            500                 505                 510

Asn Glu Lys Val Leu Pro Lys His Ser Leu Leu Tyr Glu Tyr Phe Thr
        515                 520                 525

Val Tyr Asn Glu Leu Thr Lys Val Lys Tyr Val Thr Glu Gly Met Arg
    530                 535                 540

Lys Pro Ala Phe Leu Ser Gly Glu Gln Lys Lys Ala Ile Val Asp Leu
545                 550                 555                 560

Leu Phe Lys Thr Asn Arg Lys Val Thr Val Lys Gln Leu Lys Glu Asp
                565                 570                 575

Tyr Phe Lys Lys Ile Glu Cys Phe Asp Ser Val Glu Ile Ser Gly Val
            580                 585                 590

Glu Asp Arg Phe Asn Ala Ser Leu Gly Thr Tyr His Asp Leu Leu Lys
        595                 600                 605

Ile Ile Lys Asp Lys Asp Phe Leu Asp Asn Glu Glu Asn Glu Asp Ile
    610                 615                 620

Leu Glu Asp Ile Val Leu Thr Leu Thr Leu Phe Glu Asp Arg Glu Met
625                 630                 635                 640

Ile Glu Glu Arg Leu Lys Thr Tyr Ala His Leu Phe Asp Asp Lys Val
                645                 650                 655

Met Lys Gln Leu Lys Arg Arg Arg Tyr Thr Gly Trp Gly Arg Leu Ser
            660                 665                 670

Arg Lys Leu Ile Asn Gly Ile Arg Asp Lys Gln Ser Gly Lys Thr Ile
        675                 680                 685
```

-continued

```
Leu Asp Phe Leu Lys Ser Asp Gly Phe Ala Asn Arg Asn Phe Met Gln
    690                 695                 700

Leu Ile His Asp Asp Ser Leu Thr Phe Lys Glu Asp Ile Gln Lys Ala
705                 710                 715                 720

Gln Val Ser Gly Gln Gly Asp Ser Leu His Glu His Ile Ala Asn Leu
                725                 730                 735

Ala Gly Ser Pro Ala Ile Lys Lys Gly Ile Leu Gln Thr Val Lys Val
            740                 745                 750

Val Asp Glu Leu Val Lys Val Met Gly Arg His Lys Pro Glu Asn Ile
        755                 760                 765

Val Ile Glu Met Ala Arg Glu Asn Gln Thr Thr Gln Lys Gly Gln Lys
    770                 775                 780

Asn Ser Arg Glu Arg Met Lys Arg Ile Glu Glu Gly Ile Lys Glu Leu
785                 790                 795                 800

Gly Ser Gln Ile Leu Lys Glu His Pro Val Glu Asn Thr Gln Leu Gln
                805                 810                 815

Asn Glu Lys Leu Tyr Leu Tyr Tyr Leu Gln Asn Gly Arg Asp Met Tyr
            820                 825                 830

Val Asp Gln Glu Leu Asp Ile Asn Arg Leu Ser Asp Tyr Asp Val Asp
        835                 840                 845

His Ile Val Pro Gln Ser Phe Leu Lys Asp Asp Ser Ile Asp Asn Lys
    850                 855                 860

Val Leu Thr Arg Ser Asp Lys Asn Arg Gly Lys Ser Asp Asn Val Pro
865                 870                 875                 880

Ser Glu Glu Val Val Lys Lys Met Lys Asn Tyr Trp Arg Gln Leu Leu
                885                 890                 895

Asn Ala Lys Leu Ile Thr Gln Arg Lys Phe Asp Asn Leu Thr Lys Ala
            900                 905                 910

Glu Arg Gly Gly Leu Ser Glu Leu Asp Lys Ala Gly Phe Ile Lys Arg
        915                 920                 925

Gln Leu Val Glu Thr Arg Gln Ile Thr Lys His Val Ala Gln Ile Leu
    930                 935                 940

Asp Ser Arg Met Asn Thr Lys Tyr Asp Glu Asn Asp Lys Leu Ile Arg
945                 950                 955                 960

Glu Val Lys Val Ile Thr Leu Lys Ser Lys Leu Val Ser Asp Phe Arg
                965                 970                 975

Lys Asp Phe Gln Phe Tyr Lys Val Arg Glu Ile Asn Asn Tyr His His
            980                 985                 990

Ala His Asp Ala Tyr Leu Asn Ala  Val Val Gly Thr Ala  Leu Ile Lys
        995                 1000                1005

Lys Tyr  Pro Lys Leu Glu Ser  Glu Phe Val Tyr Gly  Asp Tyr Lys
    1010                1015                1020

Val Tyr  Asp Val Arg Lys Met  Ile Ala Lys Ser Glu  Gln Glu Ile
    1025                1030                1035

Gly Lys  Ala Thr Ala Lys Tyr  Phe Phe Tyr Ser Asn  Ile Met Asn
    1040                1045                1050

Phe Phe  Lys Thr Glu Ile Thr  Leu Ala Asn Gly Glu  Ile Arg Lys
    1055                1060                1065

Arg Pro  Leu Ile Glu Thr Asn  Gly Glu Thr Gly Glu  Ile Val Trp
    1070                1075                1080

Asp Lys  Gly Arg Asp Phe Ala  Thr Val Arg Lys Val  Leu Ser Met
    1085                1090                1095

Pro Gln  Val Asn Ile Val Lys  Lys Thr Glu Val Gln  Thr Gly Gly
```

```
    1100                1105                1110

Phe Ser  Lys Glu Ser Ile Leu  Pro Lys Arg Asn Ser  Asp Lys Leu
    1115                1120                1125

Ile Ala  Arg Lys Lys Asp Trp  Asp Pro Lys Lys Tyr  Gly Gly Phe
    1130                1135                1140

Asp Ser  Pro Thr Val Ala Tyr  Ser Val Leu Val Val  Ala Lys Val
    1145                1150                1155

Glu Lys  Gly Lys Ser Lys Lys  Leu Lys Ser Val Lys  Glu Leu Leu
    1160                1165                1170

Gly Ile  Thr Ile Met Glu Arg  Ser Ser Phe Glu Lys  Asn Pro Ile
    1175                1180                1185

Asp Phe  Leu Glu Ala Lys Gly  Tyr Lys Glu Val Lys  Lys Asp Leu
    1190                1195                1200

Ile Ile  Lys Leu Pro Lys Tyr  Ser Leu Phe Glu Leu  Glu Asn Gly
    1205                1210                1215

Arg Lys  Arg Met Leu Ala Ser  Ala Gly Glu Leu Gln  Lys Gly Asn
    1220                1225                1230

Glu Leu  Ala Leu Pro Ser Lys  Tyr Val Asn Phe Leu  Tyr Leu Ala
    1235                1240                1245

Ser His  Tyr Glu Lys Leu Lys  Gly Ser Pro Glu Asp  Asn Glu Gln
    1250                1255                1260

Lys Gln  Leu Phe Val Glu Gln  His Lys His Tyr Leu  Asp Glu Ile
    1265                1270                1275

Ile Glu  Gln Ile Ser Glu Phe  Ser Lys Arg Val Ile  Leu Ala Asp
    1280                1285                1290

Ala Asn  Leu Asp Lys Val Leu  Ser Ala Tyr Asn Lys  His Arg Asp
    1295                1300                1305

Lys Pro  Ile Arg Glu Gln Ala  Glu Asn Ile Ile His  Leu Phe Thr
    1310                1315                1320

Leu Thr  Asn Leu Gly Ala Pro  Ala Ala Phe Lys Tyr  Phe Asp Thr
    1325                1330                1335

Thr Ile  Asp Arg Lys Arg Tyr  Thr Ser Thr Lys Glu  Val Leu Asp
    1340                1345                1350

Ala Thr  Leu Ile His Gln Ser  Ile Thr Gly Leu Tyr  Glu Thr Arg
    1355                1360                1365

Ile Asp  Leu Ser Gln Leu Gly  Gly Asp Asp Tyr Lys  Asp Asp Asp
    1370                1375                1380

Asp Lys
    1385
```

<210> SEQ ID NO 9
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: RPL7 promoter

<400> SEQUENCE: 9

```
gaatgctggc gacctcatga actttgttga tttttttaga attgtgtcat cgaaaaatat      60

acaatgtcga agtaaagttt atacactctg ggtactcttc ttctttgcca tccagtaggt     120

gtgggatagg agtgcgtggt aattctctga gacagttttc ctaccatgtt tcgggtccac     180

atagtacaag ttgttactcg tgacacctca tttcgctttt gtttctccac taatggacta     240

catttttcaa agcagcagcg tccgcgtttc tcgattaaga atctcccgtc cgctttgagt     300
```

```
ttgtttattt taaggattag aaggataaaa gcggagctgc aaaggtgaaa catgcctgag    360

aggactagaa gacatacgga gctgaagtgc ggggaggtta aacccgatga tcccattcct    420

tgcatttgtc aaggctcacc gcattcatag ttctaaaaag aaaatatttc cgaataatgt    480

taacacaaaa ataattaaat actgttctat gtactccgtt catttgttga tggaatcaaa    540

aggccagaaa aaaagagggg gggactccaa gctgccgcag acgctcgcct cgtctctcgt    600

tcgcggaatg ccggtcgtgg aaccgctgtg aagataccgt gccttgggga tcaattcaca    660

cattgacgag ggcgcctcac gccgtggcgt acttattcgg gccaaaatgt tatttccaag    720

gggtgacgga tggcatgctc gactcgtgtg atggctgatg catcaaccct ttcaatgctc    780

cttcctactt cctcttatcc actggtagtc tgtcatgaga tgtggtgaac cgcgtccgtg    840

ataatagtgt tctcatttaa cctaacaacc aacacaatac aaaacttgat tagataccca    900

gtgcatcgaa ttttgggtgc cttcaccgac aagcttgcac tttctcgagg gacgacaaca    960

acaaaccacc tacagcatta ccgggcaata gcagcacaac                         1000
```

```
<210> SEQ ID NO 10
<211> LENGTH: 399
<212> TYPE: DNA
<213> ORGANISM: Artificial Sequence
<220> FEATURE:
<223> OTHER INFORMATION: Aspergillus terreus
<220> FEATURE:
<221> NAME/KEY: misc_feature
<223> OTHER INFORMATION: BLAST gene codon optimized for N. gaditana

<400> SEQUENCE: 10

atggccaagc ctttatccca agaggaatcc acgctgatcg aacgtgcaac tgcgaccatc     60

aacagcatac ctattagcga ggactactcg gtggccagtg cagccctctc gtccgacggt    120

cggatcttta ccggcgtgaa tgtatatcat ttcaccggag ggccatgcgc ggagctcgtg    180

gtcctcggaa cggccgctgc ggctgctgcc ggaaatctga cgtgcatagt ggccatcggg    240

aacgaaaacc gcggcattct gtctccgtgc gggcgatgtc ggcaggtgct gcttgacttg    300

cacccgggga tcaaggcaat tgtcaaagat tccgatgggc agcccacagc ggttggcatc    360

agggagttgc ttccctctgg ctacgtctgg gagggttga                           399
```

```
<210> SEQ ID NO 11
<211> LENGTH: 999
<212> TYPE: DNA
<213> ORGANISM: Nannochloropsis gaditana
<220> FEATURE:
<221> NAME/KEY: misc_feature
<223> OTHER INFORMATION: TCTP promoter

<400> SEQUENCE: 11

cgtgcaggtg tacagattga aggaaacaat ggagatatct ttggcagttg aaaaccgtgt     60

tcgaatcatg cttttctact ctccaactga gacgaaattt atagcgccat gtcgcttctg    120

actaccaggc ttaggaaggc ctcatcacaa gctggatcgg ttcgaattaa gcaggcactg    180

aagccaagct tgcaagacag ccacctttta attccctcaa aacactttct caattcagcc    240

cggtaaatat gccgattcac agcggccaag atagagggga ggttagcaag aatgttgcga    300

tccctcccca gtcgttgcct cgcacacaac ctaggccttc acctttccat ggaaaattga    360

gaagtgaata ttggttttct tacggcatat cagatgaaat catgacccct aaacatgaag    420

agctgcaggc aaaacacctg ctctggacga gcacgatgaa atctcgagaa cccgccgtac    480
```

-continued

```
ttcagttgat cccgcatgat gacggccgcc attgaaataa gccacctcac tttattctag    540

caccgatttc caccgttgtg agggccgaac gaggacaatt tcgtgcgaaa caagcacgaa    600

cacgcacacg attagtagta cagacgagca gatcgatggc atgcggcacg gtctcgcgtt    660

ctcggcgacc aggacaacgg agcagaggga ggcctgccga gttccgaggg gcattttagt    720

ccaaaattgt gttgacacgt gaacaagtgg cttgaaaaga ggaaggaaat gcctgggttt    780

cccttcgaga gcgggaactc gcttgtgcgt catcctagct acccatggtc cctttgtggg    840

ggaggctgtt tcgtcctacc gaatgtgtgg cgctccatgc atcttctgcc tcccaaacca    900

ccaacatgag cacgcgaagg aaggagaaaa aagtggccgc aacgttctct tctcatattt    960

attgtctcat cacaaacata ggtacataat acaacaatc                           999
```

<210> SEQ ID NO 12
<211> LENGTH: 318
<212> TYPE: DNA
<213> ORGANISM: Nannochloropsis gaditana
<220> FEATURE:
<221> NAME/KEY: misc_feature
<223> OTHER INFORMATION: EIF3 terminator

<400> SEQUENCE: 12

```
ggcactgtaa ccccggttcc gctcgacgaa ggctgggagc gccctttcgg tgggataaaa     60

tggatgcttt accgctgcgc ttcggctgag gaagagagaa atgcgagcgg ggatcggggt    120

cctagaaacg aagaaaggag aacaagttcc tggccaaaga aaaacaagac aaataccctc    180

tccaggcctg ggcccattac ttttttttgc tgtttcttat acctgcactc gtgcttctct    240

agtctgtcga gaccttacct gatcttcctc cctccatcgc tccccgcccc ccccatccga    300

gcaaccgtcg accatacg                                                  318
```

<210> SEQ ID NO 13
<211> LENGTH: 112
<212> TYPE: RNA
<213> ORGANISM: Artificial Sequence
<220> FEATURE:
<223> OTHER INFORMATION: Chimeric guide RNA targeting acyl-CoA oxidase gene

<400> SEQUENCE: 13

```
gacgggggcu guggcgcgcg guuuuagagc uagaaauagc aaguuaaaau aaggcuaguc     60

cguuaucaac uugaaaaagu ggcaccgagu cggugcuuuu uuuuuuccuu uu           112
```

<210> SEQ ID NO 14
<211> LENGTH: 20
<212> TYPE: DNA
<213> ORGANISM: Nannochloropsis gaditana
<220> FEATURE:
<221> NAME/KEY: misc_feature
<223> OTHER INFORMATION: 20 nucleotide target sequence of acyl-CoA oxidase gene

<400> SEQUENCE: 14

```
gacgggggct gtggcgcgcg                                                 20
```

<210> SEQ ID NO 15
<211> LENGTH: 861
<212> TYPE: DNA
<213> ORGANISM: Nannochloropsis gaditana
<220> FEATURE:
<221> NAME/KEY: misc_feature
<223> OTHER INFORMATION: U6 promoter -continued

<400> SEQUENCE: 15
gcaaaatcct tttcgatgct gccatttact tccacagtct tcaggtttaa ttgcttctcg 60
atgtcagcag tcatcaggag taccatcaaa ctttgaatta tcaagacccg cgcgaccaag 120
aatgccggga acgaatgaat taatatgcat aatacttata tatgtatgga tttgaagatg 180
caattcaaaa gctgggtctg agtacgtctc cgaaaaggac tcccaaaata ggacaagcca 240
tacgtacgcg tcttgcacgt aaaaggagac cgtcgaaaac gccactttta cgcattccag 300
gaaggaatag tctcttgcat ggcgacatca aaagtaacca cgtcaaattt caataacgtg 360
ttacatgttg ttggtcaatg ggtgcatgag tgtccgtatg tcacaagagg gtggggggct 420
cgagctggaa catctgctta ctgcacgcta ggaaggtcgc cataagtact ttgtgcaaat 480
tgtggaacca tcactccttc actacactac tcattatcaa tgaaatgttg acagctgttc 540
ctagtcgtgg ttgtgtcaga ttttccctgc atttgcccaa ctaaaggcac taaagccgac 600
tggcatgcca gtaggattat ggtagttgcc tcgcattata tctctctcgt ccgtcttgat 660
agccagaaaa tacgtaacca ctacccatac ggcaagcatg tccatgtata aaggttactc 720
tgcaaagaaa caatttgaaa atcccagaaa agagagtgtt tgaaaaaacc ctgcccgata 780
tccacatgtt ccaaggccat tgcaaacaac accaagcttt atagctagca tggtatccgt 840
atttctcgtt tacgggaaac c 861

<210> SEQ ID NO 16
<211> LENGTH: 15
<212> TYPE: DNA
<213> ORGANISM: Nannochloropsis gaditana
<220> FEATURE:
<221> NAME/KEY: misc_feature
<223> OTHER INFORMATION: U6 terminator

<400> SEQUENCE: 16
tttttttttc ctttt 15

<210> SEQ ID NO 17
<211> LENGTH: 37
<212> TYPE: DNA
<213> ORGANISM: Artificial Sequence
<220> FEATURE:
<223> OTHER INFORMATION: ACO2-upstream Forward Primer

<400> SEQUENCE: 17
tcaaagatca tttagcagag acgggggctg tggcgcg 37

<210> SEQ ID NO 18
<211> LENGTH: 36
<212> TYPE: DNA
<213> ORGANISM: Artificial Sequence
<220> FEATURE:
<223> OTHER INFORMATION: ACO2-downstream Reverse Primer

<400> SEQUENCE: 18
agtcgagaga tggtgcgttc acggatctag ccagag 36

<210> SEQ ID NO 19
<211> LENGTH: 853
<212> TYPE: DNA
<213> ORGANISM: Nannochloropsis gaditana

<400> SEQUENCE: 19
tcaaagatca tttagcagag acgggggctg tggcgcgcgc ggtacgtgtg gagtcttgct 60

```
ttcttcaggg ggggtcccgg gggggggcg agtcagacaa agggtagagc gtactggaag    120

gacagacaga tgctggcatg accctgcatc cagaacacac atttaataat tgagggtctg    180

gtgatcgagg ggctcggcaa ccgcgcggct gctagcacgt gacacggttt tttacctcta    240

ctgttccaca atcaacccct acttcccctt ctccctccct ctttccctcc ctcccctacg    300

ttaattttcc ctcccgctgt actatatcgc ttcactttca gccgattagc tcctctgcca    360

tcaatgccac gccttttgcg gcgaggacga cgcataccat ggagcgcatg gcaagggaac    420

gagccaaggc ctccttcccc gtccgagaca tgacgtactt cttggacggc gggaggagca    480

tgaccgaggt caaggtgggt gaaataaaaa cataaaaaga gaataaacaa cgaaaggcga    540

ggtctttggg ggatgcctga atacgtaggc aaccgtactg atcgttttgg acccttcttc    600

tcttggggcc gatggcccac aggagggcat gatggcggac ttggcggcga atccggtctt    660

tacggaccca gaatggaacg acttgaacag agatcaggta gggatatggg tgattggccg    720

gaaggtgggg aaggaggggg aggtgcccct tgtgagcttg ccctgtggtc ggagcgcttc    780

cctcgatcaa cccctccctc tcccttcccc ttcccccctc tggctagatc cgtgaacgca    840

ccatctctcg act                                                      853


<210> SEQ ID NO 20
<211> LENGTH: 103
<212> TYPE: RNA
<213> ORGANISM: Artificial Sequence
<220> FEATURE:
<223> OTHER INFORMATION: Chimeric guide RNA for knocking out CHORD gene

<400> SEQUENCE: 20

ggaggcuggu caggaugaaa guuuuagagc uagaaauagc aaguuaaaau aaggcuaguc     60

cguuaucaac uugaaaaagu ggcaccgagu cggugcuuuu uuu                      103


<210> SEQ ID NO 21
<211> LENGTH: 335
<212> TYPE: PRT
<213> ORGANISM: Nannochloropsis gaditana
<220> FEATURE:
<221> NAME/KEY: misc_feature
<223> OTHER INFORMATION: CHORD protein

<400> SEQUENCE: 21

Met Lys Leu Tyr Val His Tyr Glu Glu Ala Gly Gln Asp Glu Lys Ala
1               5                   10                  15

Leu Thr Leu Lys Leu Thr Leu Pro Lys Ser Trp Ala Glu Gln Pro Leu
            20                  25                  30

Leu Gln Val Leu Glu Leu Phe Ile Glu Ser Tyr Asn Lys Lys Lys Thr
        35                  40                  45

Gly Leu Pro Pro Leu Asp Lys Asp Phe Val His Met Glu Lys Ala Gly
    50                  55                  60

Gly Val Ile Leu Pro Val Gly Asn Ile Val Ser Asp Met Leu Ser Asp
65                  70                  75                  80

Arg Asp Asp Leu Tyr Ile Arg Ser Gly Pro Gly Pro Ala Arg Gly Lys
                85                  90                  95

Ile Ala His Leu Ser Ser Pro Pro Asn Ala His Ala Ser Ser Glu Ser
            100                 105                 110

Ser Thr Gly Leu Leu Arg Cys Lys Asn Tyr Gly Cys Asn Gln Ser Phe
        115                 120                 125

Ser Glu Glu Asn Asn Ser Glu Glu Ala Cys Arg Phe His Lys Ala Pro
    130                 135                 140
```

-continued

```
Pro Val Phe His Asp Thr Lys Lys Gly Trp Ser Cys Cys Ala Lys Arg
145                 150                 155                 160

Val Tyr Asp Trp Asp Glu Phe His Thr Ile Glu Gly Cys Thr Thr Gly
                165                 170                 175

Arg His Ser Leu Ile Asp Pro Lys Glu Ile Phe Ala Pro Ser Pro Thr
            180                 185                 190

Leu Ala Ala Ala Ala Gln Ala Glu Arg Gly Asp Cys Ser Asn Thr Ser
        195                 200                 205

Ser Ala Ala Thr Val Ile Lys Ser Ile Asp Glu Phe Asn Gln Ser Asn
    210                 215                 220

Pro Asn Ala Ala Ala Ala Cys Lys Thr Ala Ala Ser Met Thr Leu Ala
225                 230                 235                 240

Gly Thr Arg Cys Thr Val Lys Pro Asp Gly Ser Ala Thr Cys Leu Asn
                245                 250                 255

Lys Gly Cys Gln Lys Asp Tyr Leu Leu Lys Glu Asn His Pro Ser Ala
            260                 265                 270

Cys Arg Tyr His Ala Ala Gly Pro Val Phe His Asp Ala Gly Lys Tyr
        275                 280                 285

Trp Ser Cys Cys Pro Gly Thr Val Lys Tyr Asp Phe Asp Asp Phe Leu
    290                 295                 300

Lys Ile Pro Gly Cys Met Leu Ser Ser His Tyr Asp Gly Ser Gln Glu
305                 310                 315                 320

Ser Leu Glu Ala Phe Thr Arg His Ala Lys Thr Ser Glu Gly Thr
                325                 330                 335
```

<210> SEQ ID NO 22
<211> LENGTH: 1029
<212> TYPE: DNA
<213> ORGANISM: Artificial Sequence
<220> FEATURE:
<223> OTHER INFORMATION: Hygromycin resistance gene, codon optimized for Nannochloropsis

<400> SEQUENCE: 22

```
atggggaaga aaccggaact gaccgctacg tccgtggaga aattccttat tgagaagttc     60

gactctgtct ccgacttgat gcaactgagc gagggagagg agagtagggc gttctcgttt    120

gacgtagggg gtcggggata cgtgttgagg gttaatagtt gtgcggacgg gttctacaag    180

gatcggtatg tctaccgtca tttcgcctcc gccgctctcc ccataccaga ggtactggac    240

attggggagt ttagcgaatc tctcacgtac tgcatctcgc gccgagccca gggagtgacg    300

ttgcaagatc tgcccgaaac tgaattgcct gccgttttgc aacccgtggc cgaggccatg    360

gacgcgatcg ctgccgcaga tctgtctcag acgtccggct ttggaccttt tgggccccag    420

ggcatcgggc agtacacgac ctggcgagac ttcatctgcg ccattgccga tcctcacgtc    480

tatcattggc agacagtcat ggatgacacc gtgtctgcat ccgtggccca agcactggac    540

gaactcatgt tgtgggccga ggattgccct gaggtcaggc acctggtgca cgcggatttc    600

ggcagcaata acgtacttac agacaatggt cggattactg ctgtcatcga ctggtccgaa    660

gcgatgtttg gtgatagcca atacgaagtg gcgaacatat tcttctggcg tccctggttg    720

gcgtgcatgg agcagcagac acgctacttt gaacggaggc acccggagct ggccggctcc    780

ccacgactcc gcgcctatat gttgcgtatc ggactcgatc agctttacca gtctctcgtc    840

gacggcaact tcgacgacgc cgcgtgggcg cagggccgct gcgacgcgat agtccgcagc    900

ggggctggga cggtgggtcg gacccaaatc gcacgccggt cggctgcggt gtggacagac    960
```

ggctgtgttg aggtgcttgc ggactcgggc aaccgtaggc cgagcacccg accgcgtgca 1020
aaggagtga 1029

<210> SEQ ID NO 23
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: EIF3 promoter

<400> SEQUENCE: 23
tcataatcaa agatgagcca gccacgaagc taccggagaa ttctgtaaga aaaatgttta 60
aagttgaaaa tgctaacagt gaagtgatat cctttttaa tggagtgttg aggtgaagtc 120
tagcatcgta ggggaaaaca ggattctgtg tcttccattc tactccttga taaagcgaag 180
aaatccgaca aaaccaaaga gattgttcaa gtttaagatt tgtaagcgta caactatgaa 240
cttcttctct ttgtaggcct gagtggtcgt atgcatacga ttcatgaagt gaatcagtat 300
cgctggattt tgcttaggag taaagcacaa ctaagaaaat atgctgcctg gcaggcatcc 360
tgagacatga ggcaagcgac gtagcaattg aatcctaatt taagccaggg catctgtatg 420
actctgttag ttaattgatg aaccaatgag ctttaaaaaa aaatcgttgc gcgtaatgta 480
gttttaattc tccgccttga ggtgcggggc catttcggac aaggttcttt ggacggagat 540
ggcagcatgt gtcccttctc caaattggtc cgtgtggtag ttgagatgct gccttaaaat 600
tctgctcggt catcctgcct tcgcattcac tcctttcgag ctgtcgggtt cctcacgagg 660
cctccgggag cggattgcgc agaaaggcga cccggagaca cagagaccat acaccgacta 720
aattgcactg gacgatacgg catggcgacg acgatggcca agcattgcta cgtgattatt 780
cgccttgtca ttcagggaga aatgatgaca tgtgtgggac ggtctttaca tgggaagagg 840
gcatgaaaat aacatggcct ggcgggatgg agcgtcacac ctgtgtatgc gttcgatcca 900
caagcaactc accatttgcg tcggggcctg tctccaatct gctttaggct acttttctct 960
aatttagcct attctataca gacagagaca cacagggatc 1000

<210> SEQ ID NO 24
<211> LENGTH: 702
<212> TYPE: DNA
<213> ORGANISM: Artificial Sequence
<220> FEATURE:
<223> OTHER INFORMATION: TurboGFP gene codon optimized for N. gaditana

<400> SEQUENCE: 24
atgttggaga gcgacgagag cggcctgccc gccatggaga tcgagtgccg catcaccggc 60
accctgaacg gcgtggagtt cgagctggtg ggcggcggag agggcacccc cgagcagggc 120
cgcatgacca acaagatgaa gagcaccaaa ggcgccctga ccttcagccc ctacctgctg 180
agccacgtga tgggctacgg cttctaccac ttcggcacct accccagcgg ctacgagaac 240
cccttcctgc acgccatcaa caacggcggc tacaccaaca cccgcatcga gaagtacgag 300
gacggcggcg tgctgcacgt gagcttcagc taccgctacg aggccggccg cgtgatcggc 360
gacttcaagg tgatgggcac cggcttcccc gaggacagcg tgatcttcac cgacaagatc 420
atccgcagca acgccaccgt ggagcacctg caccccatgg gcgataacga tctggatggc 480
agcttcaccc gcaccttcag cctgcgcgac ggcggctact acagctccgt ggtggacagc 540
cacatgcact tcaagagcgc catccacccc agcatcctgc agaacggggg ccccatgttc 600

```
gccttccgcc gcgtggagga ggatcacagc aacaccgagc tgggcatcgt ggagtaccag    660

cacgccttca agaccccgga tgcagatgcc ggtgaagaat aa                       702


<210> SEQ ID NO 25
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: RPL24 promoter

<400> SEQUENCE: 25

aataagcata catcatatga atacaattca gcttaaattt atcatacaaa gatgtaagtg     60

cagcgtgggt ctgtaacgat cgggcgtaat ttaagataat gcgagggacc gggggaggtt    120

ttggaacgga atgaggaatg ggtcatggcc cataataata atatgggttt ggtcgcctcg    180

cacagcaacc gtacgtgcga aaaaggaaca gatccattta ataagttgaa cgttattctt    240

tcctatgcaa tgcgtgtatc ggaggcgaga gcaagtcata ggtggctgcg cacaataatt    300

gagtctcagc tgagcgccgt ccgcgggtgg tgtgagtggt catcctcctc ccggcctatc    360

gctcacatcg cctctcaatg gtggtggtgg ggcctgatat gacctcaatg ccgacccata    420

ttaaaaccca gtaaagcatt caccaacgaa cgaggggctc ttttgtgtgt gttttgagta    480

tgattttaca cctctttgtg catctctctg gtcttccttg gttcccgtag tttgggcatc    540

atcactcacg cttccctcga ccttcgttct tcctttacaa ccccgacaca ggtcagagtt    600

ggagtaatca aaaaaggggt gcacgaatga gatacattag attttgacag atatcctttt    660

actggagagg gttcaaggga tcaaatgaac agcgggcgtt ggcaatctag ggagggatcg    720

gaggttggca gcgagcgaaa gcgtgtccat ccttttggct gtcacacctc acgaaccaac    780

tgttagcagg ccagcacaga tgacatacga gaatctttat tatatcgtag accttatgtg    840

gatgaccttt ggtgctgtgt gtctggcaat gaacctgaag gcttgatagg gaggtggctc    900

ccgtaaaccc tttgtccttt ccacgctgag tctcccccgc actgtccttt atacaaattg    960

ttacagtcat ctgcaggcgg tttttctttg gcaggcaaag                         1000


<210> SEQ ID NO 26
<211> LENGTH: 317
<212> TYPE: DNA
<213> ORGANISM: Nannochloropsis gaditana
<220> FEATURE:
<221> NAME/KEY: misc_feature
<223> OTHER INFORMATION: Bidirectional terminator 2

<400> SEQUENCE: 26

agtgatgcgg cctttaggaa acaccacaaa agtaattgac aatctcagga acgatctgcg     60

tgtttacagc ttcccaaata acaattatac cacgtaccaa aaggggttta atgtatctca    120

caaattcttc taataggtac agcttctcaa attgggtgta tgatgtgaca cttcgtctca    180

cacacgtcac gataattcag cgtatggctt cccttcatca cattcacgca aacttctaca    240

caaccctggg catatttctt gtgttggcaa cactcccgaa atcgattctg cacacaatgg    300

ttcattcaat gattcaa                                                   317


<210> SEQ ID NO 27
<211> LENGTH: 10103
<212> TYPE: DNA
<213> ORGANISM: Artificial Sequence
<220> FEATURE:
```

-continued

<223> OTHER INFORMATION: Chord3-KOvector

<400> SEQUENCE: 27

```
ctgtcagacc aagtttactc atatatactt tagattgatt taaaacttca tttttaattt     60
aaaaggatct aggtgaagat cctttttgat aatctcatga ccaaaatccc ttaacgtgag    120
ttttcgttcc actgagcgtc agaccccgta gaaaagatca aaggatcttc ttgagatcct    180
tttttctgc gcgtaatctg ctgcttgcaa acaaaaaaac caccgctacc agcggtggtt    240
tgtttgccgg atcaagagct accaactctt tttccgaagg taactggctt cagcagagcg    300
cagataccaa atactgtcct tctagtgtag ccgtagttag gccaccactt caagaactct    360
gtagcaccgc ctacatacct cgctctgcta atcctgttac cagtggctgc tgccagtggc    420
gataagtcgt gtcttaccgg gttggactca agacgatagt taccggataa ggcgcagcgg    480
tcgggctgaa cggggggttc gtgcacacag cccagcttgg agcgaacgac ctacaccgaa    540
ctgagatacc tacagcgtga gctatgagaa agcgccacgc ttcccgaagg gagaaaggcg    600
gacaggtatc cggtaagcgg cagggtcgga acaggagagc gcacgaggga gcttccaggg    660
ggaaacgcct ggtatcttta tagtcctgtc gggtttcgcc acctctgact tgagcgtcga    720
tttttgtgat gctcgtcagg ggggcggagc ctatggaaaa acgccagcaa cgcggccttt    780
ttacggttcc tggccttttg ctggcctttt gctcacatgt tctttcctgc gttatcccct    840
gattctgtgg ataaccgtat taccgccttt gagtgagctg ataccgctcg ccgcagccga    900
acgaccgagc gcagcgagtc agtgagcgag gaagcggaag agtttaaaca gggggcatca    960
gaatctatgc cgtatatgag cttatgaatg tcatccatta tctcatgtct gtcaacgcgg   1020
tcctcgggtg taacaaaaca caggaggagc gtctcacttt tgaccagcag ctttctgcct   1080
tagagcgcac cgtccgtgtc aaagaaaatg agctcaaaga attggagctt ctatctagta   1140
cgtgacatta tataaggagg caaagtgctc tattaatatg ttgacgagaa ggtttaatac   1200
atgcagcagg taacagatgc aggacaagtg tgtgaaattt aaccggctac ttcctatgaa   1260
tcaaacagaa gatgcttaca atgcacagga gatcgctgaa caagaactag caaaagagcg   1320
ctctgaatat aatgaggagc gtgcgcgaag ggaaagaagg ctacgggaac gacagcgtaa   1380
tgcaaaatat tgtttacaaa gacaaatgca agagcaggag aagtcgcaag gcgaaagtgc   1440
gggtggtagc atatgccaac aggaaactga ccagcaggac gagcaagacg acgaagctgg   1500
tagcgaagat tacgtgacta cacagcaagt ggaagcggac agattaagaa ctttgacaat   1560
gcttgtcaaa agtataactg ggatcggtga tgcacaggca ttgcgctcaa aacttgagca   1620
ccaaggggag gtcttgcgga agtcacaaga aattagcaaa gataatcagg tgactacaag   1680
aatgatagac tggtactacc ccagactcgt tgacatccgg cgtgtcgagc gttcacatca   1740
gagatatgaa ggtagatgac ggtaaaagtt tcctaaaatc gagcacgcga cttttttttc   1800
ttcttcaata tctgagcagg atcgcttaga gaagctacag aaagagcggg acatcctctg   1860
gaatcaatta cagagttcca gatattcacc gcgccccctc aaggtctgta acgaataata   1920
agagaggtca tcacttggcc ctgatcgcga tgctgtagag gttattgatg aaaggggagg   1980
aaagaatggc aggggccgta tagaaataat cctcaggatt ttgaaggcgt gcgtcatcct   2040
agaccaaatt tgcaggaaag atgcttagaa atctcaaaat tgacgcggat atttttgact   2100
aatcgacaaa catgctttca cgaccacagt ccgaaggcct acttcgccag ctgttgcacg   2160
acaaggaaaa agtcaaggag atcgaaaata ggtgcgagta cttagcacaa cttgtggcac   2220
atttgcagtg tggtttagtg gagcgtttat ggcctttagt aatgcgaagc aatcggaatc   2280
```

accttgctgc ttcgccaaag acggaaaatc tcgatcgagt ggcgcttcaa cgtatgctta 2340
aaaagttaga agtccgctgc ttgcagctgc ttgacaccaa atccatccca caaaagcatt 2400
gaaattctca aatatgggga accaaacgct catccaaccc atcccaagcc ccaggcttgc 2460
ttctgtcgaa tccgcagcac tcagcacgca tgtgtagtat cttttggata aatcattgca 2520
aagaaggtgt ataaggcttt ttcccggaag caaaagctcc cgtgggcact gtagaaacaa 2580
aagtgaggtg atagttattt ttcgatgcac ggaacggtat atatattcgc aaagcttgtg 2640
gaggctatcg ctgtcctttg tttgaagcag tcttcagcga agctgccacg gagcttcgtt 2700
caggaccgtt tcttggcatt caaaactcta cgactatgat actatcgagc attccgcatg 2760
attacagcgc aaagcctacc aaaaagatgc ggtaattcac ttgcgggacc gcaatcattg 2820
tcagccatca gcgcactgta ctcgtaaaaa ggcgaacatt gtccggtaac tcgctcatgt 2880
ctcacttgag ctgatgtcct ctctaaaata atagggtcgg tcccaaactc ttttaaactc 2940
cgatgaaact ctatgtgcac tacgagcggc cgcaataagc atacatcata tgaatacaat 3000
tcagcttaaa tttatcatac aaagatgtaa gtgcagcgtg ggtctgtaac gatcgggcgt 3060
aatttaagat aatgcgaggg accgggggag gttttggaac ggaatgagga atgggtcatg 3120
gcccataata ataatatggg tttggtcgcc tcgcacagca accgtacgtg cgaaaaagga 3180
acagatccat ttaataagtt gaacgttatt ctttcctatg caatgcgtgt atcggaggcg 3240
agagcaagtc ataggtggct gcgcacaata attgagtctc agctgagcgc cgtccgcggg 3300
tggtgtgagt ggtcatcctc ctcccggcct atcgctcaca tcgcctctca atggtggtgg 3360
tggggcctga tatgacctca atgccgaccc atattaaaac ccagtaaagc attcaccaac 3420
gaacgagggg ctcttttgtg tgtgttttga gtatgatttt acacctcttt gtgcatctct 3480
ctggtcttcc ttggttcccg tagtttgggc atcatcactc acgcttccct cgaccttcgt 3540
tcttccttta caaccccgac acaggtcaga gttggagtaa tcaaaaaagg ggtgcacgaa 3600
tgagatacat tagattttga cagatatcct tttactggag agggttcaag ggatcaaatg 3660
aacagcgggc gttggcaatc tagggaggga tcggaggttg gcagcgagcg aaagcgtgtc 3720
catccttttg gctgtcacac ctcacgaacc aactgttagc aggccagcac agatgacata 3780
cgagaatctt tattatatcg tagaccttat gtggatgacc tttggtgctg tgtgtctggc 3840
aatgaacctg aaggcttgat agggaggtgg ctcccgtaaa ccctttgtcc tttccacgct 3900
gagtctcccc cgcactgtcc tttatacaaa ttgttacagt catctgcagg cggtttttct 3960
ttggcaggca aacatgttgg agagcgacga gagcggcctg cccgccatgg agatcgagtg 4020
ccgcatcacc ggcaccctga acggcgtgga gttcgagctg gtgggcggcg gagagggcac 4080
ccccgagcag ggccgcatga ccaacaagat gaagagcacc aaaggcgccc tgaccttcag 4140
cccctacctg ctgagccacg tgatgggcta cggcttctac cacttcggca cctaccccag 4200
cggctacgag aacccctcc tgcacgccat caacaacggc ggctacacca acacccgcat 4260
cgagaagtac gaggacggcg gcgtgctgca cgtgagcttc agctaccgct acgaggccgg 4320
ccgcgtgatc ggcgacttca aggtgatggg caccggcttc cccgaggaca gcgtgatctt 4380
caccgacaag atcatccgca gcaacgccac cgtggagcac ctgcacccca tgggcgataa 4440
cgatctggat ggcagcttca cccgcacctt cagcctgcgc gacggcggct actacagctc 4500
cgtggtggac agccacatgc acttcaagag cgccatccac cccagcatcc tgcagaacgg 4560
gggccccatg ttcgccttcc gccgcgtgga ggaggatcac agcaacaccg agctgggcat 4620

-continued cgtggagtac cagcacgcct tcaagacccc ggatgcagat gccggtgaag aataaattta 4680
aatagtgatg cggcctttag gaaacaccac aaaagtaatt gacaatctca ggaacgatct 4740
gcgtgtttac agcttcccaa ataacaatta taccacgtac caaaaggggt ttaatgtatc 4800
tcacaaattc ttctaatagg tacagcttct caaattgggt gtatgatgtg acacttcgtc 4860
tcacacacgt cacgataatt cagcgtatgg cttcccttca tcacattcac gcaaacttct 4920
acacaaccct gggcatattt cttgtgttgg caacactccc gaaatcgatt ctgcacacaa 4980
tggttcattc aatgattcaa tcactccttt gcacgcggtc gggtgctcgg cctacggttg 5040
cccgagtccg caagcacctc aacacagccg tctgtccaca ccgcagccga ccggcgtgcg 5100
atttgggtcc gacccaccgt cccagccccg ctgcggacta tcgcgtcgca gcggccctgc 5160
gcccacgcgg cgtcgtcgaa gttgccgtcg acgagagact ggtaaagctg atcgagtccg 5220
atacgcaaca tataggcgcg gagtcgtggg gagccggcca gctccgggtg cctccgttca 5280
aagtagcgtg tctgctgctc catgcacgcc aaccagggac gccagaagaa tatgttcgcc 5340
acttcgtatt ggctatcacc aaacatcgct tcggaccagt cgatgacagc agtaatccga 5400
ccattgtctg taagtacgtt attgctgccg aaatccgcgt gcaccaggtg cctgacctca 5460
gggcaatcct cggcccacaa catgagttcg tccagtgctt gggccacgga tgcagacacg 5520
gtgtcatcca tgactgtctg ccaatgatag acgtgaggat cggcaatggc gcagatgaag 5580
tctcgccagg tcgtgtactg cccgatgccc tggggcccaa aaggtccaaa gccggacgtc 5640
tgagacagat ctgcggcagc gatcgcgtcc atggcctcgg ccacgggttg caaaacggca 5700
ggcaattcag tttcgggcag atcttgcaac gtcactccct gggctcggcg cgagatgcag 5760
tacgtgagag attcgctaaa ctccccaatg tccagtacct ctggtatggg gagagcggcg 5820
gaggcgaaat gacggtagac ataccgatcc ttgtagaacc cgtccgcaca actattaacc 5880
ctcaacacgt atccccgacc ccctacgtca aacgagaacg ccctactctc ctctccctcg 5940
ctcagttgca tcaagtcgga gacagagtcg aacttctcaa taaggaattt ctccacggac 6000
gtagcggtca gttccggttt cttccccatg atccctgtgt gtctctgtct gtatagaata 6060
ggctaaatta gagaaaagta gcctaaagca gattggagac aggccccgac gcaaatggtg 6120
agttgcttgt ggatcgaacg catacacagg tgtgacgctc catcccgcca ggccatgtta 6180
ttttcatgcc ctcttcccat gtaaagaccg tcccacacat gtcatcattt ctccctgaat 6240
gacaaggcga ataatcacgt agcaatgctt ggccatcgtc gtcgccatgc cgtatcgtcc 6300
agtgcaattt agtcggtgta tggtctctgt gtctccgggt cgcctttctg cgcaatccgc 6360
tcccggaggc ctcgtgagga acccgacagc tcgaaaggag tgaatgcgaa ggcaggatga 6420
ccgagcagaa ttttaaggca gcatctcaac taccacacgg accaatttgg agaagggaca 6480
catgctgcca tctccgtcca aagaaccttg tccgaaatgg ccccgcacct caaggcggag 6540
aattaaaact acattacgcg caacgatttt tttttaaagc tcattggttc atcaattaac 6600
taacagagtc atacagatgc cctggcttaa attaggattc aattgctacg tcgcttgcct 6660
catgtctcag gatgcctgcc aggcagcata ttttcttagt tgtgctttac tcctaagcaa 6720
aatccagcga tactgattca cttcatgaat cgtatgcata cgaccactca ggcctacaaa 6780
gagaagaagt tcatagttgt acgcttacaa atcttaaact tgaacaatct ctttggtttt 6840
gtcggatttc ttcgctttat caaggagtag aatggaagac acagaatcct gttttcccct 6900
acgatgctag acttcacctc aacactccat taaaaaagga tatcacttca ctgttagcat 6960
tttcaacttt aaacattttt cttacagaat tctccggtag cttcgtggct ggctcatctt 7020
tgattatgag gcgcgccagg cattgacgct taagttgact ctgcccaaaa gctgggcgga 7080
gcagccgttg cttcaagtac tggagctgtt catcgaatcc tacaacaaga aaaagaccgg 7140
tctacctccc ttggacaaag actttgtcca catggaaaaa gctgggtaag tccttactcg 7200
tgacagcgtt ccctttctcc agactagacg cctaatagtg ttctaatgta ccactgggac 7260
acgcctcgct gcctgtgcac catgctccat actcaacgct gctacagggg cgtaatcctt 7320
ccagtcggca acattgtgag cgacatgttg agcgatagag atgatttgta tatcagatcc 7380
gggccagggc ctgctcgtgg gaagattgcc catctcagtt cgcccccaaa cgcgcacgct 7440
tcgagtgagt cgagcacagg attgttgcgc tgcaaaaact atggatgcaa tcagtcattt 7500
tcggaagaaa acaattcaga agaggcgtgc cgctttcaca aggcaccccc cgtctttcat 7560
gatacgaaga aagggtggtc gtgctgcgcg aagcgagtat atgactggga cgagttccat 7620
acggtaagcg tggaagtgtt cgttctcggc cccaggactt tgttttgagg caattggtgt 7680
actttaattg gcggataaag ggaggactca caactttcga tattcaccgt ctccagatcg 7740
aggggtgcac cacaggacgg cacagtctca tcgatccgaa ggaaattttc gcgccgtccc 7800
ccaccctggc tgcagccgcg caggccgaga ggggagattg cagcaatacg tcaagcgctg 7860
ctacagtcat caagagcatt gatgaattca atcagtcgaa tccaaatgcc gccgctgcat 7920
gcaaaacagc agcctcgatg acgctggcgg gcacgcgctg caccgtcaaa ccggacgggt 7980
ctgccacctg tttgaacaaa ggctgccaaa aggactactt gctcaaggag aatcacccct 8040
ctgcatgtcg gtaaggacac cgcgctcgat ggaatcgtga gctttacgtt cccacgccaa 8100
cacttcgcca tttctcctcc cttcctttct ttagctacca cgcagccggc cccgtcttcc 8160
acgacgcggg taaatactgg tcatgttgcc ctggaacggt caagtacgac ttcgacgact 8220
ttctcaagat ccctggatgc atgctcagta gtcattacga cggaagccag gagagcctgg 8280
aggcgttcac tagacacgcc aaaacgtctg agggcacatg agaatgtggg atggggagaa 8340
agaaccacgt atccccacga ggaatggcgc attgggagcg agggggatcg acataggaag 8400
aagcaataaa aattctgctc aatacggtat tttttatttt ttggcgtctt ccgttcgtag 8460
ccggcggacg aacagcgatg caaactcgag acggacagtg ccccacggtc ttcgttcgaa 8520
aacatcattg ccaacaacct cgcacactta cttccaggat cctataaata tcttacaacc 8580
accatccgcc tcttccttct cacgcgcatg gataatcaac gccacgattc acaccgttgc 8640
ctggacattt ccccccatg acgggtaatc ctacccgttt ccttccagcg ttccccttct 8700
cttccattcg aacttgaatg cactttactt atttctcttg tgagcatcgt gcatccgctt 8760
gctggcaacg gcaatgggaa tgataatcac aagcaggatc gccaggattg ccagtcccat 8820
aaccatttc atctagatcg tatggagcaa aggaagagag agggggtaag ggcgagaaga 8880
tcgcaatgaa aagggatgac ggcccacgcc gcctcctgcg acttccaatc gtccgaggtt 8940
tacacacatg gcacagccag aaacaccccc ggcataggag caggataggg gtaagacaac 9000
caagcacgta ctcggagctg tttccagcac atctgtttaa acgacgaaag ggcctcgtga 9060
tacgcctatt tttataggtt aatgtcatga taataatggt ttcttagacg tcaggtggca 9120
cttttcgggg aaatgtgcgc ggaaccccta tttgtttatt tttctaaata cattcaaata 9180
tgtatccgct catgagacaa taaccctgat aaatgcttca ataatattga aaaaggaaga 9240
gtatgagtat tcaacatttc cgtgtcgccc ttattccctt ttttgcggca ttttgccttc 9300
ctgtttttgc tcacccagaa acgctggtga aagtaaaaga tgctgaagat cagttgggtg 9360
cacgagtggg ttacatcgaa ctggatctca acagcggtaa gatccttgag agttttcgcc 9420
ccgaagaacg ttttccaatg atgagcactt ttaaagttct gctatgtggc gcggtattat 9480
cccgtattga cgccgggcaa gagcaactcg gtcgccgcat acactattct cagaatgact 9540
tggttgagta ctcaccagtc acagaaaagc atcttacgga tggcatgaca gtaagagaat 9600
tatgcagtgc tgccataacc atgagtgata acactgcggc caacttactt ctgacaacga 9660
tcggaggacc gaaggagcta accgcttttt tgcacaacat gggggatcat gtaactcgcc 9720
ttgatcgttg ggaaccggag ctgaatgaag ccataccaaa cgacgagcgt gacaccacga 9780
tgcctgtagc aatggcaaca acgttgcgca aactattaac tggcgaacta cttactctag 9840
cttcccggca acaattaata gactggatgg aggcggataa agttgcagga ccacttctgc 9900
gctcggccct tccggctggc tggtttattg ctgataaatc tggagccggt gagcgtgggt 9960
ctcgcggtat cattgcagca ctggggccag atggtaagcc ctcccgtatc gtagttatct 10020
acacgacggg gagtcaggca actatggatg aacgaaatag acagatcgct gagataggtg 10080
cctcactgat taagcattgg taa 10103

<210> SEQ ID NO 28
<211> LENGTH: 2016
<212> TYPE: DNA
<213> ORGANISM: Nannochloropsis gaditana
<220> FEATURE:
<221> NAME/KEY: misc_feature
<223> OTHER INFORMATION: CHORD target upstream homology arm

<400> SEQUENCE: 28
agggggcatc agaatctatg ccgtatatga gcttatgaat gtcatccatt atctcatgtc 60
tgtcaacgcg gtcctcgggt gtaacaaaac acaggaggag cgtctcactt ttgaccagca 120
gctttctgcc ttagagcgca ccgtccgtgt caaagaaaat gagctcaaag aattggagct 180
tctatctagt acgtgacatt atataaggag gcaaagtgct ctattaatat gttgacgaga 240
aggtttaata catgcagcag gtaacagatg caggacaagt gtgtgaaatt taaccggcta 300
cttcctatga atcaaacaga agatgcttac aatgcacagg agatcgctga acaagaacta 360
gcaaaagagc gctctgaata taatgaggag cgtgcgcgaa gggaaagaag gctacgggaa 420
cgacagcgta atgcaaaata ttgtttacaa agacaaatgc aagagcagga gaagtcgcaa 480
ggcgaaagtg cgggtggtag catatgccaa caggaaactg accagcagga cgagcaagac 540
gacgaagctg gtagcgaaga ttacgtgact acacagcaag tggaagcgga cagattaaga 600
actttgacaa tgcttgtcaa aagtataact gggatcggtg atgcacaggc attgcgctca 660
aaacttgagc accaagggga ggtcttgcgg aagtcacaag aaattagcaa agataatcag 720
gtgactacaa gaatgataga ctggtactac cccagactcg ttgacatccg gcgtgtcgag 780
cgttcacatc agagatatga aggtagatga cggtaaaagt ttcctaaaat cgagcacgcg 840
actttttttt cttcttcaat atctgagcag gatcgcttag agaagctaca gaaagagcgg 900
gacatcctct ggaatcaatt acagagttcc agatattcac cgcgcccccct caaggtctgt 960 aacgaataat aagagaggtc atcacttggc cctgatcgcg atgctgtaga ggttattgat 1020
gaaaggggag gaaagaatgg caggggccgt atagaaataa tcctcaggat tttgaaggcg 1080
tgcgtcatcc tagaccaaat ttgcaggaaa gatgcttaga aatctcaaaa ttgacgcgga 1140
tatttttgac taatcgacaa acatgctttc acgaccacag tccgaaggcc tacttcgcca 1200
gctgttgcac gacaaggaaa aagtcaagga gatcgaaaat aggtgcgagt acttagcaca 1260

-continued acttgtggca catttgcagt gtggtttagt ggagcgttta tggcctttag taatgcgaag 1320
caatcggaat caccttgctg cttcgccaaa gacggaaaat ctcgatcgag tggcgcttca 1380
acgtatgctt aaaaagttag aagtccgctg cttgcagctg cttgacacca aatccatccc 1440
acaaaagcat tgaaattctc aaatatgggg aaccaaacgc tcatccaacc catcccaagc 1500
cccaggcttg cttctgtcga atccgcagca ctcagcacgc atgtgtagta tcttttggat 1560
aaatcattgc aaagaaggtg tataaggctt tttcccggaa gcaaaagctc ccgtgggcac 1620
tgtagaaaca aaagtgaggt gatagttatt tttcgatgca cggaacggta tatatattcg 1680
caaagcttgt ggaggctatc gctgtccttt gtttgaagca gtcttcagcg aagctgccac 1740
ggagcttcgt tcaggaccgt ttcttggcat tcaaaactct acgactatga tactatcgag 1800
cattccgcat gattacagcg caaagcctac caaaaagatg cggtaattca cttgcgggac 1860
cgcaatcatt gtcagccatc agcgcactgt actcgtaaaa aggcgaacat tgtccggtaa 1920
ctcgctcatg tctcacttga gctgatgtcc tctctaaaat aatagggtcg gtcccaaact 1980
cttttaaact ccgatgaaac tctatgtgca ctacga 2016

<210> SEQ ID NO 29
<211> LENGTH: 1997
<212> TYPE: DNA
<213> ORGANISM: Nannochloropsis gaditana
<220> FEATURE:
<221> NAME/KEY: misc_feature
<223> OTHER INFORMATION: CHORD target upstream homology arm

<400> SEQUENCE: 29
aggcattgac gcttaagttg actctgccca aaagctgggc ggagcagccg ttgcttcaag 60
tactggagct gttcatcgaa tcctacaaca agaaaaagac cggtctacct cccttggaca 120
aagactttgt ccacatggaa aaagctgggt aagtccttac tcgtgacagc gttccctttc 180
tccagactag acgcctaata gtgttctaat gtaccactgg gacacgcctc gctgcctgtg 240
caccatgctc catactcaac gctgctacag gggcgtaatc cttccagtcg gcaacattgt 300
gagcgacatg ttgagcgata gagatgattt gtatatcaga tccgggccag ggcctgctcg 360
tgggaagatt gcccatctca gttcgccccc aaacgcgcac gcttcgagtg agtcgagcac 420
aggattgttg cgctgcaaaa actatggatg caatcagtca ttttcggaag aaaacaattc 480
agaagaggcg tgccgctttc acaaggcacc ccccgtcttt catgatacga agaaagggtg 540
gtcgtgctgc gcgaagcgag tatatgactg ggacgagttc catacggtaa gcgtggaagt 600
gttcgttctc ggccccagga ctttgttttg aggcaattgg tgtactttaa ttggcggata 660
aagggaggac tcacaacttt cgatattcac cgtctccaga tcgaggggtg caccacagga 720
cggcacagtc tcatcgatcc gaaggaaatt ttcgcgccgt cccccaccct ggctgcagcc 780
gcgcaggccg agaggggaga ttgcagcaat acgtcaagcg ctgctacagt catcaagagc 840
attgatgaat tcaatcagtc gaatccaaat gccgccgctg catgcaaaac agcagcctcg 900
atgacgctgg cgggcacgcg ctgcaccgtc aaaccggacg ggtctgccac ctgtttgaac 960
aaaggctgcc aaaaggacta cttgctcaag gagaatcacc cctctgcatg tcggtaagga 1020
caccgcgctc gatggaatcg tgagctttac gttcccacgc caacacttcg ccatttctcc 1080
tcccttcctt tctttagcta ccacgcagcc ggccccgtct tccacgacgc gggtaaatac 1140
tggtcatgtt gccctggaac ggtcaagtac gacttcgacg actttctcaa gatccctgga 1200
tgcatgctca gtagtcatta cgacggaagc caggagagcc tggaggcgtt cactagacac 1260

-continued gccaaaacgt ctgagggcac atgagaatgt gggatgggga gaaagaacca cgtatcccca 1320
cgaggaatgg cgcattggga gcgaggggga tcgacatagg aagaagcaat aaaaattctg 1380
ctcaatacgg tattttttat tttttggcgt cttccgttcg tagccggcgg acgaacagcg 1440
atgcaaactc gagacggaca gtgccccacg gtcttcgttc gaaaacatca ttgccaacaa 1500
cctcgcacac ttacttccag gatcctataa atatcttaca accaccatcc gcctcttcct 1560
tctcacgcgc atggataatc aacgccacga ttcacaccgt tgcctggaca tttccccccc 1620
atgacgggta atcctacccg tttccttcca gcgttcccct tctcttccat tcgaacttga 1680
atgcacttta cttatttctc ttgtgagcat cgtgcatccg cttgctggca acggcaatgg 1740
gaatgataat cacaagcagg atcgccagga ttgccagtcc cataaccatt ttcatctaga 1800
tcgtatggag caaaggaaga gagagggggt aagggcgaga agatcgcaat gaaaagggat 1860
gacggcccac gccgcctcct gcgacttcca atcgtccgag gtttacacac atggcacagc 1920
cagaaacacc cccggcatag gagcaggata ggggtaagac aaccaagcac gtactcggag 1980
ctgtttccag cacatct 1997

<210> SEQ ID NO 30
<211> LENGTH: 23
<212> TYPE: DNA
<213> ORGANISM: Nannochloropsis gaditana
<220> FEATURE:
<221> NAME/KEY: misc_feature
<223> OTHER INFORMATION: CHORD-CRISPR target, including PAM sequence

<400> SEQUENCE: 30
ggaggctggt caggatgaaa agg 23

<210> SEQ ID NO 31
<211> LENGTH: 20
<212> TYPE: RNA
<213> ORGANISM: Artificial Sequence
<220> FEATURE:
<223> OTHER INFORMATION: 20 nucleotide targeting sequence homologous to
CHORD gene

<400> SEQUENCE: 31
ggaggcuggu caggaugaaa 20

<210> SEQ ID NO 32
<211> LENGTH: 103
<212> TYPE: RNA
<213> ORGANISM: Artificial Sequence
<220> FEATURE:
<223> OTHER INFORMATION: Entire chimeric guide RNA for targeting CHORD
gene

<400> SEQUENCE: 32
ggaggcuggu caggaugaaa guuuuagagc uagaaauagc aaguuaaaau aaggcuaguc 60
cguuaucaac uugaaaaagu ggcaccgagu cggugcuuuu uuu 103

<210> SEQ ID NO 33
<211> LENGTH: 120
<212> TYPE: DNA
<213> ORGANISM: Artificial Sequence
<220> FEATURE:
<223> OTHER INFORMATION: oligo-chord3 sense oligonucleotide

<400> SEQUENCE: 33
taatacgact cactatagga ggctggtcag gatgaaagtt ttagagctag aaatagcaag 60
ttaaaataag gctagtccgt tatcaacttg aaaaagtggc accgagtcgg tgcttttttt 120

<210> SEQ ID NO 34
<211> LENGTH: 120
<212> TYPE: DNA
<213> ORGANISM: Artificial Sequence
<220> FEATURE:
<223> OTHER INFORMATION: Oligo-chord3 reverse complement oligonucleotide

<400> SEQUENCE: 34
aaaaaaagca ccgactcggt gccacttttt caagttgata acggactagc cttattttaa 60
cttgctattt ctagctctaa aactttcatc ctgaccagcc tcctatagtg agtcgtatta 120

<210> SEQ ID NO 35
<211> LENGTH: 19
<212> TYPE: DNA
<213> ORGANISM: Artificial Sequence
<220> FEATURE:
<223> OTHER INFORMATION: T7 Promoter

<400> SEQUENCE: 35
taatacgact cactatagg 19

<210> SEQ ID NO 36
<211> LENGTH: 25
<212> TYPE: DNA
<213> ORGANISM: Artificial Sequence
<220> FEATURE:
<223> OTHER INFORMATION: oligo- KFchord3 Forward primer

<400> SEQUENCE: 36
gtcggtccca aactctttta aactc 25

<210> SEQ ID NO 37
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: oligo- KFchord3 Reverse primer

<400> SEQUENCE: 37
gtcggtccca aactctttta aactc 25

<210> SEQ ID NO 38
<211> LENGTH: 11263
<212> TYPE: DNA
<213> ORGANISM: Artificial Sequence
<220> FEATURE:
<223> OTHER INFORMATION: pSGE-6206 vector

<400> SEQUENCE: 38
gcggccgccg tatggtcgac ggttgctcgg atgggggggg cggggagcga tggagggagg 60
aagatcaggt aaggtctcga cagactagag aagcacgagt gcaggtataa gaaacagcaa 120
aaaaaagtaa tgggcccagg cctggagagg gtatttgtct tgtttttctt tggccaggaa 180
cttgttctcc tttcttcgtt tctaggaccc cgatccccgc tcgcatttct ctcttcctca 240
gccgaagcgc agcggtaaag catccatttt atcccaccga aagggcgctc ccagccttcg 300
tcgagcggaa ccggggttac agtgcctcaa ccctcccaga cgtagccaga gggaagcaac 360
tccctgatgc caaccgctgt gggctgccca tcggaatctt tgacaattgc cttgatcccc 420

-continued

```
gggtgcaagt caagcagcac ctgccgacat cgcccgcacg gagacagaat gccgcggttt    480
tcgttcccga tggccactat gcacgtcaga tttccggcag cagccgcagc ggccgttccg    540
aggaccacga gctccgcgca tggccctccg gtgaaatgat atacattcac gccggtaaag    600
atccgaccgt cggacgagag ggctgcactg gccaccgagt agtcctcgct aataggtatg    660
ctgttgatgg tcgcagttgc acgttcgatc agcgtggatt cctcttggga taaaggcttg    720
gccatcgagc tcggtacccg gggatccatg attgttgtat tatgtaccta tgtttgtgat    780
gagacaataa atatgagaag agaacgttgc ggccactttt ttctccttcc ttcgcgtgct    840
catgttggtg gtttgggagg cagaagatgc atggagcgcc acacattcgg taggacgaaa    900
cagcctcccc cacaaaggga ccatgggtag ctaggatgac gcacaagcga gttcccgctc    960
tcgaagggaa acccaggcat ttccttcctc ttttcaagcc acttgttcac gtgtcaacac   1020
aattttggac taaaatgccc ctcggaactc ggcaggcctc cctctgctcc gttgtcctgg   1080
tcgccgagaa cgcgagaccg tgccgcatgc catcgatctg ctcgtctgta ctactaatcg   1140
tgtgcgtgtt cgtgcttgtt tcgcacgaaa ttgtcctcgt tcggccctca caacggtgga   1200
aatcggtgct agaataaagt gaggtggctt atttcaatgg cggccgtcat catgcgggat   1260
caactgaagt acggcgggtt ctcgagattt catcgtgctc gtccagagca ggtgttttgc   1320
ctgcagctct tcatgtttag ggtcatgat ttcatctgat atgccgtaag aaaaccaata   1380
ttcacttctc aattttccat ggaaaggtga aggcctaggt tgtgtgcgag gcaacgactg   1440
gggagggatc gcaacattct tgctaacctc ccctctatct tggccgctgt gaatcggcat   1500
atttaccggg ctgaattgag aaagtgtttt gagggaatta aaaggtggct gtcttgcaag   1560
cttggcttca gtgcctgctt aattcgaacc gatccagctt gtgatgaggc cttcctaagc   1620
ctggtagtca gaagcgacat ggcgctataa atttcgtctc agttggagag tagaaaagca   1680
tgattcgaac acggttttca actgccaaag atatctccat tgtttccttc aatctgtaca   1740
cctgcacggt gcaccagttg gtacggcata ttatggttta ataagcatac atcatatgaa   1800
tacaattcag cttaaattta tcatacaaag atgtaagtgc agcgtgggtc tgtaacgatc   1860
gggcgtaatt taagataatg cgagggaccg ggggaggttt tggaacggaa tgaggaatgg   1920
gtcatggccc ataataataa tatgggtttg gtcgcctcgc acagcaaccg tacgtgcgaa   1980
aaaggaacag atccatttaa taagttgaac gttattcttt cctatgcaat gcgtgtatcg   2040
gaggcgagag caagtcatag gtggctgcgc acaataattg agtctcagct gagcgccgtc   2100
cgcgggtggt gtgagtggtc atcctcctcc cggcctatcg ctcacatcgc ctctcaatgg   2160
tggtggtggg gcctgatatg acctcaatgc cgacccatat taaaacccag taaagcattc   2220
accaacgaac gaggggctct tttgtgtgtg ttttgagtat gattttacac ctctttgtgc   2280
atctctctgg tcttccttgg ttcccgtagt ttgggcatca tcactcacgc ttccctcgac   2340
cttcgttctt cctttacaac cccgacacag gtcagagttg gagtaatcaa aaaaggggtg   2400
cacgaatgag atacattaga ttttgacaga tatcctttta ctggagaggg ttcaagggat   2460
caaatgaaca gcgggcgttg gcaatctagg gagggatcgg aggttggcag cgagcgaaag   2520
cgtgtccatc cttttggctg tcacacctca cgaaccaact gttagcaggc cagcacagat   2580
gacatacgag aatctttatt atatcgtaga ccttatgtgg atgacctttg gtgctgtgtg   2640
tctggcaatg aacctgaagg cttgataggg aggtggctcc cgtaaaccct ttgtcctttc   2700
cacgctgagt ctcccccgca ctgtccttta tacaaattgt tacagtcatc tgcaggcggt   2760
ttttctttgg caggcaaaga tgcccaagaa aaagcggaag gtcggcgact acaaggatga   2820
```

-continued

```
cgatgacaag ttggagcctg gagagaagcc ctacaaatgc cctgagtgcg gaaagagctt   2880
cagccaatct ggagccttga cccggcatca acgaacgcat acacgagaca agaagtactc   2940
catcgggctg gacatcggga cgaactccgt gggatgggcc gtgatcacag acgaatacaa   3000
ggtgccttcc aagaagttca aggtgctggg gaacacggac agacactcca tcaagaagaa   3060
cctcatcggg gccttgctct tcgactccgg agaaaccgcc gaagcaacgc gattgaaaag   3120
aaccgccaga agacgataca cacgacggaa gaaccgcatc tgctacctcc aggagatctt   3180
cagcaacgag atggccaagg tggacgactc gttctttcat cgcctggagg agagcttcct   3240
ggtggaggaa gacaagaaac atgagcgcca cccgatcttc gggaacatcg tggacgaagt   3300
ggcctaccac gagaaatacc ccacgatcta ccacttgcgc aagaaactcg tggactccac   3360
ggacaaagcg gacttgcggt tgatctactt ggccttggcc cacatgatca aatttcgggg   3420
ccacttcctg atcgagggcg acttgaatcc cgacaattcc gacgtggaca agctcttcat   3480
ccagctggtg cagacctaca accagctctt cgaggagaac cccatcaatg cctccggagt   3540
ggacgccaaa gccatcttgt ccgcccgatt gtccaaatcc agacgcttgg agaacttgat   3600
cgcacaactt cctggcgaga agaagaacgg cctcttcggc aacttgatcg cgctgtcgct   3660
gggattgacg cctaacttca agtccaactt cgacttggcc gaggacgcca agttgcaact   3720
gtccaaggac acctacgacg acgacctcga caacctgctg gcccaaattg gcgaccaata   3780
cgcggacttg tttttggcgg ccaagaactt gagcgacgcc atcttgttga gcgacatctt   3840
gcgcgtgaat acggagatca ccaaagcccc tttgtccgcc tctatgatca agcggtacga   3900
cgagcaccac caagacttga ccctgttgaa agccctcgtg cggcaacaat tgcccgagaa   3960
gtacaaggag atcttcttcg accagtccaa gaacgggtac gccggctaca tcgacggagg   4020
agcctcccaa gaagagttct acaagttcat caagcccatc ctggagaaga tggacggcac   4080
cgaggagttg ctcgtgaagc tgaaccgcga agacttgttg cgaaaacagc ggacgttcga   4140
caatggcagc atcccccacc aaatccattt gggagagttg cacgccatct tgcgacggca   4200
agaggacttc tacccgttcc tgaaggacaa ccgcgagaaa atcgagaaga tcctgacgtt   4260
cagaatcccc tactacgtgg gacccttggc ccgaggcaat tcccggtttg catggatgac   4320
gcgcaaaagc gaagagacga tcaccccctg gaacttcgaa gaagtggtcg acaaaggagc   4380
atccgcacag agcttcatcg agcgaatgac gaacttcgac aagaacctgc ccaacgagaa   4440
ggtgttgccc aagcattcgc tgctgtacga gtacttcacg gtgtacaacg agctgaccaa   4500
ggtgaagtac gtgaccgagg gcatgcgcaa acccgcgttc ctgtcgggag agcaaaagaa   4560
ggccattgtg gacctgctgt tcaagaccaa ccggaaggtg accgtgaaac agctgaaaga   4620
ggactacttc aagaagatcg agtgcttcga ctccgtggag atctccggcg tggaggaccg   4680
attcaatgcc tccttgggaa cctaccatga cctcctgaag atcatcaagg acaaggactt   4740
cctggacaac gaggagaacg aggacatcct ggaggacatc gtgctgaccc tgaccctgtt   4800
cgaggaccga gagatgatcg aggaacggtt gaaaacgtac gcccacttgt tcgacgacaa   4860
ggtgatgaag cagctgaaac gccgccgcta caccggatgg ggacgattga gccgcaaact   4920
gattaatgga attcgcgaca agcaatccgg aaagaccatc ctggacttcc tgaagtccga   4980
cgggttcgcc aaccgcaact tcatgcagct catccacgac gactccttga ccttcaagga   5040
ggacatccag aaggcccaag tgtccggaca aggagactcc ttgcacgagc acatcgccaa   5100
tttggccgga tcccccgcaa tcaaaaaagg catcttgcaa accgtgaaag tggtcgacga   5160
```

-continued

```
actggtgaag gtgatgggac ggcacaagcc cgagaacatc gtgatcgaaa tggcccgcga   5220
gaaccaaacc acccaaaaag gacagaagaa ctcccgagag cgcatgaagc ggatcgaaga   5280
gggcatcaag gagttgggct cccagatcct gaaggagcat cccgtggaga atacccaatt   5340
gcaaaacgag aagctctacc tctactacct ccagaacggg cgggacatgt acgtcgacca   5400
agagctggac atcaaccgcc tctccgacta cgatgtggat catattgtgc cccagagctt   5460
cctcaaggac gacagcatcg acaacaaggt cctgacgcgc agcgacaaga accggggcaa   5520
gtctgacaat gtgccttccg aagaagtcgt gaagaagatg aagaactact ggcggcagct   5580
gctcaacgcc aagctcatca cccaacggaa gttcgacaac ctgaccaagg ccgagagagg   5640
aggattgtcc gagttggaca aagccggctt cattaaacgc caactcgtgg agacccgcca   5700
gatcacgaag cacgtggccc aaatcttgga ctcccggatg aacacgaaat acgacgagaa   5760
tgacaagctg atccgcgagg tgaaggtgat cacgctgaag tccaagctgg tgagcgactt   5820
ccggaaggac ttccagttct acaaggtgcg ggagatcaac aactaccatc acgcccatga   5880
cgcctacctg aacgccgtgg tcggaaccgc cctgatcaag aaatacccca agctggagtc   5940
cgaattcgtg tacggagatt acaaggtcta cgacgtgcgg aagatgatcg cgaagtccga   6000
gcaggagatc ggcaaagcca ccgccaagta cttcttttac tccaacatca tgaacttctt   6060
caagaccgag atcacgctcg ccaacggcga gatccgcaag cgccccctga tcgagaccaa   6120
cggcgagacg ggagagattg tgtgggacaa aggaagagat tttgccacag tgcgcaaggt   6180
gctgtccatg cctcaggtga acatcgtgaa gaagaccgag gtgcaaacag gagggttttc   6240
caaagagtcc attttgccta agaggaattc cgacaagctc atcgcccgca agaaggactg   6300
ggacccaag aagtacgggg gcttcgactc ccccacggtg gcctactccg tgttggtggt   6360
ggccaaagtg gagaaaggga agagcaagaa gctgaaatcc gtgaaggagt tgctcggaat   6420
cacgatcatg gaacgatcgt cgttcgagaa aaaccccatc gacttcctcg aagccaaagg   6480
gtacaaagag gtgaagaagg acctgatcat caagctgccc aagtactccc tgttcgagct   6540
ggagaacggc cgcaagcgga tgctggcctc cgccggggaa ctgcagaaag ggaacgaatt   6600
ggccttgccc tccaaatacg tgaacttcct ctacttggcc tcccattacg aaaagctcaa   6660
aggatcccct gaggacaatg agcagaagca actcttcgtg gaacaacaca agcactacct   6720
ggacgagatc atcgagcaga tcagcgagtt ctccaagcgc gtgatcctcg ccgacgccaa   6780
cctggacaag gtgctctccg cctacaacaa gcaccgcgac aagcctatcc gcgagcaagc   6840
cgagaatatc attcacctgt ttaccctgac gaatttggga gcccctgccg cctttaaata   6900
ctttgacacc accatcgacc gcaaaagata cacctccacc aaggaagtct tggacgccac   6960
cctcatccac cagtccatca cgggcctcta cgagacgcgc atcgacctct cccaattggg   7020
cggcgactaa agtgatgcgg cctttaggaa acaccacaaa agtaattgac aatctcagga   7080
acgatctgcg tgtttacagc ttcccaaata acaattatac cacgtaccaa aaggggttta   7140
atgtatctca caaattcttc taataggtac agcttctcaa attgggtgta tgatgtgaca   7200
cttcgtctca cacacgtcac gataattcag cgtatggctt cccttcatca cattcacgca   7260
aacttctaca caaccctggg catatttctt gtgttggcaa cactcccgaa atcgattctg   7320
cacacaatgg ttcattcaat gattcaagta cgttttagac ggactaggca gtttaattaa   7380
aaacatctat cctccagatc accagggcca gtgaggccgg cataaaggac ggcaaggaaa   7440
gaaaagaaag aaagaaaagg acacttatag catagtttga agttataagt agtcgcaatc   7500
tgtgtgcagc cgacagatgc tttttttttc cgtttggcag gaggtgtagg gatgtcgaag   7560
```

```
accagtccag ctagtatcta tcctacaagt caatcatgct gcgacaaaaa tttctcgcac   7620
gaggcctctc gataaacaaa actttaaaag cacacttcat tgtcatgcag agtaataact   7680
cttccgcgtc gatcaattta tcaatctcta tcatttccgc ccctttcctt gcatagagca   7740
agaaaagcga cccggatgag gataacatgt cctgcgccag tagtgtggca ttgcctgtct   7800
ctcatttaca cgtactgaaa gcataatgca cgcgcatacc aatatttttc gtgtacggag   7860
atgaagagac gcgacacgta agatcacgag aaggcgagca cggttgccaa tggcagacgc   7920
gctagtctcc attatcgcgt tgttcggtag cttgctgcat gtcttcagtg gcactatatc   7980
cactctgcct cgtcttctac acgagggcca catcggtgca agttcgaaaa atcatatctc   8040
aatcttcaga tcctttccag aaacggtgct caggcgggaa agtgaaggtt ttctactcta   8100
gtggctaccc caattctctc cgactgtcgc agacggtcct tcgttgcgca cgcaccgcgc   8160
actacctctg aaattcgaca accgaagttc aattttacat ctaacttctt tcccattctc   8220
tcaccaaaag cctagcttac atgttggaga gcgacgagag cggcctgccc gccatggaga   8280
tcgagtgccg catcaccggc accctgaacg gcgtggagtt cgagctggtg ggcggcggag   8340
agggcacccc cgagcagggc cgcatgacca acaagatgaa gagcaccaaa ggcgccctga   8400
ccttcagccc ctacctgctg agccacgtga tgggctacgg cttctaccac ttcggcacct   8460
accccagcgg ctacgagaac cccttcctgc acgccatcaa caacggcggc tacaccaaca   8520
cccgcatcga gaagtacgag gacggcggcg tgctgcacgt gagcttcagc taccgctacg   8580
aggccggccg cgtgatcggc gacttcaagg tgatgggcac cggcttcccc gaggacagcg   8640
tgatcttcac cgacaagatc atccgcagca acgccaccgt ggagcacctg caccccatgg   8700
gcgataacga tctggatggc agcttcaccc gcaccttcag cctgcgcgac ggcggctact   8760
acagctccgt ggtggacagc cacatgcact tcaagagcgc catccacccc agcatcctgc   8820
agaacggggg ccccatgttc gccttccgcc gcgtggagga ggatcacagc aacaccgagc   8880
tgggcatcgt ggagtaccag cacgccttca agaccccgga tgcagatgcc ggtgaagaat   8940
aagggtggga aggagtcggg gagggtcctg gcagagcggc gtcctcatga tgtgttggag   9000
acctggagag tcgagagctt cctcgtcacc tgattgtcat gtgtgtatag gttaaggggg   9060
cccactcaaa gccataaaga cgaacacaaa cactaatctc aacaaagtct actagcatgc   9120
cgtctgtcca tctttatttc ctggcgcgcc tatgcttgta aaccgttttg tgaaaaaatt   9180
tttaaaataa aaaaggggac ctctagggtc cccaattaat tagtaatata atctattaaa   9240
ggtcattcaa aaggtcatcc agacgaaagg gcctcgtgat acgcctattt ttataggtta   9300
atgtcatgat aataatggtt tcttagacgt caggtggcac ttttcgggga aatgtgcgcg   9360
gaacccctat ttgtttattt ttctaaatac attcaaatat gtatccgctc atgagacaat   9420
aaccctgata aatgcttcaa taatattgaa aaaggaagag tatgagtatt caacatttcc   9480
gtgtcgccct tattcccttt tttgcggcat tttgccttcc tgtttttgct cacccagaaa   9540
cgctggtgaa agtaaaagat gctgaagatc agttgggtgc acgagtgggt tacatcgaac   9600
tggatctcaa cagcggtaag atccttgaga gttttcgccc cgaagaacgt tttccaatga   9660
tgagcacttt taaagttctg ctatgtggcg cggtattatc ccgtattgac gccgggcaag   9720
agcaactcgg tcgccgcata cactattctc agaatgactt ggttgagtac tcaccagtca   9780
cagaaaagca tcttacggat ggcatgacag taagagaatt atgcagtgct gccataacca   9840
tgagtgataa cactgcggcc aacttacttc tgacaacgat cggaggaccg aaggagctaa   9900
```

```
ccgctttttt gcacaacatg ggggatcatg taactcgcct tgatcgttgg gaaccggagc   9960

tgaatgaagc cataccaaac gacgagcgtg acaccacgat gcctgtagca atggcaacaa  10020

cgttgcgcaa actattaact ggcgaactac ttactctagc ttcccggcaa caattaatag  10080

actggatgga ggcggataaa gttgcaggac cacttctgcg ctcggccctt ccggctggct  10140

ggtttattgc tgataaatct ggagccggtg agcgtgggtc tcgcggtatc attgcagcac  10200

tggggccaga tggtaagccc tcccgtatcg tagttatcta cacgacgggg agtcaggcaa  10260

ctatggatga acgaaataga cagatcgctg agataggtgc ctcactgatt aagcattggt  10320

aactgtcaga ccaagtttac tcatatatac tttagattga tttaaaactt catttttaat  10380

ttaaaaggat ctaggtgaag atcctttttg ataatctcat gaccaaaatc ccttaacgtg  10440

agttttcgtt ccactgagcg tcagaccccg tagaaaagat caaaggatct tcttgagatc  10500

cttttttct gcgcgtaatc tgctgcttgc aaacaaaaaa accaccgcta ccagcggtgg  10560

tttgtttgcc ggatcaagag ctaccaactc tttttccgaa ggtaactggc ttcagcagag  10620

cgcagatacc aaatactgtc cttctagtgt agccgtagtt aggccaccac ttcaagaact  10680

ctgtagcacc gcctacatac ctcgctctgc taatcctgtt accagtggct gctgccagtg  10740

gcgataagtc gtgtcttacc gggttggact caagacgata gttaccggat aaggcgcagc  10800

ggtcgggctg aacggggggt tcgtgcacac agcccagctt ggagcgaacg acctacaccg  10860

aactgagata cctacagcgt gagctatgag aaagcgccac gcttcccgaa gggagaaagg  10920

cggacaggta tccggtaagc ggcagggtcg gaacaggaga gcgcacgagg gagcttccag  10980

ggggaaacgc ctggtatctt tatagtcctg tcgggtttcg ccacctctga cttgagcgtc  11040

gatttttgtg atgctcgtca ggggggcgga gcctatggaa aaacgccagc aacgcggcct  11100

ttttacggtt cctggccttt tgctggcctt ttgctcacat gttctttcct gcgttatccc  11160

ctgattctgt ggataaccgt attaccgcct ttgagtgagc tgataccgct cgccgcagcc  11220

gaacgaccga gcgcagcgag tcagtgagcg aggaagcgga aga                    11263
```

<210> SEQ ID NO 39
<211> LENGTH: 147
<212> TYPE: DNA
<213> ORGANISM: Artificial Sequence
<220> FEATURE:
<223> OTHER INFORMATION: Encodes N-terminal peptide linker

<400> SEQUENCE: 39

```
atgcccaaga aaaagcggaa ggtcggcgac tacaaggatg acgatgacaa gttggagcct     60

ggagagaagc cctacaaatg ccctgagtgc ggaaagagct tcagccaatc tggagccttg    120

acccggcatc aacgaacgca tacacga                                        147
```

<210> SEQ ID NO 40
<211> LENGTH: 822
<212> TYPE: DNA
<213> ORGANISM: Nannochloropsis gaditana
<220> FEATURE:
<221> NAME/KEY: misc_feature
<223> OTHER INFORMATION: 4A-III promoter

<400> SEQUENCE: 40

```
ggcataaagg acggcaagga aagaaaagaa agaaagaaaa ggacacttat agcatagttt     60

gaagttataa gtagtcgcaa tctgtgtgca gccgacagat gctttttttt tccgtttggc    120

aggaggtgta gggatgtcga agaccagtcc agctagtatc tatcctacaa gtcaatcatg    180
```

ctgcgacaaa aatttctcgc acgaggcctc tcgataaaca aaactttaaa agcacacttc 240
attgtcatgc agagtaataa ctcttccgcg tcgatcaatt tatcaatctc tatcatttcc 300
gcccctttcc ttgcatagag caagaaaagc gacccggatg aggataacat gtcctgcgcc 360
agtagtgtgg cattgcctgt ctctcattta cacgtactga aagcataatg cacgcgcata 420
ccaatatttt tcgtgtacgg agatgaagag acgcgacacg taagatcacg agaaggcgag 480
cacggttgcc aatggcagac gcgctagtct ccattatcgc gttgttcggt agcttgctgc 540
atgtcttcag tggcactata tccactctgc ctcgtcttct acacgagggc cacatcggtg 600
caagttcgaa aaatcatatc tcaatcttca gatcctttcc agaaacggtg ctcaggcggg 660
aaagtgaagg ttttctactc tagtggctac cccaattctc tccgactgtc gcagacggtc 720
cttcgttgcg cacgcaccgc gcactacctc tgaaattcga caaccgaagt tcaattttac 780
atctaacttc tttcccattc tctcaccaaa agcctagctt ac 822

<210> SEQ ID NO 41
<211> LENGTH: 200
<212> TYPE: DNA
<213> ORGANISM: Nannochloropsis gaditana
<220> FEATURE:
<221> NAME/KEY: misc_feature
<223> OTHER INFORMATION: bidirectional terminator 5

<400> SEQUENCE: 41
gggtgggaag gagtcgggga gggtcctggc agagcggcgt cctcatgatg tgttggagac 60
ctggagagtc gagagcttcc tcgtcacctg attgtcatgt gtgtataggt taagggggcc 120
cactcaaagc cataaagacg aacacaaaca ctaatctcaa caaagtctac tagcatgccg 180
tctgtccatc tttatttcct 200

<210> SEQ ID NO 42
<211> LENGTH: 213
<212> TYPE: DNA
<213> ORGANISM: Nannochloropsis gaditana
<220> FEATURE:
<221> NAME/KEY: misc_feature
<223> OTHER INFORMATION: 6487 terminator

<400> SEQUENCE: 42
tgagatgcgg aactcgcatc ttatattgca atttgatata cacagacatg acttggaaag 60
taaaagcaag ctgggtatcg gcgttacaag aaataccagg cctctggtga tgtattacac 120
tcaaaaaatt aaaaggtggt agagacaatc atgcatatgc attgtctttt gcctaatgag 180
gaaatttcga ggtgttcttc agaaaaaatc tta 213

<210> SEQ ID NO 43
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5'ID sequence

<400> SEQUENCE: 43
tccacagccc gaacccatga gagagaa 27

<210> SEQ ID NO 44
<211> LENGTH: 27
<212> TYPE: DNA

<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3'ID sequence

<400> SEQUENCE: 44
gcccgaatcg agttgatggc ccgcaaa 27

<210> SEQ ID NO 45
<211> LENGTH: 2346
<212> TYPE: DNA
<213> ORGANISM: Artificial Sequence
<220> FEATURE:
<223> OTHER INFORMATION: HygR Cassette

<400> SEQUENCE: 45
tcataatcaa agatgagcca gccacgaagc taccggagaa ttctgtaaga aaaatgttta 60
aagttgaaaa tgctaacagt gaagtgatat ccttttttaa tggagtgttg aggtgaagtc 120
tagcatcgta ggggaaaaca ggattctgtg tcttccattc tactccttga taaagcgaag 180
aaatccgaca aaaccaaaga gattgttcaa gtttaagatt tgtaagcgta caactatgaa 240
cttcttctct ttgtaggcct gagtggtcgt atgcatacga ttcatgaagt gaatcagtat 300
cgctggattt tgcttaggag taaagcacaa ctaagaaaat atgctgcctg gcaggcatcc 360
tgagacatga ggcaagcgac gtagcaattg aatcctaatt taagccaggg catctgtatg 420
actctgttag ttaattgatg aaccaatgag ctttaaaaaa aaatcgttgc gcgtaatgta 480
gttttaattc tccgccttga ggtgcggggc catttcggac aaggttcttt ggacggagat 540
ggcagcatgt gtcccttctc caaattggtc cgtgtggtag ttgagatgct gccttaaaat 600
tctgctcggt catcctgcct tcgcattcac tcctttcgag ctgtcgggtt cctcacgagg 660
cctccgggag cggattgcgc agaaaggcga cccggagaca cagagaccat acaccgacta 720
aattgcactg gacgatacgg catggcgacg acgatggcca agcattgcta cgtgattatt 780
cgccttgtca ttcagggaga aatgatgaca tgtgtgggac ggtctttaca tgggaagagg 840
gcatgaaaat aacatggcct ggcgggatgg agcgtcacac ctgtgtatgc gttcgatcca 900
caagcaactc accatttgcg tcggggcctg tctccaatct gctttaggct acttttctct 960
aatttagcct attctataca gacagagaca cacagggatc atggggaaga aaccggaact 1020
gaccgctacg tccgtggaga aattccttat tgagaagttc gactctgtct ccgacttgat 1080
gcaactgagc gagggagagg agagtagggc gttctcgttt gacgtagggg gtcggggata 1140
cgtgttgagg gttaatagtt gtgcggacgg gttctacaag gatcggtatg tctaccgtca 1200
tttcgcctcc gccgctctcc ccataccaga ggtactggac attggggagt ttagcgaatc 1260
tctcacgtac tgcatctcgc gccgagccca gggagtgacg ttgcaagatc tgcccgaaac 1320
tgaattgcct gccgttttgc aacccgtggc cgaggccatg gacgcgatcg ctgccgcaga 1380
tctgtctcag acgtccggct ttggaccttt tgggccccag ggcatcgggc agtacacgac 1440
ctggcgagac ttcatctgcg ccattgccga tcctcacgtc tatcattggc agacagtcat 1500
ggatgacacc gtgtctgcat ccgtggccca agcactggac gaactcatgt tgtgggccga 1560
ggattgccct gaggtcaggc acctggtgca cgcggatttc ggcagcaata acgtacttac 1620
agacaatggt cggattactg ctgtcatcga ctggtccgaa gcgatgtttg gtgatagcca 1680
atacgaagtg gcgaacatat tcttctggcg tccctggttg gcgtgcatgg agcagcagac 1740
acgctacttt gaacggaggc acccggagct ggccggctcc ccacgactcc gcgcctatat 1800
gttgcgtatc ggactcgatc agctttacca gtctctcgtc gacggcaact tcgacgacgc 1860
cgcgtgggcg cagggccgct gcgacgcgat agtccgcagc ggggctggga cggtgggtcg 1920
gacccaaatc gcacgccggt cggctgcggt gtggacagac ggctgtgttg aggtgcttgc 1980
ggactcgggc aaccgtaggc cgagcacccg accgcgtgca aaggagtgat tgaatcattg 2040
aatgaaccat tgtgtgcaga atcgatttcg ggagtgttgc caacacaaga aatatgccca 2100
gggttgtgta gaagtttgcg tgaatgtgat gaagggaagc catacgctga attatcgtga 2160
cgtgtgtgag acgaagtgtc acatcataca cccaatttga gaagctgtac ctattagaag 2220
aatttgtgag atacattaaa ccccttttgg tacgtggtat aattgttatt tgggaagctg 2280
taaacacgca gatcgttcct gagattgtca attacttttg tggtgtttcc taaaggccgc 2340
atcact 2346

<210> SEQ ID NO 46
<211> LENGTH: 2400
<212> TYPE: DNA
<213> ORGANISM: Artificial Sequence
<220> FEATURE:
<223> OTHER INFORMATION: HygR Cassette with flanking ID sequences

<400> SEQUENCE: 46
tccacagccc gaacccatga gagagaatca taatcaaaga tgagccagcc acgaagctac 60
cggagaattc tgtaagaaaa atgtttaaag ttgaaaatgc taacagtgaa gtgatatcct 120
tttttaatgg agtgttgagg tgaagtctag catcgtaggg gaaaacagga ttctgtgtct 180
tccattctac tccttgataa agcgaagaaa tccgacaaaa ccaaagagat tgttcaagtt 240
taagatttgt aagcgtacaa ctatgaactt cttctctttg taggcctgag tggtcgtatg 300
catacgattc atgaagtgaa tcagtatcgc tggattttgc ttaggagtaa agcacaacta 360
agaaaatatg ctgcctggca ggcatcctga gacatgaggc aagcgacgta gcaattgaat 420
cctaatttaa gccagggcat ctgtatgact ctgttagtta attgatgaac caatgagctt 480
taaaaaaaaa tcgttgcgcg taatgtagtt ttaattctcc gccttgaggt gcggggccat 540
ttcggacaag gttctttgga cggagatggc agcatgtgtc ccttctccaa attggtccgt 600
gtggtagttg agatgctgcc ttaaaattct gctcggtcat cctgccttcg cattcactcc 660
tttcgagctg tcgggttcct cacgaggcct ccgggagcgg attgcgcaga aaggcgaccc 720
ggagacacag agaccataca ccgactaaat tgcactggac gatacggcat ggcgacgacg 780
atggccaagc attgctacgt gattattcgc cttgtcattc agggagaaat gatgacatgt 840
gtgggacggt ctttacatgg gaagagggca tgaaaataac atggcctggc gggatggagc 900
gtcacacctg tgtatgcgtt cgatccacaa gcaactcacc atttgcgtcg gggcctgtct 960
ccaatctgct ttaggctact tttctctaat ttagcctatt ctatacagac agagacacac 1020
agggatcatg gggaagaaac cggaactgac cgctacgtcc gtggagaaat tccttattga 1080
gaagttcgac tctgtctccg acttgatgca actgagcgag ggagaggaga gtagggcgtt 1140
ctcgtttgac gtagggggtc ggggatacgt gttgagggtt aatagttgtg cggacgggtt 1200
ctacaaggat cggtatgtct accgtcattt cgcctccgcc gctctcccca taccagaggt 1260
actggacatt ggggagttta gcgaatctct cacgtactgc atctcgcgcc gagcccaggg 1320
agtgacgttg caagatctgc ccgaaactga attgcctgcc gttttgcaac ccgtggccga 1380
ggccatggac gcgatcgctg ccgcagatct gtctcagacg tccggctttg gaccttttgg 1440
gccccagggc atcgggcagt acacgacctg gcgagacttc atctgcgcca ttgccgatcc 1500
tcacgtctat cattggcaga cagtcatgga tgacaccgtg tctgcatccg tggcccaagc 1560
actggacgaa ctcatgttgt gggccgagga ttgccctgag gtcaggcacc tggtgcacgc 1620
ggatttcggc agcaataacg tacttacaga caatggtcgg attactgctg tcatcgactg 1680
gtccgaagcg atgtttggtg atagccaata cgaagtggcg aacatattct tctggcgtcc 1740
ctggttggcg tgcatggagc agcagacacg ctactttgaa cggaggcacc cggagctggc 1800
cggctcccca cgactccgcg cctatatgtt gcgtatcgga ctcgatcagc tttaccagtc 1860
tctcgtcgac ggcaacttcg acgacgccgc gtgggcgcag ggccgctgcg acgcgatagt 1920
ccgcagcggg gctgggacgg tgggtcggac ccaaatcgca cgccggtcgg ctgcggtgtg 1980
gacagacggc tgtgttgagg tgcttgcgga ctcgggcaac cgtaggccga gcacccgacc 2040
gcgtgcaaag gagtgattga atcattgaat gaaccattgt gtgcagaatc gatttcggga 2100
gtgttgccaa cacaagaaat atgcccaggg ttgtgtagaa gtttgcgtga atgtgatgaa 2160
gggaagccat acgctgaatt atcgtgacgt gtgtgagacg aagtgtcaca tcatacaccc 2220
aatttgagaa gctgtaccta ttagaagaat ttgtgagata cattaaaccc cttttggtac 2280
gtggtataat tgttatttgg gaagctgtaa acacgcagat cgttcctgag attgtcaatt 2340
acttttgtgg tgtttcctaa aggccgcatc actgcccgaa tcgagttgat ggcccgcaaa 2400

<210> SEQ ID NO 47
<211> LENGTH: 9533
<212> TYPE: DNA
<213> ORGANISM: Artificial Sequence
<220> FEATURE:
<223> OTHER INFORMATION: pSGE-6281

<400> SEQUENCE: 47
ctgtcagacc aagtttactc atatatactt tagattgatt taaaacttca tttttaattt 60
aaaaggatct aggtgaagat cctttttgat aatctcatga ccaaaatccc ttaacgtgag 120
ttttcgttcc actgagcgtc agaccccgta gaaaagatca aaggatcttc ttgagatcct 180 tttttctgc gcgtaatctg ctgcttgcaa acaaaaaaac caccgctacc agcggtggtt 240
tgtttgccgg atcaagagct accaactctt tttccgaagg taactggctt cagcagagcg 300
cagataccaa atactgtcct tctagtgtag ccgtagttag gccaccactt caagaactct 360
gtagcaccgc ctacatacct cgctctgcta atcctgttac cagtggctgc tgccagtggc 420
gataagtcgt gtcttaccgg gttggactca agacgatagt taccggataa ggcgcagcgg 480
tcgggctgaa cggggggttc gtgcacacag cccagcttgg agcgaacgac ctacaccgaa 540
ctgagatacc tacagcgtga gctatgagaa agcgccacgc ttcccgaagg gagaaaggcg 600
gacaggtatc cggtaagcgg cagggtcgga acaggagagc gcacgaggga gcttccaggg 660
ggaaacgcct ggtatcttta tagtcctgtc gggtttcgcc acctctgact tgagcgtcga 720
tttttgtgat gctcgtcagg ggggcggagc ctatggaaaa acgccagcaa cgcggccttt 780
ttacggttcc tggccttttg ctggcctttt gctcacatgt tctttcctgc gttatcccct 840
gattctgtgg ataaccgtat taccgccttt gagtgagctg ataccgctcg ccgcagccga 900
acgaccgagc gcagcgagtc agtgagcgag gaagcggaag agtttaaaca gggggcatca 960
gaatctatgc cgtatatgag cttatgaatg tcatccatta tctcatgtct gtcaacgcgg 1020
tcctcgggtg taacaaaaca caggaggagc gtctcacttt tgaccagcag ctttctgcct 1080

-continued

```
tagagcgcac cgtccgtgtc aaagaaaatg agctcaaaga attggagctt ctatctagta   1140
ctgtcagacc aagtttactc atatatactt tagattgatt taaaacttca tttttaattt   1200
aaaaggatct aggtgaagat cctttttgat aatctcatga ccaaaatccc ttaacgtgag   1260
ttttcgttcc actgagcgtc agaccccgta gaaaagatca aaggatcttc ttgagatcct   1320
tttttctgc gcgtaatctg ctgcttgcaa acaaaaaaac caccgctacc agcggtggtt   1380
tgtttgccgg atcaagagct accaactctt tttccgaagg taactggctt cagcagagcg   1440
cagataccaa atactgtcct tctagtgtag ccgtagttag gccaccactt caagaactct   1500
gtagcaccgc ctacatacct cgctctgcta atcctgttac cagtggctgc tgccagtggc   1560
gataagtcgt gtcttaccgg gttggactca agacgatagt taccggataa ggcgcagcgg   1620
tcgggctgaa cggggggttc gtgcacacag cccagcttgg agcgaacgac ctacaccgaa   1680
ctgagatacc tacagcgtga gctatgagaa agcgccacgc ttcccgaagg gagaaaggcg   1740
gacaggtatc cggtaagcgg cagggtcgga acaggagagc gcacgaggga gcttccaggg   1800
ggaaacgcct ggtatcttta tagtcctgtc gggtttcgcc acctctgact tgagcgtcga   1860
tttttgtgat gctcgtcagg ggggcggagc ctatggaaaa acgccagcaa cgcggccttt   1920
ttacggttcc tggccttttg ctggcctttt gctcacatgt tctttcctgc gttatcccct   1980
gattctgtgg ataaccgtat taccgccttt gagtgagctg ataccgctcg ccgcagccga   2040
acgaccgagc gcagcgagtc agtgagcgag gaagcggaag agtttaaaca gggggcatca   2100
gaatctatgc cgtatatgag cttatgaatg tcatccatta tctcatgtct gtcaacgcgg   2160
tcctcgggtg taacaaaaca caggaggagc gtctcacttt tgaccagcag ctttctgcct   2220
tagagcgcac cgtccgtgtc aaagaaaatg agctcaaaga attggagctt ctatctagta   2280
cgtgacatta tataaggagg caaagtgctc tattaatatg ttgacgagaa ggtttaatac   2340
atgcagcagg taacagatgc aggacaagtg tgtgaaattt aaccggctac ttcctatgaa   2400
tcaaacagaa gatgcttaca atgcacagga gatcgctgaa caagaactag caaaagagcg   2460
ctctgaatat aatgaggagc gtgcgcgaag ggaaagaagg ctacgggaac gacagcgtaa   2520
tgcaaaatat tgtttacaaa gacaaatgca agagcaggag aagtcgcaag gcgaaagtgc   2580
gggtggtagc atatgccaac aggaaactga ccagcaggac gagcaagacg acgaagctgg   2640
tagcgaagat tacgtgacta cacagcaagt ggaagcggac agattaagaa ctttgacaat   2700
gcttgtcaaa agtataactg ggatcggtga tgcacaggca ttgcgctcaa aacttgagca   2760
ccaaggggag gtcttgcgga agtcacaaga aattagcaaa gataatcagg tgactacaag   2820
aatgatagac tggtactacc ccagactcgt tgacatccgg cgtgtcgagc gttcacatca   2880
gagatatgaa ggtagatgac ggtaaaagtt tcctaaaatc gagcacgcga cttttttttc   2940
ttcttcaata tctgagcagg atcgcttaga gaagctacag aaagagcggg acatcctctg   3000
gaatcaatta cagagttcca gatattcacc gcgcccccctc aaggtctgta acgaataata   3060
agagaggtca tcacttggcc ctgatcgcga tgctgtagag gttattgatg aaaggggagg   3120
aaagaatggc aggggccgta tagaaataat cctcaggatt ttgaaggcgt gcgtcatcct   3180
agaccaaatt tgcaggaaag atgcttagaa atctcaaaat tgacgcggat atttttgact   3240
aatcgacaaa catgctttca cgaccacagt ccgaaggcct acttcgccag ctgttgcacg   3300
acaaggaaaa agtcaaggag atcgaaaata ggtgcgagta cttagcacaa cttgtggcac   3360
atttgcagtg tggtttagtg gagcgtttat ggcctttagt aatgcgaagc aatcggaatc   3420
accttgctgc ttcgccaaag acggaaaatc tcgatcgagt ggcgcttcaa cgtatgctta   3480
```

-continued

```
aaaagttaga agtccgctgc ttgcagctgc ttgacaccaa atccatccca caaaagcatt   3540
gaaattctca aatatgggga accaaacgct catccaaccc atcccaagcc ccaggcttgc   3600
ttctgtcgaa tccgcagcac tcagcacgca tgtgtagtat cttttggata aatcattgca   3660
aagaaggtgt ataaggcttt ttcccggaag caaaagctcc cgtgggcact gtagaaacaa   3720
aagtgaggtg atagttattt ttcgatgcac ggaacggtat atatattcgc aaagcttgtg   3780
gaggctatcg ctgtcctttg tttgaagcag tcttcagcga agctgccacg gagcttcgtt   3840
caggaccgtt tcttggcatt caaaactcta cgactatgat actatcgagc attccgcatg   3900
attacagcgc aaagcctacc aaaaagatgc ggtaattcac ttgcgggacc gcaatcattg   3960
tcagccatca gcgcactgta ctcgtaaaaa ggcgaacatt gtccggtaac tcgctcatgt   4020
ctcacttgag ctgatgtcct ctctaaaata atagggtcgg tcccaaactc ttttaaactc   4080
cgatgaaact ctatgtgcac tacgagcggc cgcagtgatg cggcctttag gaaacaccac   4140
aaaagtaatt gacaatctca ggaacgatct gcgtgtttac agcttcccaa ataacaatta   4200
taccacgtac caaaaggggt ttaatgtatc tcacaaattc ttctaatagg tacagcttct   4260
caaattgggt gtatgatgtg acacttcgtc tcacacacgt cacgataatt cagcgtatgg   4320
cttcccttca tcacattcac gcaaacttct acacaaccct gggcatattt cttgtgttgg   4380
caacactccc gaaatcgatt ctgcacacaa tggttcattc aatgattcaa tcactccttt   4440
gcacgcggtc gggtgctcgg cctacggttg cccgagtccg caagcacctc aacacagccg   4500
tctgtccaca ccgcagccga ccggcgtgcg atttgggtcc gacccaccgt cccagccccg   4560
ctgcggacta tcgcgtcgca gcggccctgc gcccacgcgg cgtcgtcgaa gttgccgtcg   4620
acgagagact ggtaaagctg atcgagtccg atacgcaaca tataggcgcg gagtcgtggg   4680
gagccggcca gctccgggtg cctccgttca aagtagcgtg tctgctgctc catgcacgcc   4740
aaccagggac gccagaagaa tatgttcgcc acttcgtatt ggctatcacc aaacatcgct   4800
tcggaccagt cgatgacagc agtaatccga ccattgtctg taagtacgtt attgctgccg   4860
aaatccgcgt gcaccaggtg cctgacctca gggcaatcct cggcccacaa catgagttcg   4920
tccagtgctt gggccacgga tgcagacacg gtgtcatcca tgactgtctg ccaatgatag   4980
acgtgaggat cggcaatggc gcagatgaag tctcgccagg tcgtgtactg cccgatgccc   5040
tggggcccaa aaggtccaaa gccggacgtc tgagacagat ctgcggcagc gatcgcgtcc   5100
atggcctcgg ccacgggttg caaaacggca ggcaattcag tttcgggcag atcttgcaac   5160
gtcactccct gggctcggcg cgagatgcag tacgtgagag attcgctaaa ctccccaatg   5220
tccagtacct ctggtatggg gagagcggcg gaggcgaaat gacggtagac ataccgatcc   5280
ttgtagaacc cgtccgcaca actattaacc ctcaacacgt atccccgacc ccctacgtca   5340
aacgagaacg ccctactctc ctctccctcg ctcagttgca tcaagtcgga gacagagtcg   5400
aacttctcaa taaggaattt ctccacggac gtagcggtca gttccggttt cttccccatg   5460
atccctgtgt gtctctgtct gtatagaata ggctaaatta gagaaaagta gcctaaagca   5520
gattggagac aggccccgac gcaaatggtg agttgcttgt ggatcgaacg catacacagg   5580
tgtgacgctc catcccgcca ggccatgtta ttttcatgcc ctcttcccat gtaaagaccg   5640
tcccacacat gtcatcattt ctccctgaat gacaaggcga ataatcacgt agcaatgctt   5700
ggccatcgtc gtcgccatgc cgtatcgtcc agtgcaattt agtcggtgta tggtctctgt   5760
gtctccgggt cgcctttctg cgcaatccgc tcccggaggc ctcgtgagga acccgacagc   5820
```

-continued

```
tcgaaaggag tgaatgcgaa ggcaggatga ccgagcagaa ttttaaggca gcatctcaac   5880
taccacacgg accaatttgg agaagggaca catgctgcca tctccgtcca aagaaccttg   5940
tccgaaatgg ccccgcacct caaggcggag aattaaaact acattacgcg caacgatttt   6000
tttttaaagc tcattggttc atcaattaac taacagagtc atacagatgc cctggcttaa   6060
attaggattc aattgctacg tcgcttgcct catgtctcag gatgcctgcc aggcagcata   6120
ttttcttagt tgtgctttac tcctaagcaa aatccagcga tactgattca cttcatgaat   6180
cgtatgcata cgaccactca ggcctacaaa gagaagaagt tcatagttgt acgcttacaa   6240
atcttaaact tgaacaatct ctttggtttt gtcggatttc ttcgctttat caaggagtag   6300
aatggaagac acagaatcct gttttcccct acgatgctag acttcacctc aacactccat   6360
taaaaaagga tatcacttca ctgttagcat tttcaacttt aaacattttt cttacagaat   6420
tctccggtag cttcgtggct ggctcatctt tgattatgag gcgcgccagg cattgacgct   6480
taagttgact ctgcccaaaa gctgggcgga gcagccgttg cttcaagtac tggagctgtt   6540
catcgaatcc tacaacaaga aaaagaccgg tctacctccc ttggacaaag actttgtcca   6600
catggaaaaa gctgggtaag tccttactcg tgacagcgtt ccctttctcc agactagacg   6660
cctaatagtg ttctaatgta ccactgggac acgcctcgct gcctgtgcac catgctccat   6720
actcaacgct gctacagggg cgtaatcctt ccagtcggca acattgtgag cgacatgttg   6780
agcgatagag atgatttgta tatcagatcc gggccagggc ctgctcgtgg gaagattgcc   6840
catctcagtt cgcccccaaa cgcgcacgct tcgagtgagt cgagcacagg attgttgcgc   6900
tgcaaaaact atggatgcaa tcagtcattt tcggaagaaa acaattcaga agaggcgtgc   6960
cgctttcaca aggcaccccc cgtctttcat gatacgaaga aagggtggtc gtgctgcgcg   7020
aagcgagtat atgactggga cgagttccat acggtaagcg tggaagtgtt cgttctcggc   7080
cccaggactt tgttttgagg caattggtgt actttaattg gcggataaag ggaggactca   7140
caactttcga tattcaccgt ctccagatcg aggggtgcac cacaggacgg cacagtctca   7200
tcgatccgaa ggaaattttc gcgccgtccc ccaccctggc tgcagccgcg caggccgaga   7260
ggggagattg cagcaatacg tcaagcgctg ctacagtcat caagagcatt gatgaattca   7320
atcagtcgaa tccaaatgcc gccgctgcat gcaaaacagc agcctcgatg acgctggcgg   7380
gcacgcgctg caccgtcaaa ccggacgggt ctgccacctg tttgaacaaa ggctgccaaa   7440
aggactactt gctcaaggag aatcacccct ctgcatgtcg gtaaggacac cgcgctcgat   7500
ggaatcgtga gctttacgtt cccacgccaa cacttcgcca tttctcctcc cttcctttct   7560
ttagctacca cgcagccggc cccgtcttcc acgacgcggg taaatactgg tcatgttgcc   7620
ctggaacggt caagtacgac ttcgacgact ttctcaagat ccctggatgc atgctcagta   7680
gtcattacga cggaagccag gagagcctgg aggcgttcac tagacacgcc aaaacgtctg   7740
agggcacatg agaatgtggg atggggagaa agaaccacgt atccccacga ggaatggcgc   7800
attgggagcg agggggatcg acataggaag aagcaataaa aattctgctc aatacggtat   7860
tttttatttt ttggcgtctt ccgttcgtag ccggcggacg aacagcgatg caaactcgag   7920
acggacagtg ccccacggtc ttcgttcgaa aacatcattg ccaacaacct cgcacactta   7980
cttccaggat cctataaata tcttacaacc accatccgcc tcttccttct cacgcgcatg   8040
gataatcaac gccacgattc acaccgttgc ctggacattt cccccccatg acgggtaatc   8100
ctacccgttt ccttccagcg ttccccttct cttccattcg aacttgaatg cactttactt   8160
atttctcttg tgagcatcgt gcatccgctt gctggcaacg gcaatgggaa tgataatcac   8220
```

aagcaggatc gccaggattg ccagtcccat aaccattttc atctagatcg tatggagcaa 8280
aggaagagag agggggtaag ggcgagaaga tcgcaatgaa aagggatgac ggcccacgcc 8340
gcctcctgcg acttccaatc gtccgaggtt tacacacatg gcacagccag aaacaccccc 8400
ggcataggag caggataggg gtaagacaac caagcacgta ctcggagctg tttccagcac 8460
atctgtttaa acgacgaaag ggcctcgtga tacgcctatt tttataggtt aatgtcatga 8520
taataatggt ttcttagacg tcaggtggca cttttcgggg aaatgtgcgc ggaaccccta 8580
tttgtttatt tttctaaata cattcaaata tgtatccgct catgagacaa taaccctgat 8640
aaatgcttca ataatattga aaaaggaaga gtatgagtat tcaacatttc cgtgtcgccc 8700
ttattccctt ttttgcggca ttttgccttc ctgtttttgc tcacccagaa acgctggtga 8760
aagtaaaaga tgctgaagat cagttgggtg cacgagtggg ttacatcgaa ctggatctca 8820
acagcggtaa gatccttgag agttttcgcc ccgaagaacg ttttccaatg atgagcactt 8880
ttaaagttct gctatgtggc gcggtattat cccgtattga cgccgggcaa gagcaactcg 8940
gtcgccgcat acactattct cagaatgact tggttgagta ctcaccagtc acagaaaagc 9000
atcttacgga tggcatgaca gtaagagaat tatgcagtgc tgccataacc atgagtgata 9060
acactgcggc caacttactt ctgacaacga tcggaggacc gaaggagcta accgcttttt 9120
tgcacaacat gggggatcat gtaactcgcc ttgatcgttg ggaaccggag ctgaatgaag 9180
ccataccaaa cgacgagcgt gacaccacga tgcctgtagc aatggcaaca acgttgcgca 9240
aactattaac tggcgaacta cttactctag cttcccggca acaattaata gactggatgg 9300
aggcggataa agttgcagga ccacttctgc gctcggccct tccggctggc tggtttattg 9360
ctgataaatc tggagccggt gagcgtgggt ctcgcggtat cattgcagca ctggggccag 9420
atggtaagcc ctcccgtatc gtagttatct acacgacggg gagtcaggca actatggatg 9480
aacgaaatag acagatcgct gagataggtg cctcactgat taagcattgg taa 9533

<210> SEQ ID NO 48
<211> LENGTH: 5712
<212> TYPE: DNA
<213> ORGANISM: Nannochloropsis gaditana
<220> FEATURE:
<221> NAME/KEY: misc_feature
<223> OTHER INFORMATION: acyl-CoA oxidase gene, genomic sequence

<400> SEQUENCE: 48
atgacgaccg ccaatgcccg tttgtcgagg ctcaaagatc atttagcaga gacgggggct 60
gtggcgcgcg cggtacgtgt ggagtcttgc tttcttcagg gggggtcccg ggggggggc 120 gagtcagaca aagggtagag cgtactggaa ggacagacag atgctggcat gaccctgcat 180
ccagaacaca catttaataa ttgagggtct ggtgatcgag gggctcggca accgcgcggc 240
tgctagcacg tgacacggtt ttttacctct actgttccac aatcaacccc tacttcccct 300
tctccctccc tctttccctc cctcccctac gttaattttc cctcccgctg tactatatcg 360
cttcactttc agccgattag ctcctctgcc atcaatgcca cgccttttgc ggcgaggacg 420
acgcatacca tggagcgcat ggcaagggaa cgagccaagg cctccttccc cgtccgagac 480
atgacgtact tcttggacgg cgggaggagc atgaccgagg tcaaggtggg tgaaataaaa 540
acataaaaag agaataaaca acgaaaggcg aggtctttgg gggatgcctg aatacgtagg 600
caaccgtact gatcgttttg gacccttctt ctcttggggc cgatggccca caggagggca 660
tgatggcgga cttggcggcg aatccggtct ttacggaccc agaatggaac gacttgaaca 720

```
gagatcaggt agggatatgg gtgattggcc ggaaggtggg gaaggagggg gaggtgcccc    780
ttgtgagctt gccctgtggt cggagcgctt ccctcgatca acccctccct ctcccttccc    840
cttccccccct ctggctagat ccgtgaacgc accatctctc gactgagagc tgcgtacaag    900
ctcctgatcc gagacggtgc cgatgtcagc cgccggaatg cccggcttga gattcacgcc    960
ctccatgact tgggtagccc ttcctccctc cctccctccc tccctccctt gctccctacc   1020
tcctccccgt gtcctcacct tcgttttttc caagcattta ttacttttca gtttcatgtg   1080
gacgatcatc aaaatgatgc cttcctcgcc cgacgcgatt ggtcctccct ccctccctct   1140
ttctctccct ccctccctcc ctccctccct ttgcagggtg gtacgtgcgg cagggtgtgc   1200
atttcggcct ctttatgggc gccttggccg ggcaggggag cgacgaacaa cgcgctgagt   1260
ggctgcccag gaccatgatg tgtgaggtag gagggaggga gggagggagg gagggagggg   1320
aaggacaaac aggctggtgg aaaccacttg caggaaggtt tgggaatgta cttcggtctg   1380
tccaatccgc catacagcat tttcattcct cccctccctc cctccccccc ctccttcctg   1440
ctctagatct acgggtgctt cgggatgacg gagttggggc acggctcatt cttgcggggc   1500
ctggagacca cagcgatgta cgacaaggta ggtacggagc gagggaggga gcgagggagg   1560
gagcaaggga gggagggagc gagggaggga gggagacagg gaccgacgga gggacgctac   1620
cgaccggttg tggttgttct ctcctttccg tacaggacac gcaagaattt gtaatcaatt   1680
cccccactga cacaagcacc aaatggtagg tgccctccct ccctccctcc ctccctcgcc   1740
tccctgtccc ctgcgaccat ccatccttcc tccctccctc cctccctccc tccctccagg   1800
tggatcggtg cggccgggca gacggccaca cattcggtgg ttttcgcccg cctcctcctt   1860
ccctcagggg acgacatggg tgtgcacaac ttcatcatac ccctccggga tatggaaacg   1920
cacttgcccc tccctggcat ccacattggt acctacctcc ctccctacct gcctccctcc   1980
ctccctcccg ccctgctcat tcctctggct ccctctctaa ttgtcgaaaa aaatatgcga   2040
agacttgtga caacgtcgag ccgcacgctt acttcctctc ctcctccccc tcctccccctc   2100
cttcccgccc tccttcctcc cctccttcct cccctccctt cctcgccctc cttcctcccc   2160
ctccgttccc cctcttcctc cccctccgtt ccccccctccc caggcgattt gggggccaag   2220
atgggcttga atggcatcga caacgggtgg atgcaatttg accacgtccg cgtgccccgg   2280
gacaacatgc tttgtcgcta cgcacaggtg cccctccctc cctccctccc tccctccctc   2340
cctcttttcc tccctccctc cctacctcct tcctcctttc tcgctttgtg acacacacac   2400
accctttcgg gtctcccccc cgcgctcagc tccctgcctt ctctccctcc ctccctccct   2460
ccctcgatcc ctccctccct ccctccctcc ctccctcccc ccctcccagg tcaccccgga   2520
ggggaaatac atccgtcctc ccaggaagga gatggcttac ggcgctctca tcggcactcg   2580
ggcggctctg gtcaagacag ccgtggactt tcaaaaaaag gtgggtcctc cctccctccc   2640
tccctccctc cctccctccc tccctccctt ctttttcctg ttgcatgctt tctactcttg   2700
tcctctgtta tttgtgcctt tttcccctcc ctctctccct ccctccctcc tttcactgac   2760
aacgacggcg tgtgtaccga ccacccttcc ctccctccct ccctccctcc ctccctccct   2820
ccctccccca ggccctcatg atcgggatcc gctacaccgc cctccggaca cagggcgtgg   2880
tggaggaagg ccaaagggaa gagaccgcca tcatcgacta ccccatccac cgggacaaac   2940
tcctgaaact cttggcaagc cccgccctcc ctccctccct ccctccctcc ctccctcttt   3000
cccgtcctgc cgctccacgc cacggcctgc tactgacccc caccacctcc tcctccctcc   3060
```

```
ctccctccct ccctccctca ggcggccgcc tacgcctggc acttccaagc cgcctacgtt   3120
ctccacctga acgattcctt ggaggagggg ctcgaggcgg gggacctctc catcctcaag   3180
gatgtgcatg ggaccatggc tggtaccccc cgccctccct ccctccctcc ctccctccct   3240
ccctgtttcc cgccctgtgg ggcctcgcag ccttttgcat ccgcttcccc gtgacgctgc   3300
cctccctccc tccctcgctc cctccctccc gccctccctc caggcctcaa ggctttcgga   3360
acctggttca cgtacaacac gatcgaggcc tgccggcaag tgtgcggggg ccacgggtac   3420
agcaagtaca acggcctctc caacaccctc caggtccctc cttccctccc tccctccctc   3480
cctccctccc tcccttcctc cctttcctcc tttcttgtcg tatgatcgga gcgacgcact   3540
gcgtgacgcg ttcctacttc cttgtggtgc tgccgatttc atccctacct ccctccttcc   3600
ctccctccct tcctccctcc cttcctccct ccctcaggac tttgctgtca tgtgcacctg   3660
ggagggcgac aacaccgtga tggctctaca gacggcgcgg tatctagttc ggtcctacga   3720
gaaggcgaag cgggggggcg gtagggaggg agggagggag ggagggaggg agggagggag   3780
ggaaagagga ggaaagaaac ggccaaagaa aggagaacat ccattgcctt cacctcggtc   3840
aaatcctaaa cactgcagcg cacatgaaat taaatcaacc cctccctccc tccctccctc   3900
ctctctccct ccatccctcc ctccctcctt ccctcgttca gagaccctgg caggctccgt   3960
ctcatacctg caggatgcgc atcccccggc ttggcgggcg aggtctgcgg aggacttgat   4020
gaacatggaa gtgcagatgg aggtagggac cgaggaaggg atagggaggg gggaggaagg   4080
gccgggccgg gaggggggga gggagtgaag gaggggagga cggaaggaaa gagggaggga   4140
gggagggagg gagggagaga gggagagagt aggaaatgag ggggataaga gatgagaata   4200
gcacggtttg ttcaatgtgc agcagagatg atcctctccg cacctcctcc actccctttc   4260
accccttcca tccctccctc cctcgctccc tcccttcctc cctccttcca ggcctggcgg   4320
gccctcctag ccgccaaggt ctccagagcc tcagagcggg tcttggcaag gcaggcggcg   4380
ttgcggggga acgaggcgca ggtagggagg gagggaggga gggagggcgg gagggaggga   4440
gggagggagg gaaggcgagg aggacggtga ggggaaaaga tctcctgaaa attgatgggg   4500
acagagtcgt tcaaggagtg tcaaaccaga atttcatgta tgcacacccg tccttccttc   4560
cctccatccc tccctccctc cctccctggc aggccttcaa cgagcatcag gtggagcttt   4620
tcgagtgcgc caagacccat gtctacttca atgtggcggc gcggtttgcc gaggcggtcg   4680
tggaggtcgg gtggaagaaa gggagggagg gagggaggga gggagggagg gagggaggga   4740
gggggaaaga ttgaaagcct accttgtcgt ctctttgcat acgcgcctat ttgtccagcg   4800
gttccaacgt tttcttttcc tccctccctc cctcatttcc tccctccctc cctccctcat   4860
ttcctccctc cctctctccc tccctccctc cctccctccc tccctccctc cctccctccc   4920
tccctccctc cctccaggcc ggcaccaccc accccgccct ggcccctgtc ctcgcccgcc   4980
tctgccacct cttctctctc tcgagccttc tagaagacga agcctccctg ctcgccagcg   5040
gtttcgcctc cgcggggcag atgcagctca ttcgcgaggt ggggaaggag ggagagaggg   5100
agagacggag ggagggacgg aaggagggag ggagggccat gtccatgtcg ctgctaaagg   5160
gcctgacgga caagaaatgg gaagatccaa tcgccgtgac tcatccctcc ctccctccgt   5220
cccgccctcc ctcccgccct ccctccaggc cgtgggcgcc ctcctcctcg ccctccgccc   5280
ggacgcggtg gcccttgtcg acgccttcaa ctattccgac gaagttttga actcacattt   5340
aggcaccgcc aacggcgata tttatacggg ctacctccaa caggtgcagc gcctcgtccc   5400
tgagaacaag gtccgcccgc tcgccctccc tccctccctc cctcccgccc tcccgccctc   5460
```

-continued cctccctctt cttctcttcc ggggccttgt gcccgtgttg acgacgagca cttgacccgc 5520
ttctcgcttt cctcgatccc tccctcctac ttcccctctt tttccctccc cccttctcct 5580
ccctccttcc cttccaatta cgtcctcttc ccctccttca tccagctggc cgtcgccccc 5640
tacatcatga gggaggtgaa gcctttaatg caaggagcag acctgatctc cacggacgag 5700
gaggaggact ga 5712

<210> SEQ ID NO 49
<211> LENGTH: 23
<212> TYPE: DNA
<213> ORGANISM: Nannochloropsis gaditana
<220> FEATURE:
<221> NAME/KEY: misc_feature
<223> OTHER INFORMATION: aco2-CRISPR target sequence including PAM sequence

<400> SEQUENCE: 49
ggcgaggacg acgcatacca tgg 23

<210> SEQ ID NO 50
<211> LENGTH: 103
<212> TYPE: RNA
<213> ORGANISM: Artificial Sequence
<220> FEATURE:
<223> OTHER INFORMATION: Entire chimeric guide RNA for targeting N. gaditana aco2 gene

<400> SEQUENCE: 50
ggcgaggacg acgcauacca guuuuagagc uagaaauagc aaguuaaaau aaggcuaguc 60
cguuaucaac uugaaaaagu ggcaccgagu cggugcuuuu uuu 103

<210> SEQ ID NO 51
<211> LENGTH: 120
<212> TYPE: DNA
<213> ORGANISM: Artificial Sequence
<220> FEATURE:
<223> OTHER INFORMATION: aco2 sense oligonucleotide

<400> SEQUENCE: 51
taatacgact cactataggc gaggacgacg cataccagtt ttagagctag aaatagcaag 60
ttaaaataag gctagtccgt tatcaacttg aaaaagtggc accgagtcgg tgcttttttt 120

<210> SEQ ID NO 52
<211> LENGTH: 120
<212> TYPE: DNA
<213> ORGANISM: Artificial Sequence
<220> FEATURE:
<223> OTHER INFORMATION: aco2 reverse complement oligonucleotide

<400> SEQUENCE: 52
aaaaaaagca ccgactcggt gccacttttt caagttgata acggactagc cttattttaa 60
cttgctattt ctagctctaa aactggtatg cgtcgtcctc gcctatagtg agtcgtatta 120

<210> SEQ ID NO 53
<211> LENGTH: 6956
<212> TYPE: DNA
<213> ORGANISM: Artificial Sequence
<220> FEATURE:
<223> OTHER INFORMATION: pSGE6282

<400> SEQUENCE: 53
ctgtcagacc aagtttactc atatatactt tagattgatt taaaacttca tttttaattt 60

```
aaaaggatct aggtgaagat cctttttgat aatctcatga ccaaaatccc ttaacgtgag    120
ttttcgttcc actgagcgtc agaccccgta gaaaagatca aaggatcttc ttgagatcct    180
tttttctgc gcgtaatctg ctgcttgcaa acaaaaaaac caccgctacc agcggtggtt    240
tgtttgccgg atcaagagct accaactctt tttccgaagg taactggctt cagcagagcg    300
cagataccaa atactgtcct tctagtgtag ccgtagttag gccaccactt caagaactct    360
gtagcaccgc ctacatacct cgctctgcta atcctgttac cagtggctgc tgccagtggc    420
gataagtcgt gtcttaccgg gttggactca agacgatagt taccggataa ggcgcagcgg    480
tcgggctgaa cggggggttc gtgcacacag cccagcttgg agcgaacgac ctacaccgaa    540
ctgagatacc tacagcgtga gctatgagaa agcgccacgc ttcccgaagg gagaaaggcg    600
gacaggtatc cggtaagcgg cagggtcgga acaggagagc gcacgaggga gcttccaggg    660
ggaaacgcct ggtatcttta tagtcctgtc gggtttcgcc acctctgact tgagcgtcga    720
tttttgtgat gctcgtcagg ggggcggagc ctatggaaaa acgccagcaa cgcggccttt    780
ttacggttcc tggccttttg ctggcctttt gctcacatgt tctttcctgc gttatcccct    840
gattctgtgg ataaccgtat taccgccttt gagtgagctg ataccgctcg ccgcagccga    900
acgaccgagc gcagcgagtc agtgagcgag gaagcggaag agtttaaaca tatatgagtg    960
cgattcgatg caaggggggg aggggggaag gttcgaaagc cgtcgacctt ctggataaag   1020
tacggagttt gtcagccctc cctcgcggtg tggccacgat aagtaacaaa gcatgtaata   1080
aggatgcagc ctggagattg atgtgcgatc agaatcatca tgacacgtca aaacacaggc   1140
ggcgacatgg cgagacccgt gaccaacgtg atagagaaac ctgtcctgag gcacgtattg   1200
taaacaaccc agagatgtca gaaaaacaaa ggcatgtcaa cgctgtttaa ggcagcatct   1260
ccaggcaatc tttcctccgt gaggtggatc tatcctccct cctttctctt taaaagcggc   1320
cgtccgtccg tggtcgcctt ttccccactc tccctgcacg ttctgcccac acgtcccttc   1380
catcaccaca aaaagagcac attattctgt catgtacata cacagctggg acgggacgtt   1440
gcggagggcg ggccggggct tgtggcccgg gcaacaggac acctttccct gcccttaaac   1500
cccgactgtc tcctttttgc tcgtggagcc atgaccttcc tcctaactac cccacatccc   1560
gatacctgtc tatggtggaa agaagagtcc tcattgcgcg gtgtctgcac gagcaattac   1620
gaaagttaac ttctccagcc ccagccctag cgggcctctg tcgccctata tccctcatga   1680
gagccatggc agcctcttgc tgcgcccctt tccatccttt ttctacctca agtcatttta   1740
agatacattt tcaagggaac gtgggggatt gttgtgcgat cgaggcttct attctccgac   1800
acactttgaa tgagagcggt gcctctccta gtgagctcat ttgcaacagg agaaggccct   1860
cctcccttta caaatataaa gtgcccctgg tcgtctcctt gccactgtat accattgctg   1920
tgtctttgat tgaaaaaaat cgtaaccatg gctttggagg gccccatcgc cacgtttgcg   1980
cgagaacagc aatacttatc ccttttagtt ccttcctttc tcgcatttgt ggtagccccg   2040
tgcgcgcggg gaaatgagtt aaagtcatgt gcaccagaaa ctacacattc cattttttac   2100
cacagcataa aagccttatt ttctactgct acccagagcg gggccaccat ttctacggtg   2160
acacccgcca aaataaagga catatgcccg tgtgacgtat cgcggggcta tggaggggta   2220
cctgcgagtt gctgttgaag tgcccccccc cccccgtatg taaaaccacg tccttcggtc   2280
cgtacccatc tcaccgcaca ttgattacac tttacggcag aaatgacgac cgccaatgcc   2340
cgtttgtcga ggctcaaaga tcatttagca gagacggggg ctgtggcgcg cgcggtacgt   2400
```

-continued

```
gtggagtctt gctttcttca ggggggggtcc cgggggggggg gcgagtcaga caaagggtag   2460
agcgtactgg aaggacagac agatgctggc atgaccctgc atccagaaca cacatttaat   2520
aattgagggt ctggtgatcg aggggctcgg caaccgcgcg gctgctagca cgtgacacgg   2580
tttttacct ctactgttcc acaatcaacc cctacttccc cttctccctc cctctttccc   2640
tccctcccct acgttaattt tccctcccgc tgtactatat cgcttcactt tcagccgatt   2700
agctcctctg ccatcagcgg ccgctccaca gcccgaaccc atgagagaga atcataatca   2760
aagatgagcc agccacgaag ctaccggaga attctgtaag aaaaatgttt aaagttgaaa   2820
atgctaacag tgaagtgata tcctttttta atggagtgtt gaggtgaagt ctagcatcgt   2880
aggggaaaac aggattctgt gtcttccatt ctactccttg ataaagcgaa gaaatccgac   2940
aaaaccaaag agattgttca agtttaagat ttgtaagcgt acaactatga acttcttctc   3000
tttgtaggcc tgagtggtcg tatgcatacg attcatgaag tgaatcagta tcgctggatt   3060
ttgcttagga gtaaagcaca actaagaaaa tatgctgcct ggcaggcatc ctgagacatg   3120
aggcaagcga cgtagcaatt gaatcctaat ttaagccagg gcatctgtat gactctgtta   3180
gttaattgat gaaccaatga gctttaaaaa aaaatcgttg cgcgtaatgt agttttaatt   3240
ctccgccttg aggtgcgggg ccatttcgga caaggttctt tggacggaga tggcagcatg   3300
tgtcccttct ccaaattggt ccgtgtggta gttgagatgc tgccttaaaa ttctgctcgg   3360
tcatcctgcc ttcgcattca ctcctttcga gctgtcgggt tcctcacgag gcctccggga   3420
gcggattgcg cagaaaggcg acccggagac acagagacca tacaccgact aaattgcact   3480
ggacgatacg gcatggcgac gacgatggcc aagcattgct acgtgattat tcgccttgtc   3540
attcagggag aaatgatgac atgtgtggga cggtctttac atgggaagag ggcatgaaaa   3600
taacatggcc tggcgggatg gagcgtcaca cctgtgtatg cgttcgatcc acaagcaact   3660
caccatttgc gtcggggcct gtctccaatc tgctttaggc tacttttctc taatttagcc   3720
tattctatac agacagagac acacagggat catggggaag aaaccggaac tgaccgctac   3780
gtccgtggag aaattcctta ttgagaagtt cgactctgtc tccgacttga tgcaactgag   3840
cgagggagag gagagtaggg cgttctcgtt tgacgtaggg ggtcggggat acgtgttgag   3900
ggttaatagt tgtgcggacg ggttctacaa ggatcggtat gtctaccgtc atttcgcctc   3960
cgccgctctc cccataccag aggtactgga cattggggag tttagcgaat ctctcacgta   4020
ctgcatctcg cgccgagccc agggagtgac gttgcaagat ctgcccgaaa ctgaattgcc   4080
tgccgttttg caacccgtgg ccgaggccat ggacgcgatc gctgccgcag atctgtctca   4140
gacgtccggc tttggacctt ttgggcccca gggcatcggg cagtacacga cctggcgaga   4200
cttcatctgc gccattgccg atcctcacgt ctatcattgg cagacagtca tggatgacac   4260
cgtgtctgca tccgtggccc aagcactgga cgaactcatg ttgtgggccg aggattgccc   4320
tgaggtcagg cacctggtgc acgcggattt cggcagcaat aacgtactta cagacaatgg   4380
tcggattact gctgtcatcg actggtccga agcgatgttt ggtgatagcc aatacgaagt   4440
ggcgaacata ttcttctggc gtccctggtt ggcgtgcatg gagcagcaga cacgctactt   4500
tgaacggagg cacccggagc tggccggctc cccacgactc cgcgcctata tgttgcgtat   4560
cggactcgat cagctttacc agtctctcgt cgacggcaac ttcgacgacg ccgcgtgggc   4620
gcagggccgc tgcgacgcga tagtccgcag cggggctggg acggtgggtc ggacccaaat   4680
cgcacgccgg tcggctgcgg tgtggacaga cggctgtgtt gaggtgcttg cggactcggg   4740
caaccgtagg ccgagcaccc gaccgcgtgc aaaggagtga ttgaatcatt gaatgaacca   4800
```

-continued

```
ttgtgtgcag aatcgatttc gggagtgttg ccaacacaag aaatatgccc agggttgtgt   4860
agaagtttgc gtgaatgtga tgaagggaag ccatacgctg aattatcgtg acgtgtgtga   4920
gacgaagtgt cacatcatac acccaatttg agaagctgta cctattagaa gaatttgtga   4980
gatacattaa accccttttg gtacgtggta taattgttat ttgggaagct gtaaacacgc   5040
agatcgttcc tgagattgtc aattactttt gtggtgtttc ctaaaggccg catcactgcc   5100
cgaatcgagt tgatggcccg caaaggcgcg ccgagcatga ccgaggtcaa ggtgggtgaa   5160
ataaaaacat aaaaagagaa taaacaacga aaggcgaggt ctttggggga tgcctgaata   5220
cgtaggcaac cgtactgatc gttttggacc cttcttctct tggggccgat ggcccacagg   5280
agggcatgat ggcggacttg gcggcgaatc cggtctttac ggacccagaa tggaacgact   5340
tgaacagaga tcaggtaggg atatgggtga ttggccggaa ggtggggaag gagggggagg   5400
tgccccttgt gagcttgccc tgtggtcgga gcgcttccct cgatcaaccc ctccctctcc   5460
cttccccttc ccccctctgg ctagatccgt gaacgcacca tctctcgact gagagctgcg   5520
tacaagctcc tgatccgaga cggtgccgat gtcagccgcc ggaatgcccg gcttgagatt   5580
cacgccctcc atgacttggg tagcccttcc tccctccctc cctccctccc tcccttgctc   5640
cctacctcct ccccgtgtcc tcaccttcgt tttttccaag catttattac ttttcagttt   5700
catgtggacg atcatcaaaa tgatgccttc ctcgcccgac gcgattggtc ctccctccct   5760
ccctctttct ctccctccct ccctccctcc ctccctttgc agggtggtac gtgcggcagg   5820
gtgtgcattt cggcctcttt atgggcgcct tggccgggca ggggagcgac gaacaacgcg   5880
ctgagtggtt taaacgacga aagggcctcg tgatacgcct atttttatag gttaatgtca   5940
tgataataat ggtttcttag acgtcaggtg gcacttttcg gggaaatgtg cgcggaaccc   6000
ctatttgttt atttttctaa atacattcaa atatgtatcc gctcatgaga caataaccct   6060
gataaatgct tcaataatat tgaaaaagga agagtatgag tattcaacat ttccgtgtcg   6120
cccttattcc cttttttgcg gcattttgcc ttcctgtttt tgctcaccca gaaacgctgg   6180
tgaaagtaaa agatgctgaa gatcagttgg gtgcacgagt gggttacatc gaactggatc   6240
tcaacagcgg taagatcctt gagagttttc gccccgaaga acgttttcca atgatgagca   6300
cttttaaagt tctgctatgt ggcgcggtat tatcccgtat tgacgccggg caagagcaac   6360
tcggtcgccg catacactat tctcagaatg acttggttga gtactcacca gtcacagaaa   6420
agcatcttac ggatggcatg acagtaagag aattatgcag tgctgccata accatgagtg   6480
ataacactgc ggccaactta cttctgacaa cgatcggagg accgaaggag ctaaccgctt   6540
ttttgcacaa catgggggat catgtaactc gccttgatcg ttgggaaccg gagctgaatg   6600
aagccatacc aaacgacgag cgtgacacca cgatgcctgt agcaatggca acaacgttgc   6660
gcaaactatt aactggcgaa ctacttactc tagcttcccg gcaacaatta atagactgga   6720
tggaggcgga taaagttgca ggaccacttc tgcgctcggc ccttccggct ggctggttta   6780
ttgctgataa atctggagcc ggtgagcgtg ggtctcgcgg tatcattgca gcactggggc   6840
cagatggtaa gccctcccgt atcgtagtta tctacacgac ggggagtcag gcaactatgg   6900
atgaacgaaa tagacagatc gctgagatag gtgcctcact gattaagcat tggtaa       6956
```

<210> SEQ ID NO 54
<211> LENGTH: 1767
<212> TYPE: DNA
<213> ORGANISM: Nannochloropsis gaditana
<220> FEATURE:

<221> NAME/KEY: misc_feature
<223> OTHER INFORMATION: aco2 target upstream homology arm

<400> SEQUENCE: 54
atatatgagt gcgattcgat gcaagggggg gagggggga ggttcgaaag ccgtcgacct 60
tctggataaa gtacggagtt tgtcagccct ccctcgcggt gtggccacga taagtaacaa 120
agcatgtaat aaggatgcag cctggagatt gatgtgcgat cagaatcatc atgacacgtc 180
aaaacacagg cggcgacatg gcgagacccg tgaccaacgt gatagagaaa cctgtcctga 240
ggcacgtatt gtaaacaacc cagagatgtc agaaaaacaa aggcatgtca acgctgttta 300
aggcagcatc tccaggcaat ctttcctccg tgaggtggat ctatcctccc tcctttctct 360
ttaaaagcgg ccgtccgtcc gtggtcgcct tttccccact ctccctgcac gttctgccca 420
cacgtccctt ccatcaccac aaaaagagca cattattctg tcatgtacat acacagctgg 480
gacgggacgt tgcggagggc gggccggggc ttgtggcccg ggcaacagga cacctttccc 540
tgcccttaaa ccccgactgt ctcctttttg ctcgtggagc catgaccttc ctcctaacta 600
ccccacatcc cgatacctgt ctatggtgga aagaagagtc ctcattgcgc ggtgtctgca 660
cgagcaatta cgaaagttaa cttctccagc cccagcccta gcgggcctct gtcgccctat 720
atccctcatg agagccatgg cagcctcttg ctgcgcccct ttccatcctt tttctacctc 780
aagtcatttt aagatacatt ttcaagggaa cgtgggggat tgttgtgcga tcgaggcttc 840
tattctccga cacactttga atgagagcgg tgcctctcct agtgagctca tttgcaacag 900
gagaaggccc tcctcccttt acaaatataa agtgcccctg gtcgtctcct tgccactgta 960
taccattgct gtgtctttga ttgaaaaaaa tcgtaaccat ggctttggag ggccccatcg 1020
ccacgtttgc gcgagaacag caatacttat cccttttagt tccttccttt ctcgcatttg 1080
tggtagcccc gtgcgcgcgg ggaaatgagt taaagtcatg tgcaccagaa actacacatt 1140 ccattttta ccacagcata aaagccttat tttctactgc tacccagagc ggggccacca 1200
tttctacggt gacacccgcc aaaataaagg acatatgccc gtgtgacgta tcgcggggct 1260
atggaggggt acctgcgagt tgctgttgaa gtgccccccc ccccccgtat gtaaaaccac 1320
gtccttcggt ccgtacccat ctcaccgcac attgattaca ctttacggca gaaatgacga 1380
ccgccaatgc ccgtttgtcg aggctcaaag atcatttagc agagacgggg gctgtggcgc 1440
gcgcggtacg tgtggagtct tgctttcttc aggggggtc ccgggggggg ggcgagtcag 1500
acaaagggta gagcgtactg gaaggacaga cagatgctgg catgaccctg catccagaac 1560
acacatttaa taattgaggg tctggtgatc gaggggctcg gcaaccgcgc ggctgctagc 1620
acgtgacacg gttttttacc tctactgttc cacaatcaac ccctacttcc ccttctccct 1680
ccctctttcc ctccctcccc tacgttaatt ttccctcccg ctgtactata tcgcttcact 1740
ttcagccgat tagctcctct gccatca 1767

<210> SEQ ID NO 55
<211> LENGTH: 755
<212> TYPE: DNA
<213> ORGANISM: Nannochloropsis gaditana
<220> FEATURE:
<221> NAME/KEY: misc_feature
<223> OTHER INFORMATION: aco2 target downstream homology arm

<400> SEQUENCE: 55
gagcatgacc gaggtcaagg tgggtgaaat aaaaacataa aaagagaata aacaacgaaa 60
ggcgaggtct ttgggggatg cctgaatacg taggcaaccg tactgatcgt tttggaccct 120

```
tcttctcttg gggccgatgg cccacaggag ggcatgatgg cggacttggc ggcgaatccg    180

gtctttacgg acccagaatg gaacgacttg aacagagatc aggtagggat atgggtgatt    240

ggccggaagg tggggaagga gggggaggtg ccccttgtga gcttgccctg tggtcggagc    300

gcttccctcg atcaacccct ccctctccct tccccttccc ccctctggct agatccgtga    360

acgcaccatc tctcgactga gagctgcgta caagctcctg atccgagacg gtgccgatgt    420

cagccgccgg aatgcccggc ttgagattca cgccctccat gacttgggta gcccttcctc    480

cctccctccc tccctccctc ccttgctccc tacctcctcc ccgtgtcctc accttcgttt    540

tttccaagca tttattactt ttcagtttca tgtggacgat catcaaaatg atgccttcct    600

cgcccgacgc gattggtcct ccctccctcc ctctttctct ccctccctcc ctccctccct    660

ccctttgcag ggtggtacgt gcggcagggt gtgcatttcg gcctctttat gggcgccttg    720

gccgggcagg ggagcgacga acaacgcgct gagtg                               755
```

<210> SEQ ID NO 56
<211> LENGTH: 5607
<212> TYPE: DNA
<213> ORGANISM: Artificial Sequence
<220> FEATURE:
<223> OTHER INFORMATION: Cas9 with FLAG tag, nuclear localization sequences, peptide linker, and introns, codon optimized for expression in Parachlorella

<400> SEQUENCE: 56

```
atgcccaaga agaagcggaa agtcggggac tacaaggacg acgatgacaa actggagcct     60

ggggagaagc cctataagtg tcctgagtgc gggaagagct tcagccaatc tggagcactg    120

acaaggcacc agaggacaca tacacgcgac aagaagtaca gcatcgggct ggatatcggg    180

accaattctg tgggatgggc cgtgattacc gacgagtata aggtgcccag caagaagttc    240

aaggtgctgg ggaacacaga ccgccacagc attaagaaga acctgatcgg ggcgctgctg    300

tttgattctg gagagacagc agaggcaacc gtgagtgaga acagttttca gatcgaatag    360

cacccccccg cctctgcagc agtcgcatac cggctgcagt aatagcttgg ttcaacggcg    420

acctgaacaa gtactgtagt ttctatgcat acgaacttta tcgaatagaa tcacgcttgg    480

gtatcgatca taccttagcg ctcaatttca ttggctgcta cagaccatat tttcctcttc    540

acttgttgca gcgcctgaaa agaacagcaa gaaggcgcta cacccgccgc aagaatagga    600

tttgctacct gcaagagatc ttcagcaacg agatggccaa ggtggacgac agcttcttcc    660

atagactgga ggagtcgttc ctggtggagg aggataagaa gcacgagagg caccccatct    720

tcggtgagaa gagtttggct accaaatcta tcttttcata tcacatatac cgcctgatat    780

tctgaggtgg tggcttttgt ctttttcttt cagtattttt cttcgttggg aacctaccgc    840

gagggcattc attgtggcgg atctgtaagt gcgaccaggc tgtatccaat attttttcct    900

atcgcaggga acattgtgga tgaggtggcc taccacgaga agtaccccac aatctaccac    960

ctgcgcaaga agctggtgag aatctctgct tgtcgaatgt gtccagttgt gtcttgaatc   1020

ctggcaagat gttcttttca ccatccgtcc tgcaaaagtg tcagaagtag catctctcga   1080

tcgcgttgtc acttcaacgc ctccgcaact ccccccgttg tgaatcctgt ggtcatggct   1140

cagcttttca gatctctacc tgcatgttgt ttgcctgtct cagtcctgcc tgcacaaatc   1200

atcgcccttg tttactcctt gcaatcacgg attgtgtgca ggtggacagc acagataagg   1260

ccgatctgag gctgatctac ctggcattgg cccacatgat caagtttagg gggcacttcc   1320
```

-continued tcatcgaggg ggatttgaac cccgacaaca gcgatgtgga caagctgttc atccagctgg 1380
tgagtggagg gctggggttt gggggtgggg ggtggggagg gaggcacgga tggtgttttc 1440
tcatgtccaa ccgtggttca tgcaaccgaa cagcagtttc acaagatggt tccaacaggg 1500
tgctccattt ctccctgaca aaacctcgtg cggtccatct ggtatagctg ggttagtagg 1560
gggttgtggg ctgtccacag tcagtgcgaa gcaggctcta ttgagcgtgt gctagtgtgt 1620
gctgtgctga ttggcatttt gttgggccga gtgttaggat tagggtaaat caccctaatt 1680
aaccttacat aataggactg tatgcaaatt tgttttccaa aaactctacc cagcgtggtc 1740
agactgcatg cactgtggag catgcatggg gctgaccctg ttgatcctgc tcattctgct 1800
tcctccaggt gcagacctac aaccagctgt ttgaggagaa ccccatcaac gcatctgggg 1860
ttgacgcaaa ggccattctg tctgcaaggt aggtgcagga agaagtgaat gatgcacaca 1920
tggtggaatc gtgatacaag cagcagcaag tgttggacca agacatgtgc gtgctttgct 1980
gctgccaagc tggcactgca ccaggtcgtg cattgatctg cacatttgat atactgtgag 2040
agtcagacga cgtcctttca gagcctgtgt gtgattctcc aggggttaac acgagtttcc 2100
tttctgccag tgagtcaccc tctcgctgct cgctcctggt gcaggctgag caagtcaagg 2160
agactggaga acctgatcgc ccaattgcct ggagagaaga agaacgggct gttcgggaac 2220
ctgatcgcat tgtctctggg gttgaccccc aacttcaaga gcaacttcga cctggcagag 2280
gacgcaaaac tgcagctgag caaggacacc tacgacgatg atctggacaa cctgctggcc 2340
cagattggag atcagtacgc agacctgttc ctggcagcca agaatctgag cgacgcaatt 2400
ctgctgagcg acattctgcg cgtgaacacc gagatcacca aggcacctct gagcgcaagc 2460
atgatcaaga ggtacgacga gcaccaccaa gacctgacac tgctgaaagc actggtgaga 2520
cagcagctgc ctgagaagta caaggagatc ttcttcgacc agagcaagaa cgggtacgct 2580
gggtacattg atggaggagc aagccaagag gagttctaca agttcatcaa gcccatcctg 2640
gagaagatgg acgggacaga agagttgctg gtgaagctga atcgcgagga tctgctgagg 2700
aagcagagga cattcgacaa tgggagcatc ccacaccaga tccatctggg agagctgcac 2760
gcaattctga ggagacaaga ggacttctac ccgttcctga aggacaatcg cgagaagatc 2820
gagaagatcc tcacgttccg catcccgtac tatgtgggac ctctggcaag gggggaactct 2880
agatttgcct ggatgacccg caagagcgag gagacaatta caccctggaa cttcgaggag 2940
gtggtggata aaggggcatc tgcacagagc ttcatcgaga ggatgaccaa cttcgacaag 3000
aacctgccca acgagaaggt actgcctaag cattcactgc tgtacgagta cttcaccgtg 3060
tacaacgagc tgaccaaggt gaagtacgtg acagagggga tgaggaagcc agcatttctg 3120
agcggagagc aaaagaaggc catcgtggat ctgctgttca agaccaaccg caaggtgacc 3180
gtgaagcagc tgaaggagga ctacttcaag aagatcgagt gcttcgacag cgtggagatt 3240
tctggagtgg aggaccgctt caacgcatct ttggggacat accacgacct gctgaagatc 3300
atcaaggaca aggacttcct ggacaacgag gagaacgagg acatcctgga ggacattgtg 3360
ctgacactga ccctgttcga ggatagggag atgatcgagg agcgcctgaa gacatacgca 3420
cacctgtttg acgacaaggt gatgaagcag ctgaagagga ggcgctatac tggatgggga 3480
aggctgtcaa ggaagctgat taacgggatc cgcgacaagc agagcgggaa gacaattctg 3540
gacttcctga agagcgacgg gttcgcaaac cgcaacttca tgcagctgat ccacgacgat 3600
agcctgacct tcaaggagga catccagaag gcccaagtgt ctggacaagg ggatagcctg 3660
catgagcaca tcgcaaatct ggctgggtca cccgcaatca agaagggaat tctgcagacc 3720
gtgaaggtgg tggatgagct ggtgaaggtg atgggaaggc acaaacccga gaacatcgtg 3780
atcgagatgg caagggagaa ccagacaacc cagaagggac agaagaactc tagggagcgc 3840
atgaagcgca tcgaggaggg aattaaggag ctgggaagcc agatcctgaa ggagcatcct 3900
gtggagaaca cccaactgca gaacgagaag ctgtacctgt actacctgca gaacgggagg 3960
gacatgtacg tggatcaaga gctggacatc aaccgcctga gcgactatga cgtggaccac 4020
attgtgcctc agtcgttcct gaaggacgac agcatcgaca acaaggtgct gacaaggagc 4080
gacaagaatc gcggaaagag cgacaacgtg ccttcagaag aggtggtgaa gaagatgaag 4140
aactactggc gccagctgct gaacgcaaag ctgattacac agcgcaagtt cgacaacctg 4200
accaaggcag agaggggagg actgtcagaa ctggataagg ccgggttcat caagaggcaa 4260
ctggtggaga cacgccagat cacaaagcat gtggcccaga ttctggacag ccgcatgaac 4320
accaagtacg acgagaacga caagctgatc cgcgaggtga aggtgattac cctgaagagc 4380
aagctggtga gcgactttcg caaggacttc cagttctaca aggtgcgcga gatcaacaac 4440
taccaccacg cacacgacgc ctacctgaat gcagttgtgg gaacagccct gatcaagaag 4500
taccccaagc tggagagcga gttcgtgtat ggggactaca aggtgtacga cgtgcgcaag 4560
atgatcgcca agtctgagca agagatcggg aaggcaaccg ccaagtactt cttctacagc 4620
aacatcatga acttcttcaa gaccgagatc accctggcca atggggagat taggaagaga 4680
cccctgatcg agaccaacgg agagactgga gagatcgtgt gggataaggg gagggacttt 4740
gcaacagtgc gcaaagtgct gagcatgcct caagtgaaca tcgtgaagaa gaccgaggtg 4800
cagactgggg gattctcaaa ggagagcatt ctgcccaagc gcaacagcga taagctgatt 4860
gcacgcaaga aggactggga ccccaagaag tatgggggt ttgatagccc caccgtggca 4920
tattctgtgt tggttgtggc caaggtggag aaggggaaga gcaagaagct gaagagcgtg 4980
aaggagctgc tggggatcac cattatggag aggagcagct tcgagaagaa ccccatcgac 5040
ttcctggagg caaaggggta taaggaggtg aagaaggacc tgatcatcaa gctgcccaag 5100
tacagcctgt tcgagctgga gaatgggagg aagaggatgc tggcatctgc tggagaactg 5160
cagaagggga atgagttggc actgcctagc aagtacgtga acttcctgta cctggccagc 5220
cactacgaga agctgaaggg atcacccgag gacaatgagc agaagcagct gtttgtggag 5280
cagcacaagc actacctgga cgagatcatc gagcagatca gcgagttcag caagcgcgtg 5340
attctggcag acgcaaacct ggataaggtg ctgagcgcct acaacaagca ccgcgataag 5400
cccattcgcg agcaagcaga gaacatcatc cacctgttca ccctgaccaa cctgggagca 5460
cctgcagcat tcaagtactt cgacaccacc atcgaccgca agaggtacac aagcaccaag 5520
gaagtgctgg acgcaaccct gattcaccag agcattactg ggctgtacga gacacgcatc 5580
gacctgtcac aactgggagg ggactga 5607

<210> SEQ ID NO 57
<211> LENGTH: 588
<212> TYPE: DNA
<213> ORGANISM: Parachlorella sp.
<220> FEATURE:
<221> NAME/KEY: misc_feature
<223> OTHER INFORMATION: RPS17 promoter

<400> SEQUENCE: 57
caacacctag ttggtaaata ccgttgctga tattgctctg taccagtaaa agagggctgc 60
gatgagcgtt tttagtgcac ttcttcaaca cggaatattt ttcacaaatt ggtatgagaa 120

```
ccaattttgc aaaatgttcg ccctgtaaag tatcgctctg ggacgatcag cttgacgtaa    180

ttgtaggcga aaagggcgtt caaagtgcag ctttatgtat gaacgtcata aaatataaag    240

catagcacaa tcactgatag aaaatatttg tgcgcattaa aactctcact tctgttgcgg    300

atacaacgac ggaaatgaga agcttgtgta agaagcaatt caagttttca ttttgtcatc    360

taaggtgtga tcctccgata ttcattaccg aatgctgatc tgagttggaa agatggcaat    420

atttagctgt gcacactttg acctccaggc cttggcggga atttagtatt ctagctttcc    480

tattggaacg ataggccagc caagtctcca gcttgtatac gctacaccag cagacatgct    540

ctcaatttag ctgacagtgt cttcatattt gtattatctg ttgtgtct                 588
```

```
<210> SEQ ID NO 58
<211> LENGTH: 455
<212> TYPE: DNA
<213> ORGANISM: Parachlorella sp.
<220> FEATURE:
<221> NAME/KEY: misc_feature
<223> OTHER INFORMATION: RPS17 terminator

<400> SEQUENCE: 58

ggtgcgaata gtgcttcagt aaaaaagtag caacttggtg caatatcgtc agggtcgtgt     60

ggtctgctcg ccagcaagtt ttttggcaca ggagagcgct ttttccgagt accgccaaag    120

ttcaagcatg tgctgtgatt cgctgttgcc tcttatgata attgctcaaa gtttccaagc    180

attctatgtc caccctgcac cactaagttg tatggtgctt attctgcagg ggatgattca    240

tggtgcctaa aaattttgtg ctgctgtcgc gtctgttttc tgtcgcagtt tagtgaatgt    300

aactccaaat accaaacttt tcatcacaat catattgatg cctttgtaag tgaattacag    360

cgtttttttgc cataaaaaga agtaccgtga cattggggtc gtcataacaa gaagctttat    420

gaacaagcag cttgatctac gagacttata cataa                               455
```

```
<210> SEQ ID NO 59
<211> LENGTH: 2691
<212> TYPE: DNA
<213> ORGANISM: Artificial Sequence
<220> FEATURE:
<223> OTHER INFORMATION: BlastR gene codon optimized for Parachlorella
      and containing introns

<400> SEQUENCE: 59

atggcaaaac ctctctccca ggaagagtct accctgattg aaagggcaac agcaaccatc     60

aacagcattc ccattagcga ggactactct gttgtgagtt ctgagaagct gattgttgtt    120

taacttcttt gaaagcttta tcgaagattc tgcaagcgat gaacattgct tgtcaagacc    180

gagagctgca tgcccacttg acatccagct ttgaacggct cttcatgttt gatttgtttc    240

tgattgtagg catctgcagc attgagctct gatggaagga tctttacagg agtgagtgca    300

gcgtcagctg tggcagttgt tggctttcgt ctcagtcagt agtttgctgg gattgattat    360

ggagggcaca gttgcaattt tgagttgcac gttgcgacaa gcgtgttgac aaagcgtggt    420

caagccggcc agtcttgccg gtggcgggtg gcttggtcta acttccgctc tacggcaatc    480

gttttgttca tggttacggg gctggcgtgc cagaaagtcc tggtcagcca ccctcgcttc    540

aaagccgtag cccaacaact ttgcgaatat gttcgatttg caggtgaacg tgtaccactt    600

tacaggagga ccttgtgcag aattggtggt gttaggtaca gctctgcgtg caacaggttg    660

caagatgcag cgcaggtctt ccctggtcaa acgatgtatg cagagttgag aggcacttga    720
```

-continued

```
gctgggtgaa tggcgtgggc tcgtaggtag tgtgcagggc aggaagggca gccaattttg    780

gagttgtggt ccggtgtcgt tgcttcgagc cttattagga ctcttgctca tcaaagcgtt    840

agttgtgaat aagttgatct gaaaggatgt tatgtacagc aagcagcagc agttaagagt    900

ctggggagta gctgcacagg gcgaggtgtc aagatgggaa gggtcctgcc tccttatgtg    960

tttttccctg taggggagga agcctcttat gggcaatggt tgggcatatt ttccagccag   1020

cccttctttc tatagggggcc agggtgggcc cagctcgtct tggcttccac caccaggaga   1080

gtgagggcat tgaagggcca taaatagtcc tcccatctac gtgcaccaga gggtgtcgtc   1140

taggctgtgc atgccacgag gggaaggagc caagaatgag tgtatgggtt gttttcatgt   1200

ttaggctggg ataaaactgt tttcaattgc gcctgccggg tgaaaaccac agcagcatca   1260

gcaagcttgg agaaggccag cccgcccagc acaggctcac gttcccactc aggcggtcag   1320

tcgggcgggg gtgtgagtca ggcaggcgag ggtgtctgtg cctgacatca gcacctctgc   1380

ttagccactg cagcccctgg agcagggtag ggcgtcattt gcagcaatca cctgctgcct   1440

cacacgtcgc agcttggaat ttcaacgacc atcagcgctg gggttgttga gggatcatag   1500

cagattttgg tgcagcctgg ttgtcatgct ctttgtggaa tggcctctat gttcgagcaa   1560

ttcgttggat gttgaggtgc ttggggacag agagtcgaat gatgggccag ggtcaaacat   1620

gcgagcgttt ggctgagtca gcggtttttg ctggtcactt tttcttttgt ttcttattta   1680

ggtttgatgg atgtgttttg tgctgctgcc ctgaagctgc agcagcgtgt ctgccctgcg   1740

ctactgcggg caccaaggct atgtgctggt gcactcggct gcgctgcacc tgtgcacctc   1800

gcactccgtc cagcctccat gcagcacacg tactcacggt gtcctcctga cctgtcgtac   1860

gctattccaa acttgctctt ttgctgccgc tgctctcgta cacaattgct gttgattatc   1920

gatatctaat cgagcgcctg ctgactgaac tccgcaggta cagcagctgc agcagcagca   1980

ggaaatttga catgcattgt ggcaataggt gggtgggctc tgaaggagga ggagggagcg   2040

ggtgattaaa cagggcctgc atgaagagga gcaggggctg cgtggacagc agggggaagg   2100

tgcagaaggg agggtcaagc ggggttcagg tggctgtggg tttctgcacg agcagtgaaa   2160

gaagctgtat ccttccacct gcttccactg gcgaaaggtt gaaaacagga tgtcgcagct   2220

ggaaagatgt tgcgctgtca agtgcaagcc atggttgagg gtatgcctgt gtgcatgtgc   2280

ttcttaaagt tactcctgtt ctatggttct gggtgcttgt tgtttgtggt gcagggaacg   2340

agaatagggg gattttgtca ccttgcggaa gatgtagaca ggtgttgttg gatctgcatc   2400

ccgggattaa ggtgaggggg catgtaagca atggcaggca attcaagaac gaatcattgc   2460

tgcaaatgct gggatggtat gcagctgagg tatctattgc cttgtatttt gtctcgcatt   2520

gcatcggtgg tgcgttctgt ggcctgaggc acagttcttg ctgtttgata agggttcgac   2580

tgagttgtcg tgtgtgctgt gctgcaggca atcgtgaagg attcagatgg gcagcctaca   2640

gcagtgggaa ttagagaact gctgccttct gggtatgtgt gggaaggata a            2691
```

<210> SEQ ID NO 60
<211> LENGTH: 531
<212> TYPE: DNA
<213> ORGANISM: Parachlorella sp.
<220> FEATURE:
<221> NAME/KEY: misc_feature
<223> OTHER INFORMATION: RPS4 promoter

<400> SEQUENCE: 60

```
ccaccatggg ggaggtttga agtgtgcgcc tgatataatc atacacctaa aagcaccact     60
```

tgctgattgt gaagggacta tgtcgtttat gacgggacgt tacgctggcc gatggtttga 120
atttggacgc tgtggtagaa tgttatatgg acgtaaaggt tggcatattg aaaatcgtct 180
tcacaggcaa acttctagac gtgtgaccca ccggtaaaac gacaagcgtg gcgcgtcgat 240
tgcgctttga acgtcgtttg ttggactcca gatgaacctc aaaatcaaag cggtgattga 300
cgaaaatcaa atgacagccc gcaaaatttc atcagccttc ggatcggatt ctcagaatct 360
gattgtccct gctggctaca tttatgaaat ttcgtacatt ttggcagaaa tgtcccaata 420
ccatagcact gccgcctgag ctcacccgag caatgcatac tgggtacctc gcccatctcg 480
ccctctttcc aagcccagtg ctgttgtaaa tagccaaagg gctcagtaac a 531

<210> SEQ ID NO 61
<211> LENGTH: 546
<212> TYPE: DNA
<213> ORGANISM: Parachlorella sp.
<220> FEATURE:
<221> NAME/KEY: misc_feature
<223> OTHER INFORMATION: RPS4 terminator

<400> SEQUENCE: 61
gcatagcatc agcctgtggc agggttgtgg tagggctgag tggcagggtt aaaggggttg 60
cctaccccac ccctactctc atgacaccag caacagcagc agctcatgca gtactcaaat 120
cactgatgtc aatggtgtga cacatttggt taaggctgct ttttaaagtg ctgctttggg 180
ggcagtgact gtgcagagct tggagcgtat ccccatgtaa tcagaaccga cgagagttcg 240
gggcaacctt tcatcttcac attttttgtg atcagctaca gagtctgaaa tcaaatagag 300
gctgccatct aaacgcagga gtcacaacga aggcgaaaac tccaattgct gtactcaatg 360
cactaagtga ttgttcaatg gataaataca ctatgctcaa ttcatgccag cagagctgct 420
ccttccagcc agctacaatg gctttttcca cgccttttga agtatgaatg ttcagcttgc 480
tgtgcttgat gcatcaccat aaacacaatt ctacaacatt tcatgccaac aacagtacgg 540
gctttc 546

<210> SEQ ID NO 62
<211> LENGTH: 572
<212> TYPE: DNA
<213> ORGANISM: Parachlorella sp.
<220> FEATURE:
<221> NAME/KEY: misc_feature
<223> OTHER INFORMATION: ACP1 promoter

<400> SEQUENCE: 62
agtttgcata gttaagtatg ctggctattg cagtacctta tatgcaaaca agtgctcaat 60
ctgtttcatc attgtctgtg ggcaaattgc ctgccaatat tctccagtta ttgcctgttg 120
tttcaaatga ttgaaattgg aagttgtatt gctctacatt tttgacttgt gattttttca 180
tttgttgata tctgacaact gtgaactgca ctgaacttgc tgtgcttata aatgcatttt 240
tttgttttgg gccacgttga ttccttgtga tactttcctg ctatcaaacc aaaaatatac 300
tctcatgact gacgtgcaac aaatgcatgg aagctttcaa cgttacgaca gctgcttgcc 360
ccccatcagc tattctacat gtgtaaccta ccttgcatgg ccaccacaac gctactgcat 420
gcaagatctg gcgcaactgg atgtcccaat agtagaagta tccggattat ctccgagagt 480
tttacatatg taatcgacgc catttctgtc atcaactata aatccattgc tcctgcattt 540
ctggcactga cattctacca caagcaatac ca 572

<210> SEQ ID NO 63
<211> LENGTH: 869
<212> TYPE: DNA
<213> ORGANISM: Parachlorella sp.
<220> FEATURE:
<221> NAME/KEY: misc_feature
<223> OTHER INFORMATION: ACP1 terminator

<400> SEQUENCE: 63
gcagcagctt gttatgcctt ccccatgggc atcagcatgc tgcaagctgt ctagatatcc 60
agctttcagt ggaggttgag cgagggtcag cagcggttcc ctggcgatgg cggtcagctt 120
ttctggaagc cttcactagg actgcgccca gcgcatgtga cgccaatcga acttgtgtgc 180
aaggccaaat tttgtgaccc tgtgctgcac ttcatgtatt caagaattga gaagaaattt 240
cattgctgcc cttctttcac tttaatttcc atccctggat ccacctccca ccattgtggt 300
tgatgggtag gggttttggg taggtgcagt tcgttgtgca cgttgacatg tgtaacggtg 360
agcaaaggaa ttgctgggca agtagctatt gcagcttaag ggcatggtga aacacttgtg 420
ctgtatttac agaggaagcc agacaggtaa ggagtgtgtg gcagcttgga acaggagggc 480
tggtcgcaac aagtatgcat atcccatgat tgttgacata agagcagcag gtgcatattg 540
ccagcctttg tgaaagtgga ttgaaaatcg attagttggt gtgatagctg aggctaggca 600
ctgccaacct gcagtgaaat gaggctccaa gaccgggtaa taatacaggc aatcgaatcc 660
agttgaaatt acggcgatta aatccaagcg agcgttgtaa gaacatctgc acctgtctga 720
agtagtgagc ggataatgag cattgcttgc cttctatcac tatacctgac agttacgtgt 780
cacacactct caagcacaac acacagcggc aaagttactt gctaaacctc acagtcaagc 840
tgaaaataaa ggctaaatta cgtgagacc 869

<210> SEQ ID NO 64
<211> LENGTH: 23
<212> TYPE: DNA
<213> ORGANISM: Parachlorella sp.
<220> FEATURE:
<221> NAME/KEY: misc_feature
<223> OTHER INFORMATION: SRP54 CRISPR target sequence (including PAM)

<400> SEQUENCE: 64
ggcgtgggac atggtgcgca agg 23

<210> SEQ ID NO 65
<211> LENGTH: 1707
<212> TYPE: DNA
<213> ORGANISM: Parachlorella sp.
<220> FEATURE:
<221> NAME/KEY: misc_feature
<223> OTHER INFORMATION: encodes cpSRP54

<400> SEQUENCE: 65
atgcttcggc agcagctgtt gcacagcggc aggcagccgg gtgcgacatg cagcttacta 60
acctgctcga catggcgacc gtctgccttg ttcggccgtc ctaagcccca aaaactgcac 120
agccagcgct tgcagcatca gggccgcccc tcccgcctcg tcgtgcgcag cgcaatgttc 180
gacaacctga gccgcagcct ggagagggcg tgggacatgg tgcgcaagga cgggcggcta 240
acggcggaca acatcaagga gcccatgcgg gagattcgca gggcgctgct tgaggcggat 300
gtgaggctgg gggcgccgct gatcagattc ttggtatcta cccccccccc ctcccaggtc 360
tccctccccg tggtgcgcaa gtttgtgaag gcggtggagg agaaggcgct gggttctgca 420
gtgaccaagg gtgtcacccc cgaccagcag ctggtgaagg tggtgtacga ccagctgcgg 480

-continued gagctgatgg gggggcagca ggaagggctg gtgcccactt cgccagagga gccgcaggtg 540
atcttgatgg cggggctgca gggcacgggg aagacgacag ctgcggggaa gctggccttg 600
ttcctgcaga agaaggggca gaaggtgctg ctggtggcca ccgacatcta ccgccccgcc 660
gccatcgacc agctggtgaa gctgggcgac aggatagggg tgccggtgtt ccagctggga 720
acccaggtgc agccgccgga gattgcaagg caggggctgg agaaggcgcg agcagagggg 780
tttgacgccg tcatcgtcga cacggcgggg cggctgcaga tcgaccagag catgatggag 840
gagctggtgc agatcaagtc cacggtgaag ccctccgaca cgctgctagt ggtcgatgcg 900
atgacggggc aggaggcagc cgggctggtg aaggcgttca atgatgccgt ggacatcaca 960
ggcgccgtgc tgaccaagct tgacggggac agccgcggcg gcgccgcgct gagcgtgcgc 1020
caggtcagcg ggcggcccat caagtttgtg ggcatggggg agggcatgga ggcgctggag 1080
cccttctacc ccgagcgcat ggccagcagg attctgggca tgggtgacgt ggtcaccctg 1140
gtggagaagg ctgaggagag catcaaggaa gaggaggcgc aggagatatc gcggaagatg 1200
ctgtcggcca aatttgactt tgacgacttc ctgaagcagt acaagatggt ggcggggatg 1260
gggaacatgg cccaaatcat gaagatgctg ccaggcatga acaagtttac ggagaagcag 1320
ctggcgggcg ttgagaagca gtacaaggtg tacgagagca tgatccagag catgacggtg 1380
aaggagcgca agcagccgga gctgttggtg aagtcgccct ccaggaggcg gcgcatagcg 1440
cgcgggtcgg ggcgctcgga gcgggaggtc acagagctgc tgggggtgtt caccaacctg 1500
cggacgcaga tgcagagctt ctccaaaatg atggccatgg gggggatggg catgggctcc 1560
atgatgagcg acgaggagat gatgcaggcc acgctggcag gcgccggccc ccgccccgtg 1620
ccagctggca aggtgcggcg gaagaagctg gccgcggcgg gcgggtcgcg gggcatggct 1680
gagctggcat ccctgaaggc agaatga 1707

<210> SEQ ID NO 66
<211> LENGTH: 2667
<212> TYPE: DNA
<213> ORGANISM: Artificial Sequence
<220> FEATURE:
<223> OTHER INFORMATION: Bleomycin resistance gene, codon optimized for Parachlorella and containing introns

<400> SEQUENCE: 66
atggccaaac tgacatccgc tgttcctgtg ttgacagcaa gagatgttgc aggtgcagtg 60
gagttttgtg agttctgaga agctgattgt tgtttaactt ctttgaaagc tttatcgaag 120
attctgcaag cgatgaacat tgcttgtcaa gaccgagagc tgcatgccca cttgacatcc 180
agctttgaac ggctcttcat gtttgatttg tttctgattg tagggacaga tagactgggg 240
tttagcaggg actttgtgga ggacgatttt gcaggagtgg tgagggatga tgtgacactg 300
tttatctcag cagtgcagga tcaagtgagt gcagcgtcag ctgtggcagt tgttggcttt 360
cgtctcagtc agtagtttgc tgggattgat tatggagggc acagttgcaa ttttgagttg 420
cacgttgcga caagcgtgtt gacaaagcgt ggtcaagccg gccagtcttg ccggtggcgg 480
gtggcttggt ctaacttccg ctctacagca atcgttttgt tcatggttac ggggctggcg 540
tgccagaaag tcctggtcag ccaccctcgc ttcaaagccg tagcccaaca actttgcgaa 600
tatgttcgat ttgcaggtgg tgcccgataa tacactggca tgggtttggg tgagaggtac 660
agctctgcgt gcaacaggtt gcaagatgca gcgcaggtct tccctggtca aacgatgtat 720
gcagagttga gaggcacttg agctgggtga atggcgtggg ctcgtaggta gtgtgcaggg 780

```
caggaagggc agccaatttt ggagttgtgg tccggtgtcg ttgcttcgag ccttattagg    840

actcttgctc atcaaagcgt tagttgtgaa taagttgatc tgaaaggatg ttatgtacag    900

caagcagcag cagttaagag tctggggagt agctgcacag ggcgaggtgt caagatggga    960

agggtcctgc ctccttatgt gtttttccct gtaggggagg aagcctctta tgggcaatgg   1020

ttgggcatat tttccagcca gcccttcttt ctataggggc cagggtgggc ccagctcgtc   1080

ttggcttcca ccaccaggag agtgagggca ttgaagggcc ataaatagtc ctcccatcta   1140

cgtgcaccag agggtgtcgt ctaggctgtg catgccacga ggggaaggag ccaagaatga   1200

gtgtatgggt tgttttcatg tttaggctgg gataaaactg ttttcaattg cgcctgccgg   1260

gtgaaaacca cagcagcatc agcaagcttg gagaaggcca gcccgcccag cacaggctca   1320

cgttcccact caggcggtca gtcgggcggg ggtgtgagtc aggcaggcga gggtgtctgt   1380

gcctgacatc agcacctctg cttagccact gcagcccctg gagcagggta gggcgtcatt   1440

tgcagcaatc acctgctgcc tcacacgtcg cagcttggaa tttcaacgac catcagcgct   1500

ggggttgttg agggatcata gcagattttg gtgcagcctg gttgtcatgc tctttgtgga   1560

atggcctcta tgttcgagca attcgttgga tgttgaggtg cttggggaca gagagtcgaa   1620

tgatgggcca gggtcaaaca tgcgagcgtt tggctgagtc agcggttttt gctggtcact   1680

ttttcttttg tttcttattt aggtttgatg gatgtgtttt gtgctgctgc cctgaagctg   1740

cagcagcgtg tctgccctgc gctactgcgg gcaccaaggc tatgtgctgg tgcactcggc   1800

tgcgctgcac ctgtgcacct cgcactccgt ccagcctcca tgcagcacac gtactcacgg   1860

tgtcctcctg acctgtcgta cgctattcca aacttgctct tttgctgccg ctgctctcgt   1920

acacaattgc tgttgattat cgatatctaa tcgagcgcct gctgactgaa ctccgcaggt   1980

ttggatgaac tgtatgcaga gtggtctgaa gtggtgagca ccaactttag gtgggtgggc   2040

tctgaaggag gaggagggag cgggtgatta aacagggcct gcatgaagag gagcaggggc   2100

tgcatggaca gcagggggaa ggtgcagaag ggagggtcaa gcggggttca ggtggctgtg   2160

ggtttctgca cgagcagtga aagaagctgt atccttccac ctgctttcac tggcgaaagg   2220

ttgaaaacag gatgtcgcag ctggaaagat gttgcgctgt caagtgcaag ccatggttga   2280

gggtatgcct gtgtgcatgt gcttcttaaa gttactcctg ttctatggtt ctgggtgctt   2340

gttgtttgtg gtgcagggat gcaagcggac ctgcaatgac agagattgga gaacaacctt   2400

ggggaaggga gtttgcattg agagatcctg caggtgaggg ggcatgtaag caatggcagg   2460

caattcaaga acgaatcatt gctgcaaatg ctgggatggt atgcagctga ggtatctatt   2520

gccttgtatt ttgtctcgca ttgcatcggt ggtgcgttct gtggcctgag gcacagttct   2580

tgctgtttga taagggttcg actgagttgt cgtgtgtgct gtgctgcagg caattgcgtg   2640

cactttgttg cagaagaaca ggactga                                       2667
```

```
<210> SEQ ID NO 67
<211> LENGTH: 32
<212> TYPE: DNA
<213> ORGANISM: Artificial Sequence
<220> FEATURE:
<223> OTHER INFORMATION: AE596 Primer

<400> SEQUENCE: 67

tgcgacatgc agcttactaa cctgctcgac at                                   32


<210> SEQ ID NO 68
```

<211> LENGTH: 28
<212> TYPE: DNA
<213> ORGANISM: Artificial Sequence
<220> FEATURE:
<223> OTHER INFORMATION: AE597 Primer

<400> SEQUENCE: 68
atgggctcct tgatgttgtc cgccgtta 28

<210> SEQ ID NO 69
<211> LENGTH: 21
<212> TYPE: DNA
<213> ORGANISM: Artificial Sequence
<220> FEATURE:
<223> OTHER INFORMATION: AE405 Primer

<400> SEQUENCE: 69
acccaaaccc atgccagtgt a 21

<210> SEQ ID NO 70
<211> LENGTH: 25
<212> TYPE: DNA
<213> ORGANISM: Artificial Sequence
<220> FEATURE:
<223> OTHER INFORMATION: AE406 Primer

<400> SEQUENCE: 70
actgtatgca gagtggtctg aagtg 25

<210> SEQ ID NO 71
<211> LENGTH: 4402
<212> TYPE: DNA
<213> ORGANISM: Artificial Sequence
<220> FEATURE:
<223> OTHER INFORMATION: Dual Promoter HygR cassette

<400> SEQUENCE: 71
cgtgcaggtg tacagattga aggaaacaat ggagatatct ttggcagttg aaaaccgtgt 60
tcgaatcatg cttttctact ctccaactga gacgaaattt atagcgccat gtcgcttctg 120
actaccaggc ttaggaaggc ctcatcacaa gctggatcgg ttcgaattaa gcaggcactg 180
aagccaagct tgcaagacag ccacctttta attccctcaa aacactttct caattcagcc 240
cggtaaatat gccgattcac agcggccaag atagagggga ggttagcaag aatgttgcga 300
tccctcccca gtcgttgcct cgcacacaac ctaggccttc acctttccat ggaaaattga 360
gaagtgaata ttggttttct tacggcatat cagatgaaat catgacccct aaacatgaag 420
agctgcaggc aaaacacctg ctctggacga gcacgatgaa atctcgagaa cccgccgtac 480
ttcagttgat cccgcatgat gacggccgcc attgaaataa gccacctcac tttattctag 540
caccgatttc caccgttgtg agggccgaac gaggacaatt tcgtgcgaaa caagcacgaa 600
cacgcacacg attagtagta cagacgagca gatcgatggc atgcggcacg gtctcgcgtt 660
ctcggcgacc aggacaacgg agcagaggga ggcctgccga gttccgaggg gcattttagt 720
ccaaaattgt gttgacacgt gaacaagtgg cttgaaaaga ggaaggaaat gcctgggttt 780
cccttcgaga gcgggaactc gcttgtgcgt catcctagct acccatggtc cctttgtggg 840
ggaggctgtt tcgtcctacc gaatgtgtgg cgctccatgc atcttctgcc tcccaaacca 900
ccaacatgag cacgcgaagg aaggagaaaa aagtggccgc aacgttctct tctcatattt 960
attgtctcat cacaaacata ggtacataat acaacaatca tgtccacagc ccgaacccat 1020
gagagagaat cataatcaaa gatgagccag ccacgaagct accggagaat tctgtaagaa 1080

-continued

```
aaatgtttaa agttgaaaat gctaacagtg aagtgatatc ctttttttaat ggagtgttga   1140
ggtgaagtct agcatcgtag gggaaaacag gattctgtgt cttccattct actccttgat   1200
aaagcgaaga aatccgacaa aaccaaagag attgttcaag tttaagattt gtaagcgtac   1260
aactatgaac ttcttctctt tgtaggcctg agtggtcgta tgcatacgat tcatgaagtg   1320
aatcagtatc gctggatttt gcttaggagt aaagcacaac taagaaaata tgctgcctgg   1380
caggcatcct gagacatgag gcaagcgacg tagcaattga atcctaattt aagccagggc   1440
atctgtatga ctctgttagt taattgatga accaatgagc tttaaaaaaa aatcgttgcg   1500
cgtaatgtag ttttaattct ccgccttgag gtgcggggcc atttcggaca aggttctttg   1560
gacggagatg gcagcatgtg tcccttctcc aaattggtcc gtgtggtagt tgagatgctg   1620
ccttaaaatt ctgctcggtc atcctgcctt cgcattcact cctttcgagc tgtcgggttc   1680
ctcacgaggc ctccgggagc ggattgcgca gaaaggcgac ccggagacac agagaccata   1740
caccgactaa attgcactgg acgatacggc atggcgacga cgatggccaa gcattgctac   1800
gtgattattc gccttgtcat tcagggagaa atgatgacat gtgtgggacg gtctttacat   1860
gggaagaggg catgaaaata acatggcctg gcgggatgga gcgtcacacc tgtgtatgcg   1920
ttcgatccac aagcaactca ccatttgcgt cggggcctgt ctccaatctg ctttaggcta   1980
cttttctcta atttagccta ttctatacag acagagacac acagggatca tggggaagaa   2040
accggaactg accgctacgt ccgtggagaa attccttatt gagaagttcg actctgtctc   2100
cgacttgatg caactgagcg agggagagga gagtagggcg ttctcgtttg acgtaggggg   2160
tcggggatac gtgttgaggg ttaatagttg tgcggacggg ttctacaagg atcggtatgt   2220
ctaccgtcat ttcgcctccg ccgctctccc cataccagag gtactggaca ttggggagtt   2280
tagcgaatct ctcacgtact gcatctcgcg ccgagcccag ggagtgacgt tgcaagatct   2340
gcccgaaact gaattgcctg ccgttttgca acccgtggcc gaggccatgg acgcgatcgc   2400
tgccgcagat ctgtctcaga cgtccggctt tggacctttt gggccccagg gcatcgggca   2460
gtacacgacc tggcgagact tcatctgcgc cattgccgat cctcacgtct atcattggca   2520
gacagtcatg gatgacaccg tgtctgcatc cgtggcccaa gcactggacg aactcatgtt   2580
gtgggccgag gattgccctg aggtcaggca cctggtgcac gcggatttcg gcagcaataa   2640
cgtacttaca gacaatggtc ggattactgc tgtcatcgac tggtccgaag cgatgtttgg   2700
tgatagccaa tacgaagtgg cgaacatatt cttctggcgt ccctggttgg cgtgcatgga   2760
gcagcagaca cgctactttg aacggaggca cccggagctg gccggctccc cacgactccg   2820
cgcctatatg ttgcgtatcg gactcgatca gctttaccag tctctcgtcg acggcaactt   2880
cgacgacgcc gcgtgggcgc agggccgctg cgacgcgata gtccgcagcg gggctgggac   2940
ggtgggtcgg acccaaatcg cacgccggtc ggctgcggtg tggacagacg gctgtgttga   3000
ggtgcttgcg gactcgggca accgtaggcc gagcacccga ccgcgtgcaa aggagtgatt   3060
gaatcattga atgaaccatt gtgtgcagaa tcgatttcgg gagtgttgcc aacacaagaa   3120
atatgcccag ggttgtgtag aagtttgcgt gaatgtgatg aagggaagcc atacgctgaa   3180
ttatcgtgac gtgtgtgaga cgaagtgtca catcatacac ccaatttgag aagctgtacc   3240
tattagaaga atttgtgaga tacattaaac cccttttggt acgtggtata attgttattt   3300
gggaagctgt aaacacgcag atcgttcctg agattgtcaa ttacttttgt ggtgtttcct   3360
aaaggccgca tcactgcccg aatcgagttg atggcccgca aaaataagca tacatcatat   3420
```

gaatacaatt cagcttaaat ttatcataca aagatgtaag tgcagcgtgg gtctgtaacg 3480
atcgggcgta atttaagata atgcgaggga ccgggggagg ttttggaacg gaatgaggaa 3540
tgggtcatgg cccataataa taatatgggt ttggtcgcct cgcacagcaa ccgtacgtgc 3600
gaaaaaggaa cagatccatt taataagttg aacgttattc tttcctatgc aatgcgtgta 3660
tcggaggcga gagcaagtca taggtggctg cgcacaataa ttgagtctca gctgagcgcc 3720
gtccgcgggt ggtgtgagtg gtcatcctcc tcccggccta tcgctcacat cgcctctcaa 3780
tggtggtggt ggggcctgat atgacctcaa tgccgaccca tattaaaacc cagtaaagca 3840
ttcaccaacg aacgaggggc tcttttgtgt gtgttttgag tatgatttta cacctctttg 3900
tgcatctctc tggtcttcct tggttcccgt agtttgggca tcatcactca cgcttccctc 3960
gaccttcgtt cttcctttac aaccccgaca caggtcagag ttggagtaat caaaaaaggg 4020
gtgcacgaat gagatacatt agattttgac agatatcctt ttactggaga gggttcaagg 4080
gatcaaatga acagcgggcg ttggcaatct agggagggat cggaggttgg cagcgagcga 4140
aagcgtgtcc atccttttgg ctgtcacacc tcacgaacca actgttagca ggccagcaca 4200
gatgacatac gagaatcttt attatatcgt agaccttatg tggatgacct ttggtgctgt 4260
gtgtctggca atgaacctga aggcttgata gggaggtggc tcccgtaaac cctttgtcct 4320
ttccacgctg agtctccccc gcactgtcct ttatacaaat tgttacagtc atctgcaggc 4380
ggtttttctt tggcaggcaa ac 4402

<210> SEQ ID NO 72
<211> LENGTH: 20
<212> TYPE: DNA
<213> ORGANISM: Artificial Sequence
<220> FEATURE:
<223> OTHER INFORMATION: ACCase target sequence 1

<400> SEQUENCE: 72
gggaaactgt gtgagaggag 20

<210> SEQ ID NO 73
<211> LENGTH: 20
<212> TYPE: DNA
<213> ORGANISM: Artificial Sequence
<220> FEATURE:
<223> OTHER INFORMATION: ACCase target sequence 2

<400> SEQUENCE: 73
ggggaggggc ttccaccaca 20

<210> SEQ ID NO 74
<211> LENGTH: 20
<212> TYPE: DNA
<213> ORGANISM: Artificial Sequence
<220> FEATURE:
<223> OTHER INFORMATION: ACCase target sequence 3

<400> SEQUENCE: 74
ggtgcgtcgc caagactgcc 20

<210> SEQ ID NO 75
<211> LENGTH: 20
<212> TYPE: DNA
<213> ORGANISM: Artificial Sequence
<220> FEATURE:
<223> OTHER INFORMATION: ACCase target sequence 4

<400> SEQUENCE: 75

```
ggcgagctct cttttccgtg                                                   20


<210> SEQ ID NO 76
<211> LENGTH: 18
<212> TYPE: DNA
<213> ORGANISM: Artificial Sequence
<220> FEATURE:
<223> OTHER INFORMATION: WX120-Accase Forward primer

<400> SEQUENCE: 76

ccttgatggt gctatatg                                                     18


<210> SEQ ID NO 77
<211> LENGTH: 18
<212> TYPE: DNA
<213> ORGANISM: Artificial Sequence
<220> FEATURE:
<223> OTHER INFORMATION: WX107-Accase Reverse primer

<400> SEQUENCE: 77

ttggagacga agagtgcc                                                     18


<210> SEQ ID NO 78
<211> LENGTH: 18
<212> TYPE: DNA
<213> ORGANISM: Nannochloropsis gaditana
<220> FEATURE:
<221> NAME/KEY: misc_feature
<223> OTHER INFORMATION: ZnCys-2845 gene target sequence

<400> SEQUENCE: 78

agtaggccat tcccggag                                                     18


<210> SEQ ID NO 79
<211> LENGTH: 120
<212> TYPE: DNA
<213> ORGANISM: Artificial Sequence
<220> FEATURE:
<223> OTHER INFORMATION: Oligonucleotide for producing chimeric guide
      targeting ZnCys-2845, first strand

<400> SEQUENCE: 79

aaaaaaagca ccgactcggt gccacttttt caagttgata acggactagc cttattttaa     60

cttgctattt ctagctctaa aacctccggg aatggcctac tcctatagtg agtcgtatta    120


<210> SEQ ID NO 80
<211> LENGTH: 120
<212> TYPE: DNA
<213> ORGANISM: Artificial Sequence
<220> FEATURE:
<223> OTHER INFORMATION: Oligonucleotide for producing chimeric guide
      targeting ZnCys-2845, opposite strand

<400> SEQUENCE: 80

taatacgact cactatagga gtaggccatt cccggaggtt ttagagctag aaatagcaag     60

ttaaaataag gctagtccgt tatcaacttg aaaaagtggc accgagtcgg tgcttttttt    120


<210> SEQ ID NO 81
<211> LENGTH: 20
<212> TYPE: DNA
<213> ORGANISM: Artificial Sequence
<220> FEATURE:
<223> OTHER INFORMATION: MA-ZnCys-Forward Primer

<400> SEQUENCE: 81
```

acctccttgt cactgagcag 20

<210> SEQ ID NO 82
<211> LENGTH: 21
<212> TYPE: DNA
<213> ORGANISM: Artificial Sequence
<220> FEATURE:
<223> OTHER INFORMATION: MA-ZnCys-Reverse Primer

<400> SEQUENCE: 82
gatcccaaag gtcatatccg t 21

<210> SEQ ID NO 83
<211> LENGTH: 20
<212> TYPE: DNA
<213> ORGANISM: Artificial Sequence
<220> FEATURE:
<223> OTHER INFORMATION: Bash-1 CRISPR target sequence

<400> SEQUENCE: 83
ggctgtcaaa tcaacaaaac 20

<210> SEQ ID NO 84
<211> LENGTH: 20
<212> TYPE: DNA
<213> ORGANISM: Artificial Sequence
<220> FEATURE:
<223> OTHER INFORMATION: Bash-2 CRISPR target sequence

<400> SEQUENCE: 84
ggagctcaga tatcttccag 20

<210> SEQ ID NO 85
<211> LENGTH: 20
<212> TYPE: DNA
<213> ORGANISM: Artificial Sequence
<220> FEATURE:
<223> OTHER INFORMATION: Bash-3 CRISPR target sequence

<400> SEQUENCE: 85
ggatcttcca gtggtgggcg 20

<210> SEQ ID NO 86
<211> LENGTH: 20
<212> TYPE: DNA
<213> ORGANISM: Artificial Sequence
<220> FEATURE:
<223> OTHER INFORMATION: Bash-4 CRISPR target sequence

<400> SEQUENCE: 86
gggggactgt cccattgtgc 20

<210> SEQ ID NO 87
<211> LENGTH: 20
<212> TYPE: DNA
<213> ORGANISM: Artificial Sequence
<220> FEATURE:
<223> OTHER INFORMATION: Bash-5 CRISPR target sequence

<400> SEQUENCE: 87
ggtctgtcta aatcagcaca 20

<210> SEQ ID NO 88
<211> LENGTH: 20
<212> TYPE: DNA

<213> ORGANISM: Artificial Sequence
<220> FEATURE:
<223> OTHER INFORMATION: Bash-6 CRISPR target sequence

<400> SEQUENCE: 88
gggccaagtg catcatgctc 20

<210> SEQ ID NO 89
<211> LENGTH: 20
<212> TYPE: DNA
<213> ORGANISM: Artificial Sequence
<220> FEATURE:
<223> OTHER INFORMATION: Bash-7 CRISPR target sequence

<400> SEQUENCE: 89
gggctcaggt acgcatctca 20

<210> SEQ ID NO 90
<211> LENGTH: 20
<212> TYPE: DNA
<213> ORGANISM: Artificial Sequence
<220> FEATURE:
<223> OTHER INFORMATION: Bash-8 CRISPR target sequence

<400> SEQUENCE: 90
ggattggaat caattttgaa 20

<210> SEQ ID NO 91
<211> LENGTH: 20
<212> TYPE: DNA
<213> ORGANISM: Artificial Sequence
<220> FEATURE:
<223> OTHER INFORMATION: Bash-9 CRISPR target sequence

<400> SEQUENCE: 91
gggctgttca tcacaaagag 20

<210> SEQ ID NO 92
<211> LENGTH: 20
<212> TYPE: DNA
<213> ORGANISM: Artificial Sequence
<220> FEATURE:
<223> OTHER INFORMATION: Bash-10 CRISPR target sequence

<400> SEQUENCE: 92
ggctctttgt gatgaacagc 20

<210> SEQ ID NO 93
<211> LENGTH: 20
<212> TYPE: DNA
<213> ORGANISM: Artificial Sequence
<220> FEATURE:
<223> OTHER INFORMATION: Bash-11 CRISPR target sequence

<400> SEQUENCE: 93
ggcgtcggtt cacgccaatc 20

<210> SEQ ID NO 94
<211> LENGTH: 20
<212> TYPE: DNA
<213> ORGANISM: Artificial Sequence
<220> FEATURE:
<223> OTHER INFORMATION: Bash-12 CRISPR target sequence

<400> SEQUENCE: 94
ggaactcgct cgtcgatcac 20

<210> SEQ ID NO 95
<211> LENGTH: 20
<212> TYPE: DNA
<213> ORGANISM: Artificial Sequence
<220> FEATURE:
<223> OTHER INFORMATION: MA-5'Bash-ZnCys Forward Primer

<400> SEQUENCE: 95
tagcagagca ggctcatcac 20

<210> SEQ ID NO 96
<211> LENGTH: 20
<212> TYPE: DNA
<213> ORGANISM: Artificial Sequence
<220> FEATURE:
<223> OTHER INFORMATION: MA-5'Bash-ZnCys Reverse primer

<400> SEQUENCE: 96
gaatatgtgg tctagctcgt 20

<210> SEQ ID NO 97
<211> LENGTH: 20
<212> TYPE: DNA
<213> ORGANISM: Artificial Sequence
<220> FEATURE:
<223> OTHER INFORMATION: MA-3'Bash-ZnCys Forward Primer

<400> SEQUENCE: 97
atggctccac cctctgtaag 20

<210> SEQ ID NO 98
<211> LENGTH: 20
<212> TYPE: DNA
<213> ORGANISM: Artificial Sequence
<220> FEATURE:
<223> OTHER INFORMATION: MA-3'Bash-ZnCys Reverse primer

<400> SEQUENCE: 98
ctgactacag ctagcacgat 20

<210> SEQ ID NO 99
<211> LENGTH: 21
<212> TYPE: DNA
<213> ORGANISM: Artificial Sequence
<220> FEATURE:
<223> OTHER INFORMATION: ZnCys-2845: Forward primer

<400> SEQUENCE: 99
atacaggaag cgtggttaca g 21

<210> SEQ ID NO 100
<211> LENGTH: 21
<212> TYPE: DNA
<213> ORGANISM: Artificial Sequence
<220> FEATURE:
<223> OTHER INFORMATION: ZnCys-2845 Reverse primer

<400> SEQUENCE: 100
gaagtattaa gggactggcc g 21

<210> SEQ ID NO 101
<211> LENGTH: 849
<212> TYPE: DNA
<213> ORGANISM: Nannochloropsis gaditana
<220> FEATURE:

<221> NAME/KEY: misc_feature
<223> OTHER INFORMATION: 1T5001704 Housekeeping gene

<400> SEQUENCE: 101
atgtcacggt cgcggtcctg ttccgaagct tctgcggcct cttcgtcatc ggcagcagca 60
gcgtcttcga ctcacgcccc ttcttcgcgc ggagcttcgg tggccgacgg tgctgcaagg 120
gagcgagaag ataatggcaa acgcctgagg tcaccgagcc ctgccggtgg tgaagcttct 180
ggttccgagg aagcggaaga ggatgatgag cccgccaaat tgcatgtttc tggtctaaca 240
agaaacgtga cagaggagca tctcaacgag atattcgcca catttgggaa gctgtcgcgt 300
gtggaactgg tacttgaccg acgagtgggc ttatcgcggg gcttcgccta tgttgagtac 360
gatcatcgga aggacgctga ggaagcccag ctgtacatgg acggtggtca gcttgacggc 420
gcacctttga aagtgaactt tgtgcttttg ggcggagccg cagccgatct cctgtatccc 480
gtggcggtgg tcgagaaagg gacctttacg atcgcaatgg cggtccgccg gagaggaggg 540
gcgggggagc tcaatgggag gggcggcggg gccggtctcg ttctccgcct cggggggtc 600 gacacgaccg aggtcggttg ccgccagggc ggtttactcg aggagagcgc ggacgcagcc 660
ccccctaccg tcgccagcca gaccctcgcg gctggtcgcc gccacggcgc gggccgggtg 720
ggcgggcatc tccgcctcgg gccgcggtcg cagccggagc agccgctcct cacgcagccg 780
ttcctagatg gagggggcgg cgccaacagg gaaggcaagc aggagtctca cccgccgctt 840
gaggcttga 849

<210> SEQ ID NO 102
<211> LENGTH: 408
<212> TYPE: DNA
<213> ORGANISM: Artificial Sequence
<220> FEATURE:
<223> OTHER INFORMATION: Region of ZnCys-2845 gene targeted by RNAi

<400> SEQUENCE: 102
gtttaaacga tcagccacga cggctctcgc atgcacaacg atggcatgga ttggcgcgcg 60
aaggatgagg actgctcgta ccacaccgcc gtggacgcca gctgccacat cgacagtagc 120
taccaccatg ttgatgcctc aggccactcc atggtcgacg cctcgggtca cagcacgata 180
gacgcgtcgg gccacgactc cctcatcgac tcaagcggcc attacgacga ctatctggcg 240
cacaaggggg acgcccgcta catggagcac agttgtgaag cctgcaagcg ctcgaagaaa 300
cgatgcaacc gccgcaaccc ctgccagatc tgcacctcca ggggcatcaa gtgtgtgccg 360
caaatccggg gtcctgggcg ccccccgggc agtaaaagca gtcggggc 408

<210> SEQ ID NO 103
<211> LENGTH: 163
<212> TYPE: DNA
<213> ORGANISM: Artificial Sequence
<220> FEATURE:
<223> OTHER INFORMATION: Terminator 9

<400> SEQUENCE: 103
gagtcaaggg ggaaggtgca tagtgtgcaa caacagcatt aacgtcaaag aaaactgcac 60
gttcaagccc gcgtgaacct gccggtcttc tgatcgccta catatagcag atactagttg 120
tacttttttt tccaaaggga acattcatgt atcaatttga aat 163

<210> SEQ ID NO 104
<211> LENGTH: 22313
<212> TYPE: DNA

<213> ORGANISM: Artificial Sequence
<220> FEATURE:
<223> OTHER INFORMATION: pSGE06337-Asc/Not Fragment
<220> FEATURE:
<221> NAME/KEY: misc_feature
<223> OTHER INFORMATION: genes with promoters and terminators

<400> SEQUENCE: 104

```
gcggccgccg tatggtcgac ggttgctcgg atgggggggg cggggagcga tggagggagg     60
aagatcaggt aaggtctcga cagactagag aagcacgagt gcaggtataa gaaacagcaa    120
aaaaaagtaa tgggcccagg cctggagagg gtatttgtct tgtttttctt tggccaggaa    180
cttgttctcc tttcttcgtt tctaggaccc cgatccccgc tcgcatttct ctcttcctca    240
gccgaagcgc agcggtaaag catccatttt atcccaccga aagggcgctc ccagccttcg    300
tcgagcggaa ccggggttac agtgcctcac tcctttgcac gcggtcgggt gctcggccta    360
cggttgcccg agtccgcaag cacctcaaca cagccgtctg tccacaccgc agccgaccgg    420
cgtgcgattt gggtccgacc caccgtccca gccccgctgc ggactatcgc gtcgcagcgg    480
ccctgcgccc acgcggcgtc gtcgaagttg ccgtcgacga gagactggta aagctgatcg    540
agtccgatac gcaacatata ggcgcggagt cgtggggagc cggccagctc cgggtgcctc    600
cgttcaaagt agcgtgtctg ctgctccatg cacgccaacc agggacgcca gaagaatatg    660
ttcgccactt cgtattggct atcaccaaac atcgcttcgg accagtcgat gacagcagta    720
atccgaccat tgtctgtaag tacgttattg ctgccgaaat ccgcgtgcac caggtgcctg    780
acctcagggc aatcctcggc ccacaacatg agttcgtcca gtgcttgggc cacggatgca    840
gacacggtgt catccatgac tgtctgccaa tgatagacgt gaggatcggc aatggcgcag    900
atgaagtctc gccaggtcgt gtactgcccg atgccctggg gcccaaaagg tccaaagccg    960
gacgtctgag acagatctgc ggcagcgatc gcgtccatgg cctcggccac gggttgcaaa   1020
acggcaggca attcagtttc gggcagatct tgcaacgtca ctccctgggc tcggcgcgag   1080
atgcagtacg tgagagattc gctaaactcc ccaatgtcca gtacctctgg tatggggaga   1140
gcggcggagg cgaaatgacg gtagacatac cgatccttgt agaacccgtc cgcacaacta   1200
ttaaccctca acacgtatcc ccgacccccct acgtcaaacg agaacgccct actctcctct   1260
ccctcgctca gttgcatcaa gtcggagaca gagtcgaact tctcaataag gaatttctcc   1320
acggacgtag cggtcagttc cggtttcttc cccatcgagc tcggtacccg gggatccatg   1380
attgttgtat tatgtaccta tgtttgtgat gagacaataa atatgagaag agaacgttgc   1440
ggccactttt ttctccttcc ttcgcgtgct catgttggtg gtttgggagg cagaagatgc   1500
atggagcgcc acacattcgg taggacgaaa cagcctcccc cacaaaggga ccatgggtag   1560
ctaggatgac gcacaagcga gttcccgctc tcgaagggaa acccaggcat ttccttcctc   1620
ttttcaagcc acttgttcac gtgtcaacac aattttggac taaaatgccc ctcggaactc   1680
ggcaggcctc cctctgctcc gttgtcctgg tcgccgagaa cgcgagaccg tgccgcatgc   1740
catcgatctg ctcgtctgta ctactaatcg tgtgcgtgtt cgtgcttgtt tcgcacgaaa   1800
ttgtcctcgt tcggccctca caacggtgga aatcggtgct agaataaagt gaggtggctt   1860
atttcaatgg cggccgtcat catgcgggat caactgaagt acggcgggtt ctcgagattt   1920
catcgtgctc gtccagagca ggtgttttgc ctgcagctct tcatgtttag ggtcatgat   1980
ttcatctgat atgccgtaag aaaaccaata ttcacttctc aattttccat ggaaaggtga   2040
aggcctaggt tgtgtgcgag gcaacgactg gggagggatc gcaacattct tgctaacctc   2100
```

```
ccctctatct tggccgctgt gaatcggcat atttaccggg ctgaattgag aaagtgtttt   2160
gagggaatta aaaggtggct gtcttgcaag cttggcttca gtgcctgctt aattcgaacc   2220
gatccagctt gtgatgaggc cttcctaagc ctggtagtca gaagcgacat ggcgctataa   2280
atttcgtctc agttggagag tagaaaagca tgattcgaac acggttttca actgccaaag   2340
atatctccat tgtttccttc aatctgtaca cctgcacggt gcaccagttg gtacggcata   2400
ttatggtttg aatgctggcg acctcatgaa ctttgttgat ttttttagaa ttgtgtcatc   2460
gaaaaatata caatgtcgaa gtaaagttta tacactctgg gtactcttct tctttgccat   2520
ccagtaggtg tgggatagga gtgcgtggta attctctgag acagttttcc taccatgttt   2580
cgggtccaca tagtacaagt tgttactcgt gacacctcat ttcgcttttg tttctccact   2640
aatggactac atttttcaaa gcagcagcgt ccgcgtttct cgattaagaa tctcccgtcc   2700
gctttgagtt tgtttatttt aaggattaga aggataaaag cggagctgca aaggtgaaac   2760
atgcctgaga ggactagaag acatacggag ctgaagtgcg gggaggttaa acccgatgat   2820
cccattcctt gcatttgtca aggctcaccg cattcatagt tctaaaaaga aaatatttcc   2880
gaataatgtt aacacaaaaa taattaaata ctgttctatg tactccgttc atttgttgat   2940
ggaatcaaaa ggccagaaaa aaagaggggg ggactccaag ctgccgcaga cgctcgcctc   3000
gtctctcgtt cgcggaatgc cggtcgtgga accgctgtga agataccgtg ccttggggat   3060
caattcacac attgacgagg gcgcctcacg ccgtggcgta cttattcggg ccaaaatgtt   3120
atttccaagg ggtgacggat ggcatgctcg actcgtgtga tggctgatgc atcaaccctt   3180
tcaatgctcc ttcctacttc ctcttatcca ctggtagtct gtcatgagat gtggtgaacc   3240
gcgtccgtga taatagtgtt ctcatttaac ctaacaacca acacaataca aaacttgatt   3300
agatacccag tgcatcgaat tttgggtgcc ttcaccgaca agcttgcact ttctcgaggg   3360
acgacaacaa caaaccacct acagcattac cgggcaatag cagcacaaca tggaggacat   3420
cgtgattgcc ggaatttccg gaagattgcc tgagagcaac aacttggagg agttttggca   3480
gaacctcttc aatggcgtgg acatggtgac agaggatgac cgaaggtgga aacctggatt   3540
gtacggattg cctagacgga atgggaagtt gaaggagatt gaccggtttg acgccgcatt   3600
ttttggcgtg catcctaaac aagcccatac gatggaccct caattgcggt tgatgttgga   3660
gatcagttac gaggcgattg tggatggagg aattaatccc gtgagcatga gagggagcaa   3720
aactggcgtg tacatcggag tgagcggatc tgaagcagga gaggcctttt ctaaagaccc   3780
tgaagagttg ttgggatact ccatgacagg atgtcaacga gccatgttcg ccaataggct   3840
cagctacttc ttcgacttta acggacctag cacggcaatc gacacagctt gttcttctag   3900
cttgttggcc ttggaaaacg ccttcaatgc catccggcac ggacaatgtg atgccgcctt   3960
gattggagga gtgaatttgt tgttgaagcc caatacctcc gtgcaattca tgaagctcgg   4020
gatgttgtcc cctgagggaa cctgtaagtc ctttgatgcc tccggaaatg gatactgtcg   4080
gtctgaagca gctgtggctg tgttgttgac gaaaaagtct atggcaaagc ggatctacgc   4140
caccgtgttg aatgcgggga acaatacaga tggatacaaa gagcaaggag tgacctttcc   4200
tagcggagag atgcaacaac gattggtgcg gtccctttac caagaagcca acatctcccc   4260
tgagcaagtg gagtacattg aggcccatgg aaccggaacc aaagtcggag atcctcaaga   4320
agtgaatgga atcgtgagcg tgttttgcca atcccctaga gatcctttgt tgattggatc   4380
caccaagtcc aatatggggc accctgaacc tgcatctgga ttagccgcat tggccaaagt   4440
cgtgttgtca ttggagcatg gagtgtgggc acctaacgtg cactttaacg agcctaaccc   4500
```

```
tgacatccct gccttgacag atggaagatt gtgtgtggtc tccaaaccta cacctgtgag   4560
aggaggaatt gtcggaatta attcctttgg atttggggga tcgaacgtcc acgtcatctt   4620
gtctccccat gtgagcgact cttctgacaa aacacctgcc ccttctgtgc cccgattgtt   4680
gcaagcttct ggacgaactg aagaggccgt tacagccttg ttttctaatg cccaacaaca   4740
ccaagagaac tcctcctact tgtccctgtt gaatgatgtg tctggtgtgc ctactgctgg   4800
aatgccttac cgaggataca ctttgattgg cgcccaagga gaattgaccg aagtccaaca   4860
gacccaacct acgcctcgac ctttgtggta catctgctcc ggaatgggaa cgcaatgggc   4920
tggaatggga caatctttga tgcaattgtc tgagtttcga gagtccatta aaagatccga   4980
tatcgccctg aaggacaccg gattgtgcgt gtctcgattg ttgatggagg ccgatgagag   5040
cacctttgaa gacaccgtcc atgcatttgt gggattggcc gccattcaag tggcccaaat   5100
cgacatgttg cggaagatgg ggttggagcc taatggaatt gtgggacatt ctgtgggaga   5160
attggcatgt ggatatgctg atggatcttt gagccattcc gaagccattt tggcagcata   5220
ctggcgagga agatgcatta aagaggcgaa cttgcccccct ggaggtatgg cagcagtggg   5280
attgacatgg gaagagtgta aagcgcaatg ccctcaagga gtggtgccag cttgccataa   5340
tgcagaagat acagtgacaa tttctggacc ccaagactcc gtgtccaaat ttgtggccca   5400
attgaaagaa tctggcgtgt ttgcgaaaga ggtgcgatct gctggagtgg cctttcattc   5460
gtactacatg gcctccattg cccctgcctt gttgtctgcc ttgcaaaaag tgatcaagtc   5520
cccccgccct agaacagcac gatggatttc tacatctatt ccccaatccg actgggaatc   5580
tcctcttgcc ttgtactctt ctgctgagta tcatgtgaac aatcttgtgt cccctgtcct   5640
cttccaagag gggttgaatc atgtccccga taatgccgtg gtcgtcgaaa tcgcccctca   5700
tgctttgttg caagccatcc tcaaacggtc cttgaagcct acctgttcca ttttgccctt   5760
gatgaaacgt ggccatgcca acaacctcga gttctttttg tcccatgtcg gaaaagtgta   5820
catgaacggg atcaacgtgg attccaacaa gctttaccct gccgtgaaat accctgtgcc   5880
tcgtggaacc cctctgattt cccccttacat ccagtgggat cactcccaat cctgggatgt   5940
gcctaaagtg gaagactttc ctgccggatc tggcggatct acatctgcaa ctgtgtacaa   6000
tatcgacatg aatcctgaat cccctgacta ctacatgatt ggacattgta tcgacggccg   6060
agtgttgtat cctgcaacgg gctacctggt gttggcttgg agaaccttga tgcgctcttt   6120
gggaacggtg atggaccata cccctgtgac gtttgaagat gtgaccatcc atcgagccac   6180
gatcttgcct aaaactggat ctgtgcaatt ggaagtgcgg ttgatgcctg caacaaatag   6240
atttgaagtg tccgagaatg gcaatttggc tgtgtccggg aaggtgtccg tgttggaaga   6300
ctctgggttg gatgcgtttc atgccgagct gaacaagccc attaccgctg acaatgaaga   6360
ccctaagctc cgcctgaaat ctggagatat ctacaaggag ttgcgattga ggggatacga   6420
ctacggaaag acctttcaag gaattttgga gagcaataat gccggagact ccgggaaact   6480
ccactggacg ggaaattggg tgacgttctt ggacacgatg ctgcagatga tcgtcgtggg   6540
attgcctgga agaagcttga gactccctac ccgaattcga tctgtgtgtg tggatcctaa   6600
attgcatgag gaacgcgtga atgactacga aggagaccaa aaagccgtga atgtttttgt   6660
gaatcggtgc ctcgacaaca tcacagccgg aggagtgcaa atctgtgggt tgcatgctac   6720
agccgcccct cgaagacaac aacaacaaac accccctacc ttggaggaat tcgtctttgt   6780
cccctacgaa gatgccgatt gcttgagaac caatgagaaa ttggccgacc aattgcgaca   6840
```

-continued

```
ctgtaaagga ttggtgcaac gattgcaacg caaattggcc aaacaaggcg tgaagatctc   6900
catccctggc ttggaaggag cgtccgaagg gcaattgatt gaagcagagg ccgagaaagg   6960
gttgttgagg ttgttgtccg tgttgtgcgg cttggagttg aatgggaatt tgagatccga   7020
attggaacaa acggtgcaaa aagagagaga ctgcttgctg caagatcccc tgttgaatgg   7080
cttgttggat tctcaagcgt tgcggcattg cctggatacc gcgctggaaa attccacacc   7140
tggcaagttc aaggtcttgg aggcccttgc tgctgatgga cgcgtgtttt ctcaagctgt   7200
gtctttgctg aatattcaac ctatgttgcg tttggactac actgcctctg atatttccgc   7260
cgaccaattg tccgcccaac aatcttcttt ggaagagcag ggaatctcta ccgcccagtg   7320
ggatcctctt caaggacccg tgacaggagg attggatgga gccgatcttg tggtgtgcaa   7380
ttgtgctgtt ggatctgcca cgaatcctgc attgttgatt gagaatttga catctgccgc   7440
tagagaagga ggattcatct tgttgcacac gttgttgaga ggagatacgt tgggagaaac   7500
agtggcgttc ctcacgagcc agaataaccg gaagggcctg ttgacgcaaa ccgagtggga   7560
agagctgttc caaaaagcct ccctgaatgt ggtgatgttg cggaagtcct attacggaag   7620
tgccttgttt ttgtgtcgaa gaagccaaca atccagccaa aagcaaccta ttcacatctt   7680
cgtggaccct accgactaca aatgggtgga gaccttgaaa tccacactcg ccgagtcctc   7740
cgatatcccc gtctggttga ttgccaccaa aggccataat ggagtcgtgg gaatggtgaa   7800
ctgcttgcgt caagagcctg gaggaaatag aattcgatgc acatttgtct ccaatttgtc   7860
caaaggagct gcagtgcctt ccttgttgcc taatgagaag gtgatgaaag ccctgttgaa   7920
gaaggacctg gtgatgaacg tccaccgcga cggactgtgg ggagtgtttc gacatcaatt   7980
gctgacccaa gacctgtccg aagaattgac cgagcaggcc tacgtgaatg tgttgacaag   8040
aggagatttg tctagtttga gatggattgc gtcccccttg aggcattttg tggcatcttc   8100
tcctaatgtg caattgtgca gagtgtacta ctcctccctg aacttccgcg acatcatgct   8160
cgccaccgga aaattgcccc ctgacgccat ccctggagat gtggcattgc agcaatgtat   8220
gttgggaatg gagttctccg gaagagatcc ttctggaaga agagtgatgg gattgttgcc   8280
tgctaaagga ttggccacat gtgtggatgc cgataaaaga tttttgtggg atgtgccttc   8340
ttcttggacg ttggagcaag ccgcctctgt gcctgtcgtc tacgctaccg cctactactc   8400
cttggtggtc agaggaagat tgagacctgg agaaagtgtg ttgattcatt ccggatctgg   8460
tggagttgga caagccgcta ttgcaattgc cttgagcatg cgctgtagag tgtttacaac   8520
agtgggatct aaagagaaga agcaatactt gcaagagcgc ttcccccagt tgacagccga   8580
gtccttcgcc aattcccgcg attcctcctt cgagcaacat gtgatgctga acacacaagg   8640
aaaaggagtg gacctcgtct tgaattccct cgccgaagag aaattgcaag cctccttgag   8700
atgtcttgcc agacatggac gatttttgga aatcggaaaa tacgatttgt ccaacaacac   8760
cccccctgggc atggccctgt tcctgaagaa cgtcgccttt cacgggatct tgctcgatgc   8820
actgtttgaa gagggcaatc gtgaatggga agaggtgtcc gacctgttga agaaaggaat   8880
ttcctccgga gtggtgcaac ctttgagaac gaccgtgttt gagagaaacc aagtggaaga   8940
agcatttaga tatatggcgc agggaaagca catcggcaag gtgttgctgc aagtgcgctc   9000
cgaagaatcc tcctcctctg gacctgcagt gtctgctttg agtattcctg ccatttgccg   9060
aacgttttgt cctgcaagtt tgtcctacat catcaccgga ggcttgggcg gatttggatt   9120
ggaattggcc caatggttga cagaaagagg agcaagaaaa ttggtgttga cgtctagatc   9180
cggaatccgc aacggctacc aagctaagag agtccgagag tggcaagcca tgggaattca   9240
```

-continued

```
agtgttggtc tccacatccg acgtgtctac cttggatgga acagaacgat tgatcacaga   9300
ggcctgtagg ttgggacctg tgggaggaat tttccatttg gcaatggtgt tgaaagatgg   9360
aatgctcgag aatttgaccc ctcaggagtt catcgaggtg aatcggccca agtacgacgg   9420
gacgatcaat ttggacagcg tgacccgaca aaaatgcccc caattgcagc aattcgtcgt   9480
gttttcttcc gtgtcttgtg gacgagggaa tgccggacag tccaattacg gatttgcaaa   9540
ctccacaatg gaaagaatct gcgaacaaag acgacaggag aatttgcctg gattggccgt   9600
gcaatgggga gccatcggag atgtgggagt ggtcttggag acaatgggag gcaatgatgc   9660
cgtgatcgga ggaacattac ctcaaagaat gtcttcctgc ttggaggtgt tggaccgctt   9720
tttgtgtcaa caacgacctg tgatgtcctc ttttgtgttg gcagaaaaag tggtggtgac   9780
aaaaggagag ggatccggac aaaaggacct ggtggaagct gtggcgcaca tcttgggagt   9840
gagggacgtg aatagcttga atgccgacgc atcattggcc gatttgggat tggatagctt   9900
gatgggagtg gaagtgagac aaaccttgga gagagactac gacattgtga tggctatgag   9960
agagatcaga caattgacga tcaacaagtt gcgggagttg agcaagcaat ccggcgggaa  10020
ggaggaatcc cctgtgaaga ggtctggagc ccaagcattg ttggaaagcg acttgtcccg  10080
aatgttggtg aatcctgacg gacctacaat ggcacccttg aatgaagtcc aatccgcaga  10140
aagacccttg tttttggtac atcctatcga aggatctatt gccgcatttc gaaccttgac  10200
agcgaagctc agcgtgccct gctacggatt gcaatgtacc aaagccgccc ctttggactc  10260
tatccaatct ttggccgcct actatgtcga atgtgtgagg caagtgcagt tggaaggacc  10320
ctacagaatt gccggatact cctttggagc ttgtgtcgct tttgaaatgt gttcccaatt  10380
gcaattggcg aaatgccctg tggagtacct gttcctgttc gacggatccc actcttacgt  10440
cgccgcgtac actcaatctt atcgagccaa gttgaccccc ggaaaagaag ctgaagcaga  10500
aacagaagcc ttgtgtgcct ttatccagca gttcaccgga atcgagtaca acaaactctt  10560
ggagaccttg ttgcctttgt ctgatttgga agccagagtg gacaaagcag tggacctgat  10620
cacctcctcc cacaagaacg tgtcccgcga tatgttgcat tttgccgcct ccacgtttta  10680
ccacaagttg aaagccgccg acagatacgt gcctacatcc aaataccacg ggaatgtgac  10740
cttgttgaga gccaaagcat cttctgagta tggagacgga ttgggatctg actacaaatt  10800
gcacgaagtc tgtgacggga aggtgtccgt gcatgtgatc gagggcgacc atagaacctt  10860
tttggaggga gaaggagtgg agtctatttc cagcatcatc cacagcagct tgtctgagcc  10920
tagagtgtcc acgagagaag gataaagtga tgcggccttt aggaaacacc acaaaagtaa  10980
ttgacaatct caggaacgat ctgcgtgttt acagcttccc aaataacaat tataccacgt  11040
accaaaaggg gtttaatgta tctcacaaat tcttctaata ggtacagctt ctcaaattgg  11100
gtgtatgatg tgacacttcg tctcacacac gtcacgataa ttcagcgtat ggcttccctt  11160
catcacattc acgcaaactt ctacacaacc ctgggcatat ttcttgtgtt ggcaacactc  11220
ccgaaatcga ttctgcacac aatggttcat tcaatgattc aagtacgttt tagacggact  11280
aggcagttca taatcaaaga tgagccagcc acgaagctac cggagaattc tgtaagaaaa  11340
atgtttaaag ttgaaaatgc taacagtgaa gtgatatcct tttttaatgg agtgttgagg  11400
tgaagtctag catcgtaggg gaaaacagga ttctgtgtct tccattctac tccttgataa  11460
agcgaagaaa tccgacaaaa ccaaagagat tgttcaagtt taagatttgt aagcgtacaa  11520
ctatgaactt cttctctttg taggcctgag tggtcgtatg catacgattc atgaagtgaa  11580
```

-continued

```
tcagtatcgc tggattttgc ttaggagtaa agcacaacta agaaaatatg ctgcctggca  11640
ggcatcctga gacatgaggc aagcgacgta gcaattgaat cctaatttaa gccagggcat  11700
ctgtatgact ctgttagtta attgatgaac caatgagctt taaaaaaaaa tcgttgcgcg  11760
taatgtagtt ttaattctcc gccttgaggt gcggggccat ttcggacaag gttctttgga  11820
cggagatggc agcatgtgtc ccttctccaa attggtccgt gtggtagttg agatgctgcc  11880
ttaaaattct gctcggtcat cctgccttcg cattcactcc tttcgagctg tcgggttcct  11940
cacgaggcct ccgggagcgg attgcgcaga aaggcgaccc ggagacacag agaccataca  12000
ccgactaaat tgcactggac gatacggcat ggcgacgacg atggccaagc attgctacgt  12060
gattattcgc cttgtcattc agggagaaat gatgacatgt gtgggacggt ctttacatgg  12120
gaagagggca tgaaaataac atggcctggc gggatggagc gtcacacctg tgtatgcgtt  12180
cgatccacaa gcaactcacc atttgcgtcg gggcctgtct ccaatctgct ttaggctact  12240
tttctctaat ttagcctatt ctatacagac agagacacac agggatcatg gatggagtga  12300
gatgggcctt tagatgtgga tcttgggtgc cttccagatc tgagtggaca ttggcagcaa  12360
gatgtgtgca acaagaggag aagttgagga tcggacagtt cgtgtttgcc aaagacgcca  12420
aatctgcaat ggccggacga ttgttgatca ggaagttggt gtgcgagaaa atggggtttg  12480
cctgggacgg atttaggttg caaagaacag agcggggaaa accttacttg ccccaaacaa  12540
gttccgcccc ttcttggagc tttaatgtga gccatcaagg cgattacgca gtgttagcag  12600
ccgaagctgg aagacaagtg ggaattgacg tcatgaaaac gtccagacct ggaagctctt  12660
ctgtgcaaga gttcttccgc atcatgaatc gccaatttac cgacctcgag tggaccaata  12720
tccgaaccgc aggatctgac tgggaccaac tgcatatgtt ttaccgccat tgggccttga  12780
aagagtcctt caacaaggca atcggaaccg gattgggctt cgacttgcaa cgtgccgaat  12840
ttcatatctc ccccaaccaa atgcgagaag gccaagtgta ccgacaaaca agaatgtacc  12900
tcgactccga agaagaagaa gactggacct tcgaggagtc cttgctcgac aaagatcacc  12960
atgtggctgt ggccttggga aaacctgaca tctctatgtc caagaaagac ggaggatcct  13020
cctgtgaggc accacctgca gcttttacag tgttgtcctt ttccgacttg gtgtcccaag  13080
caacacctct tttggacgaa gaccctacat attgggagga gtttcagaag aagaaggagg  13140
ccccttcccg acaatccgat caagagtaac cgtcaaaggc aaaggaggaa aagaagaagg  13200
cttacaccag tggcaccgaa atgttaatag cttgatgttt gcataaattg tcaaagtaaa  13260
tgaaggtcta gagcttgaag gttgcatctg aaaaaaatca acaacagatg gcgaaatcga  13320
tcgcatgctg accgtcaggc cttcagaatt accatcgcac tgcatagtcc gagcaggatg  13380
tcaatatagg gccgtcgtta aggatacgta ggccgttgct gtttgctgcc gcctgtggcc  13440
cgttcatcga atgaaaaaaa atgtgtatgt tcaagttaat ggttactaaa tggttcgcaa  13500
ggccgagttt cacagagcgg cagaagacat ccattgaaaa ctcgcaagta tgcaggagga  13560
atgaatatac tcagggtacg tgtatattta aaactattgt gaagcattag gatagaaagg  13620
aaggatctgc tacaaagtaa attcaggaac aatgtcggac acaccaaaga ttccgaccct  13680
gactgcccgc aaaaatggac gctattccaa aaacataaag gtaatgatac aaccccacgt  13740
accttggcat ttacgcatcc catacttatt tgtttggcac ccgttggtgt gttagtgggt  13800
agcgcttgtt cttactttcg ttcctgaacg cctgaaagcc aggaagagag gcacgatttg  13860
agtctttata ggggtcctcc ccggccaggc aacgcttctc tcccccagct gctctcgcaa  13920
aatttctctg agggctgtca tagctctgcg catcccctta tgtgacgtcg ccaccggtag  13980
```

atttcacgcg gacacgggca tatctcccat gtgcgggagg aacaaatgac gatggggtcg 14040
cattccatca tagacttggg ggcctctccc gtcatccagc tctgcgtcca gccttccggc 14100
actttgtctt gtgctcgtcg agcatcttcc ttcactccga cgcccatggt tcgcttgcgc 14160
gcttgcgttc gttgtccctt gggtacgaag gcgatgctgt tgtaatgaac gtcgataccc 14220
cggtggaggg atgggcgaag tttgtgaaag cgaggagagg tcatatgcag caggaagaga 14280
gagccaaccc gccctctccg attcgagatg aacccttcta aagctgtgtg tcactcatgc 14340
tcatgcattt ccctacaatg cccatctata atgcgcgaat agagaagaga tggccgctac 14400
tctccgaatg gatgaggcgg gagccaacga ggcagggggt cgtgttggtg gcgccggcgt 14460
ggaggaggtc cgggaacaag acagatattt gcccattgcc aacatcagtc ggataatgaa 14520
gaagtctttg gtaagtgtcg tgacgcatcc taatagtgcg ctccttctag atgtcccaac 14580
atctgtcgcc gatagacctt gttttgtccc acaagtctcc tgttcccatc ctcttctacc 14640
atgttctctt tcctcactca tgtgctccct ctctcgccac taatccgggc agccggcgaa 14700
tgccaaaata gccaaggacg ccaaagaaac cgtccaagaa tgtgtttcag agttcatttc 14760
tttcatcacc tccgaagcca gcgacaaatg ccaacaggag aagcgaaaga cgatcaacgg 14820
ggacgatctc ctctgggcca tgagcaccct gggcttcgac aaatacgtcg agcctctgaa 14880
acattatttg gtcaagtacc gtgagtcagt gaaggggggt gagaaggcgg acggagggaa 14940
gaaagggaag tctgagggca cccaagtgac aggaagtagc gcggcgggtc ctgtcacggc 15000
gaccgcgcta gctgagcctc agggtgacag tcgggtggaa tcgaccgaaa gcagtagtct 15060
ccccgagcag caacatcaca gttatgcagc ccgtgctgtg tcaaggcagc cgccttcctg 15120
aagacctgaa ggcgagacag taaattattt tcagagtcgt acaggaaatg gagagatgtt 15180
gcggaaaagt tatgccagta acgtacgcga cacacataca aactaaagat aaaagcaaaa 15240
ttgcccacgc acagtctaaa ttgaatattt tgctgcgaga ggctacatga tcaagtggag 15300
agcatccatt ttttgagccc catgaggttc attcaagtct acttaagttg tctttttttaa 15360
cttttcattg acatttttcg cctgttgtct cctctctgtg tcgatggcca ttcaataaaa 15420
gcactgtccc ggcattcaag agctgtagcg gtatcatgtc aacaatcagt aggaataagc 15480
atacatcata tgaatacaat tcagcttaaa tttatcatac aaagatgtaa gtgcagcgtg 15540
ggtctgtaac gatcgggcgt aatttaagat aatgcgaggg accgggggag gttttggaac 15600
ggaatgagga atgggtcatg gcccataata ataatatggg tttggtcgcc tcgcacagca 15660
accgtacgtg cgaaaaagga acagatccat ttaataagtt gaacgttatt ctttcctatg 15720
caatgcgtgt atcggaggcg agagcaagtc ataggtggct gcgcacaata attgagtctc 15780
agctgagcgc cgtccgcggg tggtgtgagt ggtcatcctc ctcccggcct atcgctcaca 15840
tcgcctctca atggtggtgg tggggcctga tatgacctca atgccgaccc atattaaaac 15900
ccagtaaagc attcaccaac gaacgagggg ctcttttgtg tgtgttttga gtatgatttt 15960
acacctcttt gtgcatctct ctggtcttcc ttggttcccg tagtttgggc atcatcactc 16020
acgcttccct cgaccttcgt tcttccttta caaccccgac acaggtcaga gttggagtaa 16080
tcaaaaaagg ggtgcacgaa tgagatacat tagattttga cagatatcct tttactggag 16140
agggttcaag ggatcaaatg aacagcgggc gttggcaatc tagggaggga tcggaggttg 16200
gcagcgagcg aaagcgtgtc catccttttg gctgtcacac ctcacgaacc aactgttagc 16260
aggccagcac agatgacata cgagaatctt tattatatcg tagaccttat gtggatgacc 16320

-continued

```
tttggtgctg tgtgtctggc aatgaacctg aaggcttgat agggaggtgg ctcccgtaaa  16380
ccctttgtcc tttccacgct gagtctcccc cgcactgtcc tttatacaaa ttgttacagt  16440
catctgcagg cggtttttct ttggcaggca aacatggaga cttcgacgag aaaaggcttt  16500
catgaacgca gtgacgcacg atttccagct ggagcgcttc atgattccat gaacttgaca  16560
tcaaatgatt cattcagaag ctctcagttt ggcaaggaag gcgccttcaa cgaagtcaag  16620
aaagaccctg gacgctggac ggctgaggaa catatgttgt ttcttagggg tctgcaatta  16680
cacggtaaat catggaagaa aatatccgag attgttacaa cgcggacagt ggtccaaatt  16740
cgtacacatg cccagaaata ccttataaag ttggaaaagg ctagaaaggc tggtcatcag  16800
ggtgtcttaa tgatggatgg gaaaggcgtc gataacactg aacgtcgagg cacttccaag  16860
aaatcatctt tgtccacgga aacggtgagt ttcacatcta cttctcctga atcttctgtt  16920
ctcgagcaga agagacagaa aaatgagcca gcggctcacc tgccaggtcc tgtgcagcat  16980
actactgtac gccctttttgc acctgtcaca agagccgcac cttcaggctg ccccccaact  17040
gcgcccgcag gattcgtgcc atggatggta ggcccatacg cttgtgtccc tccaacatac  17100
tacaacatgc aaatgatggc ccatggatat gactttggtg ctccgctggt atcgccatca  17160
tcacaatatc gtgcgagttt ttcaaatccc ctgtctgcac ccggaggaaa ttgccaagag  17220
caggacttgg gactaaacgc acctcaatct gtgagaatgc ccttggaggc tgaaatggct  17280
gcacaaattc attacctggg cattgacaac gaggaaacta tcgcgcaaaa tcagccaaat  17340
tcctataagc gtctacgtgt ccccgcaggt ctggctatgg cgacgcctgc cgcggtttct  17400
acggcacaat cctctcattg taaagtctac gttgccccgc agcagtcatg cacctcgcct  17460
tctgatatga ctccgactct aaccgcatca gccttacatc agccaccgca gggatctctt  17520
tgcccgttca tgacatcaaa tcctttagac gagctcatgc aaagcctgtc gcaggagaat  17580
ctttcttcct cctgctcctc gacctctcca tctatcgcac ccgaagttga tgtacccagc  17640
atgcatgaca tactcatttg ggacctaaat gggaaacata gccgcccttc ttcccttagc  17700
tcctgggacg aggagggctt cgatggagtc tcaacctcat cttcccctgc aagcattgac  17760
aatcacgttg tttgccaacc tccggatttg agcgagcttc agtatgcgaa agctgcgtga  17820
gagtcaaggg ggaaggtgca tagtgtgcaa caacagcatt aacgtcaaag aaaactgcac  17880
gttcaagccc gcgtgaacct gccggtcttc tgatcgccta catatagcag atactagttg  17940
tactttttt tccaaaggga acattcatgt atcaatttga aatcaccaga tataggtgac  18000
ccgataacgg agccaataga gtccaggctt ttgcgtgtga cttgtacgtt tgggggcagc  18060
agcatagctg ggacggggtc gctcgtccct gtttcgagta tggcgcgcac tctgacgcct  18120
tcaagtgtgg ttgccatctt cgccgcaatc agctgagctg tcccgtcctc ataacccacc  18180
acgacagcta cttttcccat gccctccgct gacatcatca ctaagctttt ccctgccctt  18240
attgcacatg aatccttcag cgttgtccgt ggtggagcta gaaagcccca tgctccttgt  18300
tgcagcaaag tcagaaccgt gaagatcata aagccccaca atactgagaa atgcctgtgc  18360
catacacttt gtcttgcgcc tatcgacatt tttttactca ctatcactga tttggatccc  18420
agcttgtcct ccccgtcctg tatcgtgcat tgttgacttg agtttgatac cagaaatgct  18480
tcgaaagtag tcagtcagca tccatgcgag tgttacaaag gacatgtccg tgcgccgacg  18540
cgcttccatg caactttcac tgattggggc ttaaaaggag acaccccgcg gtacgcgata  18600
ccttgagacg gacgccggga gacggtctaa agcgggttcc caggggccag caagggggga  18660
ggtcgcttcc tgcgggggcg acggaggtga gcgctctctc cgtccatgtc cagccccgcc  18720
```

```
ccgccaggca ggtgtgatgc gggcgttgca tgcgtggtca ggcagcgaag agagcctgag  18780
acacctgcgc caaccactgc tgcctcaccc gtgcgcggtg gtggccgggc aagtgcgtgt  18840
aaggagggag ccggacatgg aggcgaggag gatgagagtg cacctcaagg ctctcctctt  18900
ctgctgtcca catcgcccaa ataaaaacca ccatccttta tatcattgga gcacatatcc  18960
tgttgaatca cagatcaacg ttttaaagag tcgtcaatcc gcgacgacag gagagggggc  19020
cgaagacagc gacgccacca tgtctatcag agggaagata tacctcattt ctggctccgc  19080
tgaaatcact gacctccccc gtggcgtctt cggtgttcga ggcggatgcg aagcagcagc  19140
aactcttgaa agattccctc accgcagacc ttaaactgct cttgcacgag tttgaacgct  19200
tccagcaagc gacagcatta gtgtcgagag agggctcgaa agaggtggag gcaatggagc  19260
gggcggcgaa agtggaattc ttcctaggct acatcggaaa ggtgcttcag gaacttgccg  19320
gcgccgacgc accgaagctc caggaattag aggttcggat caagaccagc ctccttccat  19380
tgaaggggca agtggtgaac aagcttgcat cttccctgct ctcgtcctcc gccctcggtg  19440
gtctgcagca tgagccttcc tcctccgcat ccatcccgtc gccttcctct tctccttcct  19500
cctcatgcag cacccacacc actcccccca tctcccccgt atcaggggag aagatgacag  19560
tccaggatga tggccggagg gagaggacgc atccgacggc cgccgcgctc atgccctccg  19620
tgcgagtcca acgcctcgac agctcctcca gtggcgccac cacctgctcg gagaactccg  19680
aggaggggcg cggacagctt gacgatatgg agtgcctgag cctgctcatg gaggaagacg  19740
gccagggact ggggaggcca cgatccggca ctgtctttgc ctttctctct gcgtcctctc  19800
cctccggcca tcatcctgga ctgtcatctt ctcccctgat acgggggaga tgggggagt  19860
ggtgtgggtg ctgcatgagg aggaaggaga agaggaaggc gacgggatgg atgcggagga  19920
ggaaggctca tgctgcagac caccgagggc ggaggacgag agcagggaag atgcaagctt  19980
gttcaccact tgccccttca atggaaggag gctggtcttg atccgaacct ctaattcctg  20040
gagcttcggt gcgtcggcgc cggcaagttc ctgaagcacc tttccgatgt agcctaggaa  20100
gaattccact ttcgccgccc gctccattgc ctccacctct ttcgagccct ctctcgacac  20160
taatgctgtc gcttgctgga agcgttcaaa ctcgtgcaag agcagtttaa ggtctgcggt  20220
gagggaatct ttcaagagtt gctgctgctt cgcgtccgcc tcgaacaccg aagacgccac  20280
gggggaggtc agtgatttca gcggagccac cggtgatccg gcactgtctt tgcctttctc  20340
tccacaggtg tccactccca ggttcaatac agctagagag aaaatgatgt gaagaggaag  20400
agataggttt ggaaaaagca tgtacaaagt aattacgatg gagattttgg tgctcttgcc  20460
aggaagaata tatgcttttt gtacactgct gcctctcagg actattttct cgggccttaa  20520
taacacacag tctacttaat taaaaacatc tatcctccag atcaccaggg ccagtgaggc  20580
cggcataaag gacggcaagg aaagaaaaga aagaaagaaa aggacactta tagcatagtt  20640
tgaagttata agtagtcgca atctgtgtgc agccgacaga tgcttttttt ttccgtttgg  20700
caggaggtgt agggatgtcg aagaccagtc cagctagtat ctatcctaca agtcaatcat  20760
gctgcgacaa aaatttctcg cacgaggcct ctcgataaac aaaactttaa aagcacactt  20820
cattgtcatg cagagtaata actcttccgc gtcgatcaat ttatcaatct ctatcatttc  20880
cgcccctttc cttgcataga gcaagaaaag cgacccggat gaggataaca tgtcctgcgc  20940
cagtagtgtg gcattgcctg tctctcattt acacgtactg aaagcataat gcacgcgcat  21000
accaatattt ttcgtgtacg gagatgaaga gacgcgacac gtaagatcac gagaaggcga  21060
```

-continued gcacggttgc caatggcaga cgcgctagtc tccattatcg cgttgttcgg tagcttgctg 21120
catgtcttca gtggcactat atccactctg cctcgtcttc tacacgaggg ccacatcggt 21180
gcaagttcga aaaatcatat ctcaatcttc agatcctttc cagaaacggt gctcaggcgg 21240
gaaagtgaag gttttctact ctagtggcta ccccaattct ctccgactgt cgcagacggt 21300
ccttcgttgc gcacgcaccg cgcactacct ctgaaattcg acaaccgaag ttcaatttta 21360
catctaactt ctttcccatt ctctcaccaa aagcctagct tacatgttgg agagcgacga 21420
gagcggcctg cccgccatgg agatcgagtg ccgcatcacc ggcaccctga acggcgtgga 21480
gttcgagctg gtgggcggcg gagagggcac ccccgagcag ggccgcatga ccaacaagat 21540
gaagagcacc aaaggcgccc tgaccttcag cccctacctg ctgagccacg tgatgggcta 21600
cggcttctac cacttcggca cctaccccag cggctacgag aaccccttcc tgcacgccat 21660
caacaacggc ggctacacca acacccgcat cgagaagtac gaggacggcg gcgtgctgca 21720
cgtgagcttc agctaccgct acgaggccgg ccgcgtgatc ggcgacttca aggtgatggg 21780
caccggcttc cccgaggaca gcgtgatctt caccgacaag atcatccgca gcaacgccac 21840
cgtggagcac ctgcacccca tgggcgataa cgatctggat ggcagcttca cccgcacctt 21900
cagcctgcgc gacggcggct actacagctc cgtggtggac agccacatgc acttcaagag 21960
cgccatccac cccagcatcc tgcagaacgg gggccccatg ttcgccttcc gccgcgtgga 22020
ggaggatcac agcaacaccg agctgggcat cgtggagtac cagcacgcct tcaagacccc 22080
ggatgcagat gccggtgaag aataagggtg ggaaggagtc ggggagggtc ctggcagagc 22140
ggcgtcctca tgatgtgttg gagacctgga gagtcgagag cttcctcgtc acctgattgt 22200
catgtgtgta taggttaagg gggcccactc aaagccataa agacgaacac aaacactaat 22260
ctcaacaaag tctactagca tgccgtctgt ccatctttat ttcctggcgc gcc 22313

<210> SEQ ID NO 105
<211> LENGTH: 20
<212> TYPE: DNA
<213> ORGANISM: Artificial Sequence
<220> FEATURE:
<223> OTHER INFORMATION: HygR-forward primer

<400> SEQUENCE: 105
atggggaaga aaccggaact 20

<210> SEQ ID NO 106
<211> LENGTH: 80
<212> TYPE: RNA
<213> ORGANISM: Artificial Sequence
<220> FEATURE:
<223> OTHER INFORMATION: Cas9 Tracr RNA

<400> SEQUENCE: 106
ggaaccauuc aaaacagcau agcaaguuaa aauaaggcua guccguuauc aacuugaaaa 60
aguggcaccg agucggugcu 80

<210> SEQ ID NO 107
<211> LENGTH: 42
<212> TYPE: RNA
<213> ORGANISM: Artificial Sequence
<220> FEATURE:
<223> OTHER INFORMATION: crRNA targeting Nannochloropsis acyl-CoA
      oxidase gene

<400> SEQUENCE: 107
gacgggggcu guggcgcgcg guuuuagagc uaugcuguuu ug 42

<210> SEQ ID NO 108
<211> LENGTH: 42
<212> TYPE: RNA
<213> ORGANISM: Artificial Sequence
<220> FEATURE:
<223> OTHER INFORMATION: crRNA targeting Parachlorella cpSRP54 gene

<400> SEQUENCE: 108
ggcgugggac auggugcgca guuuuagagc uaugcuguuu ug 42

<210> SEQ ID NO 109
<211> LENGTH: 103
<212> TYPE: RNA
<213> ORGANISM: Artificial Sequence
<220> FEATURE:
<223> OTHER INFORMATION: Entire chimeric guide RNA for targeting Nannochloropsis LAR1 gene

<400> SEQUENCE: 109
ggugugggug cugcaugagg guuuuagagc uagaaauagc aaguuaaaau aaggcuaguc 60
cguuaucaac uugaaaaagu ggcaccgagu cggugcuuuu uuu 103

<210> SEQ ID NO 110
<211> LENGTH: 342
<212> TYPE: PRT
<213> ORGANISM: P1 bacteriophage
<220> FEATURE:
<221> NAME/KEY: misc_feature
<223> OTHER INFORMATION: Cre recombinase

<400> SEQUENCE: 110

Ser Asn Leu Leu Thr Val His Gln Asn Leu Pro Ala Leu Pro Val Asp
1 5 10 15

Ala Thr Ser Asp Glu Val Arg Lys Asn Leu Met Asp Met Phe Arg Asp
20 25 30

Arg Gln Ala Phe Ser Glu His Thr Trp Lys Met Leu Leu Ser Val Cys
35 40 45

Arg Ser Trp Ala Ala Trp Cys Lys Leu Asn Asn Arg Lys Trp Phe Pro
50 55 60

Ala Glu Pro Glu Asp Val Arg Asp Tyr Leu Leu Tyr Leu Gln Ala Arg
65 70 75 80

Gly Leu Ala Val Lys Thr Ile Gln Gln His Leu Gly Gln Leu Asn Met
85 90 95

Leu His Arg Arg Ser Gly Leu Pro Arg Pro Ser Asp Ser Asn Ala Val
100 105 110

Ser Leu Val Met Arg Arg Ile Arg Lys Glu Asn Val Asp Ala Gly Glu
115 120 125

Arg Ala Lys Gln Ala Leu Ala Phe Glu Arg Thr Asp Phe Asp Gln Val
130 135 140

Arg Ser Leu Met Glu Asn Ser Asp Arg Cys Gln Asp Ile Arg Asn Leu
145 150 155 160

Ala Phe Leu Gly Ile Ala Tyr Asn Thr Leu Leu Arg Ile Ala Glu Ile
165 170 175

Ala Arg Ile Arg Val Lys Asp Ile Ser Arg Thr Asp Gly Gly Arg Met
180 185 190

Leu Ile His Ile Gly Arg Thr Lys Thr Leu Val Ser Thr Ala Gly Val
195 200 205

-continued

```
Glu Lys Ala Leu Ser Leu Gly Val Thr Lys Leu Val Glu Arg Trp Ile
    210                 215                 220

Ser Val Ser Gly Val Ala Asp Asp Pro Asn Asn Tyr Leu Phe Cys Arg
225                 230                 235                 240

Val Arg Lys Asn Gly Val Ala Ala Pro Ser Ala Thr Ser Gln Leu Ser
                245                 250                 255

Thr Arg Ala Leu Glu Gly Ile Phe Glu Ala Thr His Arg Leu Ile Tyr
            260                 265                 270

Gly Ala Lys Asp Asp Ser Gly Gln Arg Tyr Leu Ala Trp Ser Gly His
        275                 280                 285

Ser Ala Arg Val Gly Ala Ala Arg Asp Met Ala Arg Ala Gly Val Ser
    290                 295                 300

Ile Pro Glu Ile Met Gln Ala Gly Gly Trp Thr Asn Val Asn Ile Val
305                 310                 315                 320

Met Asn Tyr Ile Arg Asn Leu Asp Ser Glu Thr Gly Ala Met Val Arg
                325                 330                 335

Leu Leu Glu Asp Gly Asp
            340


<210> SEQ ID NO 111
<211> LENGTH: 1511
<212> TYPE: DNA
<213> ORGANISM: Artificial Sequence
<220> FEATURE:
<223> OTHER INFORMATION: Synthetic cre gene codon optimized for
      Nannochloropsis with nuclear localization sequence and intron

<400> SEQUENCE: 111

atgccgaaaa agaaacgcaa ggtggggtcc aacctgttga cggtgcatca gaacttgcct     60

gccttgcctg tggatgccac atccgatgaa gtgcggaaga acctgatgga catgttccga    120

gacagacaag ccttcagcga gcacacctgg aagatgctgc tgtccgtgtg tagatcttgg    180

gcagcatggt gcaagctcaa taaccggaag tggttcccag ccgaacctga ggacgtgaga    240

gactacctgc tgtacctgca agccagagga ttggcagtga aaaccatcca gcagcacttg    300

ggccagctga acatgttgca tcgacgatcc gggttgccta gacctagcga ctctaatgcc    360

gtgtctctgg tgatgcgccg aatcagaaag gagaacgtgg atgccggaga acgggccaaa    420

caagcattgg cctttgagcg aaccgacttc gaccaagtga gatccttgat ggagaactcc    480

gaccggtgcc aagacatccg gaatctggcg ttcttgggaa tcgcctacaa cacgttgttg    540

agaatagccg agatcgcccg gatccgcgtg aaagacatct ccagaacaga cggaggacgg    600

atgttgatcc atatcggacg gacgaagacc ctggtgtcta cagctggagt ggaaaaggcc    660

ctgtccttgg gagtgacgaa attggtggag cgatggatct ccgtgtctgg agtggccgat    720

gatcccaaca actacctgtt ctgcagagtg cggaagaatg gagtggcagc ccctagtgcc    780

acgtcccaat tgtccacaag agccttagag ggaatcttcg aagccacaca tcgcctgatc    840

tacggcgcca aggacgattc cggacaacgg tatttggcct ggtctggaca ttctgcaaga    900

gtgggagcag cccgagatat ggtaagtgtt tgcaagaggt cgtgcggagg atgaagaggt    960

gcctgagaac gatagatgga aagggtcggg tggccttggt gatggcattc ttttcagagc   1020

tttccgaaca cagtcttgta tctgcagtat taattgatgt atgcagtgtg tatgatccca   1080

cccagtgcct ttatgcagca tgggattgtt aaatagatat gaaagcataa ccggtagaaa   1140

agaaagagag atgagacgct tggtagaacg ccataatcta tgcgttatat gaggagatac   1200

aagcataggc tgtcactcaa tatgtaaatg ggagaagaag cgtatgttac ttgtagatca   1260
```

gggagacgtg tggataaagc gcgcagcgat ttgtcttccc ctctccgtct cgataccttt 1320
ctgctcggta acaaactgac atggactcta tcttatataa atcacaacgt ttgtaggcgc 1380
gcgctggagt gtccattccc gagatcatgc aagctggagg atggaccaac gtgaacatcg 1440
tgatgaacta catccggaac ctggactccg agacgggagc aatggtgcgg ctgttggaag 1500
atggagatta a 1511

<210> SEQ ID NO 112
<211> LENGTH: 683
<212> TYPE: DNA
<213> ORGANISM: Nannochloropsis gaditana
<220> FEATURE:
<221> NAME/KEY: misc_feature
<223> OTHER INFORMATION: Nitrite/Sulfite Reductase Promoter

<400> SEQUENCE: 112
ctggtgtcgt caacagccag ctgccacaag aaagtgaaca tgcgtctatt tatgacgtca 60
ttcatcaacc accccgtttc caaacaccgt cccacgcgct gttgagagat gatttttga 120 atgccatatg gtgctcaaac atgtgcatcg acgctgtcgc acaagcagga gcgggcttgc 180
ccactcgttc ttgttaacgg cttgattcaa aatccccgcc cggaacaaaa tatgccggag 240
cgatccaacg aagcaaaagt caaccagagc ctctctttcc gtccaacacc cgtgttggtg 300
ccatgttaac aatagattca tgcatggata ggcgaagacg tgagaagtta cggagtttgg 360
gtcatgcttg cgtacatcac tcaacccttt tccccaaaaa aaaatcccgc catgcgattg 420
ccttcgttgc accgcaaaac ggaaattagt tatggcgtca ttgctcaaga ttactgtttt 480
tcgacaaggt gctgcacaac cttggaagaa aactctgcaa atccgtcaat cacatgagtt 540
gtagtttttt tcggcaaggc gggtgagcgt agtgaattat attccttgta aggcaaagcg 600
gatactaatt ttcacgtagt tgccctgacc tcctatgctc ggaaacgccg ccgtactgcc 660
ccacccgaac tcagatcacc agt 683

<210> SEQ ID NO 113
<211> LENGTH: 990
<212> TYPE: DNA
<213> ORGANISM: Nannochloropsis gaditana
<220> FEATURE:
<221> NAME/KEY: misc_feature
<223> OTHER INFORMATION: Nitrite/Sulfite Reductase Terminator

<400> SEQUENCE: 113
aggcagggtc cccgccaaaa agggtggcga ggacaagaag aagaaacagg aagggggggg 60
gcacgacgga ggacttgtcg agtccatcag ggaggtaggg gcgggaagcc tcgaatctgc 120
tagttggtag ggataaatag agttcaagga ccgaaggagg aggcgccagg atcagcgaaa 180
gcctggatta agagcgagac tccttgcgct gcagtcaagg cgattacagg acccccggtg 240
tctgggtttg gagatgacct cttggaggac ggcttgatgc gggtttttga ggaaggttgt 300
acatttttgt ttgaaatttg caaggaaagc gtcgcgctcc ggcatagagg gataggggga 360
ggaaagggca cttgtgcccg ctccgtctct gtacgggtct ttgaagaaaa gattcgagaa 420
accacccaaa gggcatcaaa tgcgaaacct ccctgaaaaa agtttcgatt ttctttattt 480
gttgaggagg agagggaaga gtggtatcca atgtggggtg tattcacgcc aacaaagcgg 540
ggggagctga cccagaggcc acctgccaca ggctccatcc aaacaagctt tcagggctga 600
ttccagaatt agggttagag taagaatgag ggctacgcca gcagtcatcc tttgcgggcg 660
tcttgagtcg caagaagctc tccaaggaaa gcgaaggcga attttcccca aaaacaaagg 720
cagtggcgag ctccttgtcc ctctttgagc acccctcctc gctaattttc ttactctgat 780
tttttgggga agtgtttctc cttctttcgg agacgtggcc ttatgctcca tcgccttcgc 840
gcaccgactc gaccatgccc acacactctc cgtgcccccc ttccctctgc acccttccc 900 tctcccccc tcccttcctc cctccctccc tccctccctc cctccctcct cccaggcaca 960
cccctattgt ccacttcgcg ccccaggctc 990

<210> SEQ ID NO 114
<211> LENGTH: 34
<212> TYPE: DNA
<213> ORGANISM: P1 bacteriophage
<220> FEATURE:
<221> NAME/KEY: misc_feature
<223> OTHER INFORMATION: loxP sequence

<400> SEQUENCE: 114
ataacttcgt ataatgtatg ctatacgaag ttat 34

<210> SEQ ID NO 115
<211> LENGTH: 4341
<212> TYPE: DNA
<213> ORGANISM: Artificial Sequence
<220> FEATURE:
<223> OTHER INFORMATION: Floxed HygR-GFP fragment

<400> SEQUENCE: 115
tccacagccc gaacccctta agctagacga acacagttag cgcggccgca taacttcgta 60
tagcatacat tatacgaagt tatgatgcta gcgtgtttaa gaagtcactt aattaacgta 120
tggtcgacgg ttgctcggat gggggggcg gggagcgatg gagggaggaa gatcaggtaa 180
ggtctcgaca gactagagaa gcacgagtgc aggtataaga aacagcaaaa aaaagtaatg 240
ggcccaggcc tggagagggt atttgtcttg tttttcttg gccaggaact tgttctcctt 300
tcttcgtttc taggaccccg atccccgctc gcatttctct cttcctcagc cgaagcgcag 360
cggtaaagca tccattttat cccaccgaaa gggcgctccc agccttcgtc gagcggaacc 420
ggggttacag tgcctcactc ctttgcacgc ggtcgggtgc tcggcctacg gttgcccgag 480
tccgcaagca cctcaacaca gccgtctgtc cacaccgcag ccgaccggcg tgcgatttgg 540
gtccgaccca ccgtcccagc cccgctgcgg actatcgcgt cgcagcggcc ctgcgcccac 600
gcggcgtcgt cgaagttgcc gtcgacgaga gactggtaaa gctgatcgag tccgatacgc 660
aacatatagg cgcggagtcg tggggagccg gccagctccg ggtgcctccg ttcaaagtag 720
cgtgtctgct gctccatgca cgccaaccag ggacgccaga agaatatgtt cgccacttcg 780
tattggctat caccaaacat cgcttcggac cagtcgatga cagcagtaat ccgaccattg 840
tctgtaagta cgttattgct gccgaaatcc gcgtgcacca ggtgcctgac ctcagggcaa 900
tcctcggccc acaacatgag ttcgtccagt gcttgggcca cggatgcaga cacggtgtca 960
tccatgactg tctgccaatg atagacgtga ggatcggcaa tggcgcagat gaagtctcgc 1020
caggtcgtgt actgcccgat gccctggggc ccaaaaggtc caaagccgga cgtctgagac 1080
agatctgcgg cagcgatcgc gtccatggcc tcggccacgg gttgcaaaac ggcaggcaat 1140
tcagtttcgg gcagatcttg caacgtcact ccctgggctc ggcgcgagat gcagtacgtg 1200
agagattcgc taaactcccc aatgtccagt acctctggta tggggagagc ggcggaggcg 1260
aaatgacggt agacataccg atccttgtag aacccgtccg cacaactatt aaccctcaac 1320

-continued

```
acgtatcccc gaccccctac gtcaaacgag aacgccctac tctcctctcc ctcgctcagt   1380
tgcatcaagt cggagacaga gtcgaacttc tcaataagga atttctccac ggacgtagcg   1440
gtcagttccg gtttcttccc catcgagctc ggtacccggg gatccatgat tgttgtatta   1500
tgtacctatg tttgtgatga gacaataaat atgagaagag aacgttgcgg ccactttttt   1560
ctccttcctt cgcgtgctca tgttggtggt ttgggaggca gaagatgcat ggagcgccac   1620
acattcggta ggacgaaaca gcctccccca caaagggacc atgggtagct aggatgacgc   1680
acaagcgagt tcccgctctc gaagggaaac ccaggcattt ccttcctctt ttcaagccac   1740
ttgttcacgt gtcaacacaa ttttggacta aaatgcccct cggaactcgg caggcctccc   1800
tctgctccgt tgtcctggtc gccgagaacg cgagaccgtg ccgcatgcca tcgatctgct   1860
cgtctgtact actaatcgtg tgcgtgttcg tgcttgtttc gcacgaaatt gtcctcgttc   1920
ggccctcaca acggtggaaa tcggtgctag aataaagtga ggtggcttat ttcaatggcg   1980
gccgtcatca tgcgggatca actgaagtac ggcgggttct cgagatttca tcgtgctcgt   2040
ccagagcagg tgttttgcct gcagctcttc atgtttaggg gtcatgattt catctgatat   2100
gccgtaagaa aaccaatatt cacttctcaa ttttccatgg aaaggtgaag gcctaggttg   2160
tgtgcgaggc aacgactggg gagggatcgc aacattcttg ctaacctccc ctctatcttg   2220
gccgctgtga atcggcatat ttaccgggct gaattgagaa agtgttttga gggaattaaa   2280
aggtggctgt cttgcaagct tggcttcagt gcctgcttaa ttcgaaccga tccagcttgt   2340
gatgaggcct tcctaagcct ggtagtcaga agcgacatgg cgctataaat ttcgtctcag   2400
ttggagagta gaaaagcatg attcgaacac ggttttcaac tgccaaagat atctccattg   2460
tttccttcaa tctgtacacc tgcacgggcc agtgaggcca ggaaataaag atggacagac   2520
ggcatgctag tagactttgt tgagattagt gtttgtgttc gtctttatgg ctttgagtgg   2580
gcccccttaa cctatacaca catgacaatc aggtgacgag gaagctctcg actctccagg   2640
tctccaacac atcatgagga cgccgctctg ccaggaccct ccccgactcc ttcccaccct   2700
tattcttcac cggcatctgc atccggggtc ttgaaggcgt gctggtactc cacgatgccc   2760
agctcggtgt tgctgtgatc ctcctccacg cggcggaagg cgaacatggg gcccccgttc   2820
tgcaggatgc tggggtggat ggcgctcttg aagtgcatgt ggctgtccac cacggagctg   2880
tagtagccgc cgtcgcgcag gctgaaggtg cgggtgaagc tgccatccag atcgttatcg   2940
cccatggggt gcaggtgctc cacggtggcg ttgctgcgga tgatcttgtc ggtgaagatc   3000
acgctgtcct cggggaagcc ggtgcccatc accttgaagt cgccgatcac gcggccggcc   3060
tcgtagcggt agctgaagct cacgtgcagc acgccgccgt cctcgtactt ctcgatgcgg   3120
gtgttggtgt agccgccgtt gttgatggcg tgcaggaagg ggttctcgta gccgctgggg   3180
taggtgccga agtggtagaa gccgtagccc atcacgtggc tcagcaggta ggggctgaag   3240
gtcagggcgc ctttggtgct cttcatcttg ttggtcatgc ggccctgctc gggggtgccc   3300
tctccgccgc ccaccagctc gaactccacg ccgttcaggg tgccggtgat gcggcactcg   3360
atctccatgg cgggcaggcc gctctcgtcg ctctccaaca tgtaagctag gcttttggtg   3420
agagaatggg aaagaagtta gatgtaaaat tgaacttcgg ttgtcgaatt tcagaggtag   3480
tgcgcggtgc gtgcgcaacg aaggaccgtc tgcgacagtc ggagagaatt ggggtagcca   3540
ctagagtaga aaccttcac tttcccgcct gagcaccgtt tctggaaagg atctgaagat   3600
tgagatatga tttttcgaac ttgcaccgat gtggccctcg tgtagaagac gaggcagagt   3660
ggatatagtg ccactgaaga catgcagcaa gctaccgaac aacgcgataa tggagactag   3720
```

```
cgcgtctgcc attggcaacc gtgctcgcct tctcgtgatc ttacgtgtcg cgtctcttca   3780

tctccgtaca cgaaaaatat tggtatgcgc gtgcattatg ctttcagtac gtgtaaatga   3840

gagacaggca atgccacact actggcgcag gacatgttat cctcatccgg gtcgcttttc   3900

ttgctctatg caaggaaagg ggcggaaatg atagagattg ataaattgat cgacgcggaa   3960

gagttattac tctgcatgac aatgaagtgt gcttttaaag ttttgtttat cgagaggcct   4020

cgtgcgagaa atttttgtcg cagcatgatt gacttgtagg atagatacta gctggactgg   4080

tcttcgacat ccctacacct cctgccaaac ggaaaaaaaa agcatctgtc ggctgcacac   4140

agattgcgac tacttataac ttcaaactat gctataagtg tccttttctt tctttctttt   4200

ctttccttgc cgtcctttat gcccctgcag ggtacgtttt agacggacta ggcagtataa   4260

cttcgtatag catacattat acgaagttat ggcgcgccag gctacgttag ttcagcagct   4320

gagaacgacc acgaacggga a                                               4341
```

<210> SEQ ID NO 116
<211> LENGTH: 7536
<212> TYPE: DNA
<213> ORGANISM: Artificial Sequence
<220> FEATURE:
<223> OTHER INFORMATION: Encodes fatty acid synthase of Danio rerio, codon optimized for Nannochloropsis

<400> SEQUENCE: 116

```
atggaggaca tcgtgattgc cggaatttcc ggaagattgc ctgagagcaa caacttggag     60

gagttttggc agaacctctt caatggcgtg gacatggtga cagaggatga ccgaaggtgg    120

aaacctggat tgtacggatt gcctagacgg aatgggaagt tgaaggagat tgaccggttt    180

gacgccgcat tttttggcgt gcatcctaaa caagcccata cgatggaccc tcaattgcgg    240

ttgatgttgg agatcagtta cgaggcgatt gtggatggag gaattaatcc cgtgagcatg    300

agagggagca aaactggcgt gtacatcgga gtgagcggat ctgaagcagg agaggccttt    360

tctaaagacc ctgaagagtt gttgggatac tccatgacag gatgtcaacg agccatgttc    420

gccaataggc tcagctactt cttcgacttt aacggaccta gcacggcaat cgacacagct    480

tgttcttcta gcttgttggc cttggaaaac gccttcaatg ccatccggca cggacaatgt    540

gatgccgcct tgattggagg agtgaatttg ttgttgaagc ccaatacctc cgtgcaattc    600

atgaagctcg ggatgttgtc ccctgaggga acctgtaagt cctttgatgc ctccggaaat    660

ggatactgtc ggtctgaagc agctgtggct gtgttgttga cgaaaaagtc tatggcaaag    720

cggatctacg ccaccgtgtt gaatgcgggg aacaatacag atggatacaa agagcaagga    780

gtgacctttc ctagcggaga gatgcaacaa cgattggtgc ggtcccttta ccaagaagcc    840

aacatctccc ctgagcaagt ggagtacatt gaggcccatg gaaccggaac caaagtcgga    900

gatcctcaag aagtgaatgg aatcgtgagc gtgttttgcc aatcccctag agatcctttg    960

ttgattggat ccaccaagtc caatatgggg caccctgaac ctgcatctgg attagccgca   1020

ttggccaaag tcgtgttgtc attggagcat ggagtgtggg cacctaacgt gcactttaac   1080

gagcctaacc ctgacatccc tgccttgaca gatggaagat tgtgtgtggt ctccaaacct   1140

acacctgtga gaggaggaat tgtcggaatt aattcctttg gatttggggg atcgaacgtc   1200

cacgtcatct tgtctcccca tgtgagcgac tcttctgaca aaacacctgc cccttctgtg   1260

ccccgattgt tgcaagcttc tggacgaact gaagaggccg ttacagcctt gttttctaat   1320

gcccaacaac accaagagaa ctcctcctac ttgtccctgt tgaatgatgt gtctggtgtg   1380
```

```
cctactgctg gaatgcctta ccgaggatac actttgattg gcgcccaagg agaattgacc   1440
gaagtccaac agacccaacc tacgcctcga cctttgtggt acatctgctc cggaatggga   1500
acgcaatggg ctggaatggg acaatctttg atgcaattgt ctgagtttcg agagtccatt   1560
aaaagatccg atatcgccct gaaggacacc ggattgtgcg tgtctcgatt gttgatggag   1620
gccgatgaga gcacctttga agacaccgtc catgcatttg tgggattggc cgccattcaa   1680
gtggcccaaa tcgacatgtt gcggaagatg gggttggagc ctaatggaat tgtgggacat   1740
tctgtgggag aattggcatg tggatatgct gatggatctt tgagccattc cgaagccatt   1800
ttggcagcat actggcgagg aagatgcatt aaagaggcga acttgccccc tggaggtatg   1860
gcagcagtgg gattgacatg ggaagagtgt aaagcgcaat gccctcaagg agtggtgcca   1920
gcttgccata atgcagaaga tacagtgaca atttctggac cccaagactc cgtgtccaaa   1980
tttgtggccc aattgaaaga atctggcgtg tttgcgaaag aggtgcgatc tgctggagtg   2040
gcctttcatt cgtactacat ggcctccatt gcccctgcct tgttgtctgc cttgcaaaaa   2100
gtgatcaagt ccccccgccc tagaacagca cgatggattt ctacatctat tccccaatcc   2160
gactgggaat ctcctcttgc cttgtactct tctgctgagt atcatgtgaa caatcttgtg   2220
tcccctgtcc tcttccaaga ggggttgaat catgtccccg ataatgccgt ggtcgtcgaa   2280
atcgcccctc atgctttgtt gcaagccatc ctcaaacggt ccttgaagcc tacctgttcc   2340
attttgccct tgatgaaacg tggccatgcc aacaacctcg agttcttttt gtcccatgtc   2400
ggaaaagtgt acatgaacgg gatcaacgtg gattccaaca agctttaccc tgccgtgaaa   2460
taccctgtgc ctcgtggaac ccctctgatt tccccttaca tccagtggga tcactcccaa   2520
tcctgggatg tgcctaaagt ggaagacttt cctgccggat ctggcggatc tacatctgca   2580
actgtgtaca atatcgacat gaatcctgaa tcccctgact actacatgat tggacattgt   2640
atcgacggcc gagtgttgta tcctgcaacg ggctacctgg tgttggcttg gagaaccttg   2700
atgcgctctt tgggaacggt gatggaccat acccctgtga cgtttgaaga tgtgaccatc   2760
catcgagcca cgatcttgcc taaaactgga tctgtgcaat tggaagtgcg gttgatgcct   2820
gcaacaaata gatttgaagt gtccgagaat ggcaatttgg ctgtgtccgg gaaggtgtcc   2880
gtgttggaag actctgggtt ggatgcgttt catgccgagc tgaacaagcc cattaccgct   2940
gacaatgaag accctaagct ccgcctgaaa tctggagata tctacaagga gttgcgattg   3000
aggggatacg actacggaaa gacctttcaa ggaattttgg agagcaataa tgccggagac   3060
tccgggaaac tccactggac gggaaattgg gtgacgttct tggacacgat gctgcagatg   3120
atcgtcgtgg gattgcctgg aagaagcttg agactcccta cccgaattcg atctgtgtgt   3180
gtggatccta aattgcatga ggaacgcgtg aatgactacg aaggagacca aaaagccgtg   3240
aatgtttttg tgaatcggtg cctcgacaac atcacagccg gaggagtgca aatctgtggg   3300
ttgcatgcta cagccgcccc tcgaagacaa caacaacaaa cacccccctac cttggaggaa   3360
ttcgtctttg tcccctacga agatgccgat tgcttgagaa ccaatgagaa attggccgac   3420
caattgcgac actgtaaagg attggtgcaa cgattgcaac gcaaattggc caaacaaggc   3480
gtgaagatct ccatccctgg cttggaagga gcgtccgaag ggcaattgat tgaagcagag   3540
gccgagaaag ggttgttgag gttgttgtcc gtgttgtgcg gcttggagtt gaatgggaat   3600
ttgagatccg aattggaaca aacggtgcaa aaagagagag actgcttgct gcaagatccc   3660
ctgttgaatg gcttgttgga ttctcaagcg ttgcggcatt gcctggatac cgcgctggaa   3720
```

-continued

```
aattccacac ctggcaagtt caaggtcttg gaggcccttg ctgctgatgg acgcgtgttt   3780
tctcaagctg tgtctttgct gaatattcaa cctatgttgc gtttggacta cactgcctct   3840
gatatttccg ccgaccaatt gtccgcccaa caatcttctt tggaagagca gggaatctct   3900
accgcccagt gggatcctct tcaaggaccc gtgacaggag gattggatgg agccgatctt   3960
gtggtgtgca attgtgctgt tggatctgcc acgaatcctg cattgttgat tgagaatttg   4020
acatctgccg ctagagaagg aggattcatc ttgttgcaca cgttgttgag aggagatacg   4080
ttgggagaaa cagtggcgtt cctcacgagc cagaataacc ggaagggcct gttgacgcaa   4140
accgagtggg aagagctgtt ccaaaaagcc tccctgaatg tggtgatgtt gcggaagtcc   4200
tattacggaa gtgccttgtt tttgtgtcga agaagccaac aatccagcca aaagcaacct   4260
attcacatct tcgtggaccc taccgactac aaatgggtgg agaccttgaa atccacactc   4320
gccgagtcct ccgatatccc cgtctggttg attgccacca aaggccataa tggagtcgtg   4380
ggaatggtga actgcttgcg tcaagagcct ggaggaaata gaattcgatg cacatttgtc   4440
tccaatttgt ccaaaggagc tgcagtgcct tccttgttgc ctaatgagaa ggtgatgaaa   4500
gccctgttga agaaggacct ggtgatgaac gtccaccgcg acggactgtg gggagtgttt   4560
cgacatcaat tgctgaccca agacctgtcc gaagaattga ccgagcaggc ctacgtgaat   4620
gtgttgacaa gaggagattt gtctagtttg agatggattg cgtccccctt gaggcatttt   4680
gtggcatctt ctcctaatgt gcaattgtgc agagtgtact actcctccct gaacttccgc   4740
gacatcatgc tcgccaccgg aaaattgccc cctgacgcca tccctggaga tgtggcattg   4800
cagcaatgta tgttgggaat ggagttctcc ggaagagatc cttctggaag aagagtgatg   4860
ggattgttgc ctgctaaagg attggccaca tgtgtggatg ccgataaaag atttttgtgg   4920
gatgtgcctt cttcttggac gttggagcaa gccgcctctg tgcctgtcgt ctacgctacc   4980
gcctactact ccttggtggt cagaggaaga ttgagacctg gagaaagtgt gttgattcat   5040
tccggatctg gtggagttgg acaagccgct attgcaattg ccttgagcat gcgctgtaga   5100
gtgtttacaa cagtgggatc taaagagaag aagcaatact tgcaagagcg cttcccccag   5160
ttgacagccg agtccttcgc caattcccgc gattcctcct tcgagcaaca tgtgatgctg   5220
aacacacaag gaaaaggagt ggacctcgtc ttgaattccc tcgccgaaga gaaattgcaa   5280
gcctccttga gatgtcttgc cagacatgga cgatttttgg aaatcggaaa atacgatttg   5340
tccaacaaca ccccccctggg catggccctg ttcctgaaga acgtcgcctt tcacgggatc   5400
ttgctcgatg cactgtttga agagggcaat cgtgaatggg aagaggtgtc cgacctgttg   5460
aagaaaggaa tttcctccgg agtggtgcaa cctttgagaa cgaccgtgtt tgagagaaac   5520
caagtggaag aagcatttag atatatggcg cagggaaagc acatcggcaa ggtgttgctg   5580
caagtgcgct ccgaagaatc ctcctcctct ggacctgcag tgtctgcttt gagtattcct   5640
gccatttgcc gaacgttttg tcctgcaagt ttgtcctaca tcatcaccgg aggcttgggc   5700
ggatttggat tggaattggc ccaatggttg acagaaagag gagcaagaaa attggtgttg   5760
acgtctagat ccggaatccg caacggctac caagctaaga gagtccgaga gtggcaagcc   5820
atgggaattc aagtgttggt ctccacatcc gacgtgtcta ccttggatgg aacagaacga   5880
ttgatcacag aggcctgtag gttgggacct gtgggaggaa ttttccattt ggcaatggtg   5940
ttgaaagatg gaatgctcga gaatttgacc cctcaggagt tcatcgaggt gaatcggccc   6000
aagtacgacg ggacgatcaa tttggacagc gtgacccgac aaaaatgccc ccaattgcag   6060
caattcgtcg tgttttcttc cgtgtcttgt ggacgaggga atgccggaca gtccaattac   6120
```

-continued ggatttgcaa actccacaat ggaaagaatc tgcgaacaaa gacgacagga gaatttgcct 6180
ggattggccg tgcaatgggg agccatcgga gatgtgggag tggtcttgga gacaatggga 6240
ggcaatgatg ccgtgatcgg aggaacatta cctcaaagaa tgtcttcctg cttggaggtg 6300
ttggaccgct ttttgtgtca acaacgacct gtgatgtcct cttttgtgtt ggcagaaaaa 6360
gtggtggtga caaaaggaga gggatccgga caaaaggacc tggtggaagc tgtggcgcac 6420
atcttgggag tgagggacgt gaatagcttg aatgccgacg catcattggc cgatttggga 6480
ttggatagct tgatgggagt ggaagtgaga caaaccttgg agagagacta cgacattgtg 6540
atggctatga gagagatcag acaattgacg atcaacaagt tgcgggagtt gagcaagcaa 6600
tccggcggga aggaggaatc ccctgtgaag aggtctggag cccaagcatt gttggaaagc 6660
gacttgtccc gaatgttggt gaatcctgac ggacctacaa tggcaccctt gaatgaagtc 6720
caatccgcag aaagaccctt gtttttggta catcctatcg aaggatctat tgccgcattt 6780
cgaaccttga cagcgaagct cagcgtgccc tgctacggat tgcaatgtac caaagccgcc 6840
cctttggact ctatccaatc tttggccgcc tactatgtcg aatgtgtgag gcaagtgcag 6900
ttggaaggac cctacagaat tgccggatac tcctttggag cttgtgtcgc ttttgaaatg 6960
tgttcccaat tgcaattggc gaaatgccct gtggagtacc tgttcctgtt cgacggatcc 7020
cactcttacg tcgccgcgta cactcaatct tatcgagcca agttgacccc cggaaaagaa 7080
gctgaagcag aaacagaagc cttgtgtgcc tttatccagc agttcaccgg aatcgagtac 7140
aacaaactct tggagacctt gttgcctttg tctgatttgg aagccagagt ggacaaagca 7200
gtggacctga tcacctcctc ccacaagaac gtgtcccgcg atatgttgca ttttgccgcc 7260
tccacgtttt accacaagtt gaaagccgcc gacagatacg tgcctacatc caaataccac 7320
gggaatgtga ccttgttgag agccaaagca tcttctgagt atggagacgg attgggatct 7380
gactacaaat tgcacgaagt ctgtgacggg aaggtgtccg tgcatgtgat cgagggcgac 7440
catagaacct tttggagggg agaaggagtg gagtctattt ccagcatcat ccacagcagc 7500
ttgtctgagc ctagagtgtc cacgagagaa ggataa 7536

<210> SEQ ID NO 117
<211> LENGTH: 882
<212> TYPE: DNA
<213> ORGANISM: Artificial Sequence
<220> FEATURE:
<223> OTHER INFORMATION: Encodes pantetheine phosphotransferase of Danio rerio, codon optimized for Nannochloropsis

<400> SEQUENCE: 117
atggatggag tgagatgggc ctttagatgt ggatcttggg tgccttccag atctgagtgg 60
acattggcag caagatgtgt gcaacaagag gagaagttga ggatcggaca gttcgtgttt 120
gccaaagacg ccaaatctgc aatggccgga cgattgttga tcaggaagtt ggtgtgcgag 180
aaaatggggt ttgcctggga cggatttagg ttgcaaagaa cagagcgggg aaaaccttac 240
ttgccccaaa caagttccgc cccttcttgg agctttaatg tgagccatca aggcgattac 300
gcagtgttag cagccgaagc tggaagacaa gtgggaattg acgtcatgaa aacgtccaga 360
cctggaagct cttctgtgca agagttcttc cgcatcatga atcgccaatt taccgacctc 420
gagtggacca atatccgaac cgcaggatct gactgggacc aactgcatat gttttaccgc 480
cattgggcct tgaaagagtc cttcaacaag gcaatcggaa ccggattggg cttcgacttg 540
caacgtgccg aatttcatat ctcccccaac caaatgcgag aaggccaagt gtaccgacaa 600

-continued

```
acaagaatgt acctcgactc cgaagaagaa gaagactgga ccttcgagga gtccttgctc    660

gacaaagatc accatgtggc tgtggccttg ggaaaacctg acatctctat gtccaagaaa    720

gacggaggat cctcctgtga ggcaccacct gcagctttta cagtgttgtc cttttccgac    780

ttggtgtccc aagcaacacc tcttttggac gaagacccta catattggga ggagtttcag    840

aagaagaagg aggccccttc ccgacaatcc gatcaagagt aa                       882
```

```
<210> SEQ ID NO 118
<211> LENGTH: 12447
<212> TYPE: DNA
<213> ORGANISM: Artificial Sequence
<220> FEATURE:
<223> OTHER INFORMATION: Encodes Type I fatty acid synthase of
      Thraustochytrid sp., codon optimized for Nannochloropsis

<400> SEQUENCE: 118
```

```
atgtccgacc agcagcaaca acagcagatc aaggtggagg agacagcccc tgtggcccaa     60

gagcctaaaa cccacttgtt tgtggaccct gaagtgtcct cctgtattgc cgcctttgga    120

ggccaaggat ccgattggtt gggagagttg cgatccttgc acaagaacgg gaaatcctcc    180

gtgcgggagt tttggaact gggcctgtcc aaattggagg atattgccgc gtccgatgag    240

tggtacgcca accacggggg cttgaatgtg agagcctgga ttgcctccga caaatctgtg    300

ccgagcttcg acctgttgcg ctacgcccct gtgagctttc cgctgatctt catgacgcaa    360

atggccaact acatgcgggt gctggagttg ttgggaacga gccacgagaa agtcgcacaa    420

caaggctggt ttaagggagc cttgggacac agccagggag tcgtcgccgc cgctgtgact    480

gctgctgcat ctactgatcg agaattgaga aacttgtccg tcgccggttt ggagttcatg    540

tcccaaattg gattgggagc ccaaaagagc atgaacttcg agttgtcccg cagatccgcc    600

ggacctgaat cccctatgtt gtctgtgcaa ggcatgtccg aagccacgct cctgaaggcc    660

ttcaaggagg ccacgaagct cgccgtgcag aaagagacca tgatggccaa attttccacg    720

tcctccaagg acgacaaagc cgcccctaat gcctcccaaa gattgggaat tgccttgtgt    780

aatggaaccg acgactacgt ggtgtgtgga gaacctaagg acctgcgcat gttgcggaag    840

gtgatcgtgt ccatgtccgc cgaagtcggg aaagaggccc aagcccgagt gccattcagc    900

aaaagaaaac ctgtgaccca aacgacgttt ctgcgcatga cagcgccatt ccattctgcc    960

ttgaatgccg aagcctttga acaagtggcc gcttgggcag catcttctgc ttttggacag   1020

gaattggccc aacgcacctt gagaatccct gtgtgggaca ccgagaaagg agccgacctc   1080

cgcaagatgg agccttccca agtggtgaac atgttggccc gaaatacctt ggtctcctcc   1140

gccaatttgc tcagcacatt gagagccgcc gaagctgact gtaaagcctc ccacttgatc   1200

tcctttggac ctggatctgt ggccggacac cttatggcca atgcccttgt gggaactgga   1260

atccaggtga tccaggcgaa tgaccctgac tccaagagca aggaaaatgc cgccaccgcg   1320

agcagctcgt cgagccggag cagcgccaaa tctcttgccg ccatcttgac agccgaaaaa   1380

cctgagcgaa tccctgttgc aacaccttgg ggagagaaat tcgcccctaa gattgccgtg   1440

cgtgcgtgtg atggagaacg agtgttgatg accaagtaca cctccaccat cggacgagcc   1500

cctgtgatga tgtccgggat gacgcctacg acgtcgttcc acggaattga cttggtggcc   1560

gcctgtgcaa atgccggata caatgccgaa ttggctgctg gaggattgcc tacacctgac   1620

ctgtttaaga tgaaggtgca ggaactggcc tccaagttga accctggagt gggaatggcc   1680

attaacatgc tgtacctgaa cgcctaccag tggggcttcc agttcccact ggtgtgcgaa   1740
```

-continued

```
ttggcaaaag ccgggctccc catcgagagc atcacaatcg gagccggagt gcctaccgaa   1800
gaaaaagcca aggacatctt tgacggattg caaggagccg gcatcaactt gatcgggttc   1860
aaacctgggt ccaaacaagc cattagagac gtgctccaac ttgcctcctt gagaccctcc   1920
atgaacatca tgctccagtg gacctccgga cgcggcggcg gacatcacag ctttgaggac   1980
ttccacgagc ccttgttggc cacatacgaa gagatcagac aacacgacaa catcatcctg   2040
gtgatcggaa gcggctttgg agacgcccaa ggagtgatga cataccttga tggatcctgg   2100
tcccaatccc ccaaatttgg acgcttggcc aaaatgcctg tggacggcgt gctcttcggg   2160
tcccggtgta tggtggcgaa agaggcagcc acagcccctg aagtgaaaca attgatcgtc   2220
gatgctgctg gattggaaga cgagttgagc tgggagaagt cctacgacga agtggcagga   2280
ggagtcgtta ctgtgcaatc tgagttggga gaacccattc acaaattggc cacacggggc   2340
atactgttgt ggcgggagtt cgacaagcgg ttcttcagct tgcctcgggg ggagaaacgg   2400
agagatgcca tcttggcagc aaaagacgag attatcgcga agctcaatgc ggacttccag   2460
aaaccctact tcggccgcaa acgagacgga tctgtgtgtg aagtggagga catgacatat   2520
gctgaagtgc tggagcggat ggtgcagctg atgcacatca agaacggggg ggacaaggcc   2580
gggcggttgg cgcctacacg atggattgat cctacatatg cctctagagt gatgctgatg   2640
atgcaacgtt ccgccgcgag attggccaag gacaaaatgg acaaggtggt gccttccaac   2700
aagctgttga tggaagaccc tgacaaagcc atcgccgact tcttggcagc cattcctgcc   2760
ttggaggact ccctgatggc cgacgacgac gtgacctact tcctcgactt gtgcaaagtg   2820
cctacacgtg gaaaacctgt gaacttcgtg cccgtggtgg atgaggactt ggtgttttgg   2880
gtgaagaagg actccctgtg gttttccgag cagttggatg cagtgcctga cagagatcct   2940
ggacgagtgt gcgtgttgca tggacctgtg gctgcccgat actccaccat cgtggatgag   3000
cctattgccg acattatggg gaacatccac aaggacttgg tgcgggacct gaagtgtgac   3060
gaggtgaaag tgaacgtgtt ggcccctgtg gagttgcaac aagcaagcgt gctgaagatc   3120
atctccgaga caccccaatt ggtgagagga cgctcctttg tgcccaaccc catcgccaag   3180
gtgttgaaac gcgaggcctt cgagaaagtg aagtacacat ccgagggagg attggagtcc   3240
atcaacgtgc aagaccctga gcgaggattg accgtggcca ccttgtccca agtcggatcc   3300
gacaacaaat tggcagagtt gcaagtgttc gacaaagaag ccggagccgt gttgaagcag   3360
aagttcacca tcgacctgac cagcctccgc cccatctttc agacagagga ggacaacttg   3420
agcgcaacga agcagttgta cagaaccgcc tgggactgtc aaggcgagtt ccatgccgga   3480
gacacgttca ccgacgaagt ggtggtcaca tccgaaaaca ttgaggcctt taatcgaggg   3540
acgcataccg agtacaatgg atccgcagaa gcccctatcg acatcagcat catggccgga   3600
tggcggcctt tggcccgagc gttgttcgtg gaagaattgc aatccaacct cctgaagctc   3660
gtccatctga ccaacggcat ccggttgccc aaccccaaaa cccgaacacc tgtgaaagcc   3720
ggagaagtga ttagatctga ggtgcgcatt acaggaatca cgatccagcc caaagtgggc   3780
aagaaagtgg cggtgaaggg catcatcacc cgcgcctccg acaaaaatgc cacgcccgaa   3840
atgtgggtcg aaatgaattc cgccttcctc atccgcggag tcgccgagac acctgaagaa   3900
tacgccacga cgttcgaaga gtttcctgcc gaaacccatg tgattgatgt gaaagatgcc   3960
acggtggccg aattggtggc ctctagagcc tggatcaaac tggacaacgg ccgcaaggtg   4020
caagagggag accgagtgac gatttccttg tcccatgtgt ccaatcgctt tgccggaccc   4080
```

-continued

```
aaccgcttga aggacatcaa ggtgaccgga gacgtgttta tcgagtccac ctccgtgaaa   4140
tcctccaatt ccggatccac ccctttggga tcccctacga attcctccgt ctctggaaca   4200
caatccgacg acttcgtgga cgtggacacc tcctccaagg tgaaagcagg aacagtcgag   4260
tttgcctcct ccgagggcga agagttccag ttgaatcccg tgatgtcgtt cctggaaaag   4320
tactccgagc ctatgcacaa tggccatatc gccgagaatg gcgggtacga gttgatcgcc   4380
gagcctatgg tggtgcctgc acctgctgat tgtacgatgt acgcacgcgg atccagagat   4440
gccaatccta tccatcgcga atccgcattc gccgtgttgg ccgatttgcc tggaggagag   4500
cctatcgtcc atggaatgtg gacagcatgt atggctagag ctagattgga agaaggacct   4560
gccggaggaa atcctgcccg aatcgtctcc tacgaggcct cctttgtgga tatggtgcat   4620
tgcggcgacg aactggtggt gacggctaaa caaacagggg tgaaggacgg actgatgctg   4680
atcaacctga gcgtgaatcg ggcctccgac cgagcattgg tgatgactgc tagagctgaa   4740
ttggaacaac ctacaacggc ctacttgttc acggggcaag gatccgcctc tcccggaatg   4800
ggaatggaca gatatgcagc ttccgcaacg gtgcgcaaag tgtgggatgt ggcagatgag   4860
tacttgagaa accgatacgg gttcagcatc ctccagatcg tgcgggagaa ccccaagtcc   4920
ttgacggtcc actttggagg acctagagga aaggtgattc gcgaaaattt gcgctccctg   4980
cagaccgagg accctacaac cgggaaaaaa atgcccctga tccccgagat ctcctccacg   5040
accaagtcct tcaccttcaa ttcccctacc ggcttgttgt ttgccaccca attctcccaa   5100
cccgccctcg tcttggtgca gaaagccgcc tttgaagaat tgagagaagc cggccttgtc   5160
cctgaaaaag ccttctttgc cggccactct ttgggcgagt atgccgcatt ggccggattt   5220
gccgatgtcc tgtctgtgga ggaccttgtg gaaaccgtgt ttttgagggg aatggtgatg   5280
cagaatgccg tgcctaggga tgccgacgga accagcaatt acgccatggt ggcagcaaat   5340
cctttgagag tcggacgtgg atttacccct gagaccttgg gagaagtcgt ggacttgctg   5400
tgtgagcggg aggacttggg aaagcccttg ctgcagatcg tgaactacaa cgtgagatac   5460
acccagtacg tggtggcagg agagttgctc gcattggacg ccttgggaga agccctgaat   5520
ttggcctttg caaccggaaa taggaatgcc gcggaattgg ccgagaaagg agcacaagca   5580
gccttggcct ctttggcaaa gaggggagga cggaaagagc ccttgaaacg gggaaaagcc   5640
acaattcctt tgcctggaat cgatgtgccc ttccattccc ggaagttgtt gcccggagtg   5700
ggagcgttca gacaactgtt gagccctaga cttgccttga gtacgatgga gcggatctac   5760
caccggttgg tgggcaacta catccctaac gtgacagccg aggtcttgac gttggacaga   5820
tcctacgccg agaaagtgca gaaagtgacc ggaagtgccc ctatgttgga gttgttggcc   5880
gactacgatt ccgccacccc tgccgaaaaa tgccgaacgt tggtgatcga gttgttggca   5940
catcagttcg ccatgcctgt gcgctggatt gagacccaag atctgatgtt tggagcccga   6000
gtgcaacgcg tgatcgagat gggacctgca gccacattga caacaatggc caagcacacg   6060
ttgaaatccg gagcctttgg agacgccgac gagtacaacc ctgagatcat gtggtggaag   6120
aacgaccgag agcgagtgta ctacgagttg gacgacgagg gaccgagctt cgccgccttt   6180
gtggaacaat tgaaggccga gatggagtcc gaggccggag actctgagga gggagaagtg   6240
tccgaagcac ctgcagcacc tgcacctaca cctgctcctg cacctgcacc tgtggcacct   6300
aaacctgcac ctgcacctgt tgctgctcct gcacctgcac cttctggagg agcatctaca   6360
cctgatgcac ctgttgatac aaaacatgtt ttgagagtgt tgttagcctc caagctcaag   6420
aagcccattg gcgaagtccc tgcctctacg tccgtccaaa ccttgtccgc cggccgatct   6480
```

-continued

```
gctgtccaga acgagatcat gggcgagttg tccgccgagt tcaaaggcgg catccccgac   6540
aatgccggag aaatgccttt gtccgaattg gccggaaatt tgtcctccta caaagaacct   6600
ggagccgtgt ctacaaaact tgtcacccga acattgtctg cagccttgcc tggaggcttt   6660
ggagccaatg ccgccaagga ctacctcacg caacactggg ggttgggaac gggacggaac   6720
ttctccgtgc tgttgcactc ctgcacaatg gcccctgaga aacgcttgaa atctgaggag   6780
gaaggaaaac aatggctcga ctccgtctgc aaagcctacg gtgatgatgt tggagtgtct   6840
ttgtcccctg ccggagctgg aggagctgga ggagcacctt ctggaatgat gatgatgccc   6900
cagatgatgt ccatgggagg acctgccgcc gtgccgccac cggatgcacc tgtctctgca   6960
ttgcatgcta tgagagtgat gttggccaca aaattcgaga aagggttcaa cgagattagc   7020
gattctgcca cagtggcctc tctgtccaac gggaaatccg ccctccagaa cgaggtggcc   7080
ggagatttgg cagccgaatt tggagctgaa ggagacgatt ccgcccagaa gcccctcacc   7140
gaactcgccg ccgcttttca agccggatac tctggacctg gtaaagtttt gtcaagagac   7200
atcaataaag tgttgggaca atgtctcccc ggaggatttg gactgtccgc cgcacgagcc   7260
taccttgcat ctgaccgcct tttgcctgcc ggacgagttg aatccgtgat gatccactcc   7320
ctgaccatgg cccctaagga gcgcatcaag tccgccgaag acgcaaaggc ctggctggat   7380
acagtgtgtg gagcatatgg atcttttgca ggaattgata tccctagagc tggagcagga   7440
ggaggaggag gagccatgat gggatttgcg ggacctggag tgtcttctgc cgaagtgaat   7500
gggttgaaag cgaacctgca gtcgatggtg gagacccagt tggaggccct tcagcggttc   7560
atggagcagg accccttgca tgccgacaga ttgttggatg tggagagaaa attgagagga   7620
gaaacagagg ccaagttgga cgccatccac gccgagttga cagtggactt ctgcgagaga   7680
gtgcaacccc aattcgacga gaaacgtgtg cgagtgtacg actccttctg gaactgggtg   7740
gtgcaagacg cgatgcagat gcacctgcac gtgctgtccc ggttgaatga ggcccggaaa   7800
ggacaatcta caggattacc tgcaggagat gccaatcccc atttcgagga catgtccaag   7860
tggttgttgg gaacgtcgag cagcgaagtg cccccctacag cctggtttcg caatttcttg   7920
tgcaatagag ccacgcccca gttgttgcaa gccgtcaagt tcttcgccaa ctccatgcac   7980
gaggccggac acgtggacta cgcccaagcc attgctttgc ttgccgaaca ggtgcaatgc   8040
tggttgaata atgtgcctgt acatgtcgcc acctttgacc ccgtctcccc caatgtgcga   8100
gtgttggaca atggaacagt cgactacttc gagaccccta gagaaggcgt gcctgacgcc   8160
gtgagatacg tggcagaaat gagccgcggc ctgttctacg tgagaagatc tcctgccaga   8220
gtggccaatc cttcccaagc agtgaatgtg gctggagatg gacaattggc attgcctcct   8280
gctgctgatt ctaccggatt gcaacctgcc gatggagaac ttgcttctgg atggagacga   8340
cctagatccg aggccgaatt ggcccgagag ttgaacaacc ggtccggatc cggccttgaa   8400
gcattggact tggaagccga tgaagcctct gaggagtcta aagaagcctt gcccgaagga   8460
cctaccttgg accgattgag attgacggtg tctagagatg cagcctcttc tggagaagat   8520
gccggaagcc ctgggaaaat ttccacgagc tcgctgaaga acggctacga gtccatccac   8580
gtgtccaagc aggtgccctt cgtccacctc aagtccttgt ccggagtcga caaatctgtg   8640
cgcatcctca atgagcagct tacctccgag tacttttcgt gccttgacga aatcgccaca   8700
tccggagtgt cctttgccgg ccaagtcgcc ttggttacag gagcaggagc aggatccatt   8760
ggaacagagt tggtgaagtc cctgttggag ggaggagcaa ccgtgttgtg tgccatgcga   8820
```

```
accgccagat ccgagaatgc attgaccaag gaatacgccc gctttcagaa catctacaag   8880
gagtttgggg ccaaagacag caagctctac ctcgtgccgt gcaactgtgc gtccagccag   8940
gacatgaaga gcatcgtggc ctacacgtac gagcaattgg gattggacgt ggacttcgtc   9000
gtgccctttg ccgcagccgc ccaacaagga aaagatatct cctctattga cgccgcctct   9060
gaagcctctc ataggatgat gatgaccaat gtggtgcgcc tcttgggagc cttgcgtgat   9120
gccaaagcca gccggggaat tgtgacaaga cctgccatgg tgttgatccc ttgctctcct   9180
aatcatggcg agttcgggaa tgacggcctg tacgccgagt ccaaattggg atgtgaagcc   9240
ttgctcaaca agtggtcctc cgagggatgg ggagattatt tgtccttggc cgcctgcgtg   9300
atcggatgga caagaagtgc cctcatggag cacaacaaca ttgtcgcccc cggaatcgaa   9360
gccttgggat gcagaacatt tgcccctgaa gaaacgaact tcaacctggt cggcctcttg   9420
catccccgaa tggtgacctt ggccgccgaa gaacctttgt gggccgattt gacaggaaat   9480
tgggtggtga tccccaacat gaaggacgca gccgacggat tgagaagcga gttgatgacc   9540
aagtcccgca ttgccagagc tgtcgccaca tccaaccaat tggaagagtc caaaaaacct   9600
gagggaggac gggagttgcc gccaccggaa tccgccggac ctttggccgg aacgatgttg   9660
ggaatgacgc cgtttccgac cttgcctagc gaagaagccc gaaagtccct gtctgccttg   9720
gaaggaatgg tggacttgcg gaaagtcgtc gtgatcaccg gatacggaga agtgggacct   9780
tggggaaatg caagaacacg atgggaaatg gagagctacg gagagttctc cctggagggg   9840
gccatcgagt tggcctggat ggtcggattg atcaaaagac atgacggacc tttgcctagc   9900
ggacctcctc gacaacggta tgtgggatgg gtggatgcaa cgagtggaga agcagtggca   9960
gatcatgagg tgaaacggag atacgagaag accctgttgc aatcttgcgg aatccggatt  10020
gtggaacccg ccatcttcga gggctacaac cccgacgcca agcgcttttt gcatagtgtg  10080
gtgcttgacc gagatatgcc cgccatcgag ttggcctctc tggaagaagg gctgcagtac  10140
atgaaggagt tgggagagga gtgctgtgac gtgtttgcca gacctagcga tggacaatac  10200
atgatgcgcg tgaaaaaagg agccgaggtg agcatcgcca aagccctcaa gttcaaccgg  10260
aacgtggccg gacaagtgcc tacaggatgg gatgccagga gattgggatt gcctgccgat  10320
atcgcgaaca gtgtggaccc tgtgacgttg tacacgttgg tgagcaccgt ggaagccttg  10380
atggcagctg gattgtcaga cccttacgaa ttgtaccaat acgtccatgt gagcgaggtg  10440
gggaatacaa gcggaggagg aatgggggga atgaggtcgt tgaagcggat gttccatcag  10500
cggaagctcg acgaggacat ccctagtgac accttggccg agtccttcat caacacgatg  10560
cctgcctggg tgaacatgct gctcgtgtct agctccggac ctatcaaaac acctgtggga  10620
gcatgcgcaa cagcagccga atctttggat attggaatgg agaccatcct cagcggaaaa  10680
gccagagtgg tgatcgccgg aggatacgac gactttgggg aggagggatc ctacgagttc  10740
gcccaaatgg gagccacgaa caacaccgtc ttggatgccg cacgtggaag aacagtgaga  10800
gaatctagcc gacctatgtc gtcgagcagg gcaggatttg tggaatctca tggagccgga  10860
attcaagtgt tgatggatgc cgaattggcc ctggagatgg gagcccctat cttcgccatc  10920
ctggccctga caaataccgc caccgacaaa cagggacgct ccattcctgc acctggacgt  10980
ggaatcttga catctgccag agaaagcacc aaagccggag tgagccctat gctttccttg  11040
gaacgacgaa gacaaggctt ggaaatggaa ttggacgcct tgaagacgct gaatgcccag  11100
aaggagcagt ccgaggggga ggatgccgcc tttcttgaga gactcgtgca gaaacgacga  11160
gcagcagcct tggagacctg gggacaaggg tttttcaaga atgacccctc catcgcccct  11220
```

-continued

```
ttgagaggag ccttggccgt gtggggattg ggagtggatg atttgggagt tgcatcattt  11280

catggaacgt ctacgaagtt gaacgacacg aacgagtccg gcgtgctgaa caagcagatg  11340

gagcatttgg gacggagcaa gggcaacgtg ctcttcgtgg tggcccagaa gtacttgacg  11400

ggacacccta aaggagccgc ctgtgcgtgg atggtgaacg ggttggtgca gtgtatgttg  11460

gacgcacgag tgcctggaaa tagaaatttg gacaatgtgg atgtgaagtt gcagacgaac  11520

tcctacctcg tgtaccccaa tgagcccgtg caactcccca agatcgaagc cgccctgctg  11580

aagtccttcg gattcggaca agccggagca gaggtcgtga tcgtgcatcc tgaccgcttg  11640

ttggccacct tgtctcctga agccttcgcc aactacatcg aagccagaaa tattagagaa  11700

agacgaacgt tccgaaatgc ccagaacgtg atgtccggat cccgcaacat ggtgatcgtg  11760

aaggagcacc ccccctaccc tgccgagttg gaagaagccg tgtacctcga ccctcttgcc  11820

cgtgcctcct atgatgccaa ggagaatacc tggacgttcc gatccgccgc tggacttaca  11880

tcttctggaa tgcctaaaat tgcgtcgagc caagcgccgt cgtcgccgaa acctgcagca  11940

gcacctgtgt ctgaatctgc ctcccaatcc gcccagatgt ccgccaaaga ccgattgcag  12000

atgacgatgg ccgagcaagc cgccggaatc gcagcaagag ctggaggttc tggtgtggga  12060

gtcggagttg atgtcgaaaa tgtgtccact tttgctgatt acgctggatc caagcaagac  12120

ttcatccaac ggaacttcac cgaagccgag atcgcctact gcaagtccgc cgccgatcct  12180

gccgcctcct ttgctggaag atgggcagcc aaagaagccg tcgtcaaagc cttgtcctcc  12240

attgcccctg attcccgatc cttgtgggcc ggaggtcatg catctttagt tgatatcgaa  12300

gtggtcgcaa atccttctgg agcacctcaa attagattgc acggtcaccc tgagcaagtc  12360

tcccagatgc tcgccgtgaa cgacctgagc gtctccatct cccataccgc cgaagtggca  12420

atcgccaacg ccatcgcccg aaagtga                                      12447
```

RNA-GUIDED ENDONUCLEASE EXPRESSING ALGAL STRAIN FOR HIGH EFFICIENCY IN VIVO GENOME EDITING

CROSS-REFERENCE TO RELATED APPLICATIONS

This application is a Continuation application of application Ser. No. 14/986,492, filed Dec. 31, 2015, now pending; which claims the benefit under 35 USC § 119(e) to U.S. Application Ser. No. 62/099,014 filed Dec. 31, 2014. The disclosure of each of the prior applications is considered part of and is incorporated by reference in the disclosure of this application.

INCORPORATION OF SEQUENCE LISTING

The material in the accompanying sequence listing is hereby incorporated by reference into this application. The accompanying sequence listing text file, name SGI1850_2_Sequence_Listing.txt, was created on Sep. 29, 2020, and is 238 kb. The file can be accessed using Microsoft Word on a computer that uses Windows OS.

BACKGROUND

The present invention relates to genetic engineering of eukaryotic organisms and in particular to genome editing using cas/CRISPR systems.

The genome editing capability of CRISPR systems, while only recently developed, has significantly expanded the spectrum of cells and organisms that can be genetically engineered (Sander & Joung (2014) *Nature Biotechnology*). US2014/0068797, incorporated herein by reference discloses Cas9/CRISPR systems and methods of use in genome editing.

SUMMARY

The present invention provides methods for developing cell lines and microbial strains that can be used for highly efficient genome editing using an RNA-guided endonuclease, such as a Cas/CRISPR system. The cell lines and microbial strains comprise a gene encoding an RNA-guided nuclease, which can be, for example, a Cas nuclease, e.g., a Cas9 nuclease, where the RNA-guided nuclease exhibits fully penetrant expression in a population of the cell line or microbial strain. The fully penetrant expression of the RNA-guided nuclease is determined by assessing the expression of a linked gene encoding a detectable marker, e.g., a fluorescent protein.

The methods provided herein for isolating a fully penetrant cas-expressing cell line or microbial strain include introducing the RNA-guided nuclease gene on a nucleic acid molecule that also includes a gene encoding a detectable marker, preferably a fluorescent marker. Transformed cell lines that include the nucleic acid molecule that includes a gene encoding an RNA-guided nuclease such as a Cas protein and a detectable marker gene are screened by flow cytometry to select a strain or cell line in which essentially all the cells of the culture express the detectable marker, which can be, for example, a fluorescent protein. A strain or line selected for culture-wide expression of the detectable marker is identified as a fully penetrant stain or line.

The invention thus provides cell lines and microbial strains that are fully penetrant for a heterologous RNA-guided nuclease such as a Cas gene, e.g., a Cas9 gene. The fully penetrant Cas strains and lines provided herein demonstrate highly efficient genome editing, for example, when cells of the fully penetrant strain or cell line are transformed with a guide RNA targeting a genetic locus of interest, at least about 10%, at least about 20%, at least about 30%, at least about 40%, or at least about 50% of the cells transformed with the guide RNA (e.g., a chimeric guide RNA, or a crRNA that promotes site-specific DNA editing in combination with a transactivator RNA (tracrRNA)) become genetically altered at the targeted locus. For example, in various examples, when transformed with a guide RNA and donor fragment, at least about 10%, at least about 20%, at least about 30%, or at least about 40% of the cells transformed with the guide RNA incorporate the donor DNA at the targeted locus. In some examples, at least 50%, at least 60%, at least 70%, or at least 80%, at least 90%, at least 95%, or greater than 95% of the cells of a fully penetrant Cas cell line transformed with a guide RNA and donor fragment incorporate the donor DNA the targeted locus.

In one aspect, provided herein are methods for generating a high efficiency genome editing cell line that expresses an exogenous RNA-guided nuclease, in which the methods include introducing into a population of host cells a non-native nucleic acid molecule comprising a nucleic acid sequence encoding an RNA-guided nuclease and a nucleic acid sequence encoding a detectable marker to obtain one or more RNA-guided nuclease-transformed cell lines comprising the at least one non-native nucleic acid molecule; individually culturing at least one of the RNA-guided nuclease-transformed cell lines; using flow cytometry to assess the expression of the detectable marker in the RNA-guided nuclease-transformed cell line culture; and identifying a RNA-guided nuclease-transformed cell line demonstrating fully penetrant expression of the detectable marker in culture to identify a high efficiency genome editing cell line. The detectable marker can be a fluorescent protein. By "fully penetrant expression" is meant that the RNA-guided nuclease-transformed cell line, when analyzed by flow cytometry, gives rise to a single peak of fluorescence intensity, where the transformed cell fluorescence intensity peak is at a higher intensity than the peak of fluorescence exhibited by non-transformed cells, i.e., is at a higher than background intensity. As demonstrated in the examples herein, cell lines exhibiting full penetrance of a detectable marker gene physically linked to a non-native RNA-guided nuclease protein gene demonstrate highly efficient genome editing when transformed with a genome-targeting guide RNA. Highly efficient genome editing can successfully generate mutations (altered target site) in at least 10%, at least 20%, at least 30%, at least 40%, at least 50%, at least 60%, or at least 70% of the cells transformed with a donor DNA.

The methods can be performed with any cells that can be cultured, including prokaryotic cells (bacteria and archaea) and eukaryotic cells, including, without limitation, plant cells, animal cells, and protozoans, including mesomycetozoea, fungi, heterokonts, and algae.

The RNA-guided nuclease can be, for example, a Cas protein, such as a Cas9 protein, of which a large number have been identified, and can be for example a Cas9 protein of *Streptococcus pyogenes, Streptococcus thermophilus*, or *Neisseria meningitidis*. Other Cas proteins of interest include, without limitation, the Cpf1 RNA-guided endonuclease (Zetsche et al. (2015) *Cell* 163:1-13) as well as the C2c1, C2c2, C2c3 RNA-guided nucleases (Shmakov et al. (2015) *Molecular Cell* 60:1-13). The nucleic acid sequence encoding the Cas protein can be codon optimized for the host cell of interest. In some instances, a Cas9 protein encoded by a nucleic acid molecule introduced into a host cell can comprise at least one mutation with respect to a wild-type Cas9 protein; for example, the Cas9 protein can be inactivated in one of the cleavage domains of the protein resulting in a "nickase" variant. Nonlimiting examples of mutations include D10A, H840A, N854A, and N863A.

The methods can be used to screen for full penetrance of proteins other than cas proteins, so that methods are provided for generating cell lines fully penetrant for expression of a gene of interest, in which the methods include introducing into a population of host cells a non-native nucleic acid molecule comprising a gene of interest and a nucleic acid sequence encoding a detectable marker to obtain one or more transformed cell lines comprising the at least one non-native nucleic acid molecule; individually culturing at least one of the transformed cell lines; using flow cytometry to assess the expression of the detectable marker in the transformed cell line culture; and identifying a transformed cell line demonstrating fully penetrant expression of the detectable marker in culture to identify a cell line having fully penetrant expression of the gene of interest. The detectable marker can be a fluorescent protein. By "fully penetrant expression" is meant that the transformed cell line, when analyzed by flow cytometry, gives rise to a single peak of fluorescence intensity, where the transformed cell fluorescence intensity peak is shifted a higher intensity than the peak of fluorescence exhibited by non-transformed cells, i.e., is at a higher than background intensity.

The gene encoding a Cas polypeptide can include, in addition to sequences encoding the cas enzyme, sequences encoding at least one nuclear localization sequence (NLS) as part of the recombinant cas protein. An NLS can optionally be at the N-terminal or C-terminal portion of the cas enzyme, or the cas enzyme can have at least one NLS at or near the N-terminus of the protein and least one NLS at or near the C-terminus of the protein. Alternatively or in addition, the nucleic acid molecule can encode a cas protein that includes an epitope tag, such as but not limited to a histidine tag, a hemagglutinin (HA) tag, a FLAG tag, or a Myc tag.

The non-native nucleic acid molecule that includes sequences encoding a cas protein can further comprise a selectable marker gene. The selectable marker can be an auxotrophic marker, or can confer resistance to an antibiotic or toxin, and the selectable marker gene can be codon-optimized for the intended host cell.

The detectable marker encoded by the nucleic acid molecule that also includes a sequence encoding a cas protein is preferably a fluorescent protein which can be any fluorescent protein, including phycoerythrin, phycocyanin, allophycocyanin, or a green, yellow, red, blue, cyan, "fruit basket" or "paintbox" (DNA 2.0) fluorescent protein. As nonlimiting examples, a fluorescent protein encoded by a nucleic acid molecule that also encodes a cas protein can be a green fluorescent protein (GFP), YFP, RFP, CFP, BFP, Cherry, Tomato, Venus, Cerulean fluorescent protein, or a variant of any thereof, including but not limited to a monomeric variant of a fluorescent protein.

The nucleic acid molecule that encodes a cas protein, e.g., a Cas9 protein, can encode a detectable marker protein, e.g., a fluorescent protein such that the cas protein and detectable marker protein are regulated by the same promoter and transcribed as a single RNA. For example, the cas enzyme and detectable marker can be produced as a fusion protein. Alternatively, the Cas enzyme and detectable marker can be translated together but the translation product can include a cleavage sequence such as an FMDV 2A sequence that results in cleavage of the two polypeptide moieties so that separate cas and detectable marker proteins result. Further alternatively, an IRES can be provided in the construct between the two coding regions so that they are transcribed as a single transcript but translated as separate polypeptides. In yet another configuration, the cas protein and detectable marker can be operably linked to separate promoters. The promoters can optionally be derived from ("homologous to") the host cell species and can optionally be constitutive promoters.

A further aspect of the invention is a highly efficiency genome editing cell line. The high efficiency genome editing recombinant cell line includes an exogenous gene encoding an RNA-guided endonuclease and is fully penetrant for the heterologous (introduced) RNA-guided endonuclease gene. Based on results described herein that demonstrate high efficiencies of Cas9 genome editing in strains fully penetrant for a linked fluorescent protein, the high efficiency Cas9 genome editing cell line is said to be a "fully penetrant Cas9 cell line" based on identification of the cell line by screening for fully penetrant (culture-wide) expression of a fluorescent protein whose encoding gene is physically linked to the gene encoding the RNA-guided endonuclease gene. Without limiting the invention to a particular mechanism, it is considered that cell lines selected for penetrance using a linked fluorescence marker also exhibit Cas9 gene expression throughout the cells of the culture, resulting in the high efficiencies of targeted mutations observed. The fully penetrant Cas9 cell lines or microbial strains provided herein can have targeted mutation rates of at least 10%, at least 20%, at least 30%, at least 40%, or at least 50% using a guide RNA (gRNA) and donor fragment, where the efficiency is the percentage of cells that received the donor fragment that also have a targeted mutation.

The high efficiency genome editing cell line can include an exogenous gene encoding a fluorescent protein, or may not include an exogenous gene encoding a fluorescent protein. Using methods disclosed herein, a detectable marker gene, e.g. a gene encoding a fluorescent protein used to screen for full penetrance of a linked introduced gene such as a gene encoding an RNA-guided endonuclease, can subsequently be excised from the genome of the high efficiency genome editing cell line, for example, using a site specific recombinase such as the cre recombinase.

Further included herein is a high efficiency genome editing cell line that includes an exogenous gene encoding an RNA-guided endonuclease and an exogenous gene encoding a site-specific recombinase, such as a cre recombinase. The gene encoding a site-specific recombinase can optionally be operably linked to an inducible and/or repressible promoter. The high efficiency genome editing cell line that includes an exogenous gene encoding an RNA-guided endonuclease and an exogenous gene encoding a site-specific recombinase may or may not include an exogenous gene encoding a fluorescent protein. For example, a high efficiency genome editing cell line that includes an exogenous gene encoding an RNA-guided endonuclease and an exogenous gene encoding a site-specific recombinase may also include an exogenous gene encoding a fluorescent protein that is subsequently excised by the action of the site-specific recombinase. Further, a high efficiency genome editing cell line that includes an exogenous gene encoding an RNA-guided endonuclease and an exogenous gene encoding a site-specific recombinase may be "markerless", i.e., may lack a selectable marker. A selectable marker used to transform a strain with a construct that includes an RNA-guided endonuclease and/or an exogenous gene encoding a site-specific recombinase can subsequently be excised by the action of the site-specific recombinase.

Also provided herein is a method of altering the genome of a cell in vivo, where the method comprises: introducing at least one guide RNA into a fully penetrant RNA-guided endonuclease-expressing cell line or microbial strain, wherein the guide RNA targets a site in the genome of the cell; and screening cells transformed with the guide RNA for alteration of the targeted site in the genome. Alteration of the targeted genome site can be detected, for example, by PCR or by phenotypic screen. The RNA-guided endonuclease can be a Cas protein, such as a Cas9 protein.

Optionally, a donor fragment is also transformed into the host cell with the guide RNA, where the donor fragment optionally but preferably includes a selectable marker gene. The selectable marker gene of the donor fragment is used for selection of transformants. A donor fragment can optionally include homology regions for mediating insertion into the targeted site by homologous recombination.

A fully penetrant RNA-guided endonuclease-expressing cell line or strain can be any type of cell, for example, plant or animal, metazoan or protozoan. For example, cells derived from plants, mammals, amphibians, fish, birds, marsupials, reptiles, nematodes, crustaceans, arachnids, or insects can be transformed with a construct that encodes a cas protein, where the construct preferably but optionally includes a gene regulatory sequence such as a promoter operably linked to the cas-encoding sequence. Cell lines and strains of protozoan species are also considered, such as, but not limited to microalgae, heterokonts such as labyrinthulomycetes and oomyctes, mesomycetozoea, and fungi. Archaea and bacteria can also be hosts that express cas9 for genome editing.

Also provided herein are methods of editing the genome of a host cell, comprising, transforming a fully penetrant RNA-guided endonuclease-expressing host strain with at least one guide RNA that targets a site in the genome of the host cell and at least one donor DNA to generate at least one mutation in the targeted site of the host cell genome. The method is versatile, and allows for the donor DNA to include homology arms for recombination into the target locus, or to be free of sequences homologous to the host genome. For example, the donor DNA can be circular or linear and can include a selectable marker gene and/or one or more genes encoding a regulator, a metabolic enzyme, a transporter, an RNAi construct, an antisense RNA construct, etc. or can include a sequence bound by a DNA binding protein, transcription factor, etc.

The guide RNA can be a chimeric guide RNA or can be a guide RNA that includes crRNA having homology to a locus in the host cell genome targeted for genome alteration and, preferably, a sequence homologous to the tracr RNA ("tracr mate sequence"). A tracr RNA can be provided separately. Further, the guide RNA, tracr RNA, and/or chimeric guide RNA can be encoded by a construct transformed into the host cell.

In any of the cell lines, microbial strains, and methods herein, an RNA-guided endonuclease can be a Cas nuclease, such as, without limitation, a Cas9, Cpf1, C2c1, C2c2, or C2c3 RNA-guided nuclease, a homolog of any thereof, of a modified version of any thereof.

A host cell can be a prokaryotic cell, an animal cell, a plant cell or a single-celled eukaryotic microbe, such as a fungal cell, heterokont cell, or algal cell. A heterokont cell can be, for example, a labrynthulocycete (e.g., a member of any of the genera *Aplanochytrium, Aurantiochytrium, Diplophrys, Japonochytrium, Labryinthula, Labryinthuloides, Schizochytrium, Thraustochytrium*, or *Ulkenia*) or can be a diatom (e.g., a member of *Acnanthes, Amphora, Chaetoceros, Cyclotella, Fragilaria, Fragilariopsis, Hantzschia, Navicula, Nitzchia, Phaeodactylum*, or *Thalassiosira*). A heterokont can also be a *Eustigmatophyte*, such as, for example, a species of *Eustigmatos, Monodus, Nannochloropsis, Pseudostaurastrum*, or *Vischeria*.

While the methods provided refer to "genome editing" it is to be understood that "genome editing" as disclosed herein includes in vivo editing (e.g., mis-repair, insertion, or other target site alteration) of any DNA molecule targeted within the host cell, for example, a native chromosome, a synthetic chromosome, a naturally-occurring or synthetic episomal molecule, a viral construct etc. Without limitation, the editing can effect gene disruption by insertion of a donor fragment that "knocks out" the gene or that disrupts a noncoding sequence that results in reduced expression of the gene. Alternatively or in addition, genome editing can introduce gene expression elements such as promoters that can increase expression of a gene. Genome editing as disclosed herein can further be used to introduce genes, such as exogenous genes, into a locus. Using the genome editing methods herein, multiple genes can be introduced into a genome target site on a donor fragment. The donor fragment can optionally include a detectable marker gene, e.g., a fluorescent protein gene, that can be used to evaluate penetrance of the introduced gene or genes that are physically linked to the detectable marker gene, using the methods provided herein.

Also provided herein are methods of screening a recombinant cell lines for full penetrance of an introduced gene. The introduced gene can encode a functional RNA or polypeptide. As disclosed in the examples herein, in addition to screening for fully penetrant expression of an RNA-guided endonuclease and a site specific recombinase, the methods of screening transformants by flow cytometry to identify cell lines having a single fluorescence peak where the fluorescence peak is at a higher fluorescence intensity that the peak seen in non-transformed cells can be used to isolate cell lines having fully penetrant expression of genes encoding functional RNAs, such as RNAi molecules, and polypeptides, such as enzymes. Further, the comparison of fluorescence intensity levels of different transformed cells lines can allow for selection of cell lines with higher or lower expression levels overall. Such culture-wide screening can be more reliable than other methods, such as determining levels of expressed proteins.

BRIEF DESCRIPTION OF THE DRAWINGS

FIGS. 35 A and B provides a graph of in vivo FAS rate determination using isotope tracer (13C) incorporation for ChytFAS transgenic lines grown under phototrophic conditions (A) and mixotrophic conditions (B). ChytFAS strain 6167-B outperformed the wild type strain under photoautotrophic conditions (A). Strain 6167-A was also tested under mixotrophic conditions, where it outperformed wild type in FAME production (B).

FIGS. 36 A and B provides a graph of in vivo FAS rate determination using isotope tracer incorporation for DrFAS over-expression strains grown under photoautotrophic (A, labeled with 13C bicarbonate) and acetate-boosted mixotrophic (B, labeled with 13C acetate) conditions. All DrFAS transformants were able to outperform the wild type strain under mixotrophic conditions.

DETAILED DESCRIPTION

Figure 1:
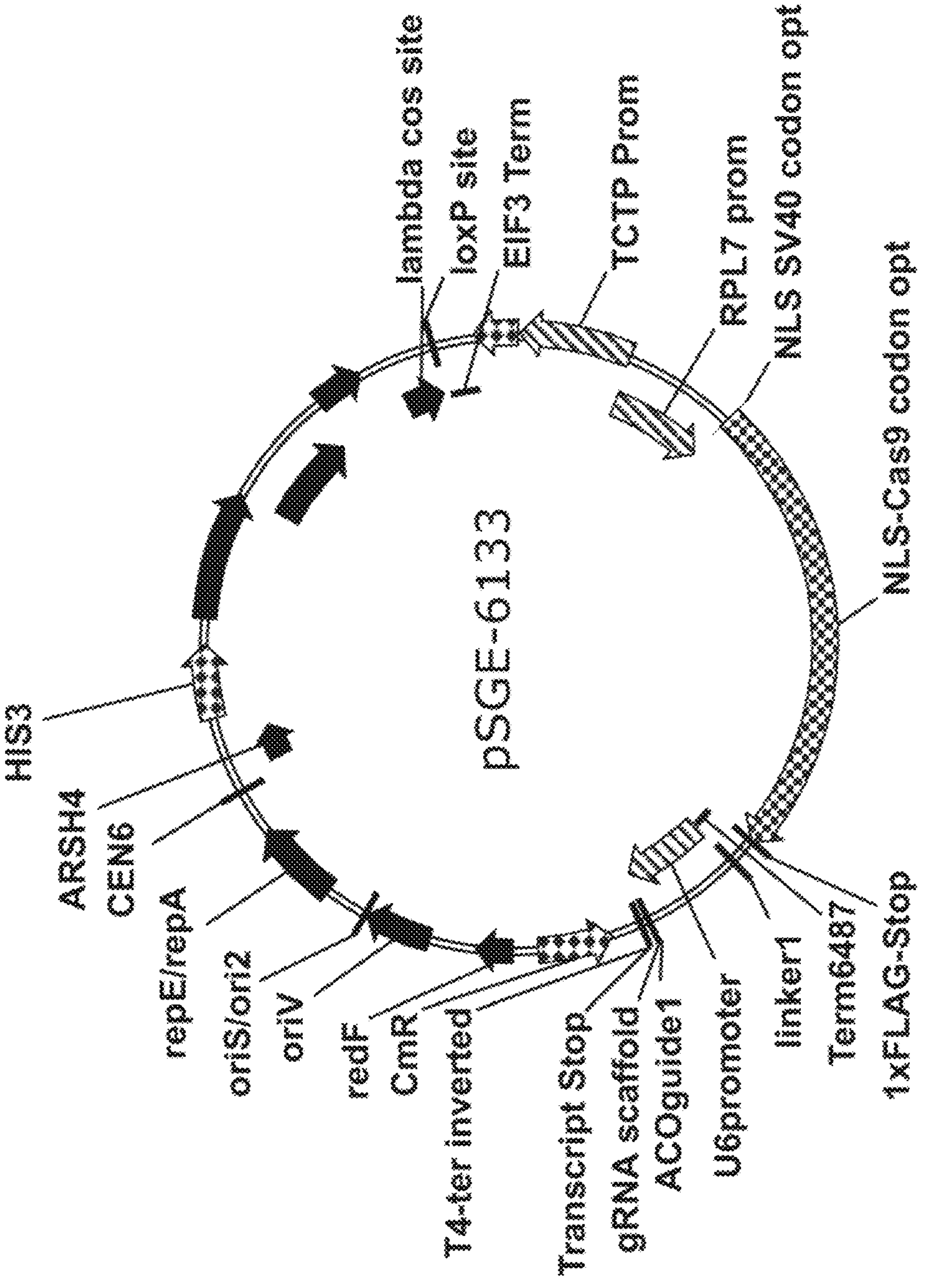
FIG. 1 is a diagram of vector pSGE-6133 that includes a Cas9 gene codon optimized for *Nannochloropsis* that includes a nuclear localization sequence (NLS) and a FLAG tag. The pSGE-6133 construct also includes a chimeric CRISPR guide RNA sequence targeting the acyl-CoA oxidase gene under the control of the *Nannochloropsis* U6 promoter.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form “a”, “an”, and “the” include plural references unless the context clearly dictates otherwise. For example, the term “a cell” includes one or more cells, including mixtures thereof. “A and/or B” is used herein to include all of the following alternatives: “A”, “B”, “A or B”, and “A and B”.

“About” means either: within plus or minus 10% of the provided value, or a value rounded to the nearest significant figure, in all cases inclusive of the provided value. Where ranges are provided, they are inclusive of the boundary values.

As used herein, “amino acid” refers to naturally-occurring and synthetic amino acids, as well as amino acid analogs and amino acid mimetics that function in a manner similar to the naturally-occurring amino acids. Naturally-occurring amino acids are those encoded by the genetic code, including D/L optical isomers, as well as those amino acids that are later modified, e.g., hydroxyproline, y-carboxyglutamate, and O-phosphoserine. Amino acid analogs refer to compounds that have the same basic chemical structure as a naturally-occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics, as used herein, refer to chemical compounds that have a structure that is different from the general chemical structure of an amino acid, but that functions in a manner similar to a naturally-occurring amino acid.

A “nucleotide” is the basic unit of a nucleic acid molecule and typically includes a base such as adenine, guanine, cytosine, thymine, or uracil linked to a pentose sugar such as ribose or deoxyribose that is in turn linked to a phosphate group. Nucleotides can also include alternative or non-naturally occurring bases or sugars that do not occur in naturally-occurring DNA or RNA. In peptide nucleic acids one or more sugars may be substituted by amino acids, and in some nucleic acid analogs at least a portion of the phosphates may be replaced by hydroxyl groups. Although nucleotides are often used to denote the length of a single-stranded nucleic acid molecule, and “base pairs” (i.e., base paired nucleotides) are often used to denote the length of double-stranded nucleic acid molecules, in the present application, “nucleotides” or “nt” may be used interchangeably with “base pairs” or “bp”, and the use of one term or the other does not meant restrict the type of nucleic acid molecule being described to being either single-stranded or double-stranded. The use of kilobases or “kb” as units of length also applies equally to single-stranded and double-stranded nucleic acid molecules.

A "nucleic acid construct", "DNA construct" or simply "construct" is a nucleic acid molecule produced by recombinant means that includes at least two juxtaposed or operably linked nucleic acid sequences that are not juxtaposed or operably linked to one another in nature.

An "episomal DNA molecule" or "EDM" is an independently replicating nucleic acid molecule that is not integrated into the genome of the host organism in which the EDM resides and replicates. An EDM may be stable, in which it persists for many generations or unstable, where the EDM is gradually diluted out of the population by successive cell divisions. A stable EDM may be maintained in a cell population by selective pressure (e.g., the presence of an antibiotic).

A "detectable marker" is a gene or the polypeptide encoded by the gene that confers some detectable phenotype on a cell that expresses the gene. Detection can be colorometric (for example, the blue color by expression of beta galactosidase or beta-glucuronidase in the presence of a colorometric substrate) or by detection of luminescence or fluorescence. A detectable marker generally encodes a detectable polypeptide, for example, a green fluorescent protein or a signal producing enzyme such as luciferase, which, when contacted with an appropriate agent (a particular, wavelength of light or luciferin, respectively) generates a signal that can be detected by eye or using appropriate instrumentation (Giacomin, Plant Sci. 116:59-72, 1996; Scikantha, J. Bacteriol. 178:121, 1996; Gerdes, FEBS Lett. 389:44-47, 1996; see, also, Jefferson, EMBO J. 6:3901-3907, 1997).

The term or "selectable marker" or "selection marker" refers to a gene (or the encoded polypeptide) that confers a phenotype that allows the organism expressing the gene to survive under selective conditions. For example, a selectable marker generally is a molecule that, when present or expressed in a cell, provides a selective advantage (or, if a negative selectable marker, disadvantage) to the cell containing the marker, for example, the ability to grow in the presence of an agent that otherwise would kill the cell, or the ability to grow in the absence of a particular nutrient.

A "cDNA" is a DNA molecule that comprises at least a portion the nucleotide sequence of an mRNA molecule, with the exception that the DNA molecule substitutes the nucleobase thymine, or T, in place of uridine, or U, occurring in the mRNA sequence. A cDNA can be single-stranded or double-stranded, and can be the complement of the mRNA sequence. In preferred embodiments, a cDNA does not include one or more intron sequences that occur in the naturally-occurring gene (in the genome of an organism) that the cDNA corresponds to. For example, a cDNA can have sequences from upstream (5') of an intron of a naturally-occurring gene juxtaposed to sequences downstream (3') of the intron of the naturally-occurring gene, where the upstream and downstream sequences are not juxtaposed in a DNA molecule (i.e., the naturally occurring gene) in nature. A cDNA can be produced by reverse transcription of mRNA molecules by a polymerase (e.g., a reverse transcriptase), or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences and/or the sequences of one or more cDNAs.

A "coding sequence" or "coding region", as used herein in reference to an mRNA or DNA molecule, refers to the portion of the mRNA or DNA molecule that codes for a polypeptide. It typically consists of the nucleotide residues of the molecule which are matched with an anticodon region of a transfer RNA molecule during translation of the mRNA molecule or which encode a stop codon. The coding sequence may include nucleotide residues corresponding to amino acid residues which are not present in the mature protein encoded by the mRNA molecule (e.g., amino acid residues in a protein export signal sequence).

"Derived from" refers to the source of a nucleotide or amino acid sequence, and typically means the sequence of the nucleic acid molecule, protein, or peptide is based on that of the referenced nucleic acid molecule, protein, or peptide. The nucleic acid molecule, protein, or peptide is either a variant having at least 60% identity (and, in various examples, at least 75%, at least 70%, at least 75%, at least 80%, or at least 85% identity) to the referenced nucleic acid molecule, protein, or peptide, and/or is a truncated or internally deleted variant of the referenced nucleic acid molecule, protein, or peptide. For example, a protein or peptide may be C-terminally or N-terminally truncated or internally deleted with respect to the protein or peptide it is derived from and may have a C-terminal, N-terminal, or internal deletion of any number of amino acids, for example, at least 1, 2, 3, 4, 5, 10, 20, 30, 40, 50, 60, 70, 80, 90, or 100 amino acids. A nucleic acid molecule may be 5' or 3' truncated or internally deleted with respect to the nucleic acid molecule it is derived from and may have a 5', 3', or internal deletion of any number of nucleotides, for example, at least 1, 2, 3, 4, 5, 10, 20, 30, 40, 50, 60, 70, 80, 90, 100, 150, or 200 nucleotides.

The term "endogenous," within the context of the present disclosure refers to any polynucleotide, polypeptide or protein sequence which is a natural part of a cell or organism.

An "exogenous" nucleic acid molecule or gene is a nucleic acid molecule or gene that has been introduced into a host cell. For example, an exogenous nucleic acid molecule or gene is from one species and has been introduced ("transformed") into another organism, microorganism, or cell by human intervention, for example via a recombinant nucleic acid construct. An exogenous nucleic acid can be a sequence from one species introduced into another species, i.e., a heterologous nucleic acid molecule. An exogenous nucleic acid molecule can also be a sequence that is homologous with respect to the host cell or organism (i.e., the nucleic acid sequence occurs naturally in that species or encodes a polypeptide that occurs naturally in the host species) and that has been reintroduced into cells of that organism. An exogenous (introduced) nucleic acid molecule that includes a sequence that is homologous (of the same species) with respect to the host organism can often be distinguished from the naturally-occurring sequence by the presence of sequences linked to the homologous nucleic acid sequence, e.g., regulatory sequences that are not native to the host organism flanking an endogenous gene sequence in a recombinant nucleic acid construct. Alternatively or in addition, a stably transformed exogenous nucleic acid molecule can be detected or distinguished from a native gene by its juxtaposition to sequences in the genome where it has integrated. A nucleic acid molecule is considered exogenous if it has been introduced into a progenitor of the cell, organism, or strain under consideration.

"Expression cassette" as used herein means a DNA sequence capable of directing expression of a particular nucleotide sequence in an appropriate host cell, comprising a promoter operably linked to a nucleotide sequence of interest, which can optionally be operably linked to termination signals and/or other regulatory elements. An expression cassette may also comprise sequences that enable, mediate, or enhance translation of the nucleotide sequence. The coding region usually codes for a protein of interest but may also code for a functional RNA of interest, for example antisense RNA or a non-translated RNA, in the sense or antisense direction. An expression cassette may be assembled entirely extracellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. The expression of the nucleotide sequence in the expression cassette may be under the control of a constitutive promoter or of an inducible promoter which initiates transcription only when the host cell is exposed to some particular external stimulus.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Examples of expression vectors known in the art include cosmids, plasmids and viruses (e.g., retroviruses, lentiviruses, adenoviruses, and adeno-associated viruses) that incorporate the recombinant polynucleotide.

An "oligonucleotide", as used herein, is a nucleic acid molecule 200 or fewer nucleotides in length. An oligonucleotide can be RNA, DNA, or a combination of DNA and RNA, a nucleic acid derivative, or a synthetic nucleic acid, for example, an oligonucleotide can be a peptide nucleic acid or a locked nucleic acid, and can be single-stranded, double-stranded, or partially single-stranded and partially double-stranded. An oligonucleotide can be, for example, between about 4 and about 200 nucleotides in length, between about 6 and about 200 nucleotides in length, between about 10 and about 200 nucleotides in length, between about 15 and about 200 nucleotides in length, between about 17 and about 200 nucleotides in length, between about 20 and about 200 nucleotides in length, or between about 40 and about 200 nucleotides in length. In additional examples, an oligonucleotide can be between about 15 and about 180 nucleotides in length, between about 15 and about 160 nucleotides in length, between about 15 and about 140 nucleotides in length, between about 15 and about 120 nucleotides in length, between about 17 and about 100 nucleotides in length, between about 17 and about 80 nucleotides in length, or between about 17 and about 70 nucleotides in length, for example between about 20 and about 65 nucleotides in length.

When used in reference to a polynucleotide, a gene, a nucleic acid, a polypeptide, or an enzyme, the term "heterologous" refers to a polynucleotide, gene, a nucleic acid, polypeptide, or an enzyme not derived from the host species, e.g., from a different species with respect to the host cell. For example, a transgenic *Nannochloropsis* microorganism transformed with the coding sequence for a fatty acid desaturase from a *Tetraselmis* microorganism or from a plant is transformed with a heterologous desaturase gene. When referring to nucleic acid sequences operably linked or otherwise joined to one another ("juxtaposed") in a nucleic acid construct or molecule, "heterologous sequences", as used herein, are those that are not operably linked or are not in proximity or contiguous to each other in nature. For example, a promoter from *Tetraselmis* sp. is considered heterologous to a *Nannochloropsis* coding region sequence. Also, a sequence encoding a *Nannochloropsis* fatty acid desaturase operably linked to a promoter from a gene encoding a tubulin gene from *Nannochloropsis* is considered to be operably linked to a heterologous promoter. Similarly, when referring to a gene regulatory sequence or to an auxiliary nucleic acid sequence used for maintaining or manipulating a gene sequence (e.g. a 5' un-translated region, 3' un-translated region, Kozak sequence, poly A addition sequence, intron sequence, splice site, ribosome binding site, internal ribosome entry sequence, genome homology region, recombination site, etc.), "heterologous" means that the regulatory sequence or auxiliary sequence is from a different source (e.g., different gene, whether from the same or different species as the host organisms) than the gene with which the regulatory or auxiliary nucleic acid sequence is juxtaposed or operably linked in a construct, genome, chromosome, or episome.

The term "hybridization", as used herein, refers generally to the ability of nucleic acid molecules to join via complementary base strand pairing. Such hybridization may occur when nucleic acid molecules are contacted under appropriate conditions. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity, i.e., when every nucleotide of one of the molecules is complementary to its base pairing partner nucleotide of the other. Two molecules are said to be "minimally complementary" if they can hybridize to one another with sufficient stability to permit them to remain annealed to one another under at least conventional low-stringency conditions. Molecules are said to be "complementary" if they can hybridize to one another with sufficient stability to permit them to remain annealed to one another under conventional high-stringency hybridization conditions. Conventional stringency conditions are described by Sambrook et al., (1989, supra), and by Haymes et al. In: Nucleic Acid Hybridization, A Practical Approach, IRL Press, Washington, D.C. (1985). Departures from complete complementarity are therefore permissible, as long as such departures do not completely preclude the capacity of the molecules to form a double-stranded structure. Thus, in order for a nucleic acid molecule or fragment thereof of the present invention to serve as a primer or probe it needs only be sufficiently complementary in sequence to be able to form a stable double-stranded structure under the particular solvent and salt concentrations and temperature employed.

Appropriate stringency conditions which promote nucleic acid hybridization include, for example, 6.0× sodium chloride/sodium citrate (SSC) at about 45° C., followed by a wash of 2.0×SSC at about 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. These conditions are known to those skilled in the art, or can be found in Current Protocols in Molecular Biology, John Wiley & Sons, N.Y. (1989), 6.3.1-6.3.6. For example, low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989, supra). In one embodiment of the present invention, high stringency conditions involve nucleic acid hybridization in about 2×SSC to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. High stringency conditions are typically provided by 6×SSC, 5×Denhardt's solution, 100 mg/mL fish sperm DNA, and 0.1% (w/v) SDS, with incubation at 55° C. for several hours. Hybridization is generally followed by several wash steps. The wash compositions generally comprise 0.5×SSC to about 1×SSC, and 0.01% (w/v) to about 0.5% (w/v) SDS with an incubation for 15-min at about 20° C. to about 70° C. Typically, complementary nucleic acid segments remain hybridized after washing at least one time in 0.1×SSC at 65° C.

"Percentage of sequence identity," as used herein for the identified centromere sequences, is determined by comparing the specified centromere sequence or fragment thereof with an optimally locally aligned sequence over a comparison window defined by the specified length of the nucleotide sequence (e.g., centromere fragment) set forth. In other contexts, the comparison window for percentage sequence identity between two sequences is defined by the local alignment between the two sequences. For example, an amino acid or nucleotide sequence in the comparison window may comprise additions or deletions (e.g., gaps or overhangs) as compared to the reference sequence (which does not comprise additions or deletions) for optimal alignment of the two sequences. In this context, local alignment between two sequences only includes segments of each sequence that are deemed to be sufficiently similar according to a criterion that depends on the algorithm used to perform the alignment (e.g. BLAST). The percentage identity is calculated by determining the number of positions at which the identical nucleic acid base or amino acid residue occurs in both sequences to yield the number of matched positions, dividing the number of matched positions by the total number of positions in the window of comparison and multiplying the result by 100. Optimal alignment of sequences for comparison may be conducted by the local homology algorithm of Smith and Waterman (Add. APL. Math. 2:482, 1981), by the global homology alignment algorithm of Needleman and Wunsch (J. Mol. Biol. 48:443, 1970), by the search for similarity method of Pearson and Lipman (Proc. Natl. Acad. Sci. USA 85: 2444, 1988), by heuristic implementations of these algorithms (NCBI BLAST, WU-BLAST, BLAT, SIM, BLASTZ), or by inspection. GAP and BESTFIT, for example, can be employed to determine their optimal alignment of two sequences that have been identified for comparison. Typically, the default values of 5.00 for gap weight and 0.30 for gap weight length are used. The term "substantial sequence identity" between polynucleotide or polypeptide sequences refers to polynucleotide or polypeptide comprising a sequence that has at least 50% sequence identity, for example, at least 70%, at least 80%, at least 85%, at least 90%, at least 95%, or at least 96%, 97%, 98% or 99% sequence identity compared to a reference sequence using the programs. In addition, pairwise sequence homology or sequence similarity, as used refers to the percentage of residues that are similar between two sequences aligned. Families of amino acid residues having similar side chains have been well defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

For example, query nucleic acid and amino acid sequences can be searched against subject nucleic acid or amino acid sequences residing in public or proprietary databases. Such searches can be done using the National Center for Biotechnology Information Basic Local Alignment Search Tool (NCBI BLAST v 2.18) program. The NCBI BLAST program is available on the internet from the National Center for Biotechnology Information (blast.ncbi.nlm.nih.gov/Blast.cgi). Exemplary parameters for NCBI BLAST include: Filter options set at "default", the Comparison Matrix set to "BLOSUM62", the Gap Costs set to "Existence: 11, Extension: 1", the Word Size set to 3, the Expect (E threshold) set to 1e-3, and the minimum length of the local alignment set to 50% of the query sequence length. Sequence identity and similarity may also be determined using GENOMEQUEST™ software (Gene-IT, Worcester, Mass. USA).

As used herein, an "isolated" nucleic acid molecule or protein is removed from its natural milieu or the context in which the nucleic acid molecule or protein exists in nature. For example, an isolated protein or nucleic acid molecule is removed from the cell or organism with which it is associated in its native or natural environment. As such, an "isolated" nucleic acid molecule typically is free of sequences that naturally flank the nucleic acid (i.e., sequences located at the 5' and 3' ends of the nucleic acid) in the cell of the organism from which the nucleic acid is derived. An isolated nucleic acid molecule or protein can be, in some instances, partially or substantially purified, but no particular level of purification is required for isolation. For example, an isolated nucleic acid molecule can be a nucleic acid sequence that has been excised from the chromosome, genome, or episome that it is integrated into in nature. Thus, an isolated nucleic acid includes, without limitation, a nucleic acid that exists as a purified molecule, or a nucleic acid molecule that is incorporated into a vector or a recombinant cell.

The terms "microbe" and "microorganism" are used interchangeably to refer to organisms that are too small to be seen with the naked eye. Microbes or microorganisms includes bacteria and protozoa, including unicellular and colonial protozoa such as, but not limited to, fungi, amoebae, mesomycetozoea, single-celled heterokonts (e.g., labyrinthylomycetes, oomyctes), and microalgae.

A "purified" nucleic acid molecule or nucleotide sequence is substantially free of cellular material and cellular components. The purified nucleic acid molecule may be free of chemicals beyond buffer or solvent, for example. "Substantially free" is not intended to mean that other components beyond the novel nucleic acid molecules are undetectable. In some circumstances "substantially free" may mean that the nucleic acid molecule or nucleotide sequence is free of at least 95% (w/w) of cellular material and components.

The term "native" is used herein to refer to nucleic acid sequences or amino acid sequences as they naturally occur in the host. The term "non-native" is used herein to refer to nucleic acid sequences or amino acid sequences that do not occur naturally in the host, or are not configured as they are naturally configured in the host. For example, non-native genes include introduced genes that are homologous with respect to the host (that is, of the same species as the host) that re-introduced into the host with a heterologous promoter and/or lacking one or more introns that occur in the native gene. A nucleic acid sequence or amino acid sequence that has been removed from a host cell, subjected to laboratory manipulation, and introduced or reintroduced into a host cell is considered "non-native." Non-native genes further include genes endogenous to the host microorganism operably linked to one or more heterologous regulatory sequences that have been recombined into the host genome, or genes endogenous to the host organism that are in a locus of the genome other than that where they naturally occur.

In reference to a nucleic acid molecule or a polypeptide, the terms "naturally-occurring" and "wild-type" refer to a form found in nature. For example, a naturally occurring or wild-type nucleic acid molecule, nucleotide sequence or protein may be present in and isolated from a natural source, and is not intentionally modified by human manipulation.

The terms "nucleic acid molecule" and "polynucleotide molecule" are used interchangeably herein, and refer to both DNA and RNA molecule, including cDNA, genomic DNA, synthetic DNA, and DNA or RNA containing nucleic acid analogs. Polynucleotides can have any three-dimensional structure. Polynucleotides can be natural-occurring or synthetic origin. A nucleic acid molecule can be double-stranded or single-stranded. Non-limiting examples of polynucleotides include genes, gene fragments, exons, introns, messenger RNA (mRNA), transfer RNA (tRNA), ribosomal RNA (rRNA), siRNA, micro-RNA, ribozymes, tracr RNAs, crRNAs, chimeric guide RNAs, cDNA, recombinant polynucleotides, branched polynucleotides, nucleic acid probes and nucleic acid primers. A polynucleotide may contain unconventional or modified nucleotides.

As used herein, "operably linked" is intended to mean a functional linkage between two or more sequences such that activity at or on one sequence affects activity at or on the other sequence(s). For example, an operable linkage between a polynucleotide of interest and a regulatory sequence (e.g., a promoter) is a functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site. Operably linked elements may be contiguous or non-contiguous. When used to refer to the joining of two protein coding regions, by "operably linked" is intended that the coding regions are in the same reading frame. When used to refer to the effect of an enhancer, "operably linked" indicated that the enhancer increases the expression of a particular polypeptide or polynucleotides of interest. "Juxtaposed with" in the context of nucleic acid sequences, means the referenced sequences are part of the same continuous nucleic acid molecule, such as a nucleic acid construct introduced into a cell. The term "physically linked", as used herein when referring to nucleic acid sequences, means that the nucleic acid sequence are either part of the same continuous nucleic acid molecule such as a nucleic acid construct introduced into a cell, for example, or, for the purposed of the invention, are positioned on genomic DNA (e.g., a chromosome) within 200 kb of one another, and generally within 100 kb of one another, within 50 kb of one another, or within 25 kb of one another.

The term "penetrance" is used in genetics to indicate the variability of phenotype observed among organisms being genetically identical for a given gene that is known to influence the phenotype. Differences in penetrance, or the degree to which a trait is expressed in an organism, can rely on the genetic background of an individual organism or can be influenced by environmental or epigenetic factors. In the present application, "penetrance" is used to refer to the presence or absence of differences in expression level of a gene introduced into a microorganisms or cells, where the transformed gene is identical and is operably linked to (regulated by) the same promoter. In a cell population resulting from a single transformant, incomplete penetrance of expression of a transgene results in subpopulations that do not express the transgene at a level greater than background. For example, where the transgene encodes a fluorescent protein, incomplete penetrance can be observed by flow cytometry as, typically, either a single fluorescence peak that coincides with the autofluorescence peak of nontransformed cells, or two expression (fluorescence intensity) peaks, one of which coincides with the autofluorescence peak of non-transformed cells, that is, a portion of the transformed population is not expressing the transgene. Without limiting the invention to any particular mechanism, it may be that the observed differences in expression of a transgene rely at least in part on the site in the genome into which the gene has integrated, e.g., "position effects" that results in inconsistent expression of the transgene throughout a clonal culture that may be due, for example, to cell cycle stages of cells at any given time throughout the culture, nutrient or environmental status of cells throughout the culture, or unknown epigenetic, stochastic, or environmental factors. "Fully penetrant" expression, where the transgene encodes a fluorescent protein, can be observed as a single fluorescence intensity peak in flow cytometry histograms, where the single fluorescence intensity peak is greater than the autofluorescence peak of nontransformed cells.

The terms "polynucleotide sequence" and "nucleic acid sequence" as used herein interchangeably refer to a sequence of a polynucleotide molecule, and can refer, for example, to DNA or RNA sequences. The nomenclature for nucleotide bases as set forth in 37 CFR § 1.822 is used herein.

A "promoter" refers to a transcription control sequence that is capable of initiating transcription in a host cell and can drive or facilitate transcription of a nucleotide sequence or fragment thereof of the instant invention. Such promoters need not be of naturally-occurring sequences. In addition, it will be understood that such promoters need not be derived from the target host cell or host organism.

"Polypeptide" and "protein" are used interchangeably herein and refer to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition. In various embodiments the polypeptides can have at least 10 amino acids or at least 25, or at least 50 or at least 75 or at least 100 or at least 125 or at least 150 or at least 175 or at least 200 amino acids.

As used herein "progeny" means a descendant, offspring, or derivative of an organism. For example, daughter cells from a transgenic alga are progeny of the transgenic alga. Because certain modifications may occur in succeeding generations due to mutations or environmental influences, such progeny, descendant, or derivatives may not, in fact, be identical to the parent cell, but are still included within the scope of the term as used herein.

The terms "recombinant" or "engineered" as used herein in reference to a nucleic acid molecule, refer to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. A "recombinant protein" is a protein produced by genetic engineering, for example, by expression of a genetically engineered nucleic acid molecule in a cell.

The term "regulatory region" "regulatory sequence", "regulatory element", or "regulatory element sequence", as used in the present invention, refer to a nucleotide sequence that influences transcription or translation initiation or rate, and stability and/or mobility of a transcription or translation product. Such regulatory regions need not be of naturally-occurring sequences. Regulatory sequences include but are not limited to promoter sequences, enhancer sequences, response elements, protein recognition sites, inducible elements, protein binding sequences, 5' and 3' un-translated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR).

As used herein, a "synthetic chromosome construct" is a DNA construct that includes a centromere and at least one ARS. The term "synthetic chromosome" is used herein to refer to a synthetic chromosome construct that is autonomously replicating and faithfully segregating in a host cell. By "faithfully segregating" is meant that the synthetic chromosome equally partitions into two daughter cells during cell division (i.e., the centromere is activated within the host cell).

As used herein, "transgenic organism" refers to an organism which comprises a heterologous polynucleotide. When applied to organisms, the terms "transgenic" or "recombinant" or "engineered" or "genetically engineered," used interchangeably herein, refer to organisms that have been manipulated by introduction into the organism of an exogenous or recombinant nucleic acid sequence. Generally, the heterologous polynucleotide is stably integrated within the genome such that the polynucleotide is passed on to successive generations, although it can also be present on an episome, and may be present on a synthetic chromosome of the transgenic organism. The non-native polynucleotide may be integrated into the genome alone or as part of a recombinant expression cassette. In additional examples, a transgenic microorganism can include an introduced exogenous regulatory sequence operably linked to an endogenous gene of the transgenic microorganism. Non-limiting examples of such manipulations include gene knockouts, targeted mutations and gene replacement, promoter replacement, deletion, or insertion, as well as introduction of transgenes into the organism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases, TALENs, zinc finger nucleases, or CRISPR nucleases. As used herein, "recombinant microorganism" or "recombinant host cell" includes progeny or derivatives of the recombinant microorganisms of the invention. Because certain modifications may occur in succeeding generations from either mutation or environmental influences, such progeny or derivatives may not, in fact, be identical to the parent cell, but are still included within the scope of the term as used herein.

For nucleic acids and polypeptides, the term "variant" is used herein to denote a polypeptide, protein, or polynucleotide molecule with some differences, generated synthetically or naturally, in their base or amino acid sequences as compared to a reference polypeptide or polynucleotide, respectively, such that the variant has at least 70% sequence identity with the reference polypeptide or polynucleotide. In other embodiments the variant can have at least 80%, at least 85%, at least 90%, at least 95%, at least 96%, at least 97%, at least 98%, or at least 99% sequence identity with the reference polypeptide or polynucleotide. Alternatively or in addition, a variant can have one or more insertions or deletions in response to a reference polypeptide or polynucleotide. For example, protein variants may be N-terminally truncated or C-terminally truncated with respect to the reference sequence, or can have one or more internal deletions, while nucleic acid variants may have a 5' end and/or 3'end sequence truncation and/or can have one or more internal deletions. Further, a protein variant may have an additional sequence added to the N-terminus and/or C-terminus with respect to the reference sequence, or can have one or more internal additional sequences, while nucleic acid variants may have a 5' end and/or 3'end sequence addition and/or can have one or more internal sequence additions. A variant can have any desired combination of substitutions, insertions, and/or deletions with respect to a reference polypeptide or polynucleotide. Polypeptide and protein variants can further include differences in post-translational modifications (such as glycosylation, methylation. phosphorylation, etc.). When the term "variant" is used in reference to a microorganism, it typically refers to a strain microbial strain having identifying characteristics of the species to which it belongs, while having at least one nucleotide sequence variation or identifiably different trait with respect to the parental strain, where the trait is genetically based (heritable).

A "vector" is any genetic element capable of serving as a vehicle of genetic transfer, expression, or replication for a foreign polynucleotide in a host cell. For example, a vector may be an artificial chromosome or a plasmid, and may be capable of stable integration into a host cell genome, or it may exist as an independent genetic element (e.g., episome, plasmid). A vector may exist as a single polynucleotide or as two or more separate polynucleotides. Vectors may be single copy vectors or multicopy vectors when present in a host cell.

"RNA-guided nuclease" is used herein to refer generically to enzymes of CRISPR systems in which the referred to nuclease hydrolyzes DNA in a site-specific manner, where the targeted site is determined by an RNA molecule that interacts with the nuclease. Examples of RNA-guided nucleases include but are not limited to Cas1, Cas1B, Cas2, Cas3, Cas4, Cas5, Cas6, Cas7, Cas8, Cas9, Cas10, Cpf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Cpf1, Csb1, Csb2, Csb3, Csx17, Csx14, Csx10, Csx16, CsaX, Csx3, Csx1, Csx15, Csf1, Csf2, Csf3, Csf4, C2c1, C2c2, C2c3, homologs thereof, and modified versions thereof.

A "CRISPR system" or "CRISPR-cas system" refers to a Cas protein, such as but not limited to a Cas9 protein or a variant thereof, or a nucleic acid molecule encoding a Cas protein, along with one or more RNAs required for targeting and/or altering a genetic locus. For example, a CRISPR-cas system can include a Cas protein or a nucleic acid molecule encoding a Cas protein and at least one tracrRNA ("trans-activating CRISPR RNA") or gene encoding a tracr RNA and at least one crRNA or "CRISPR RNA" or gene encoding a crRNA, in which the crRNA comprises sequences homologous to a target nucleic acid sequence. The crRNA may further include a "tracr mate" sequence that is able to hybridize with the tracrRNA. Alternatively, a CRISPR system can include a cas protein (or a gene or transcript encoding a cas protein) and a gene or transcript that includes both the tracrRNA and crRNA sequences. A single RNA molecule that includes both a tracr sequence and a cr (target homologous) sequence is referred to herein as a "chimeric guide RNA" or simply a "guide RNA". A crRNA or guide RNA can further include a tracr-mate sequence (encompassing a "direct repeat" and/or a tracrRNA-processed partial direct repeat as in an endogenous CRISPR system). In some embodiments, one or more elements of a CRISPR system is derived from a type I, type II, or type III CRISPR system. CRISPR-cas systems and their use in genome editing are disclosed in Jinek et al. (2012) Science 337:816-821; Brouns (2012) Science 337:808; Gaj et al. (2013) Trends in Biotechnol. 31:397-405; Hsu et al. (2013) Cell 157:1262-1278; Mali et al. (2013) Science 339:823-826; Qi et al. (2013) Cell 152:1173-1183; Walsh & Hochedlinger (2013) Proc Natl Acad Sci 110:155414-155515; Sander & Joung (2014) Nature Biotechnology; Sternberg et al. (2014) Nature 507: 63-67; U.S. Patent Application Publication No. 2014/0068797; U.S. Pat. No. 8,697,359; U.S. Patent Application Publication No. 20140170753; U.S. Patent Application Publication No. 20140179006; U.S. Patent No. 20140179770; U.S. Patent Application Publication No. 20140186843; and U.S. Patent Application Publication No. US 20150045546; all of which are incorporated by reference in their entireties.

In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. A sequence or template that may be used for recombination into the targeted locus comprising the target sequences is referred to as an "editing template" or "editing sequence", "donor sequence" or "donor DNA". In aspects of the invention, an exogenous template polynucleotide may be referred to as a donor DNA molecule.

As used herein, a "meganuclease" also known as a "homing endonuclease" is an endodeoxynuclease with a recognition site of at least 12 base pairs. Homing endonucleases are well-known to the art (e.g. Stoddard, Quarterly Reviews of Biophysics, 2006, 38:49-95). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. Examples of such endonuclease include I-Sce I, I-Chu I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I, and I-Msol.

As used herein, a "zinc finger nuclease" is an engineered restriction enzyme that includes a zinc finger DNA-binding domain fused to a restriction endonuclease, such as, for example, a meganuclease or the restriction nuclease FokI. The zinc finger domain can be engineered to bind to particular DNA sequences for targeting of specific genome sites.

A "TALE" or "Transcription activator-like effector" is a DNA-binding protein that can recognize particular bases in the DNA sequence by the sequence of amino acids in its central repeat domain. TALE proteins thus can be engineered to bind particular DNA sequences and may be fused to nuclease domains (e.g., a FokI nuclease) as "TALENs" or "Transcription activator-like effector nucleases".

All publications and patent applications mentioned in this specification are herein incorporated by reference to the same extent as if each individual publication or patent application was specifically and individually indicated to be incorporated by reference.

No admission is made that any reference constitutes prior art. The discussion of the references states what their authors assert, and the applicants reserve the right to challenge the accuracy and pertinence of the cited documents. It will be clearly understood that, although a number of prior art publications are referred to herein; this reference does not constitute an admission that any of these documents forms part of the common general knowledge in the art.

The discussion of the general methods given herein is intended for illustrative purposes only. Other alternative methods and embodiments will be apparent to those of skill in the art upon review of this disclosure.

CRISPR Systems

CRISPR systems include, in addition to the Cas9 nuclease, a targeting RNA often denoted "crRNA" that interacts with the genome target site by complementarity with a target site sequence, a transactivating RNA that complexes with the Cas9 polypeptide and also includes a region that binds (by complementarity) the targeting crRNA.

The nuclease activity cleaves target DNA to produce double strand breaks. These breaks are then repaired by the cell in one of two ways: non-homologous end joining, and homology-directed repair. In non-homologous end joining (NHEJ), the double-strand breaks are repaired by direct ligation of the break ends to one another. In this case, no new nucleic acid material is inserted into the site, although some nucleic acid material may be lost, resulting in a deletion. In homology-directed repair, a donor polynucleotide with homology to the cleaved target DNA sequence is used as a template for repair of the cleaved target DNA sequence, resulting in the transfer of genetic information from the donor polynucleotide to the target DNA. As such, new nucleic acid material may be inserted/copied into the site. In some cases, a target DNA is contacted with a donor DNA, for example a donor DNA introduced into a host cell. The modifications of the target DNA due to NHEJ and/or homology-directed repair can lead to, for example, gene correction, gene replacement, gene tagging, transgene insertion, nucleotide deletion, gene disruption, gene mutation, etc.

In some instances, cleavage of DNA by a site-directed modifying polypeptide may be used to delete nucleic acid material from a target DNA sequence by cleaving the target DNA sequence and allowing the cell to repair the sequence in the absence of an exogenously provided donor polynucleotide.

Alternatively, if a DNA-targeting RNA and a cas polypeptide are coadministered to cells with a donor DNA, the subject methods may be used to add, i.e. insert or replace, nucleic acid material to a target DNA sequence (e.g. "knock out" by insertional mutagenesis, or "knock in" a nucleic acid that encodes for a protein, an siRNA, an miRNA, etc.), to add a tag (e.g., a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation), and the like.

The invention contemplates the use of two RNA molecules ("crRNA" and "tracrRNA") that can be cotransformed into a host strain for genome editing, or, as disclosed in the examples herein, a single guide RNA that includes a sequence complementary to a target sequence as well as a sequence that interacts with the cas9 protein. That is, a CRISPR system as used herein can comprise two separate RNA molecules (RNA polynucleotides: an "activator-RNA" and a "targeter-RNA", see below) and is referred to herein as a "double-molecule DNA-targeting RNA" or a "two-molecule DNA-targeting RNA." Alternatively, as illustrated in the examples, the DNA-targeting RNA can be a single RNA molecule (single RNA polynucleotide) and is referred to herein as a "chimeric guide RNA," a "single-guide RNA," or an "sgRNA." The term "DNA-targeting RNA" or "gRNA" is inclusive, referring both to double-molecule DNA-targeting RNAs and to single-molecule DNA-targeting RNAs (i.e., sgRNAs).

An exemplary two-molecule DNA-targeting RNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA-like molecule (targeter-RNA) comprises both the DNA-targeting segment (single stranded) of the DNA-targeting RNA and a stretch ("duplex-forming segment") of nucleotides that forms one half of the dsRNA duplex of the protein-binding segment of the DNA-targeting RNA. A corresponding tracrRNA-like molecule (activator-RNA) comprises a stretch of nucleotides (duplex-forming segment) that forms the other half of the dsRNA duplex of the protein-binding segment of the DNA-targeting RNA. In other words, a stretch of nucleotides of a crRNA-like molecule are complementary to and hybridize with a stretch of nucleotides of a tracrRNA-like molecule to form the dsRNA duplex of the protein-binding domain of the DNA-targeting RNA. As such, each crRNA-like molecule can be said to have a corresponding tracrRNA-like molecule. The crRNA-like molecule additionally provides the single stranded DNA-targeting segment. Thus, a crRNA-like and a tracrRNA-like molecule (as a corresponding pair) hybridize to form a DNA-targeting RNA. The exact sequence of a given crRNA or tracrRNA molecule is characteristic of the species in which the RNA molecules are found.

The term "activator-RNA" is used herein to mean a tracrRNA-like molecule of a double-molecule DNA-targeting RNA. The term "targeter-RNA" is used herein to mean a crRNA-like molecule of a double-molecule DNA-targeting RNA. The term "duplex-forming segment" is used herein to mean the stretch of nucleotides of an activator-RNA or a targeter-RNA that contributes to the formation of the dsRNA duplex by hybridizing to a stretch of nucleotides of a corresponding activator-RNA or targeter-RNA molecule. In other words, an activator-RNA comprises a duplex-forming segment that is complementary to the duplex-forming segment of the corresponding targeter-RNA. As such, an activator-RNA comprises a duplex-forming segment while a targeter-RNA comprises both a duplex-forming segment and the DNA-targeting segment of the DNA-targeting RNA. Therefore, a subject double-molecule DNA-targeting RNA can be comprised of any corresponding activator-RNA and targeter-RNA pair.

A "host cell," as used herein, denotes an in vivo or in vitro eukaryotic cell, a prokaryotic cell (e.g., bacterial or archaeal cell), or a cell from a multicellular organism (e.g., a cell line) cultured as a unicellular entity, in which the eukaryotic or prokaryotic cells can be or have been used as recipients for a nucleic acid. "Host cells" also include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced an exogenous nucleic acid, for example, an expression cassette or vector.

Both single-molecule guide RNAs and two RNA systems have been described in detail in the literature and for example, in US20140068797, incorporated by reference herein. Any Cas9 protein can be used in the methods herein (see, for example, the cas9 Cas9 proteins provided as SEQ ID NOs:1-256 and 795-1346 in US20140068797), including chimeric cas9 proteins that may combine domains from more than one Cas9 protein, as well variants and mutants of identified Cas9 proteins.

Figure 5:
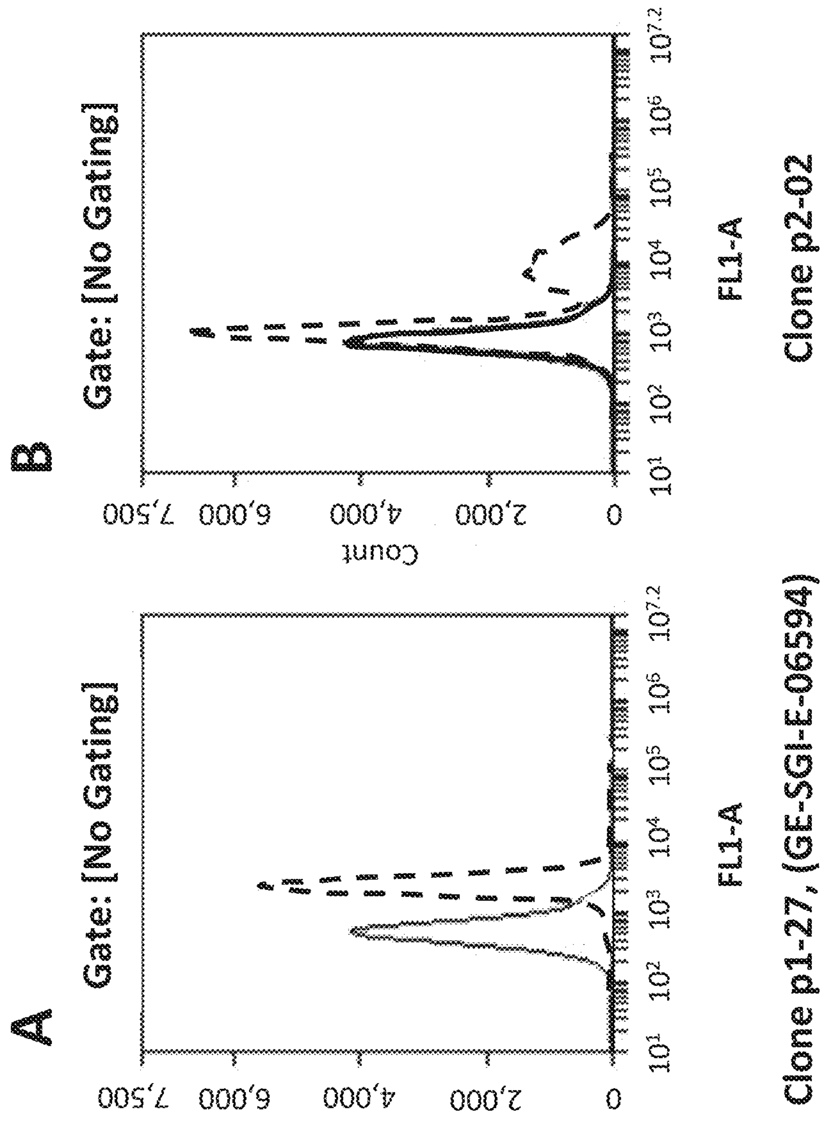
FIG. 5 A) shows the readout from flow cytometry performed on a host cell line transformed with construct pSGE6202 that demonstrates full penetrance (single peak, shifted with respect to control). B) shows the readout from flow cytometry performed on a host cell line transformed with construct pSGE6202 that does not demonstrate full penetrance (two peaks, one of which is coincident with control peak).

For example, one mutant of the Cas9 polypeptide is a D10A (aspartate to alanine at amino acid position 10) mutation (or the corresponding mutation of any of the proteins set forth as SEQ ID NOs:1-256 and 795-1346 of US20140068797) that can cleave the complementary strand of the target DNA but has reduced ability to cleave the non-complementary strand of the target DNA (thus resulting in a single strand break (SSB) instead of a double strand break (DSB)). In some embodiments, the modified form of the Cas9 polypeptide is a H840A (histidine to alanine at amino acid position 840) mutation (or the corresponding mutation of any of the proteins set forth as SEQ ID NOs: 1-256 and 795-1346) that can cleave the non-complementary strand of the target DNA but has reduced ability to cleave the complementary strand of the target DNA (thus resulting in a SSB instead of a DSB). The use of the D10A or H840A variant of Cas9 (or the corresponding mutations in any of the proteins set forth as SEQ ID NOs:1-256 and 795-1346 of US20140068797) can alter the expected biological outcome because the non-homologous end joining (NHEJ) is much more likely to occur when DSBs are present as opposed to SSBs. Other residues can be mutated to achieve the same effect (i.e. inactivate one or the other nuclease portions). As non-limiting examples, residues D10, G12, G17, E762, H840, N854, N863, H982, H983, A984, D986, and/or A987 (or the corresponding mutations of any of the proteins set forth as SEQ ID NOs:1-256 and 795-1346) can be altered (i.e., substituted) (see FIG. 3, FIG. 5, FIG. 11A, and Table 1 for more information regarding the conservation of Cas9 amino acid residues). Also, mutations other than alanine substitutions are suitable. In some embodiments when a site-directed polypeptide (e.g., site-directed modifying polypeptide) has reduced catalytic activity (e.g., when a Cas9 protein has a D10, G12, G17, E762, H840, N854, N863, H982, H983, A984, D986, and/or a A987 mutation, e.g., D10A, G12A, G17A, E762A, H840A, N854A, N863A, H982A, H983A, A984A, and/or D986A), the polypeptide can still bind to target DNA in a site-specific manner (because it is still guided to a target DNA sequence by a DNA-targeting RNA) as long as it retains the ability to interact with the DNA-targeting RNA. In some examples, the modified form of the Cas9 polypeptide harbors both the D10A and the H840A mutations (or the corresponding mutations of any of the proteins set forth as SEQ ID NOs:1-256 and 795-1346 of US20140068797) such that the polypeptide has a reduced ability to cleave both the complementary and the non-complementary strands of the target DNA (i.e., the variant can have no substantial nuclease activity).

Cas Proteins

A Cas protein encoded by a nucleic molecule introduced into a host cell can be any cas protein, such as, for example, Cas1, Cas1B, Cas2, Cas3, Cas4, Cas5, Cas6, Cas7, Cas8, Cas9 (also known as Csn1 and Csx12), Cas10, Cpf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, C2c1, C2c2, C2c3, homologs thereof, or modified versions thereof. The Cas protein can be a Cas9 protein, such as a Cas9 protein of *S. pyogenes, S. thermophilus, S. pneumonia*, or *Neisseria meningitidis*, as nonlimiting examples. The Cas9 enzyme can cleave one or both strands of DNA at the location of a target sequence, such as within the target sequence and/or within the complement of the target sequence. For example, the cas9 enzyme can directs cleavage of one or both strands within about 1, 2, 3, 4, 5, 6, 7, 8, 9, 10, 15, 20, 25, 50, 100, or 200 base pairs from the first or last nucleotide of a target sequence.

In some examples, a nucleic acid molecule introduced into a host cell for generating a high efficiency genome editing cell line encodes a cas9 enzyme that is mutated to with respect to the corresponding wild-type enzyme such that the mutated cas9 enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In some embodiments, a Cas9 nickase may be used in combination with guide sequenc(es), e.g., two guide sequences, which target respectively sense and antisense strands of the DNA target. This combination allows both strands to be nicked and used to induce NHEJ. Two nickase targets (within close proximity but targeting different strands of the DNA) can be used to inducing mutagenic NHEJ. Such targeting of a locus using enzymes that cleave opposite strains at staggered positions can also reduce nontarget cleavage, as both strands must be accurately and specifically cleaved to achieve genome mutation.

As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In some cases, the variant Cas9 site-directed polypeptide is a fusion polypeptide (a “variant Cas9 fusion polypeptide”), i.e., a fusion polypeptide comprising: i) a variant Cas9 site-directed polypeptide; and b) a covalently linked heterologous polypeptide (also referred to as a “fusion partner”). A heterologous nucleic acid sequence may be linked to another nucleic acid sequence (e.g., by genetic engineering) to generate a chimeric nucleotide sequence encoding a chimeric polypeptide. In some embodiments, a variant Cas9 fusion polypeptide is generated by fusing a variant Cas9 polypeptide with a heterologous sequence that provides for subcellular localization (i.e., the heterologous sequence is a subcellular localization sequence, e.g., a nuclear localization signal (NLS) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a hemagglutinin (HA) tag; a FLAG tag; a Myc tag; and the like). In some embodiments, an RNA-guided nuclease can be codon-optimized for optimal expression in a host cell.

Host Cells for Highly Efficient Genome Editing

Provided herein are host cells, including cell lines and microbial strains that express an RNA-guided endonuclease and have genome editing efficiencies of at least 10%, at least 20%, at least 30%, at least 40%, at least 50%, at least 60%, at least 70%, or at least 80%. The efficiency of genome editing is the percentage of cells that are transformed with a donor DNA that become altered at the targeted genetic locus. Typically a donor DNA (also referred to as an editing DNA) includes a selectable marker so that cells that receive the editing construct can be selected for. The percentage of such selected transformants that have an altered targeted locus represents the efficiency of genome editing in the cell line or strain.

Targeting of a particular genetic locus is achieved by co-transforming into the cell a guide RNA that can either be a chimeric guide (that includes, in addition to the crRNA sequence having homology to the target site in the host genome, the tracrRNA sequence that interacts with the RNA-guided endonuclease) or a crRNA that includes a sequence of from about 16 to about 20 nucleotides homologous to the genomic target site and also includes a sequence that interacts with the tracrRNA (the "tracr mate sequence"). Alternatively, a chimeric guide RNA, or a crRNA plus a tracrRNA can be expressed in the host cell by transforming an expression construct into the host cell. In another variation, the host cell can express the tracrRNA from a construct engineered into the cell, and a targeting crRNA can be transformed into the cell, for example, the crRNA can co-transformed into the host cell along with the donor DNA.

The inventors have discovered that these high efficiencies can be obtained by isolating cell lines and strains that have fully penetrant, or culture-wide, expression of the introduced RNA-guided endonuclease gene. Host strains having fully penetrant expression of an RNA-guided endonuclease gene, for example, as Type II Cas gene, such as a Cas9 gene, can be isolated by introducing the gene encoding the RNA-guided endonuclease into a population of cells on the same construct with a gene encoding a detectable marker, such as a fluorescent protein, and assessing the expression level of the physically linked detectable marker gene. Cell lines or microbial strains transformed with a construct that includes a gene encoding an RNA-guided endonuclease, e.g., Cas9, and also includes a gene encoding a fluorescent protein, are analyzed by flow cytometry. A transformed cell line displaying a single fluorescence intensity peak, in which the single fluorescence peak on the flow cytometry histogram is at a higher fluorescence level than the peak displayed by control cells (cells that do not have a fluorescent protein gene), is identified as a fully penetrant cell line.

As demonstrated herein in the examples, the histogram resulting from flow cytometry of a cell culture originating from a single transformed colony, in which fluorescence is indicated on the x axis, typically on a logarithmic scale, and cell number is indicated on the y axis, provides a distribution of the expression level in the culture. It has been found that, when compared with the fluorescence level of control cells that do not express a fluorescent protein gene (e.g., non-transformed cells) which display a single peak at background (autofluorescence) level, a transformed cell line can display a single peak that coincides with that of control cells, indicating that they are non-expressors, or can display two peaks, one of which coincides with that of control cells, indicating that the cell line is not fully penetrant for expression of the fluorescent protein gene. The examples herein demonstrate that expression of a transgene physically linked to the GFP transgene (e.g., Cas9, Cre recombinase, Type I FAS, ZnCys-2845 RNAi) demonstrates fully penetrant expression when the linked GFP gene demonstrates fully penetrant expression.

The method for isolating a fully penetrant cell line or strain analyzes a clonal cell line or strain, not a population of cells originating from independent transformation events. The flow cytometry method does not include selection of a subpopulation of the analyzed cell culture, which originates from a single clone. That is, the method in various preferred embodiments does not include cell sorting.

The method for identifying a cell line or microorganism strain having fully penetrant expression of a transgene, can be used to identify cell lines or strains having fully penetrant expression of an RNA-guided endonuclease.

Target Cells

The methods provided herein may be employed to induce DNA cleavage, DNA modification, and/or transcriptional modulation in mitotic or post-mitotic cells in vivo and/or ex vivo and/or in vitro (e.g., to produce genetically modified cells that can be reintroduced into an individual). Because the DNA-targeting RNA provide specificity by hybridizing to target DNA, a mitotic and/or post-mitotic cell of interest in the disclosed methods may include a cell from any organism (e.g. a bacterial cell, an archaeal cell, a cell of a single-cell eukaryotic organism, a plant cell, an algal cell, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.).

Any type of cell may be of interest (e.g. a stem cell, e.g. an embryonic stem (ES) cell, an induced pluripotent stem (iPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro. Target cells are in many embodiments unicellular organisms, or are grown in culture.

A host cell for genome modification can be a plant, animal, or microbial cell and may optionally be an algal cell, such as a cell of a species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Fragilaropsis, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria,*

*Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria*, or *Volvox*.

Exemplary diatoms include members of the genera *Achnanthes, Amphora, Chaetoceros, Coscinodiscus, Cylindrotheca, Cyclotella, Cymbella, Fragilaria, Fragilaropsis, Hantzschia, Navicula, Nitzschia, Pseudo-Nitzschia, Phaeodactylum, Psammodictyon, Skeletonema, Thalassionema*, and *Thalassiosira*. Examples of eustigmatophytes that may be hosts for synthetic chromosome constructs and synthetic chromosomes as provided herein include not only *Nannochloropsis* species but also species of *Monodus, Pseudostaurastrum, Vischeria*, and *Eustigmatos*. In some examples, an alga of a species of the genus *Nannochloropsis* such as, but are not limited to, *N. gaditana, N. granulata, N. limnetica, N. oceanica, N. oculata*, and *N. salina* is transformed with a synthetic chromosome constructs as provided herein.

Alternatively or in addition, a host cell that includes a synthetic chromosome construct or synthetic chromosome of the present invention may optionally be a heterokont cell, an animal cell, a plant cell, a yeast cell, a fungal cell, or a protist. For example, heterokonts include not only eustigmatophytes and diatoms such as those listed above but also chytrid species, including labrinthulids and thraustochytrids. In some examples, heterokont species considered for use in the invention include, but are not limited to, *Bacillariophytes, Eustigmatophytes, Labrinthulids*, and *Thraustochytrids*. In some examples, the strain may be a species of *Labryinthula, Labryinthuloides, Thraustochytrium, Schizochytrium, Aplanochytrium, Aurantiochytrium, Japonochytrium, Diplophrys*, or *Ulkenia*. For example, the strain may be a species of *Thraustochytrium, Schizochytrium, Oblongichytrium*, or *Aurantiochytrium*.

Also considered are prokaryotic host cells, for example, host cells can be of a species belonging to any of the following groups: Archaea, cyanobacteria, green-sulfur bacteria (e.g., *Chlorobium*), green non-sulfur bacteria, purple sulfur bacteria, or purple non-sulfur bacteria or any of the following genera: *Arthrobacter, Escherichia, Bacillus, Brevibacteria, Clostridium, Corynebacteria, Desulfovibrio, Jeotgalicoccus, Kineococcus, Lactobacillus, Micrococcus, Mycobacterium, Pantoea, Pseudomonas, Rhodococcus, Rhodopseudomonas, Rhodospirillium, Rhodomicrobium, Stenotrophomonas, Vibrio, Streptomyces*, or *Zymomonas*.

The host cells can be cells of any of the groups *Aspergillus, Mucor, Pichia, Pullularia, Saccharomyces, Schizosaccharomyces, Trichoderma, Rhodotorula, Yarrowia*, and alternatively can be mesomycetozoea (e.g., Sphaeroforma), heterokont, or algal cells.

Algal host cells can optionally be of a genus selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phxodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*.

For example, a Cas9 expressing host as provided herein can be a diatom, such as, for example a member of any of the genera *Achnanthes, Amphora, Chaetoceros, Coscinodiscus, Cylindrotheca, Cyclotella, Cymbella, Fragilaria, Fragilariopsis, Hantzschia, Navicula, Nitzschia, Pavlova, Pseudo-Nitzschia, Phaeodactylum, Psammodictyon, Skeletonema, Thalassionema*, and *Thalassiosira*. Eustigmatophytes that can be high efficiency cas9 Editor lines include, without limitation, species of *Eustigmatos, Monodus, Nannochloropsis, Pseudostaurastrum*, and *Vischeria*. For example, microorganisms for genetic modification or nucleic acid isolation as disclosed herein include members of the genus *Nannochloropsis*. Suitable species include but are not limited to *N. gaditana, N. granulata, N. limnetica, N. maritime, N. oceanica, N. oculata*, and *N. salina*. Some preferred species within the genus *Nannochloropsis* include, but are not limited to, *N. gaditana, N. oceanica, N. oculata*, and *N. salina*.

Other types of cells that may be of interest include e.g. a stem cell, e.g. an embryonic stem (ES) cell, an induced pluripotent stem (iPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where “primary cells”, “primary cell lines”, and “primary cultures” are used interchangeably herein to refer to cells and cells cultures that have been derived from a subject and allowed to grow in vitro for a limited number of passages, i.e. splittings, of the culture. For example, primary cultures include cultures that may have been passaged 0 times, 1 time, 2 times, 4 times, 5 times, 10 times, or 15 times, but not enough times go through the crisis stage. Primary cell lines can be are maintained for fewer than 10 passages in vitro. Target cells are in many embodiments unicellular organisms, or are grown in culture.

If the cells are primary cells, such cells may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, phosphate-buffered saline (PBS), Hank’s balanced salt solution, etc., conveniently supplemented with fetal calf serum or other naturally occurring factors, in conjunction with an acceptable buffer at low concentration, e.g., from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% dimethyl sulfoxide (DMSO), 50% serum, 40% buffered medium, or some other such solution as is commonly used in the art to preserve cells at such freezing temperatures, and thawed in a manner as commonly known in the art for thawing frozen cultured cells.

Introducing Nucleic Acid into a Host Cell

A DNA-targeting RNA, or a nucleic acid comprising a nucleotide sequence encoding a transactivating RNA (tracrRNA), chimeric guide RNA (chimeric gRNA) or crispr RNA that targets a genomic locus (crRNA), can be introduced into a host cell by any of a variety of well-known methods. Introducing into a host cell a nucleic acid comprising a nucleotide sequence encoding an RNA-guide endonuclease, such as a gene encoding a Cas polypeptide, such as a Cas9 polypeptide or variant thereof, can be by any of a variety of well-known methods.

Methods of introducing a nucleic acid into a host cell are known in the art, and any known method can be used to introduce a nucleic acid (e.g., an expression construct) into a stem cell, progenitor cell, cell line, primary cell, or microbial cell. Suitable methods include, include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like.

Genetic transformation can result in stable insertion and/or expression of transgenes or tracr RNAs, and in some cases can result in transient expression of transgenes tracr RNAs or guide RNAs. The transformation methods can also be used for the introduction of editing (donor) DNAs. Non-limiting examples of transformation methods that can be used on microorganisms including algae include agitation of cells in the presence of glass beads or silicon carbide whiskers as reported by, for example, Dunahay, Biotechniques, 15(3):452-460, 1993; Kindle, Proc. Natl. Acad. Sci. U.S.A., 1990; Michael and Miller, Plant J., 13, 427-435, 1998. Electroporation techniques have been successfully used for genetic transformation of several microalgal species including *Nannochloropsis* sp. (see, e.g., Chen et al., J. Phycol., 44:768-76, 2008), *Chlorella* sp. (see, e.g., Chen et al., Curr. Genet., 39:365-370, 2001; Chow and Tung, Plant Cell Rep. Vol. 18, No. 9, 778-780, 1999), *Chlamydomonas* (Shimogawara et al., Genetics, 148: 1821-1828, 1998), *Dunaliella* (Sun et al., Mol. Biotechnol., 30(3): 185-192, 2005). Micro-projectile bombardment, also referred to as microparticle bombardment, gene gun transformation, or biolistic bombardment, has been used successfully for several algal species including, for example, diatoms species such as *Phaeodactylum* (Apt et al., Mol. Gen. Genet., 252:572-579, 1996), Cyclotella and Navicula (Dunahay et al., J. Phycol., 31:1004-1012, 1995), Cylindrotheca (Fischer et al., J. Phycol., 35:113-120, 1999), and Chaetoceros sp. (Miyagawa-Yamaguchi et al., Phycol. Res. 59: 113-119, 2011), as well as green algal species such as *Chlorella* (El-Sheekh, Biologia *Plantarum*, Vol. 42, No. 2: 209-216, 1999), and Volvox species (Jakobiak et al., Protist, 155:381-93, 2004). Additionally, *Agrobacterium*-mediated gene transfer techniques can also be useful for genetic transformation of microalgae, as has been reported by, for example, Kumar, Plant Sci., 166(3):731-738, 2004, and Cheney et al., J. Phycol., Vol. 37, Suppl. 11, 2001.

A transformation vector or construct as described herein and/or a donor (editing) DNA as used in methods disclosed herein will typically comprise a marker gene that confers a selectable or scorable phenotype on target host cells. Common selectable markers include antibiotic resistance, fluorescent markers, and biochemical markers and are well-known in the art. Several different antibiotic resistance genes have been used successfully for selection of microalgal transformants, including blastocidin, bleomycin (see, for example, Apt et al., 1996, supra; Fischer et al., 1999, supra; Fuhrmann et al., Plant J., 19, 353-61, 1999, Lumbreras et al., Plant J., 14(4):441-447, 1998; Zaslavskaia et al., J. Phycol., 36:379-386, 2000), spectinomycin (Cerutti et al., Genetics, 145: 97-110, 1997; Doetsch et al., Curr. Genet., 39, 49-60, 2001; Fargo, Mol. Cell. Biol., 19:6980-90, 1999), streptomycin (Berthold et al., Protist, 153:401-412, 2002), paromomycin (Jakobiak et al., Protist, supra.; Sizova et al., Gene, 277:221-229, 2001), nourseothricin (Zaslavskaia et al., 2000, supra), G418 (Dunahay et al., 1995, supra; Poulsen and Kroger, FEBS Lett., 272:3413-3423, 2005, Zaslavskaia et al., 2000, supra), hygromycin (Berthold et al., 2002, supra), chloramphenicol (Poulsen and Kroger, 2005, supra), and many others. Additional selectable markers for use in microalgae such as *Chlamydomonas* can be markers that provide resistance to kanamycin and amikacin resistance (Bateman, Mol. Gen. Genet. 263:404-10, 2000), zeomycin and phleomycin (e.g., ZEOCIN™ pheomycin D1) resistance (Stevens, Mol. Gen. Genet. 251:23-30, 1996), and paramomycin and neomycin resistance (Sizova et al., 2001, supra).

Fluorescent or chromogenic markers that have been used include luciferase (Falciatore et al., J. Mar. Biotechnol., 1: 239-251, 1999; Fuhrmann et al., Plant Mol. Biol., 2004; Jarvis and Brown, Curr. Genet., 19: 317-322, 1991), 0-glucuronidase (Chen et al., 2001, supra; Cheney et al., 2001, supra; Chow and Tung, 1999, supra; El-Sheekh, 1999, supra; Falciatore et al., 1999, supra; Kubler et al., J. Mar. Biotechnol., 1:165-169, 1994), β-galactosidase (Gan et al., J. Appl. Phycol., 15:345-349, 2003; Jiang et al., Plant Cell Rep., 21:1211-1216, 2003; Qin et al., High Technol. Lett., 13:87-89, 2003), and green fluorescent protein (GFP) (Cheney et al., 2001, supra; Ender et al., Plant Cell, 2002, Franklin et al., Plant J., 2002; 56, 148-210).

A variety of known promoter sequences can be usefully deployed for transformation systems, including promoters useful in microalgal species. For example, promoters used to drive transgene expression in microalgae include various versions of the of cauliflower mosaic virus promoter 35S (CaMV35S), which has been used in both dinoflagellates and chlorophyta (Chow et al, Plant Cell Rep., 18:778-780, 1999; Jarvis and Brown, Curr. Genet., 317-321, 1991; Lohuis and Miller, Plant J., 13:427-435, 1998). The SV40 promoter from simian virus has also reported to be active in several algae (Gan et al., J. Appl. Phycol., 151 345-349, 2003; Qin et al., Hydrobiologia 398-399, 469-472, 1999). The promoters of RBCS2 (ribulose bisphosphate carboxylase, small subunit) (Fuhrmann et al., Plant J., 19:353-361, 1999) and PsaD (abundant protein of photosystem I complex; Fischer and Rochaix, FEBS Lett. 581:5555-5560, 2001) from *Chlamydomonas* can also be useful. The fusion promoters of HSP70A/RBCS2 and HSP70A/02TUB (tubulin) (Schroda et al., Plant J., 21:121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of an fcp gene encoding a diatom fucoxanthin-chlorophyll a/b binding protein (Falciatore et al., Mar. Biotechnol., 1:239-251, 1999; Zaslavskaia et al., J. Phycol. 36:379-386, 2000) or the vcp gene encoding a eustigmatophyte violaxanthin-chlorophyll a/b binding protein (see U.S. Pat. No. 8,318,482, incorporated by reference herein).

Inducible promoters can be useful in various aspects of the invention, including, but not limited to, expression of site-specific recombinases such as cre. For example, promoter regions of the NR genes encoding nitrate reductase can be used as inducible promoters in microorganisms including microalgae. The NR promoter activity is typically suppressed by ammonium and induced when ammonium is replaced by nitrate (Poulsen and Kroger, FEBS Lett 272: 3413-3423, 2005), thus gene expression can be switched off or on when microalgal cells are grown in the presence of ammonium/nitrate. Additional algal promoters that can find use in the constructs and transformation systems provided herein include those disclosed in U.S. Pat. No. 8,883,993; U.S. Patent Appl. Pub. No. US 2013/0023035; U.S. Patent Application Pub. No. US 2013/0323780; and U.S. Patent Application Pub. No. US 2014/0363892, all incorporated herein by reference in their entireties.

In some embodiments, a method can involve introducing into a host cell (or a population of host cells) one or more nucleic acids comprising nucleotide sequences encoding a DNA-targeting RNA and/or a variant Cas9 site-directed polypeptide. Suitable nucleic acids comprising nucleotide sequences encoding a DNA-targeting RNA and/or a site-directed polypeptide include expression vectors, where an expression vector comprising a nucleotide sequence encoding a DNA-targeting RNA and/or a site-directed polypeptide is a "recombinant expression vector."

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

In some embodiments, a nucleotide sequence encoding a DNA-targeting RNA and/or a variant Cas9 site-directed polypeptide is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some embodiments, a nucleotide sequence encoding a DNA-targeting RNA and/or a variant Cas9 site-directed polypeptide is operably linked to multiple control elements that allow expression of the nucleotide sequence encoding a DNA-targeting RNA and/or a variant Cas9 site-directed polypeptide in both prokaryotic and eukaryotic cells.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein), it may be a spatially restricted promoter (i.e., transcriptional control element, enhancer, etc.) (e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Examples of inducible promoters include, but are not limited toT7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter (e.g., Tet-ON, Tet-OFF, etc.), Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

Selectable Markers

A selectable marker can be, as nonlimiting examples, a gene conferring resistance to an antibiotic such as blasticidin, bleomycin, chloramphenicol, G418, gentamycin, glyphosate, hygromycin, kanamycin, neomycin, nourseothricin, paromomycin, phleomycin, puromycin, spectinomycin, streptomycin or zeomycin. A selectable marker can also confer resistance to methotrexate or DFMO, or an herbicide such as phosphinothricin, glyphosate, imidazolione, a sulfonylurea, atrazine, glufosinate, or a sulfonamide. A selectable marker can also allow autotorophic growth of an auxotrophic host strain, such as a gene encoding, for example, arginosuccinate lyase, for arginine synthesis, nitrate reductase for nitrogen assimilation (ability to utilize nitrate), thi10 for thiamine biosynthesis, or nic for nicotinamide biosynthesis.

Detectable markers or reporter genes can include genes encoding a variety of fluorescent proteins, including without limitation green, cyan, blue, yellow, orange, and red fluorescent proteins and their variants. Other markers that can be used include enzymes that produce fluorescent or chromogenic products include luciferase (Falciatore et al., *J. Mar. Biotechnol.,* 1: 239-251, 1999; Fuhrmann et al., *Plant Mol. Biol.,* 2004; Jarvis and Brown, *Curr. Genet.,* 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., *J. Mar. Biotechnol.,* 1:165-169, 1994), and β-galactosidase (Gan et al., *J. Appl. Phycol.,* 15:345-349, 2003; Jiang et al., Plant Cell Rep., 21:1211-1216, 2003; Qin et al., *High Technol. Lett.,* 13:87-89, 2003). Further nonlimiting examples of enzymes that can be used for detecting a colored or labeled product include aryl sulfatase (Davies et al. (1992) *Nucl. Acids. Res.* 20:2959-2965; Hallman and Sumper (1994) *Eur. J. Biochem.* 221:143-150), alkaline phosphatase (El-Sankary et al. (2001) *Drug Metab. Disposition* 29:1499-1504), and chloramphenicol acetyl transferase (Sekiya et al. (2000) *J. Biol. Chem.* 275:10738-10744).

A selectable marker can provide a means to obtain heterokont cells, algal cells, yeast cell, plant cells or any combination that express the marker and, therefore, include the synthetic chromosome construct, and can therefore be useful as a component of a synthetic chromosome of the present disclosure. Examples of selectable markers include genes encoding deaminase, such as the deaminase from *Aspergillus terreus*, which confers resistance to Blasticidin S (Tamura, *Biosci. Biotechnol. Biochem.* 59: 2336-2338, 1995), as well as genes conferring resistance to antibiotics such as bleomycin, gentamycin, glyphosate, hygromycin, kanamycin, neomycin, phleomycin, puromycin, spectinomycin, and streptomycin. For example, neomycin phosphotransferase confers resistance to the aminoglycosides neomycin, kanamycin and paromycin (Herrera-Estrella, *EMBO J.* 2:987-995, 1983) and the "hygro" gene confers resistance to hygromycin (Marsh, *Gene* 32:481-485, 1984). Several different antibiotic resistance genes have been used successfully for selection of microalgal transformants, including blastocydin, bleomycin (see, for example, Apt et al., 1996, supra; Fischer et al., 1999, supra; Fuhrmann et al., *Plant J.,* 19, 353-61, 1999, Lumbreras et al., *Plant J.,* 14(4):441-447, 1998; Zaslavskaia et al., *J. Phycol.,* 36:379-386, 2000), spectinomycin (Cerutti et al., *Genetics,* 145: 97-110, 1997; Doetsch et al., *Curr. Genet.,* 39, 49-60, 2001; Fargo, *Mol. Cell. Biol.,* 19:6980-90, 1999), streptomycin (Berthold et al., *Protist,* 153:401-412, 2002), paromomycin (Jakobiak et al., *Protist*, supra.; Sizova et al., *Gene,* 277:221-229, 2001), nourseothricin (Zaslavskaia et al., 2000, supra), G418 (Dunahay et al., 1995, supra; Poulsen and Kroger, *FEBS Lett.,* 272:3413-3423, 2005, Zaslavskaia et al., 2000, supra), hygromycin (Berthold et al., 2002, supra), chloramphenicol (Poulsen and Kroger, 2005, supra), and others. Additional selectable markers for use in microalgae can be markers that provide resistance to kanamycin and amikacin (Bateman, *Mol. Gen. Genet.* 263:404-10, 2000), zeomycin and phleomycin (e.g., ZEOCIN™ pheomycin D1) (Stevens, *Mol. Gen. Genet.* 251:23-30, 1996), and paramomycin and neomycin (Sizova et al., 2001, supra).

Also considered are genes conferring resistance to antimetabolites, such as methotrexate, e.g., genes encoding dihydrofolate reductase, (Reiss, *Plant Physiol.* (*Life Sci. Adv.*) 13:143-149, 1994); trpB, which allows cells to utilize indole in place of tryptophan; hisD, which allows cells to utilize histinol in place of histidine (Hartman, *Proc. Nat. Acad. Sci., USA* 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: *Current Communications in Molecular Biology*, Cold Spring Harbor Laboratory ed.). Additional selectable markers include those that confer herbicide resistance, for example, phosphinothricin acetyltransferase gene, which confers resistance to phosphinothricin (White et al., *Nucl. Acids Res.* 18:1062, 1990; Spencer et al., *Theor. Appl. Genet.* 79:625-631, 1990), a mutant EPSPV-synthase, which confers glyphosate resistance (Hinchee et al., *BioTechnology* 91:915-922, 1998), a mutant acetolactate synthase, which confers imidazolione or sulfonylurea resistance (Lee et al., *EMBO J.* 7:1241-1248, 1988), a mutant psbA, which confers resistance to atrazine (Smeda et al., *Plant Physiol.* 103:911-917, 1993), or a mutant protoporphyrinogen oxidase (see U.S. Pat. No. 5,767,373), or other markers conferring resistance to an herbicide such as glufosinate, sulfonamide, or phosphinothricin or sulfonylurea (see, for example, Maliga et al., *Methods in Plant Molecular Biology*, Cold Spring Harbor Laboratory Press, 1995, page 39). Genes conferring resistance to antibiotics such as tetracycline; ampicillin, kanamycin, and chloramphenicol can be used for selection of the synthetic chromosome construct in prokaryotes such as *E. coli.*

Auxotrophic markers are selectable markers that can be used in a host having a mutation in a gene encoding a metabolic enzyme, such as, for example, arginosuccinate lyase, for arginine synthesis, nitrate reductase for nitrogen assimilation (ability to utilize nitrate), thi10 for thiamine biosynthesis, and nic for nicotinamide biosynthesis.

Negative selection markers that may be included on a synthetic chromosome construct or synthetic chromosome include, without limitation, thymidine kinase (Lupton et al. (1991) *Molecular and Cellular Biology* 11: 3374-3378), DAOO (Erikson et al. (2004) *Nature Biotechnology* 22: 455-458) URA, and sacB (Quenee et al. (2005) Biotechniques 38: 63-67).

A variety of known promoter sequences can be usefully deployed for transformation systems of microalgal and heterokont species. For example, the promoters commonly used to drive transgene expression in microalgae include various versions of the of cauliflower mosaic virus promoter 35S (CaMV35S), which has been used in both dinoflagellates and chlorophyta (Chow et al, *Plant Cell Rep.,* 18:778-780, 1999; Jarvis and Brown, *Curr. Genet.,* 317-321, 1991; Lohuis and Miller, *Plant J.,* 13:427-435, 1998). The SV40 promoter from simian virus has also reported to be active in several algae (Gan et al., *J. Appl. Phycol.,* 151345-349, 2003; Qin et al., Hydrobiologia 398-399, 469-472, 1999). The promoters of RBCS2 (ribulose bisphosphate carboxylase, small subunit) (Fuhrmann et al., *Plant J.,* 19:353-361, 1999) and PsaD (abundant protein of photosystem I complex; Fischer and Rochaix, *FEBS Lett.* 581:5555-5560, 2001) from *Chlamydomonas* can also be useful. The fusion promoters of HSP70A/RBCS2 and HSP70A/02TUB (tubulin) (Schroda et al., *Plant J.,* 21:121-131, 2000) can also be useful for an improved expression of transgenes, in which HSP70A promoter may serve as a transcriptional activator when placed upstream of other promoters. High-level expression of a gene of interest can also be achieved in heterokonts, for example diatoms species, under the control of a promoter of an fcp gene encoding a diatom fucoxanthin-chlorophyll a/b binding protein (Falciatore et al., *Mar. Biotechnol.,* 1:239-251, 1999; Zaslavskaia et al., *J. Phycol.* 36:379-386, 2000) or the vcp gene encoding a eustigmatophyte violaxanthin-chlorophyll a/b binding protein (see U.S. Pat. No. 8,318,482). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, *FEBS Lett* 272: 3413-3423, 2005), thus gene expression can be switched off or on when microalgal cells are grown in the presence of ammonium/nitrate. Other regulatable promoters from *Nannochloropsis* include those disclosed in U.S. Patent Application Publication No. US2013/0023035, incorporated by reference herein. Additional *Nannochloropsis* algal promoters that can find use in the constructs and transformation systems provided herein include those disclosed in U.S. Pat. No. 8,709,766; U.S. Patent Application Publication No. US2013/0323780; U.S. patent application Ser. No. 13/693, 585, filed Dec. 4, 2012; and U.S. patent application Ser. No. 13/915,522, filed Jun. 11, 2013, all incorporated by reference herein.

EXAMPLES

Example 1. Construction of a Cas9-Expressing *Nannochloropsis* Line

A construct was engineered for the expression of a gene encoding the *Streptococcus pyogenes* Cas9 endonuclease using a vector based on a pCC1BAC backbone. The vector included an engineered Cas9 gene having a sequence codon optimized for *Nannochloropsis gaditana* (SEQ ID NO:1) that encoded the Cas9 protein from *Streptococcus pyogenes* (SEQ ID NO:2). A sequence encoding a Nuclear Localization Signal (NLS) peptide (SEQ ID NO:3) from SV40 that was also codon optimized for *Nannochloropsis gaditana* (SEQ ID NO:4) was linked to the 5' end of the Cas9-encoding sequence, and a sequence (SEQ ID NO:5) encoding a FLAG tag peptide (SEQ ID NO:6) was cloned 3' of the Cas9-encoding sequence. The entire engineered Cas9 gene (SEQ ID NO:7), encoding the engineered NLS-Cas9-Cterminal FLAG protein (SEQ ID NO:8) was cloned 3' of the *N. gaditana* RPL7 promoter (SEQ ID NO:9) and 5' of the *N. gaditana* 6487 terminator (SEQ ID NO:42). The construct also included a selectable marker expression cassette, which included the blasticidin S deaminase ("blast") gene from *Aspergillus terreus* codon-optimized for *Nannochloropsis gaditana* (SEQ ID NO:10), driven by the *N. gaditana* TCTP promoter (SEQ ID NO:11). The EIF3 terminator (SEQ ID NO:12) was positioned at the 3' end of the blast gene. In addition, the vector included an expression cassette designed to drive expression of a chimeric guide RNA (SEQ ID NO:13) designed to include a 20 bp sequence for targeting the *N. gaditana* acyl-coA oxidase gene (SEQ ID NO:14), driven by the *N. gaditana* putative U6 promoter (SEQ ID NO:15) and U6 terminator (SEQ ID NO:16). A diagram of the construct, named pSGE-6133, is provided in FIG. 1.

To target the *N. gaditana* acyl-CoA oxidase gene, the pSGE-6133 construct was linearized with SwaI restriction enzyme and transformed into *Nannochloropsis* cells by electroporation essentially according to methods known in the art (see, for example U.S. Patent Application Publication 2015/0183838, incorporated herein by reference). Blasticidin resistant colonies were obtained and colony PCR was performed on colonies to screen for the presence of the Cas9 gene. For colony screening by PCR, a small amount of cells from a colony to be screened was suspended into 100 μl of 5% Chelex 100 Resin (BioRad, Hercules, CA)/TE solution and the suspension was boiled for boiled 10 minutes at 99° C., after which the tubes were briefly spun. One microliter of the lysate supernatant was added to a PCR reaction mix, in which the PCR mixture and reactions were set up and performed according to the QIAGEN Fast Cycling PCR Master Mix Protocol (Qiagen, Germantown, MD) from the manufacturer (Handbook available at giagen.com) using primers derived from the sequence of the engineered Cas9 construct.

Twelve of the transformed strains that were found to include the Cas9 gene were then screened by Western blot to determine the level of the Cas9 protein in the cells. Samples were removed from liquid culture of the selected strains and cells were counted using an Accuri flow cytometer. Based on the cell count, an aliquot of 2×10 cells was removed from each sample culture and centrifuged at maximum speed in a microcentrifuge. The supernatant was discarded and the pelleted cells were resuspended in 2×LDS buffer that included 100 mM DTT. The samples were boiled for 10 minutes (99° C.). The lysate (10 μl) was run on a 3-8% Tris-Acetate Gel with Tris-Acetate/SDS running buffer to separate proteins, after which proteins were transferred to PVDF membrane using an iBlot Western transfer apparatus (Invitrogen; Carlsbad, CA) according to manufacturer's instructions. For detection of the FLAG-tagged Cas9 protein, membranes were first blocked with a blocking solution of 5% milk in TBST (50 mM Tris pH7.4, 150 mM NaCl, 0.15% Tween20) and then incubated with anti-FLAG alkaline phosphatase conjugated antibody (diluted 1 to 4000 in blocking solution) overnight. The membrane was washed 3 times with TBST and the membrane was then developed with BCIP/NBT chromagen and dried to visualize the antibody-bound protein.

The strain determined to have the highest level of the Cas9 protein was GE-6571. As this strain had the highest level of expression of the Cas9 protein and also was engineered to express the chimeric guide RNA (SEQ ID NO:13) targeting the *N. gaditana* acyl-CoA oxidase gene (SEQ ID NO:48), the GE-6571 strain was analyzed for mutations within the acyl-CoA oxidase gene by colony PCR as described above along with the rest of the western-positive strains. For PCR, the primers used were ACO2-upstreamF (SEQ ID NO:17) and ACO2-downstreamR (SEQ ID NO:18) which together produced an 852 bp PCR fragment (SEQ ID NO:19) that included the targeted portion of the acyl-CoA oxidase gene. PCR fragments were Sanger sequenced using the same primers to determine the presence of any mutations. No mutations were detected at the target site of the acyl-CoA oxidase gene. Subsequent Northern blots and RT-PCR experiments failed to detect any guide RNA transcript.

Figure 2:
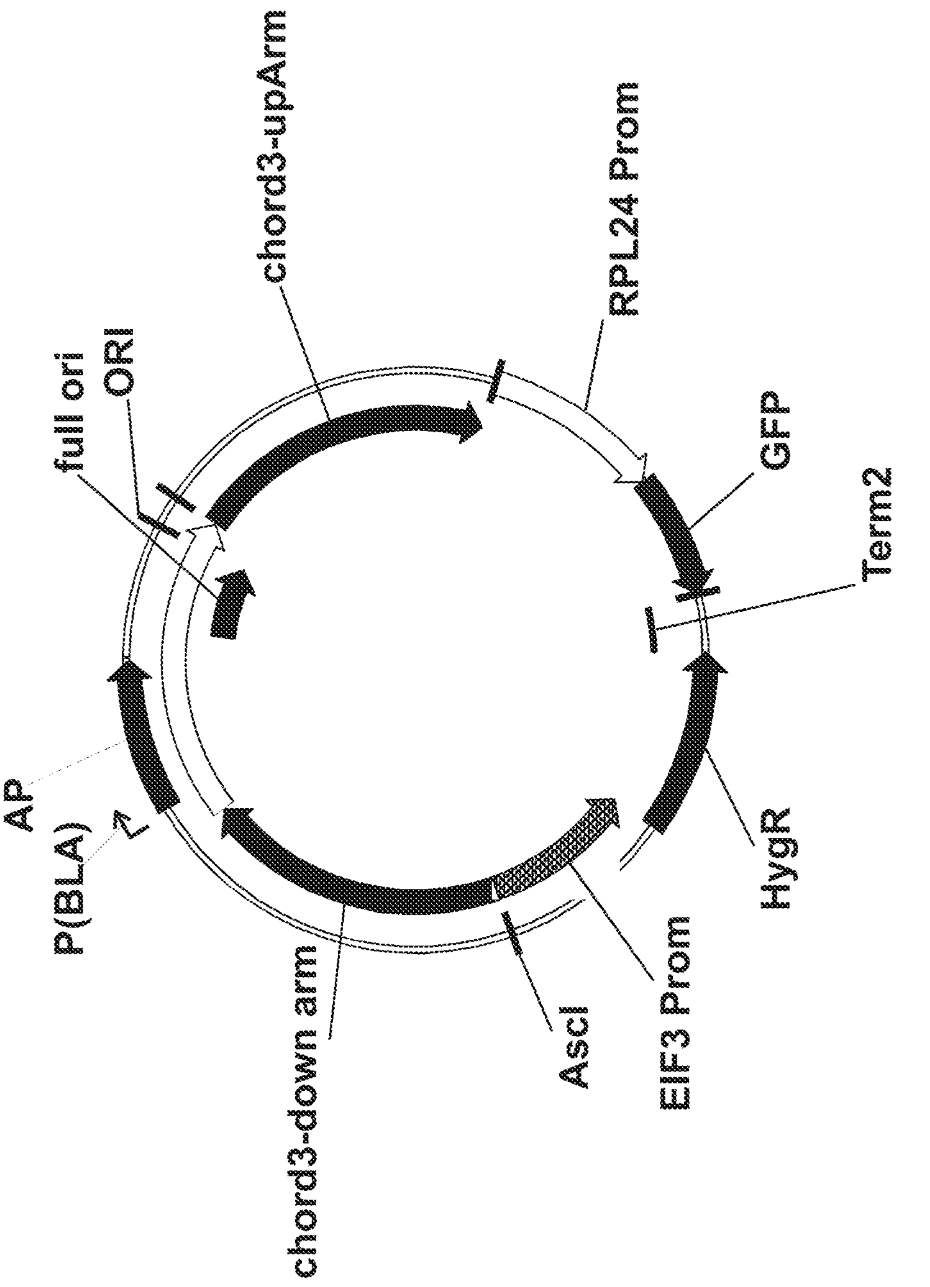
FIG. 2 is a diagram of the Chord3-KO vector that includes homology arms for the CHORD-3266 gene of *Nannochloropsis* flanking a cassette that includes a GFP gene codon optimized for *Nannochloropsis* operably linked to the *Nannochloropsis* RPL24 promoter and a hygromycin resistance gene codon optimized for *Nannochloropsis* and operably linked to the *Nannochloropsis* EIF3 promoter. The GFP gene and HygR gene are operably linked to the same bidirectional terminator at their 3' ends.

Example 2. Use of Strain GE-6571 to Generate Targeted CHORD-3266 Mutants by Co-Transformation of In Vitro Synthesized Guide RNA and Selectable Donor DNA The GE-6571 Cas9 expression strain was then tested for its ability to generate mutations in a targeted gene by co-transformation of in vitro synthesized chimeric guide RNA (gRNA) (SEQ ID NO:20) targeting a sequence in a *Nannochloropsis* gene encoding the CHORD-3266 polypeptide having a CHORD (cysteine and histidine rich) domain; SEQ ID NO:21) and one of the following three forms of selectable DNA; 1) a fragment that only included a hygromycin resistance (HygR) gene (SEQ ID NO:22) under the control of the *N. gaditana* EIF3 promoter (SEQ ID NO:23), and a TurboGFP gene (Evrogen, Moscow, Russia) codon optimized for *Nannochloropsis gaditana* (SEQ ID NO:24) under the control of the *N. gaditana* RPL24 promoter (SEQ ID NO:25), with both genes terminated by *N. gaditana* bidirectional terminator 2 (SEQ ID NO:26), found between the NADH-dependent fumarate reductase gene and D-tyrosyl-tRNA(Tyr) deacylase gene in the *N. gaditana* genome, 2) a circular form of a vector named "Chord3-KOvector" (SEQ ID NO:27; FIG. 2) which included all of the elements in the fragment described above, but in this case the elements were flanked by 2 kb "up" (SEQ ID NO:28) and "down" (SEQ ID NO:29) arms which are homologous to sequences upstream and downstream of the CRISPR target sequence (SEQ ID NO:30) and contain a puc19 vector backbone, or 3) a linear DNA molecule which was released by PmeI digest from the "Chord3-KOvector" which contains all the elements of the circular homologous vector but without the puc19 backbone. The same DNA series was transformed into GE-6571 without a gRNA as a control.

The chimeric guide RNA that was designed to target the coding region of the CHORD-3266 gene included 20 nucleotides of sequence (SEQ ID NO:31) with homology to the CRISPR target in the CHORD-3266 gene (SEQ ID NO:30) upstream of the *S. pyogenes* Cas9 PAM sequence (NGG), within a 103 total chimeric guide RNA sequence (SEQ ID NO:32) that included the transactivating CRISPR (tracr) sequence. The entire chimeric guide sequence was synthesized by first making a DNA template made up of complementary DNA oligonucleotides (SEQ ID NO:33 and SEQ ID NO:34) in which the DNA sequence encoding the guide RNA molecule was included downstream of a T7 promoter sequence (SEQ ID NO:35). The oligos were annealed to create a double stranded DNA template, which was used as the template for in vitro transcription reactions that were performed using the MEGAshortscript™ T7 Kit (Life Technologies cat #AM1354M; Carlsbad, CA) according to the manufacturer's protocol. The resulting RNA was purified using Zymo-Spin™ V-E columns (Zymo Research; Irvine, CA; cat #C1024-25) according to manufacturer's protocol.

Figure 3:
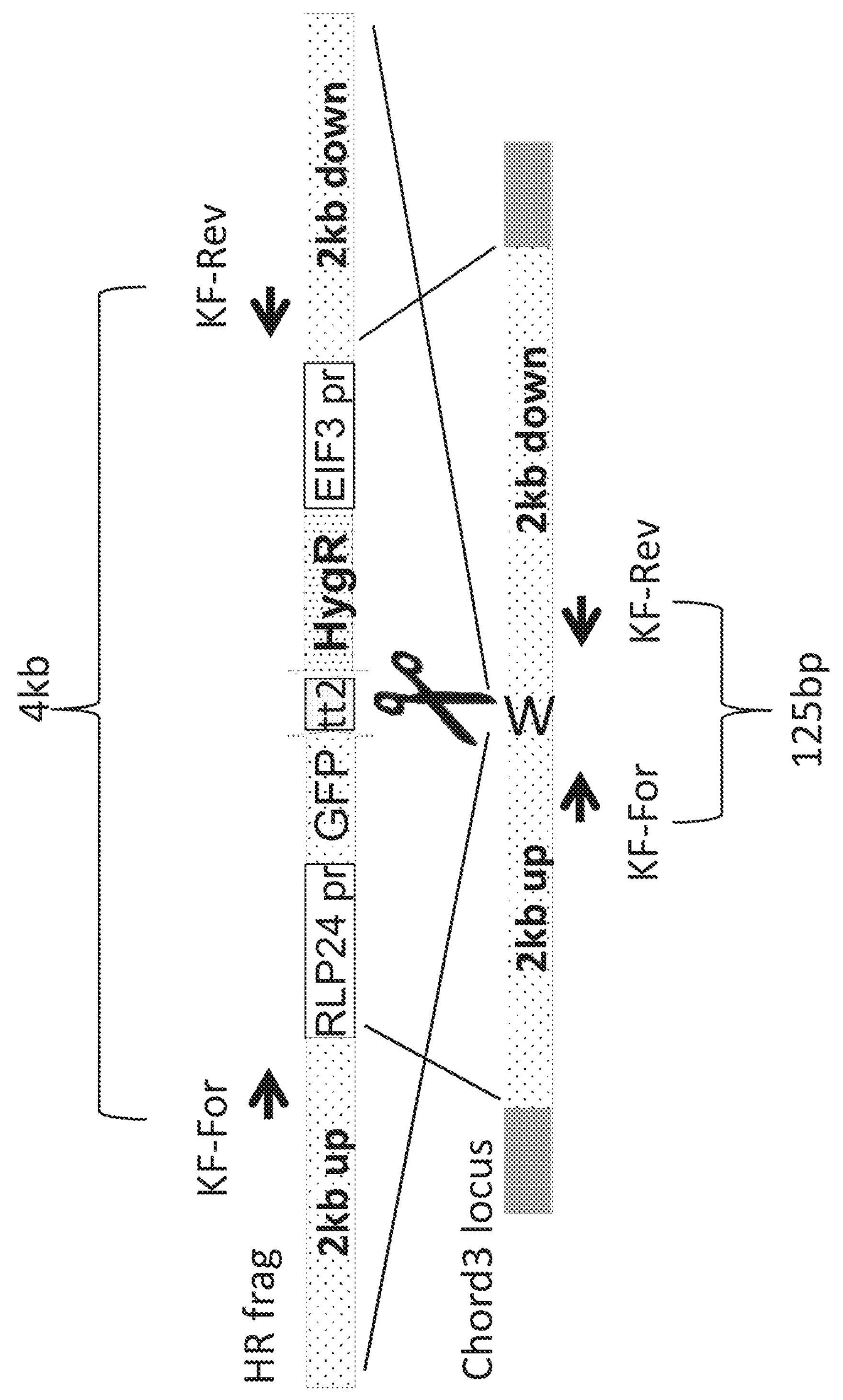
FIG. 3 depicts a strategy for disrupting the *Nannochloropsis* CHORD-3266 gene using the CRISPR system. The Chord3-KO (knockout) vector depicted in FIG. 2 is designed for double homologous recombination with homology regions that flank the CHORD-3266 CRISPR target sequence in the genome. A guide RNA molecule targeting CHORD is introduced along with the knockout vector. The guide RNA and Cas9 complex are depicted as scissors. The donor fragment can be the homologous recombination fragment (HR frag) released from the Chord3-KO (knockout) vector or the intact vector can be introduced into the host cell to generated recombinants. The diagnostic PCR primers are shown aligned over the locus that includes the donor fragment, which would result in an approximately 4 kb PCR product, and the native locus, which would result in an approximately 125 bp fragment if the donor fragment did not insert.

The GE-6571 Cas9 expression strain was transformed by electroporation using 5 µg of purified chimeric guide RNA targeting the CHORD-3266 gene and 1 µg of one of the forms of selectable donor DNA (1, 2, or 3) described previously in this example. Following electroporation, cells were plated on agar media containing hygromycin to select for transformants that incorporated the hygromycin cassette. Transformants were screened by Colony PCR using primers designed to amplify across the CHORD-CRISPR target (SEQ ID NO:36 and SEQ ID NO:37), yielding a 100 bp band if no DNA was inserted and no or very minor NHEJ mis-repair occurred, or a single 4 kb band if the selectable marker and reporter cassette was inserted by NHEJ or homologous recombination (FIG. 3). NHEJ mis-repair resulting in small insertions or deletions would likely be seen as a small shift in the 100 bp product, which should have been detectable using the 3% agarose gel electrophoresis. However, to rule out any small and hard to detect insertions or deletions due to NHEJ mis-repair, strains which initially yielded a single 100 bp band underwent an additional round of colony PCR using a different primer set in which the priming sites resided farther away from the CRISPR target site, and the PCR products were Sanger sequenced using the same primers. Out of 555 hygromycin-resistant colonies screened for the different transformation strategies (i.e., using the three different forms of selectable donor DNA as described above in this example), only 5 mutants were found, providing a mutation rate of approximately 1%. Furthermore, all 5 mutants were obtained by co-transformation of selectable DNA with homologous arms (i.e., DNA insertion was by way of double recombination within the gene homology arms, for both circular and linear donor DNA forms), and no mutants were obtained using the fragment that lacked CHORD-3266 homologous arms. This fragment that did not include homology arms was never observed to have been inserted by NHEJ "knock-in", and furthermore, no mutants were caused by apparent NHEJ mis-repair. No mutants were obtained from the transformants generated by the control transformations where gRNA was omitted.

Example 3. Development of Fully Penetrant *Nannochloropsis* Cas9 Editor Lines To improve the efficiency of making genome alterations, improved Cas9-expressing strains were produced. To do this, *Nannochloropsis* strains were engineered and isolated that exhibited expression of the introduced Cas9 genes in essentially 100% of the cell population of a growing culture.

Figure 4:
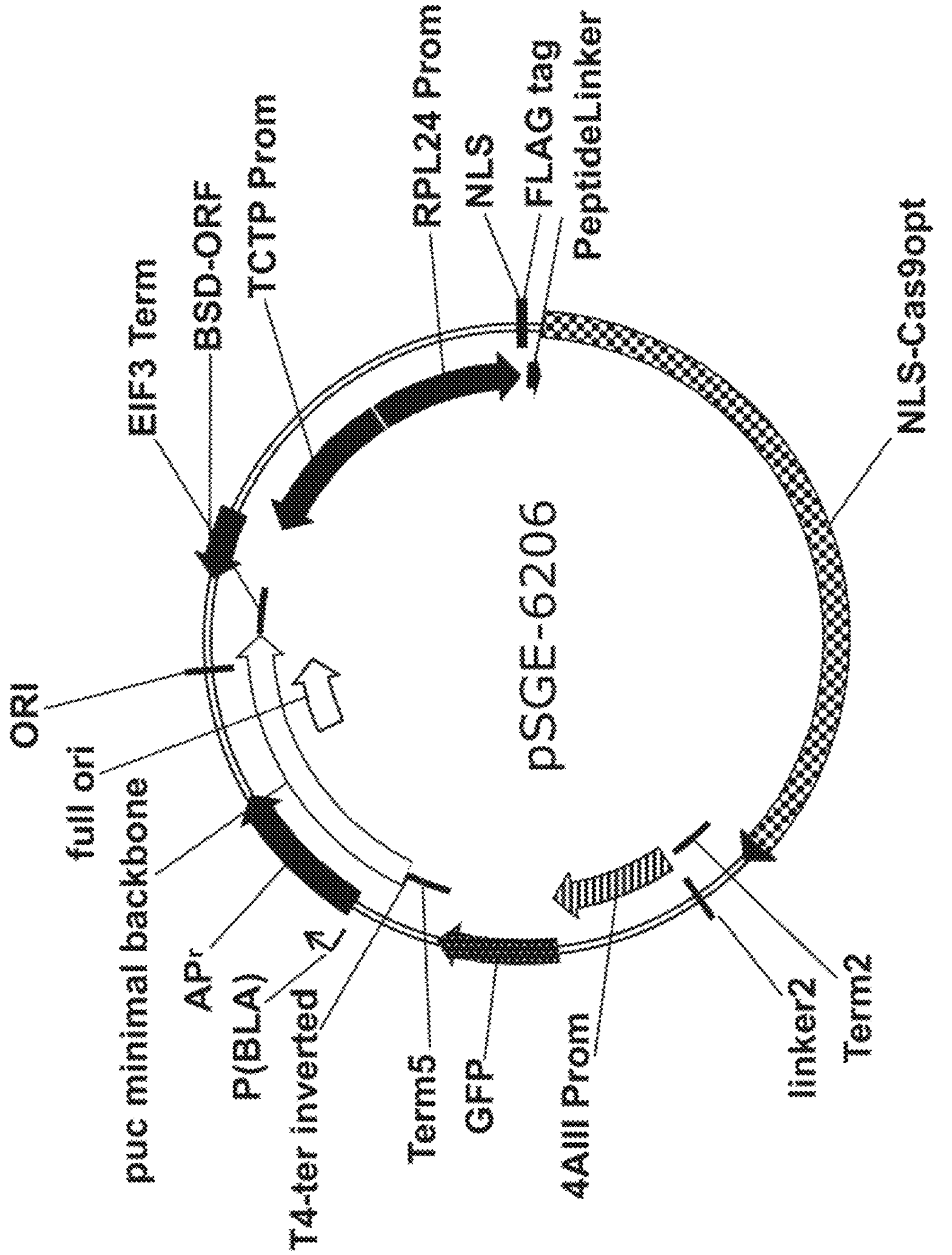
FIG. 4 is a diagram of vector pSGE-6206 that includes a Cas9 protein codon optimized for *Nannochloropsis* that includes a nuclear localization sequence (NLS) and also includes a GFP gene.

The first step in generating a fully penetrant Cas9 line was to introduce a gene encoding a fluorescent protein on the vector that included the Cas9 gene. The vector pSGE-6206 (SEQ ID NO:38) (FIG. 4) included the following three elements: 1) a Cas9 expression cassette which contained a Cas9 gene from *Streptococcus pyogenes* codon optimized for *Nannochloropsis gaditana* (SEQ ID NO:1) with an N-terminal FLAG tag (SEQ ID NO:5), nuclear localization signal (SEQ ID NO:4), and peptide linker (SEQ ID NO:39), driven by the *N. gaditana* RPL24 promoter (SEQ ID NO:25) and terminated by *N. gaditana* bidirectional terminator 2 (SEQ ID NO:26); 2) a selectable marker expression cassette, which contained the blast gene from *Aspergillus terreus* codon optimized for *N. gaditana* ("BSD"; SEQ ID NO:10), driven by the *N. gaditana* TCTP promoter (SEQ ID NO:11) and followed by the EIF3 terminator (SEQ ID NO:12); and 3) a GFP reporter expression cassette, which contained the TurboGFP gene (Evrogen, Moscow, Russia) codon-optimized for *Nannochloropsis gaditana* (SEQ ID NO:24), driven by the *N. gaditana* 4A-III promoter (SEQ ID NO:40) and followed by the *N. gaditana* bidirectional terminator 5 (SEQ ID NO:41) which occurs between the Glucosamine 6-phosphate isomerase 2 gene and the YVTN repeat like quinoprotein amine dehydrogenase gene in the *N. gaditana* genome.

An additional GFP trackable Cas9 vector (pSGE-6202) was created that was similar to pSGE-6206, except that in pSGE-6202 the Cas9 gene was driven by the *N. gaditana* RPL7 promoter (SEQ ID NO:9) and the *N. gaditana* 6487 terminator (SEQ ID NO:42), which were also used in the pSGE-6133 vector (Example 1).

Strains transformed with either pSGE-6206 or pSGE-6202 were plated onto PM74 agar medium containing 100 mg/L of blasticidin. Colonies were patched onto selection media for analysis and archiving. A small amount of biomass was taken from the patches and completely resuspended in 300 µl of 1× Instant Ocean solution (Aquatic Eco Systems, Apopka, FL). Care was taken to not add too much biomass so that a light green resuspension was obtained. This liquid was directly analyzed by flow cytometry using a BD Accuri C6 flow cytometer, using a 488 nm laser and 530/10 nm filter to measure GFP fluorescence per cell. 10,000-30,000 events were recorded for each sample using the slow fluidics setting. The resulting histograms were overlayed with histograms of wild type cells (i.e., cells not expressing a fluorescent protein) run separately. Only strains with fully penetrant expression in culture were carried forward; this meant that the flow cytometry GFP fluorescence histogram showed a single peak or bell-shaped curve in which the fluorescence peak was fully shifted higher than the wild type autofluorescence (background fluorescence) peak when plotted on a log scale (FIGS. 5A and B). These strains were designated as "fully penetrant" Cas9 expressing strains, in that the expression of the GFP gene was found throughout the cells of a culture of the strain. That is, while at any given point in time the amount (and therefore fluorescence) of GFP might vary somewhat cell-to-cell, resulting in peaks or bell-shaped curves, there was no subpopulation of cells exhibiting a distinct distribution of GFP expression with respect to the shifted peak. Thus, a fully penetrant strain was one in which there was a single peak (or bell-shaped curve having a peak) where the peak was separate from and at a higher fluorescence value than the background peak of non-expressing cells (e.g., cells not transformed with a GFP expression construct). Because the GFP gene was physically associated with the Cas9 gene in the introduced constructs, it was postulated that the Cas9 gene was also likely expressed throughout the cells of a culture of the strain in fully penetrant GFP strains.

Figure 6:
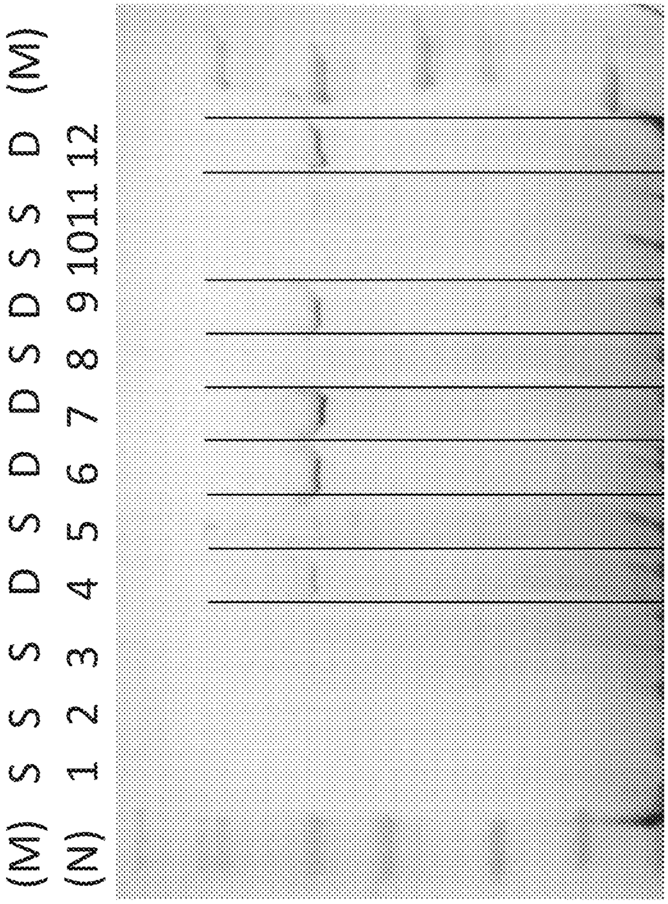
FIG. 6 is a Western blot with an antibody that recognizes the FLAG-tagged cas9 protein. "S" identifies proteins from cells that demonstrated a single shifted peak in flow cytometry performed to assess penetrance, and "D" identifies proteins from cells that demonstrated two peaks in flow cytometry analysis.

Fully GFP-penetrant Cas9 strains demonstrating a single clearly shifted fluorescence peak with respect to nontransformed cells (see FIG. 5A and Table 1, in which clones are scored by 'X's' according to whether they exhibited single or double peaks) were then tested by western blotting with an anti-FLAG antibody for evidence of Cas9 expression. An example of a strain (clone p1-27) that exhibited a single peak separated from the autofluorescence peak of nontransformed cells is provided in FIG. 5A, and compared with clone p2-02, which had two peaks, one of which coincided with the control (no GFP construct) peak (FIG. 5B). One strain resulting from transformation with each vector (pSGE-6206 and pSGE-6202) that exhibited only a single peak by flow cytometry that recorded GFP fluorescence levels, where the single peak was shifted to a higher fluorescence level than no GFP controls, and that also demonstrated Cas9 protein expression by Western (FIG. 6) was carried forward for genome editing tests. Strain GE-6594 was selected as a fully penetrant Cas9 strain resulting from transformation with pSGE-6202, and strain GE-6791 was selected as a fully penetrant Cas9 strain resulting from transformation with pSGE-6206.

TABLE 1

Nannochloropsis lines transformed with Cas9 expression vector pSGE-6202 scored for exhibiting Double or Single fluorescence peaks by flow cytometry

| | | Double | Single | FL-1 |
|---|---|---|---|---|
| B05 | p2-02 | X | | 4111.8 |
| B02 | p1-10 | X | | 3589.9 |
| C04 | p1-27 | | X | 3364.2 |
| B12 | p3-26 | | X | 2684.9 |
| B09 | p3-02 | | X | 2661.7 |
| A02 | p1-09 | X | | 2352.2 |
| C02 | p1-11 | X | | 2084.9 |
| E02 | p1-13 | X | | 2031.6 |
| B01 | p1-02 | X | | 1969.0 |
| E11 | p3-21 | X | | 1933.3 |
| E07 | p2-21 | X | | 1909.3 |
| B11 | p3-18 | X | | 1881.1 |
| C10 | p3-11 | X | | 1775.7 |
| B08 | p2-26 | X | | 1755.3 |
| H01 | p1-08 | X | | 1730.2 |
| D08 | p2-28 | X | | 1707.0 |
| C05 | p2-03 | X | | 1694.5 |
| D07 | p2-20 | X | | 1685.0 |
| E12 | p3-29 | X | | 1588.7 |
| H02 | p1-16 | X | | 1560.2 |
| C08 | p2-27 | X | | 1556.6 |
| F04 | p1-30 | X | | 1551.8 |
| H05 | p2-08 | X | | 1547.5 |
| H04 | p1-32 | X | | 1540.4 |
| H08 | p2-32 | X | | 1538.1 |
| F03 | p1-22 | X | | 1529.2 |
| A07 | p2-17 | X | | 1523.1 |
| B07 | p2-18 | X | | 1497.1 |
| F06 | p2-14 | X | | 1496.7 |
| A05 | p2-01 | X | | 1488.0 |
| F11 | p3-22 | X | | 1465.9 |
| D04 | p1-29 | X | | 1459.6 |
| G12 | p3-31 | X | | 1449.0 |
| H07 | p2-24 | X | | 1441.7 |
| D03 | p1-20 | X | | 1425.8 |
| H06 | p2-16 | X | | 1413.9 |
| H10 | p3-16 | X | | 1404.2 |
| C03 | p1-19 | X | | 1374.8 |
| E08 | p2-29 | X | | 1374.3 |
| D09 | p3-04 | X | | 1361.7 |
| B04 | p1-26 | X | | 1349.9 |
| E01 | p1-05 | X | | 1330.9 |
| G08 | p2-31 | X | | 1308.8 |
| A06 | p2-09 | X | | 1288.0 |
| H03 | p1-24 | X | | 1280.9 |
| F07 | p2-22 | X | | 1276.6 |
| C01 | p1-03 | X | | 1252.3 |
| F10 | p3-14 | X | | 1234.3 |
| C07 | p2-19 | X | | 1227.7 |
| H11 | p3-24 | X | | 1226.7 |

TABLE 1-continued

Nannochloropsis lines transformed with Cas9 expression vector pSGE-6202 scored for exhibiting Double or Single fluorescence peaks by flow cytometry

| | | Double | Single | FL-1 |
|---|---|---|---|---|
| C11 | p3-19 | X | | 1214.1 |
| E10 | p3-13 | X | | 1209.1 |
| E09 | p3-05 | X | | 1178.2 |
| F05 | p2-06 | X | | 1151.5 |
| E05 | p2-05 | X | | 1115.7 |
| D06 | p2-12 | X | | 1101.3 |
| H09 | p3-08 | X | | 1070.7 |
| B03 | p1-18 | | X | 1056.4 |
| G02 | p1-15 | | X | 996.8 |
| G03 | p1-23 | X | | 970.68 |
| D01 | p1-04 | | X | 956.46 |
| A01 | p1-01 | | X | 952.68 |
| B10 | p3-10 | | X | 948.74 |
| D12 | p3-28 | | X | 918.9 |
| F02 | p1-14 | | X | 914.78 |
| All | p3-17 | | X | 914.25 |
| Dll | p3-20 | | X | 912.9 |
| D02 | p1-12 | | X | 907.08 |
| G04 | p1-31 | | X | 892.9 |
| A08 | p2-25 | | X | 891.83 |
| A04 | p1-25 | | X | 888.76 |
| B06 | p2-10 | | X | 887.53 |
| F12 | p3-30 | | X | 886.9 |
| E03 | p1-21 | | X | 882.81 |
| DOS | p2-04 | | X | 880.78 |
| GO1 | p1-07 | | X | 878.16 |
| C06 | p2-11 | | X | 872.85 |
| E04 | p1-29 | | X | 869.05 |
| Gil | p3-23 | | X | 867 |
| GO5 | p2-07 | | X | 864.08 |
| A03 | p1-17 | | X | 861.61 |
| F01 | p1-06 | | X | 861.06 |
| G06 | p2-15 | | X | 861.02 |
| E06 | p2-13 | | X | 857.7 |
| C12 | p3-27 | | X | 854.33 |
| F09 | p3-06 | | X | 849.25 |
| F08 | p2-30 | | X | 843.08 |
| A10 | p3-09 | | X | 840.75 |
| A09 | p3-01 | | X | 834.58 |
| Al2 | p3-25 | | X | 834.53 |
| D10 | p3-12 | | X | 826.53 |
| C09 | p3-03 | | X | 818.38 |
| G07 | p2-23 | | X | 814.46 |
| G10 | p3-15 | | X | 810.45 |
| H12 | p3-32 | | X | 803.66 |
| G09 | p3-07 | | X | 800.77 |

Figure 7:
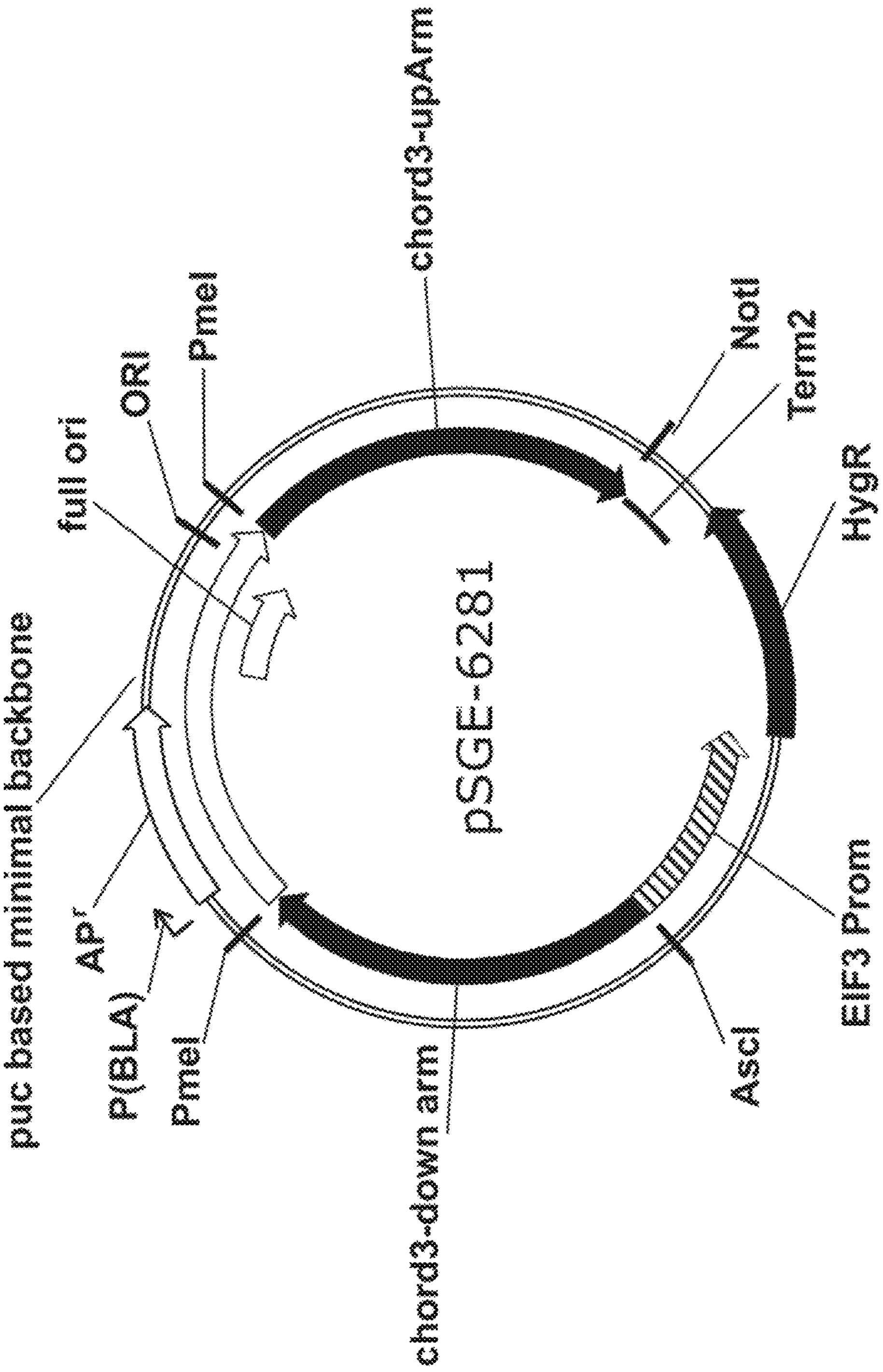
FIG. 7 is a diagram of a vector (pSGE-6281) that includes homology arms for the CHORD gene of *Nannochloropsis* flanking a cassette that includes a hygromycin resistance gene.

Example 4. High Frequency Knockout of CHORD-3266 Gene Using Fully Penetrant *Nannochloropsis* Cas9 Editor Lines To test the fully penetrant *Nannochloropsis* Cas9 strains GE-6594 and GE-6791 for genome editing capability, a genome editing approach similar to that described in Example 2 was taken, using the same in vitro synthesized chimeric gRNA. However, in this example, which used the new fully penetrant strains, the selectable donor DNA used in the co-transformation did not include the GFP gene and associated promoter and terminator. The strains were transformed with gRNA targeting the CHORD-3266 gene (encoding a protein product having a CHORD (cysteine and histidine rich) domain) and one of the following selectable DNA molecules; 1) a HygR fragment that only included a hygromycin resistance (HygR) gene (SEQ ID NO:22) under the control of the *N. gaditana* EIF3 promoter (SEQ ID NO:23) terminated by *N. gaditana* bidirectional terminator 2 (SEQ ID NO:26) (the operably linked HygR gene, promoter, and terminator referred to herein as the HygR cassette), and flanked by 27 base pair identification sequences on the 5' (SEQ ID NO:43) and 3' (SEQ ID NO:44) ends of the gene to yield an ID-sequence-flanked HygR cassette fragment (SEQ ID NO:46), or 2) a circular form of vector pSGE-6281 (SEQ ID NO:47) (FIG. 7) which included all of the elements in the fragment described above, but here those elements were flanked by 2 kb "up" (SEQ ID NO:28) and "down" (SEQ ID NO:29) arms which were homologous to the sequences upstream and downstream of the CRISPR target (SEQ ID NO:30) in the *N. gaditana* genome, and which also contained a puc19 vector backbone. The same DNA series was transformed without gRNA as a control group.

The GE-6594 and GE-6791 Cas9 fully penetrant expression strains were transformed by electroporation using 5 μg of purified chimeric guide RNA targeting the CHORD-3266 gene and 1 μg of one of the forms of selectable DNA described above. Following electroporation, cells were plated on agar medium containing hygromycin to select for transformants that incorporated the hygromycin cassette. Transformants were screened by colony PCR as described in Example 2. The results are shown in Table 2.

TABLE 2

Rates of in vivo Genome Editing targeting the CHORD-3266 locus with selection in Fully Penetrant Cas9 Editor Lines.

| Cas9 Editor Strain | Donor DNA fragment | total no. transformants analyzed | no. confirmed positive for mutation at locus | % transformants with mutated target locus |
|---|---|---|---|---|
| GE-6791 | Hyg-Frag | 61 | 19 | 31 |
| GE-6791 | pSGE-6281 (arms for HR) | 9 | 8 | 89 |
| GE-6594 | Hyg-Frag | 17 | 6 | 35 |
| GE-6594 | pSGE-6281 (arms for HR) | 5 | 5 | 100 |

The mutation frequency in these new Cas9 parental strains was drastically improved over the original parental strain GE-6571. Furthermore, using the homologous recombination vector pSGE-6281 as donor DNA, fully penetrant Cas9 strain GE-6791 yielded 8 clones with the donor DNA integrated into the target locus out of 9 hygromycin-resistant transformants analyzed, and fully penetrant Cas9 strain GE-6594 yielded 5 mutants having integrated DNA in the target locus out of 5 hygromycin-resistant transformants analyzed. Using the HygR cassette fragment (SEQ ID NO:46; lacking flanking sequences having homology to the targeted locus), GE-6791 yielded 19 clones with a donor fragment-disrupted target locus from 61 analyzed, and GE-6594 yielded 6 target locus integration mutants out of out of 17 hygromycin-resistant transformants analyzed. No mutants were obtained from transformants generated by control transformations where gRNA was omitted. PCR products of wild type size were Sanger sequenced to look for any small and hard to detect insertions or deletions due to NHEJ mis-repair, but none were observed.

In this example, using the fully penetrant Cas9 lines, mutants were obtained with the co-transformation of only a HygR cassette lacking homology to the targeted locus and thus target gene mutation was not dependent on the use of a homologous recombination (HR) vector. This wasn't observed in the original parent strain GE-6571 (Example 2), where integration of the donor fragment only occurred when there were homology arms on the donor fragment flanking the gene(s) of interest. This new mutant class not generated by homologous recombination was nonetheless found by colony PCR to yield a large band indicative of insertion at the targeted locus, and Sanger sequencing of the PCR products confirmed that all of these mutants had insertions of the HygR cassette at the targeted locus. Integration of the donor fragment was found to occur in either orientation, presumably inserted during NHEJ repair (i.e., by NHEJ "knock-in"). These NHEJ integration events were sequence-confirmed by sequencing the PCR products.

Figure 8:
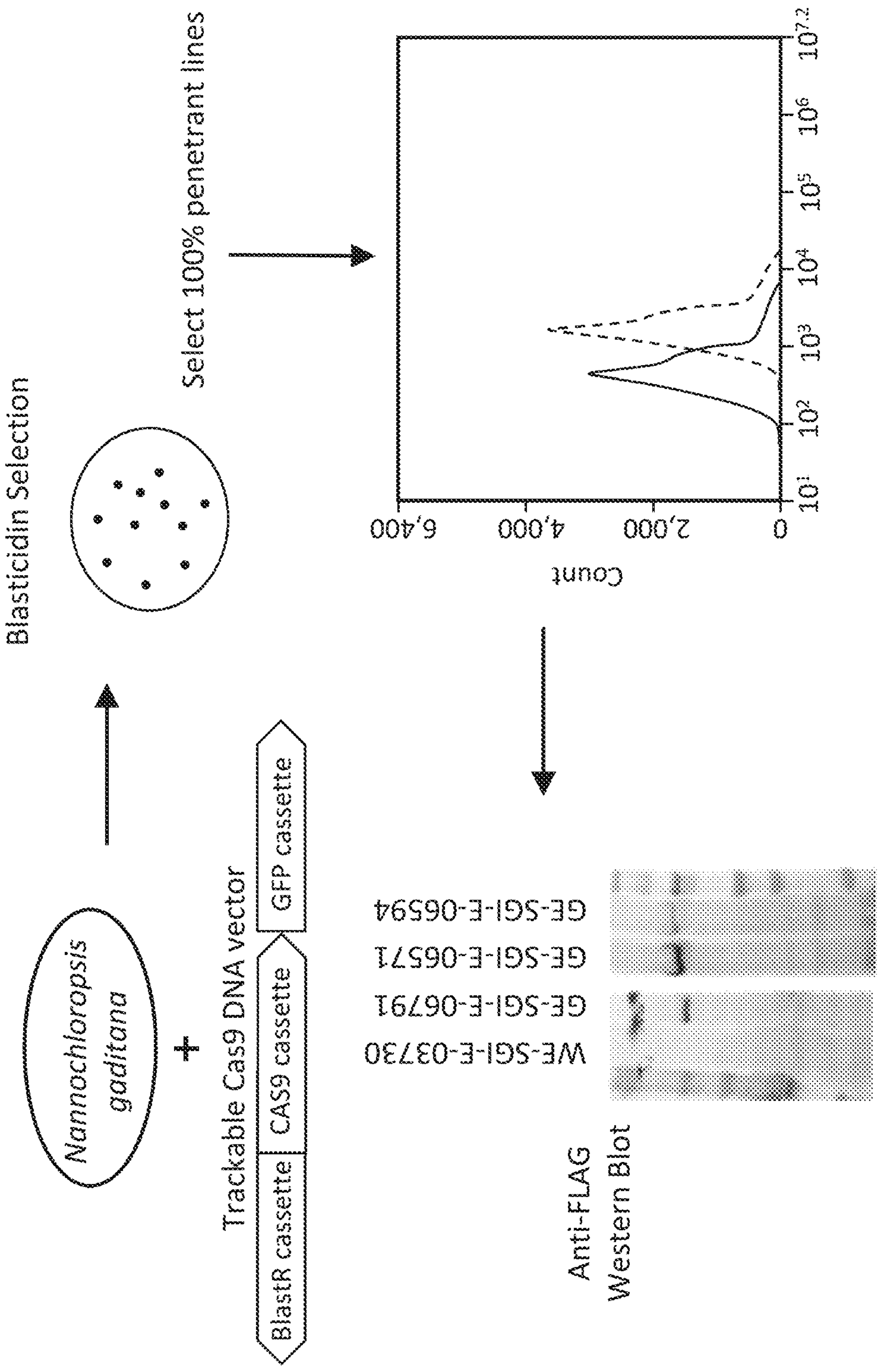
FIG. 8 depicts the strategy for developing high efficiency Cas9 genome editing lines in which colonies are transformed with a construct that includes expression cassettes for each of a selectable marker (used to isolated transformants), a Cas9 nuclease, and a fluorescent protein. Culture from individual transformants (arising from single colonies) are screened by flow cytometry for a single shifted peak indicating full penetrance of expression of Cas9. The Western step need not be included in the method.

The improvement in mutation frequency in the new Cas9 expressor strains over the original strain is best explained by the fact that these new strains were pre-screened and determined to be essentially 100% phenotypically penetrant for GFP prior to transformation. The original strain GE-6571 did not have a GFP cassette, and fully penetrant lines transformed with this construct were not isolated. Although GE-6571 arguably had higher Cas9 expression according to western blot (FIG. 8), it was likely only partially penetrant (that is, the expression level among the population was probably not consistent). FIG. 8 provides a general schema for isolating fully penetrant Cas9-expressing strains that includes transforming a strain with a construct that includes a Cas9 gene plus a selectable marker and reporter gene (preferably encoding a fluorescent protein, isolating transformants on selective media, performing a penetrance screen by flow cytometry to identify strains that have 100% penetrance of the fluorescent protein, and verifying expression of Cas9, for example, by Western blot. Interestingly, the Western blot in FIG. 8 shows that GE-6571, which was not screened for penetrance and had very poor Cas9 mutational frequency (Example 2), has a higher level of Cas9 protein than the two fully penetrant Editor lines, GE-6594 and GE-6791, which show dramatically higher Cas9 mutation rates (Example 4), demonstrating that penetrance is a far more reliable screen than assessing Cas9 protein levels.

Example 5. High Frequency Knockout of the Acyl-CoA Oxidase Gene Using Fully Penetrant *Nannochloropsis* Cas9 Editor Lines To further test the penetrant *Nannochloropsis* Cas9 Editor strains GE-6594 and GE-6791 for genome editing capability, an editing approach similar to Example 4 was taken where the CHORD-3266 gene was successfully and efficiently targeted. To target the *N. gaditana* acyl-CoA oxidase gene (SEQ ID NO:48), a chimeric guide RNA was designed to target the aco2 target sequence, which included 20 nucleotides of sequence with homology to an acyl-CoA oxidase gene sequence directly upstream of a *S. pyogenes* Cas9 PAM sequence occurring within the acyl-CoA oxidase gene (SEQ ID NO:49; 20 nucleotide target sequence plus PAM), where the 20 nucleotide targeting sequence was within a 103 base chimeric guide RNA sequence (SEQ ID NO:50) that also included the transactivating CRISPR (tracr) sequence. The entire chimeric guide sequence was synthesized by first making a DNA template made up of complementary DNA oligonucleotides (SEQ ID NO:51 and SEQ ID NO:52) in which the DNA sequence encoding the guide RNA molecule was included downstream of a T7 promoter (SEQ ID NO:35). The oligos were annealed to create a double stranded DNA template, which was used as the template for in vitro transcription reactions that were performed using the MEGAshortscript™ T7 Kit (Life Technologies #AM1354M) according to the manufacturer's protocol. The resulting RNA was purified using Zymo-Spin™ V-E columns (Zymo Research #C1024-25) according to manufacturer's protocol.

Figure 9:
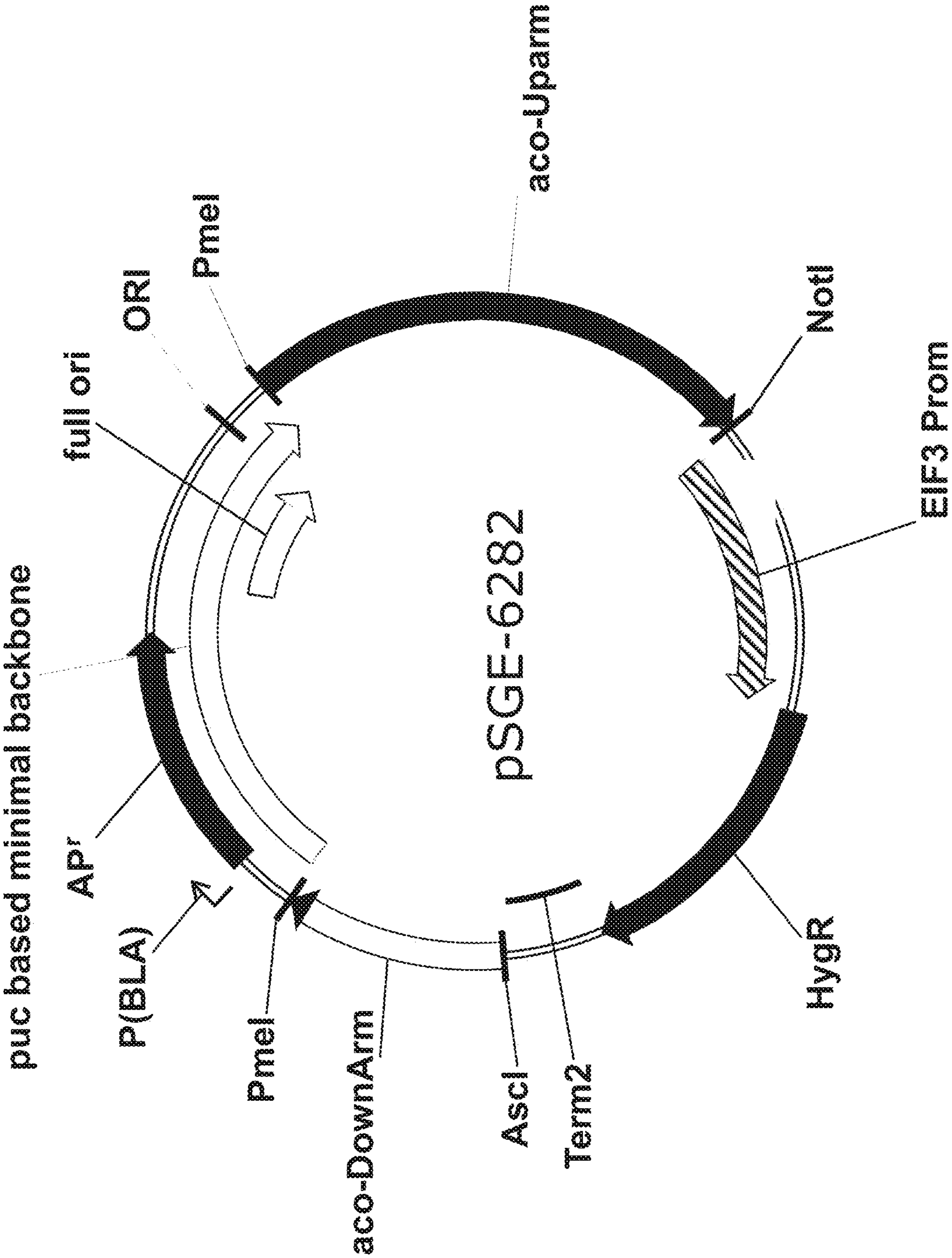
FIG. 9 is a diagram of a vector that includes homology arms for the acyl-CoA oxidase gene of *Nannochloropsis* flanking a cassette that includes a hygromycin resistance gene.

The strains were transformed with the gRNA targeting aco2 and one of the following selectable DNA molecules: 1) a HygR cassette that only included a hygromycin resistance (HygR) gene (SEQ ID NO:22) under the control of the *N. gaditana* EIF3 promoter (SEQ ID NO:23) terminated by *N. gaditana* bidirectional terminator 2 (SEQ ID NO:26) (the operably linked HygR gene, promoter, and terminator referred to herein as the HygR cassette), or 2) a circular form of vector pSGE-6282 (SEQ ID NO:53) (FIG. 9) based on a puc19 backbone which includes all of the elements in the fragment described in 1), but here those elements were flanked by 1.7 kb “up” (SEQ ID NO:54) and 0.8 kb “down” (SEQ ID NO:55) arms homologous to the sequences upstream and downstream of the aco2 target (SEQ ID NO:49). The homology arms omit 113 bp of DNA surrounding the aco2 target site. The same donor DNAs (1) and 2)) were transformed into Cas9 Editor strains GE-6594 and GE-6791 without gRNA as controls.

The GE-6594 and GE-6791 Cas9 expression strains were transformed by electroporation using 5 μg of purified chimeric guide RNA targeting the aco2 target site, and 1 μg of one of the forms of selectable donor DNA described above. Following electroporation, cells were plated on agar medium containing hygromycin to select for transformants that incorporated the hygromycin cassette. Transformants were screened by colony PCR as described previously (see Example 2) but using primers flanking the aco2 target (SEQ ID NO:17 and SEQ ID NO:18). The results are shown in Table 3.

TABLE 3

Rates of in vivo Genome Editing in Fully Penetrant Cas9 Editor Lines targeting the Acyl-CoA Oxidase locus.

| Cas9 Editor Strain | Donor DNA fragment | total no. transformants analyzed | no. confirmed positive for mutation at locus | % transformants with mutated target locus |
|---|---|---|---|---|
| GE-6791 | Hyg-Frag | 160 | 90 | 56 |
| GE-6791 | pSGE06282 (for HR) | 61 | 43 | 70 |
| GE-6594 | Hyg-Frag | 96 | 44 | 46 |
| GE-6594 | pSGE06282 (for HR) | 62 | 46 | 74 |

The mutation frequency in these new Cas9 Editor strains was drastically improved over that of the original parental strain GE-6571. Using the homologous recombination vector pSGE-6282, GE-6791 yielded 43 positive clones from 61 analyzed, and GE-6594 yielded 46 positive mutants out of 62 analyzed. Using the HygR cassette alone (without homology arms), GE-6791 yielded 90 positive clones from 160 analyzed, and GE-6594 yielded 44 positive mutants out of 96 analyzed. No mutants were obtained from the transformants generated by control transformations where gRNA was omitted. PCR products of wild type size were Sanger sequenced to look for any small and hard to detect insertions or deletions due to NHEJ mis-repair, but none were observed.

In this example, as in Example 4, mutants were again obtained with the co-transformation of only a HygR cassette fragment and not dependent on the use of an HR vector having sequences homologous to the targeted locus flanking the resistance cassette; this wasn't observed in the original parent strain GE-6571 (see Example 2). This is further evidence that the improvement in mutation frequency in the new Cas9 Editor strains over the original strain can likely be explained by the fact that these new strains were pre-screened and determined to be phenotypically fully penetrant for GFP prior to transformation.

Figure 10:
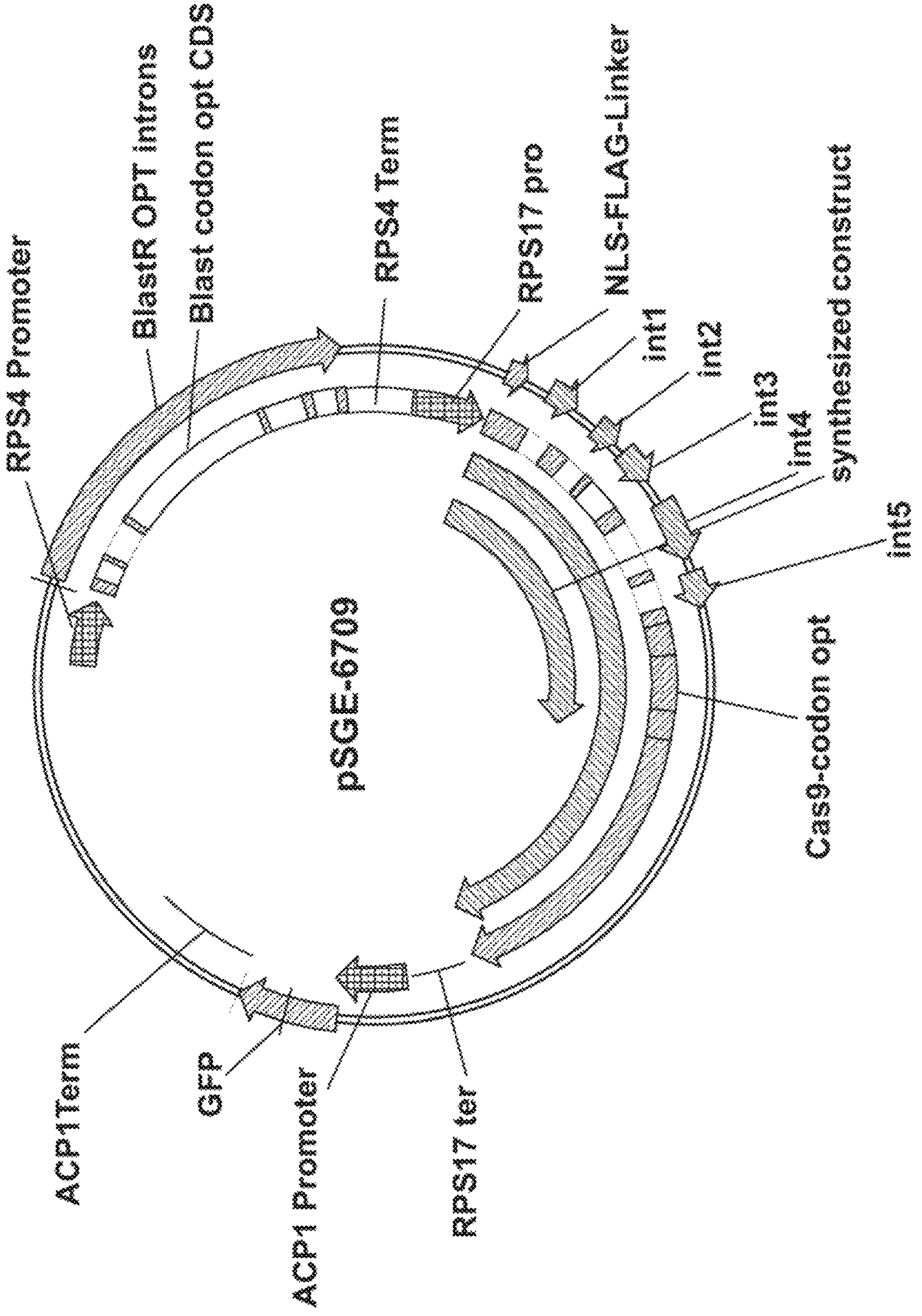
FIG. 10 is a diagram of a vector (pSGE-6709) that includes a gene encoding a Cas9 polypeptide optimized for expression in Parachlorella. The construct also includes a gene encoding GFP and a gene encoding a blast gene optimized for expression in Parachlorella. Each of the Cas9, GFP, and blast genes is operably linked to a separate Parachlorella promoter.

Example 6. Development of a Fully Penetrant Cas9-Expressing *Parachlorella* Strain A vector, pSGE-6709 (FIG. 10), was engineered for the expression of the *Streptococcus pyogenes* Cas9 gene in *Parachlorella*. The vector included the following three elements: 1) a Cas9 expression cassette which contained an engineered Cas9 gene codon optimized for *Parachlorella* and containing introns from *Parachlorella*, that also included an N-terminal FLAG tag, nuclear localization signal, and peptide linker (SEQ ID NO:56) operably linked to the *Parachlorella* RPS17 promoter (SEQ ID NO:57) and terminated by the *Parachlorella* RPS17 terminator (SEQ ID NO:58); 2) a selectable marker expression cassette, which contained the blasticidin resistance gene from *Aspergillus terreus* codon optimized for *Parachlorella* and containing *Parachlorella* introns (SEQ ID NO:59), operably linked to the *Parachlorella* RPS4 promoter (SEQ ID NO:60) and terminated by the *Parachlorella* RPS4 terminator (SEQ ID NO:61); and 3) a GFP reporter expression cassette, which contained the TurboGFP gene (Evrogen, Moscow, Russia) (SEQ ID NO:24), driven by the *Parachlorella* ACP1 promoter (SEQ ID NO:62) and terminated by the *Parachlorella* ACP1 terminator (SEQ ID:63).

The vector was transformed into *Parachlorella* by biolistics. Transformation of *Parachlorella* wild type strain WT-1185 was accomplished using the BioRad Helios® Gene Gun System essentially as described in US Patent Publication No. 2014/0154806, incorporated herein by reference. DNA for transformation was precipitated onto gold particles, the gold particles were adhered to the inside of lengths of tubing, and a burst of helium gas was fired through the tubing positioned within the Gene Gun to propel the DNA-coated gold particles into *Parachlorella* strain WT-1185 cells which were adhered on solid non-selective media (2% agar plates containing PM074 algal growth medium). The Helios® Gene Gun was used to fire two bullets per cell circle at 600 psi from a distance of 3-6 cm from the plate. The following day, cells were transferred onto selective medium for growth of transformed colonies.

Figure 11:
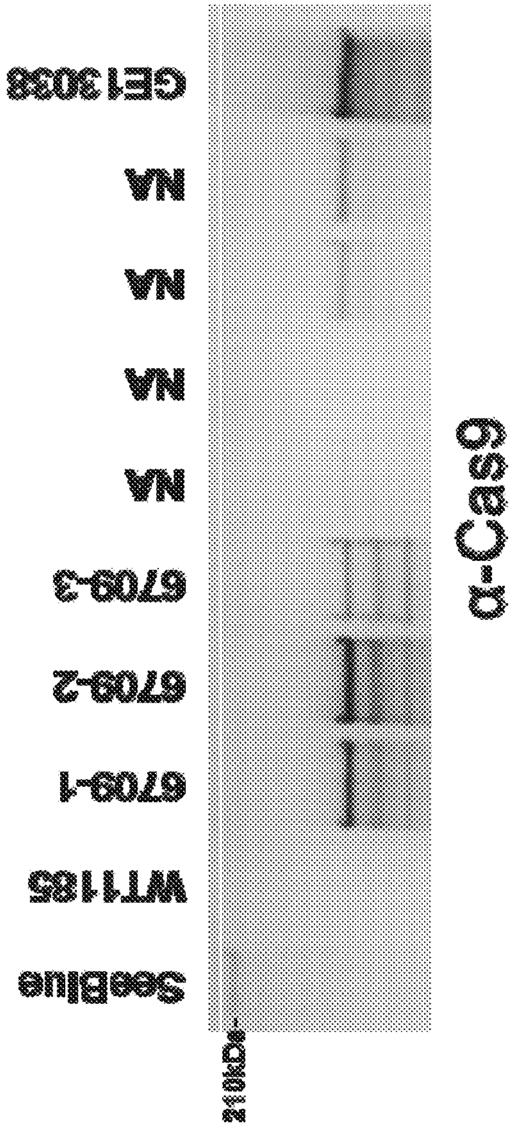
FIG. 11 is a Western blot of Parachlorella strains transformed with pSGE-6709 and confirmed to be fully penetrant by flow cytometry (6709-1, 6709-2, and 6709-3) using an antibody against Cas9. WT1185 is the wild type Parachlorella strain.

Colonies were screened for full GFP penetrance as described in Example 3 by flow cytometry and identification of transformed strains that had a single fluorescence peak shifted to a higher value than the wild type fluorescence peak. Fully penetrant Cas9 strains demonstrating a clearly shifted fluorescence peak with respect to nontransformed cells were tested for Cas9 expression by anti-Cas9 western blotting for evidence of Cas9 expression (FIG. 11). Based on these screens, isolate 6709-2 was carried forward and given strain identifier GE-15699.

Example 7. Knockout of SRP54 Using Fully Penetrant *Parachlorella* Cas9 Editor Line To test the new strain GE-15699 for genome editing capability, an editing approach was taken that was similar to that described in Examples 2 and 4. Chimeric gRNA (SEQ ID NO:64) was designed and synthesized in vitro to target the chloroplastic SRP54 gene in *Parachlorella* (SEQ ID NO:65). GE-15699 was transformed by electroporation with 1-2 μg of purified chimeric guide RNA, and 1 μg of selectable marker DNA which contained a bleomycin resistance "BleR" gene codon-optimized for *Parachlorella* and containing introns from *Parachlorella* (SEQ ID NO:66). The BleR gene was operably linked to the *Parachlorella* RPS4 promoter (SEQ ID NO:60) and terminated by the *Parachlorella* RPS4 terminator (SEQ ID NO:61).

Electroporation was performed by inoculating a 100 mL seed culture inoculated to $1\times10^6$ cells/mL six days before transformation was used to inoculate a 1 L culture to $1\times10^6$ cells/mL two days before transformation. On the day of transformation, cells were pelleted by centrifugation at 5000×g for 20 minutes, washed three times with 0.1 um filtered 385 mM sorbitol, and resuspended to $5\times10^9$ cells/mL in 385 mM sorbitol. Electroporation of 100 μL concentrated cells was performed in 0.2 cm cuvettes in a BioRad Gene Pulser Xcell™ under varied conditions. The DNA used for optimization of electroporation was linearized pSG6640 including the ble and TurboGFP expression cassettes. The TurboGFP cassette included the *Parachlorella* ACP promoter (SEQ ID NO:62) operably linked to the TurboGFP gene (SEQ ID NO:24) and the *Parachlorella* ACP terminator (SEQ ID NO:63). Immediately after electroporating pre-chilled cells and cuvettes, 1 mL cold sorbitol was added and used to transfer cells into 10 mL PM074. After overnight recovery, cells were concentrated and spread onto 13 cm-diameter PM074 media containing zeocin at 250 mg/L and grown under the conditions listed in the biolistics section.

After testing a range of voltages, resistances, and capacitances, the optimal electroporation conditions were determined to be 1.0-1.2 kV (5000-6000 V/cm), 200-300 ohms, and 25-50 μF. Use of larger quantities of DNA increased the resulting number of zeocin-resistant colonies, though the effect plateaued at amounts larger than 4 μg.

Figure 12:
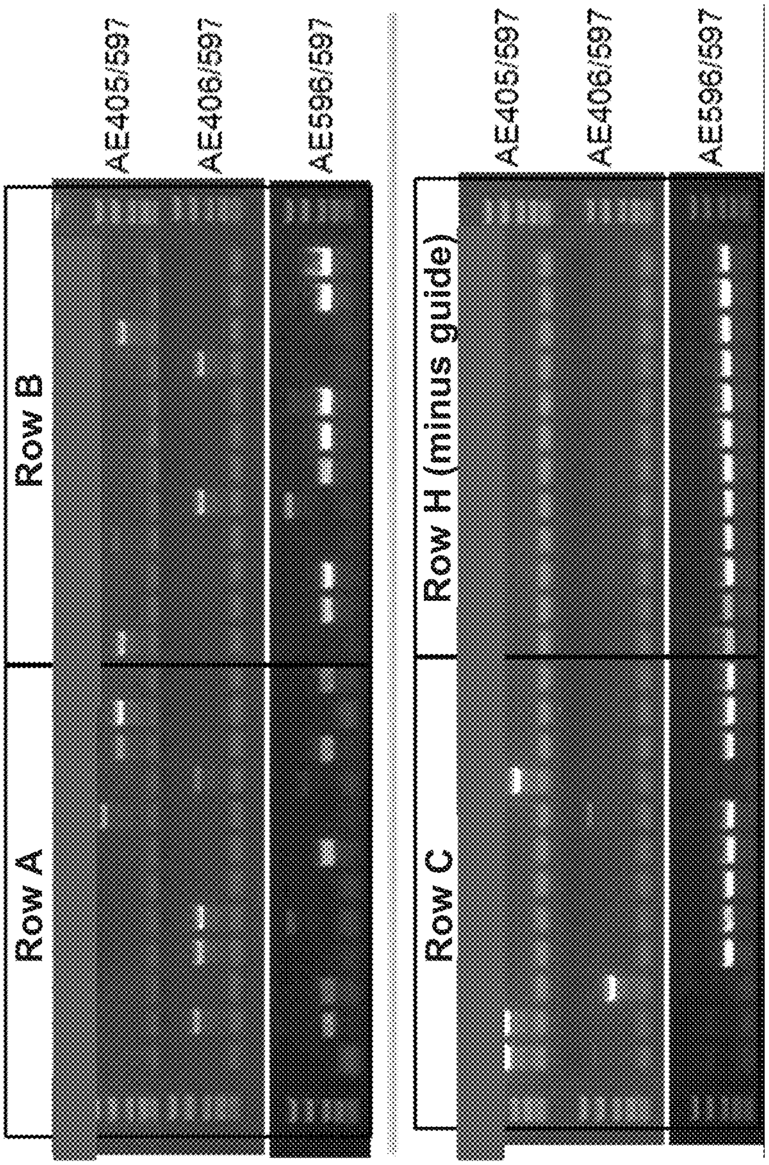
FIG. 12 shows gels of PCR products using primer sets for detecting insertion of the bleR cassette into the CRISPR-targeted cpSRP54 locus in fully penetrant Cas9-expressing Parachlorella strain GE-15699. The product of primers 596 and 597 is the wild type (unmodified) locus; the products of primers 405/597 and 406/597 result from targeted insertion of the bleR cassette.

Following electroporation, cells were plated on agar medium (PM130) containing 250 μg/ml zeocin to select for transformants that incorporated the bleR cassette. Transformants were screened by colony PCR using primers designed to amplify across the native targeted locus (oligo-AE596; SEQ ID NO:67 and oligo-AE597; SEQ ID NO:68). The primers were designed to produce a 700 bp band in the absence of integration (e.g., "knock-in" of the BleR cassette) into the locus, or a 4.3 kb band if there was integration of a single BleR cassette into the targeted locus. In addition, colony PCR was also performed using primers designed to amplify a fragment extending from the cpSRP54 gene (oligo-AE597; SEQ ID NO:68) into the selectable marker (oligo-AE405; SEQ ID NO:69 and oligo-AE406; SEQ ID NO:70). Depending on orientation of the integrated ble cassette, a 1.2 kb band would result from either amplification by primers 405/597 or 406/597 spanning from within the bleR cassette out to the cpSRP54 gene. The results show a high frequency (between 40 and 45% in this sample) of knock-in of the BleR cassette into the targeted locus (FIG. 12), in the absence of homology arms. As cpSRP54 knockouts result in a pale green phenotype, these colony patches are overlaid with the PCR results in this image.

Figure 13:
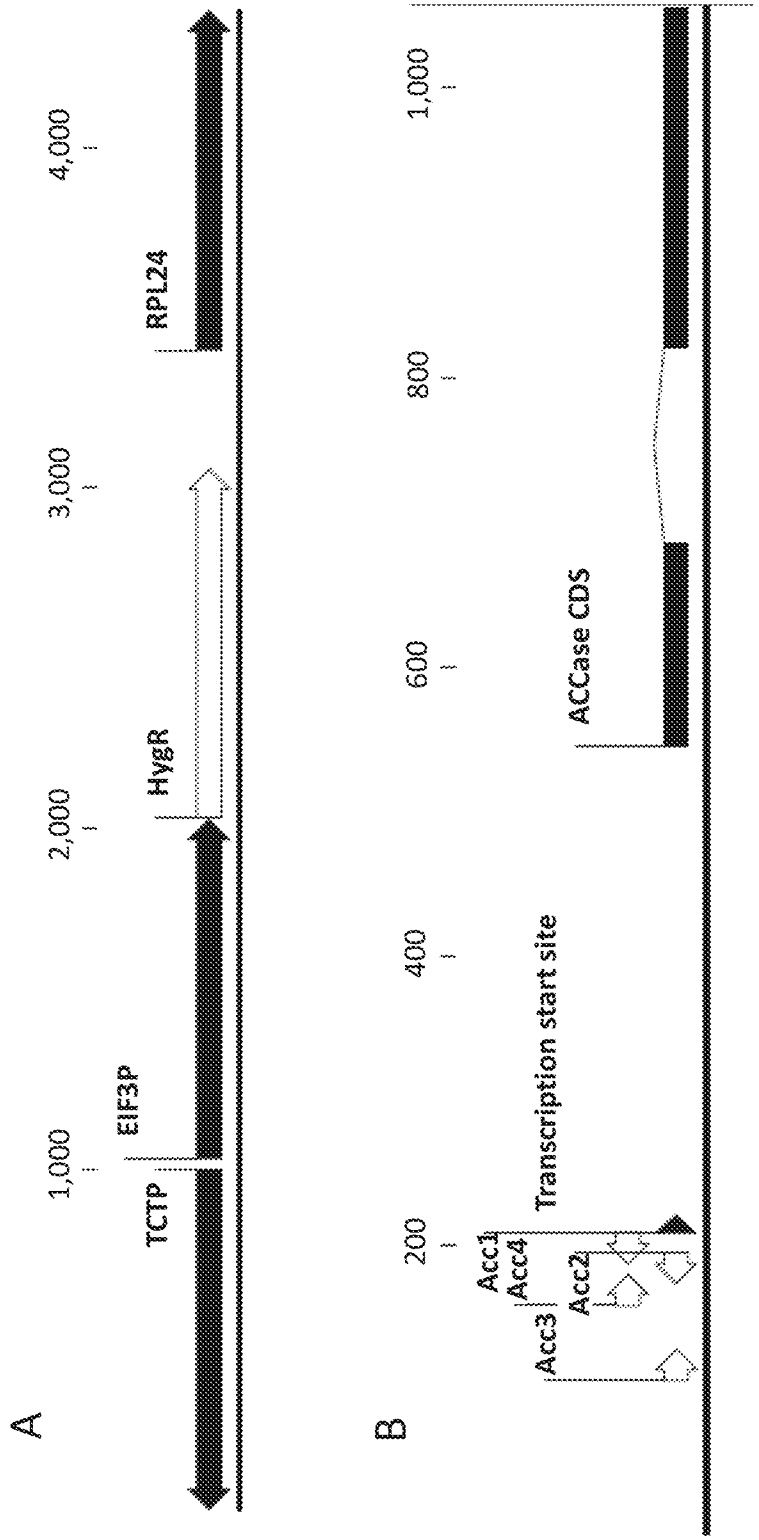
FIG. 13 A) is a diagram of a donor DNA construct for promoter boosting; B) shows insertion sites of the donor DNA in the ACCase locus upstream of the coding region.

Example 8. Promoter Boosting to Increase Expression of the Native *Nannochloropsis* Accase Gene Using Cas9/CRISPR The promoter region of the *N. gaditana* Accase gene was targeted to increase its promoter function. A construct was designed that included a hygromycin resistance cassette as described in Example 4, but lacking the 5' and 3' identification sequences (SEQ ID NO:45). The HygR cassette was flanked by strong promoters oriented in an outward direction (FIG. 13A). The outwardly-directed dual promoter design was to ensure that regardless of the orientation in which the HygR cassette integrated, one of the promoters would be positioned to enhance expression of the Accase gene when the donor fragment was targeted to the upstream region of the Accase gene (FIG. 13B). The construct lacked homology arms for the integration region and therefore the intended mode of insertion was by NHEJ. The outward directed promoter positioned "upstream" of the HygR cassette was the TCTP promoter (SEQ ID NO:11). The outward directed promoter positioned "downstream" of the HygR cassette was RPL24 promoter (SEQ ID NO:25), giving rise to a DNA fragment termed the Dual Promoter HygR cassette (SEQ ID NO:71).

Four chimeric guide RNAs were synthesized as described in Example 2, each 20 nucleotides in length (SEQ ID Nos:72-75) to target integration of the promoter flanked hygromycin cassette (SEQ ID NO:71) into different target sites (Acc1 through Acc4) as indicated in FIG. 13B. Transformation of *N. gaditana* Editor line GE-6791 described in Example 3 was performed using electroporation essentially as described in Example 4, where each of the four guide RNAs was individually co-transformed with the promoter flanked hygromycin cassette (SEQ ID NO:71). For each transformation, hygromycin-resistant colonies were selected and analyzed by PCR to identify whether or not the HygR cassette had integrated into the 5' region of the Accase gene. PCR products were sequenced for absolute confirmation of disrupted loci. The primers used were Accase-F (SEQ ID NO:76) and Accase-R (SEQ ID NO:77) that flanked the targeted upstream region of the Accase gene.

Two of the transformants with confirmed promoter region modification, designated ACC-KI-1 and ACC-KI-2, were selected for further analysis. In ACC-KI-1, the insert was targeted to the Acc1 guide RNA site 13 bp upstream of the deduced transcriptional start site, and in ACC-KI-2, it was targeted to the Acc2 guide RNA site 28 bp upstream of the deduced transcriptional start site. To determine the effect of the "promoter boosting" construct, Accase enzyme activity was measured exactly as described in Roessler P. (1988) *Archives of Biochemistry and Biophysics* 267:521-528) for the two strains ACC-KI-1 and ACC-KI-2 and the enzyme activity was compared to that of wild type cells. Increased total ACCase enzyme activity on a per total milligram protein basis in both ACC-KI-1 and ACC-KI-2 was observed (Table 4), proving that modification of a gene promoter as described gives rise to increased expression of the gene and level of the encoded protein.

TABLE 4

| | Activity nmol/min/mg | % increase |
|---|---|---|
| WE-3730 | 0.454 | 0.00 |
| ACC-KI-1 | 0.604 | 33.12 |
| ACC-KI-2 | 1.129 | 148.63 |

Example 9. Knockout of the ZnCys-2845 Locus in *Nannochloropsis*

The ZnCys-2845 lipid regulator gene was also knocked out using CRISPR technology. The *Nannochloropsis* Cas9 Editor line GE-6791, expressing a gene encoding the *Strep-*

*tococcus pyogenes* Cas9 nuclease was used as a host for transformation with a chimeric guide RNA and donor DNA for insertional knockout.

For targeting of the ZnCys-2845 gene for disruption, a DNA construct was made (SGI-DNA, La Jolla, CA) for producing a guide RNA in which the DNA molecule included the sequence of a chimeric guide engineered downstream of a T7 promoter (SEQ ID NO:35). The chimeric guide sequence included an 18 bp target sequence (SEQ ID NO:78) homologous to a sequence within the ZnCys-2845 gene sequence that was upstream of an *S. pyogenes* cas9 PAM sequence (NGG), and also included the transactivating CRISPR (tracr) sequence. The chimeric guide sequence was synthesized by first making a DNA template made up of complementary DNA oligonucleotides (SEQ ID NO:79 and SEQ ID NO:80) that were annealed to create a double-stranded DNA template that included a T7 promoter sequence which was used in in vitro transcription reactions using the MEGAshortscript™ T7 Kit (Life Technologies #AM1354M) according to the manufacturer's instructions to synthesize the guide RNA. The resulting RNA was purified using Zymo-Spin™ V-E columns (Zymo Research #C1024-25) according to manufacturer's protocol.

The donor fragment for insertion into the targeted ZnCys-2845 locus (SEQ ID NO:46) included a selectable marker cassette that included the hygromycin resistance gene (HygR, SEQ ID NO:22) downstream of the *N. gaditana* EIF3 promoter (SEQ ID NO:23) and followed by *N. gaditana* bidirectional terminator 2 (SEQ ID NO:26), with the entire promoter-hygromycin resistance gene-terminator sequence flanked by 27 base pair identification sequences on the 5' (SEQ ID NO:43 5'ID) and 3' (SEQ ID NO:44 3'ID) ends to yield the DNA fragment referred to as the "Hyg Resistance Cassette" (SEQ ID NO:46 HygR Cassette).

For targeted knockout of the ZnCys-2845 locus, Cas9 Editor line GE-6791 was transformed by electroporation using 5 μg of purified chimeric guide RNA targeting the ZnCys-2845 gene and 1 μg of the selectable donor DNA (HygR Cassette; SEQ ID NO:46) essentially as described in US 2014/0220638. Following electroporation, cells were plated on PM124 agar media containing hygromycin to select for transformants that incorporated the hygromycin resistance cassette. Transformants were patched onto a fresh plate and screened by colony PCR for insertion of the donor fragment into the ZnCys-2845 gene.

Colony PCR screening was performed as described in Example 1. The primers used to detect the insertion of the donor fragment into the targeted locus of the ZnCys-2845 gene were SEQ ID NO:81 and SEQ ID NO:82. Based on the PCR-based colony screening, knockout strains having the donor DNA (HygR cassette) inserted into the targeted ZnCys-2845 gene, GE-8564 and GE-8565 (FIG. 14A), were tested in productivity assays.

ZnCys-2845 knockout strain GE-8564 and wild type progenitor strain WT-3730 were cultured in a batch productivity assay in nitrogen replete medium PM123 that included 15 mM nitrate as the sole nitrogen source available to the cells, i.e., the culture medium had no source of reduced nitrogen. Because it had been determined that the ZnCys-2845 mutant does not grow in the absence of reduced nitrogen, the production cultures were inoculated to an initial OD730 of 0.5 from seed (scale-up) cultures that were grown in PM124 medium that included 5 mM ammonium in addition to 8.8 mM nitrate.

After inoculation, ZnCys knockout strain GE-8564 and wild type strain WT-3730 were grown in triplicate cultures in a batch assay in 75 cm2 rectangular tissue culture flasks containing 175 ml of PM123 medium, which includes 15 mM nitrate as the sole nitrogen source, for seven days. The flasks were positioned with their narrowest "width" dimension against an LED light source that was programmed for a 16 h light:8 hour dark cycle, with the light intensity following a curve designed to mimic natural daylight, in which the light intensity peaked in the middle of the light period at approximately 1200 μE. Deionized H2O was added to the cultures daily to replace evaporative losses. The temperature of the cultures was regulated by a water bath set at 25° C. Cultures were inoculated on day 0 and samples (5 mls) were removed on days 3, 5, and 7 for assessing cell density, fatty acid methyl esters (FAME) as a measure of lipid, and total organic carbon (TOC).

FAME analysis was performed on 2 mL samples that were dried using a GeneVac HT-4X. To each of the the dried pellets the following were added: 500 μL of 500 mM KOH in methanol, 200 μL of tetrahydrofuran containing 0.05% butylated hydroxyl toluene, 40 μL of a 2 mg/ml C11:0 free fatty acid/C13:0 triglyceride/C23:0 fatty acid methyl ester internal standard mix and 500 μL of glass beads (425-600 μm diameter). The vials were capped with open top PTFE septa-lined caps and placed in an SPEX GenoGrinder at 1.65 krpm for 7.5 minutes. The samples were then heated at 80° C. for five minutes and allowed to cool. For derivatization, 500 μL of 10% boron trifluoride in methanol was added to the samples prior to heating at 80° C. for 30 minutes. The tubes were allowed to cool prior to adding 2 mL of heptane and 500 μL of 5 M NaCl. The samples were vortexed for five minutes at 2K rpm and finally centrifuged for three minutes at 1K rpm. The heptane layer was sampled using a Gerstel MPS Autosampler. Quantitation used the 80 μg of C23:0 FAME internal standard.

Total organic carbon (TOC) was determined by diluting 2 mL of cell culture to a total volume of 20 mL with DI water. Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The 4 point calibration range was from 2 ppm to 200 ppm corresponding to 20-2000 ppm for non-diluted cultures with a correlation coefficient of r2>0.999.

The results of these analyses are shown in Tables 5-7. Values provided for wild type and knockout GE-8564 mutant are the average of three cultures with standard deviations (sd).

TABLE 5

Lipid (FAME) Produced by ZnCys-2845 Knockout Mutant and Wild Type Cultures in Batch Assay with Nitrate-only Culture Medium.

| | WT-3730 (NO3) | | ZnCys-KO GE-8564 ($NO_3$) | | |
|---|---|---|---|---|---|
| Day | μg/ml | sd | ng/ml | sd | % increase |
| 3 | 105.03 | 9.71 | 188.56 | 6.52 | 79.53 |
| 5 | 140.01 | 13.48 | 223.41 | 0.28 | 59.57 |
| 7 | 198.49 | 2.04 | 250.76 | 3.22 | 26.33 |

TABLE 6

Biomass (TOC) Produced by ZnCys-2845 Knockout Mutant and Wild Type Cultures in Batch Assay with Nitrate-only Culture Medium.

| | WT-3730 (NO3) | | ZnCys-KO GE-8564 (NO3) | | |
|---|---|---|---|---|---|
| Day | μg/ml | s.d. | μg/ml | s.d. | % diff |
| 3 | 375.6 | 10.18 | 261.7 | 7.07 | −30.3 |
| 4 | 474.6 | 8.34 | 283.95 | 3.61 | −40.2 |
| 5 | 534.45 | 43.20 | 269.5 | 3.68 | −49.6 |
| 6 | 644.8 | 48.65 | 311.75 | 3.18 | −51.7 |
| 7 | 804.35 | 36.13 | 329.3 | 1.70 | −59.1 |

TABLE 7

FAME/TOC ratios of ZnCys-2845 Knockout Mutant and Wild Type Strains in Batch Assay with Nitrate-only Culture Medium.

| | WT-3730 (NO3) | | ZnCys-KO GE-8564 (NO3) | | |
|---|---|---|---|---|---|
| Day | | s.d. | | s.d. | % increase |
| 3 | 0.28 | 0.018 | 0.72 | 0.044 | 157 |
| 5 | 0.26 | 0.004 | 0.83 | 0.012 | 219 |
| 7 | 0.25 | 0.009 | 0.76 | 0.006 | 204 |

Although the FAME content of the ZnCys-2845 knockout mutant culture in nitrate-only medium was at a higher level on day 3 of the culture, which was the first day assayed, as well as on days 5 and 7 (Table 5), the increase in FAME per day between days 3 and 7 was less for the ZnCys-2845 knockout strain than for the wild type strain. Table 6 demonstrates that over this time period the ZnCys-2845 gene disruption mutant cultured in nitrate-only medium increased its total organic carbon very little as compared to wild type, which showed steady growth as assessed by TOC accumulation. Thus, the ZnCys-2845 knockout strain, when cultured in a medium that included nitrate as the sole nitrogen source, behaved as though it were in nitrogen starvation. Table 7 confirms this, demonstrating that over the course of the one week productivity assay, the FAME/TOC ratio of the ZnCys-2845 knockout strain GE-8564 was significantly elevated over the wild type FAME/TOC ratio (approximately three-fold the FAME/TOC ratio of wild type).

Example 10. Cas9 ZnCys-2845 Insertional Knockdown Constructs

Figure 14:
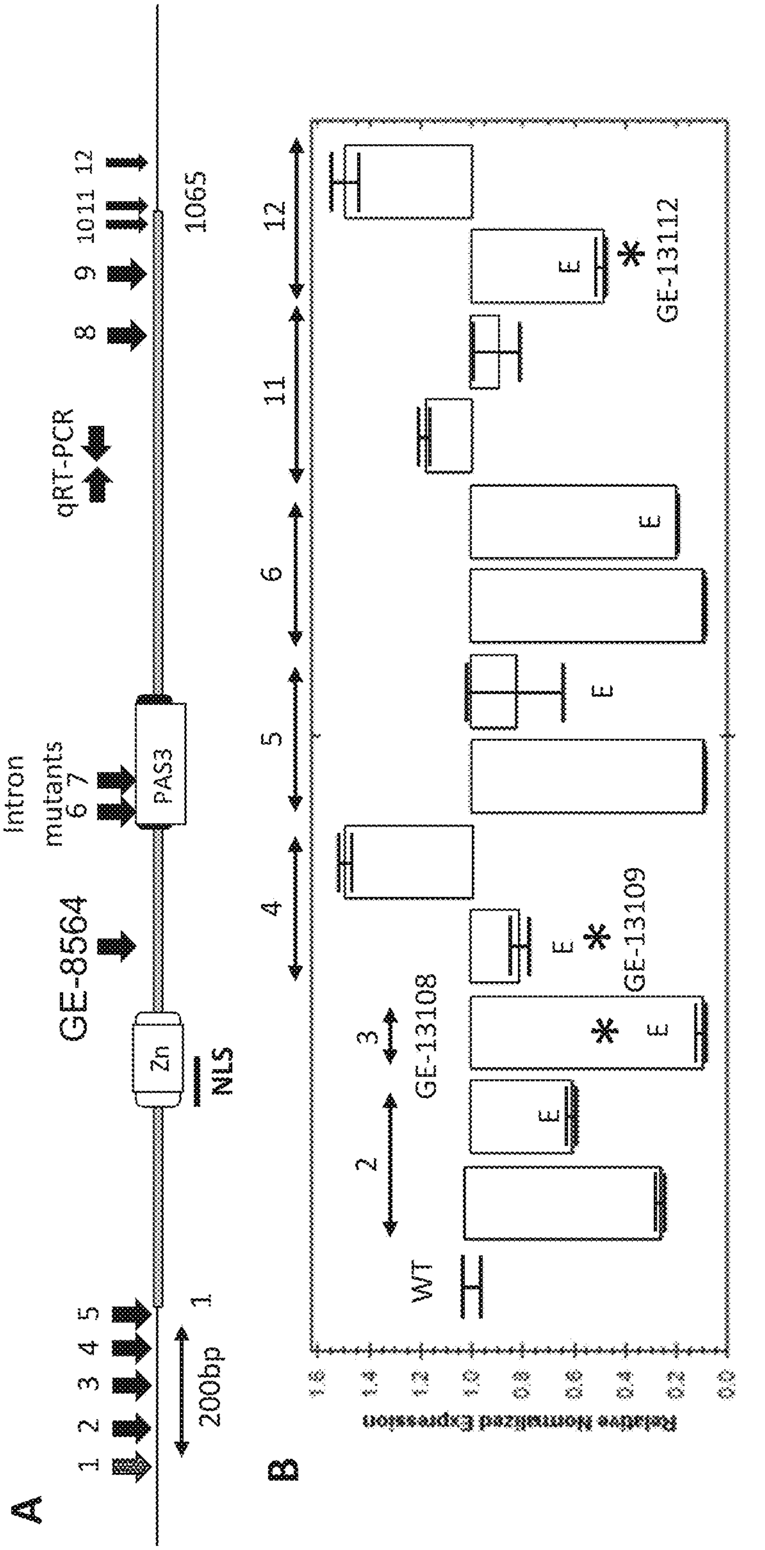
FIG. 14 A) provides a schematic map of the ZnCys-2845 gene locus in *Nannochloropsis* with arrows depicting target sites for Cas9 mediated insertion of a HygR cassette. Only locus 1 failed to result in a targeted insertion. B) provides the level of ZnCys-2845 gene knockdown for the various targeted insertion mutants.

Additional mutant strains were engineered to have decreased expression of the ZnCys-2845 gene using Cas9/CRISPR genome engineering. Twelve chimeric guide RNAs were designed to target sequences upstream of the ATG that encoded the first amino acid of the open reading frame, within an intron of the gene, in the 3' end of the gene but still within the coding sequence, or in the 3' untranslated region of the gene (FIG. 14A). These constructs described here as “Bash Knockdown constructs” or simply “Bash constructs” because they are designed to insert the donor fragment into a site in a region of the gene where the insertion is expected to disrupt native sequences to result in the targeted gene being expressed at a lower level than in wild type. (Correspondingly, the strains that include such insertions are referred to as “Bash strains”, “Bashers”, or “Bash Knockdown mutants”.) The twelve 18-nucleotide sequences having homology to the ZnCys-2845 gene (target site sequences) are provided in Table 8.

TABLE 8

Target and Chimeric Guide Sequences for Attenuating ZnCys-2845 Expression

| “Bash” Gene Attenuation Mutant | Gene Region Targeted | Target Sequence (18 nt) |
|---|---|---|
| 1 | 5’ UTR | SEQ ID NO: 83 |
| 2 | 5’ UTR | SEQ ID NO: 84 |
| 3 | 5’ UTR | SEQ ID NO: 85 |
| 4 | 5’ UTR | SEQ ID NO: 86 |
| 5 | 5’ UTR | SEQ ID NO: 87 |
| 6 | coding region | SEQ ID NO: 88 |
| 7 | coding region | SEQ ID NO: 89 |
| 8 | C-terminus | SEQ ID NO: 90 |
| 9 | C-terminus | SEQ ID NO: 91 |
| 10 | C-terminus | SEQ ID NO: 92 |
| 11 | 3’ UTR | SEQ ID NO: 93 |
| 12 | 3’ UTR | SEQ ID NO: 94 |

Chimeric guide DNA constructs were synthesized as two complementary strands that were annealed to produce a double-stranded construct with a T7 promoter positioned upstream of the guide sequence (that included the 18 nucleotide target sequence), and used to produce the chimeric guide RNAs by in vitro transcription and purified as described in Example 3. Each chimeric guide RNA was individually transformed into *Nannochloropsis* Editor strain GE-6791 along with the donor fragment that included a Hyg resistance (“HygR”) cassette (SEQ ID NO:46) as described in Example 3. Hygromycin resistant colonies were selected and screened by colony PCR as described using primers adjacent to the targeted regions of the ZnCys-2845 gene (Primers MA-ZnCys-FP (SEQ ID NO:81) and MA-ZnCys-RP (SEQ ID NO:82) were used to confirm the knockout (GE-8564) and donor fragment insertion into introns; primers MA-5'Bash-ZnCys-FP (SEQ ID NO:95) and MA-5'Bash-ZnCys-RP (SEQ ID NO:96) were used to confirm the insertion of the donor fragment into the 5' regions of the ZnCys-2845 gene; and primers MA-3'Bash-ZnCys-FP (SEQ ID NO:97) and MA-3'Bash-ZnCys-RP (SEQ ID NO:98) were used to confirm the insertion of the donor fragment into the 3' regions of the ZNCys-2845 gene. Eleven of the twelve guide RNAs resulted in isolates that were diagnosed by colony PCR as having the Hyg gene inserted at the targeted locus.

Quantitative reverse transcription-PCR (qRT-PCR) was performed on RNA isolated from the knockdown lines to determine whether expression of the ZnCys-2845 gene was in fact reduced in these lines. The ZnCys-2845 Bash Knockdown strains were grown under standard nitrogen replete conditions (PM074 (nitrate-only) medium) and harvested during early stationary phase. Total RNA was isolated from ZnCys-2845 Bash Knockdown cells and converted to cDNA BioRad’s iScript™ Reverse Transcription Supermix kit according to the manufacturer’s protocol. For PCR, Ssofast EvaGreen Supermix (Bio-Rad, Hercules, CA) was used along with gene-specific primers. The PCR reaction was carried out on C1000 Thermal Cycler coupled with a CFX Real-time System (BioRad). Primer and cDNA concentrations were according to the manufacturer’s recommendation. Primers for amplifying a sequence of the ZnCys-2845 transcript were SEQ ID NO:99 and SEQ ID NO:100. Transcript levels for each sample were normalized against a housekeeping gene with consistent expression levels under different culture conditions (1T5001704; SEQ ID NO:101) and relative expression levels were calculated using the ddCT method using BioRad’s CFX Manager software.

FIG. 14B shows that several of the strains had reduced levels of ZnCys-2845 transcript. Of these, strains GE-13108 (ZnCys-2845 Bash-3) and GE-13109 (ZnCys-2845 Bash-4), targeting the 5' end of the ZnCys-2845 gene, and strain GE-13112 (ZnCys-28453 Bash-12), targeting the 3' end of the ZnCys-2845 gene, were selected for productivity assays.

Example 11. ZnCys-2845 RNAi Knockdown Construct

Figure 15:
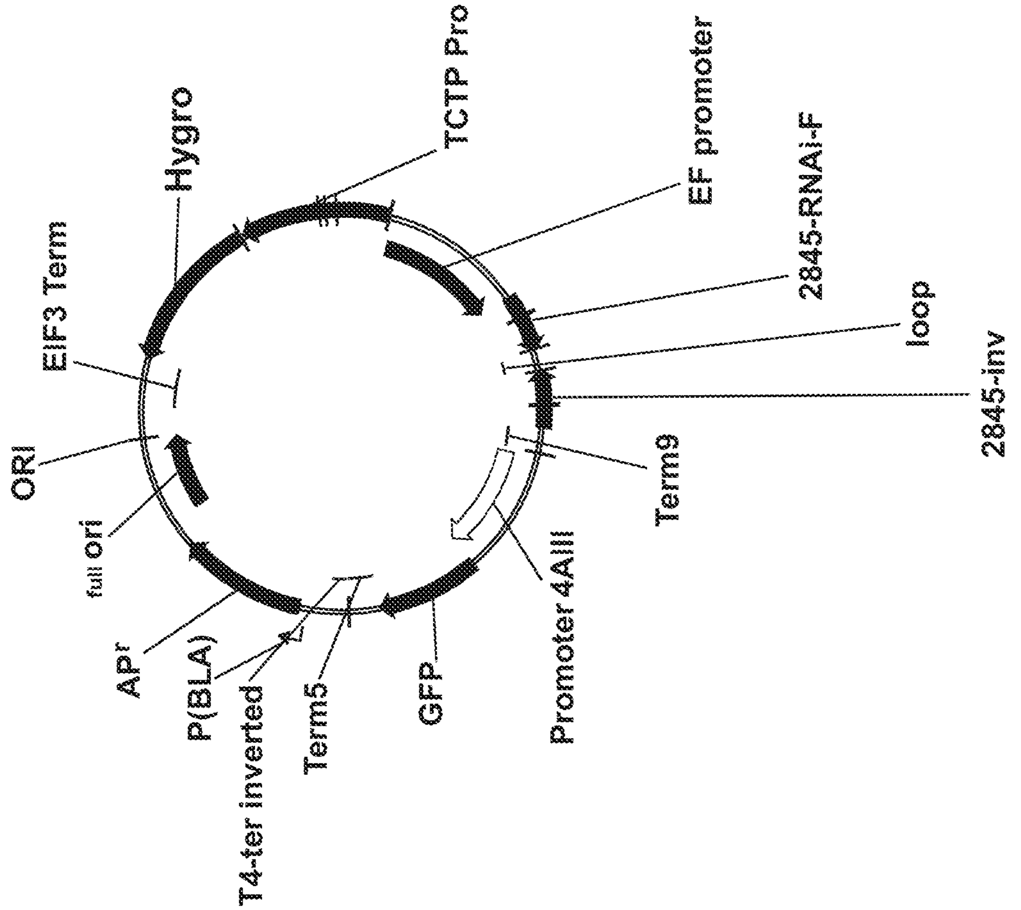
FIG. 15 is a schematic diagram of the vector than included an RNAi construct for attenuation expression of the ZnCys-2845 gene. The vector included a blast gene for selection and a GFP gene for assessing penetrance of the genes of the inserted RNAi construct.

In another strategy to determine whether decreasing expression of the ZnCys-2845 gene would allow the cells to accumulate more carbon than the Cas9-mediated ZnCys-2845 knockout (Example 9) while still producing increased amounts of lipid with respect to wild type, an interfering RNA (RNAi) construct (shown in FIG. 15) was designed for expression in *Nannochloropsis* cells. The construct included a sequence designed to form a hairpin that included a sequence homologous to a region of the ZnCys-2845 gene (SEQ ID NO:102), followed by a loop sequence and then followed by the inverse sequence to the ZnCys-2845 gene-homologous sequence, driven by the *N. gaditana* EIF3 promoter (SEQ ID NO:45) and followed by *N. gaditana* "terminator 9" (SEQ ID NO:103). The construct that included the RNAi expression cassette also included the *Nannochloropsis* codon-optimized gene encoding TurboGFP (Evrogen; Moscow, Russia) codon-optimized for *Nannochloropsis* (SEQ ID NO:24) under the control of the *Nannochloropsis* 4AIII promoter (SEQ ID NO:40) and followed by "terminator 5" (SEQ ID NO:41), as well as a gene conferring hygromycin resistance (SEQ ID NO:44) driven by the TCTP promoter (SEQ ID NO:11) and terminated by the EIF3 terminator (SEQ ID NO:12). The RNAi expression cassette for the construct was positioned between the hygromycin resistance expression cassette (which was positioned 5' of and oriented in a transcriptional direction opposite to that of the RNAi construct) and the GFP expression cassette (which was positioned 3' of the RNAi cassette and oriented in the same transcriptional direction as the RNAi cassette) The construct was linearized and transformed into wild type *Nannochloropsis gaditana* WT-3730 by electroporation as described.

Hygromycin resistant colonies were screened for the presence of the RNAi construct by PCR, and were further screened for full penetrance of GFP using flow cytometry as described in Example 3, above. Flow cytometry was performed to test the penetrance of lines 6, 7, 10, 12, 13, 21, 25, and 30 isolated from transformants that were positive for the RNAi construct and overlaid with the traces of wild type controls.

Because RNAi was employed to test different levels of gene attenuation, it was of interest to test the phenotypes of strains showing different penetrance patterns. For example, some of the RNAi construct carrying lines, such as lines 10, 13, 21, and 30, were not fully penetrant, that is, their fluorescence traces essentially coincided with that of wild-type. Interestingly, strain 25 had the most reduced RNA level with respect to wild type levels, followed by strains 7, 10, 6, and 12. A characteristic of attenuation of the ZnCys-2845 gene is the inability (or, depending on the level of attenuation of ZnCys2845 gene expression, reduced ability) to grow on media that include only nitrate as a nitrogen source. The knockout shows no growth (rightmost flask), and strain 1 and strain 12 showed very little to no growth as well. Strains 7 and 25 had reduced growth in nitrate only medium, whereas strains 10, 13, 21, and 30 demonstrated growth similar to wild type. Notably, strain 10, which appeared by RNA level to have a high level of gene attenuation (at least as high as strain 6), does not display nearly as strong a phenotype as strain 6. This difference in phenotype, while not predictable from RNA levels, correlated well with the incomplete penetrance of GFP expression of strain 10 and the fully penetrant expression of GFP in strain 6. Thus, assessment of fluorescence of a linked fluorescent protein gene in a clonal population was a highly reliable method for isolating strains with consistent expression of a gene of interest.

Strain 7, which displayed full penetrance but a less severe reduction of growth in nitrate-only medium than the knockout strain was renamed strain GE-13103 and selected for further evaluation along with the promoter and 3' end disruption strains isolated in Example 10.

Example 12. Phenotyping of ZnCys-2845 Knockdown Constructs

To rigorously test the lipid regulator phenotype, ZnCys-2845 RNAi strain GE-13103 and ZnCys-2845 knockdown insertional "basher" strains GE-13108, GE-13109, and GE-13112 were tested in the batch productivity assay by scaling up the cultures in culture medium PM124 (which includes both $NH_4$ and $NO_3$ as nitrogen sources) and by carrying out the assay in PM123 culture medium that includes nitrate as the sole nitrogen source.

Strikingly, all gene attenuation mutants, including original knockout mutant GE-8564, produced FAME in amounts greater than wild type when cultured with nitrate as the sole nitrogen source on all days sampled (Table 9). However, while the original knockout strain GE-8564 had a significantly reduced rate of total organic carbon accumulation with respect to wild type (Table 10), in these conditions, the attenuated knockdown strains—the "bash" strains and RNAi strain having reduced expression of the ZnCys-2845 gene had rates of TOC accumulation close to or (for example in the case of GE-13112) essentially identical to, wild type (Table 10). Remarkably, these ZnCys-2845 knockdown mutants demonstrated FAME to TOC ratios that were significantly enhanced with respect to wild type (Table 11).

TABLE 9

FAME productivity of ZnCys-2845 Knockdown Strains Compared to Wild Type in Batch Assay with $NO_3$-containing Culture Medium (mg/L culture)

| | | BASH-3 (GE-13108) | | BASH-4 (GE-13109) | | BASH-12 (GE-13112) | | RNAi-7 (GE-13103) | | ZnCys-KO (GE-8564) | |
|---|---|---|---|---|---|---|---|---|---|---|---|
| Day | WT | | % incr | | % incr | | % incr | | % incr | | % incr |
| 3 | 159.22 | 279.72 | 75.68 | 260.14 | 233.36 | 233.36 | 40.64 | 233.36 | 46.56 | 242.05 | 52.02 |
| 5 | 191.33 | 446.40 | 133.31 | 377.8 | 368.41 | 368.41 | 55.98 | 368.41 | 92.55 | 360.89 | 88.67 |
| 7 | 270.37 | 599.06 | 121.57 | 431.41 | 460.69 | 460.69 | 27.96 | 460.69 | 70.39 | 473.53 | 75.14 |

TABLE 10

TOC productivity of ZnCys-2845 Knockdown Strains Compared to Wild Type in Batch Assay with NO3-containing Culture Medium (mg/L culture)

| | | BASH-3 (GE-13108) | | BASH-4 (GE-13109) | | BASH-12 (GE-13112) | | RNAi-7 (GE-13103) | | ZnCys-KO (GE-8564) | |
|---|---|---|---|---|---|---|---|---|---|---|---|
| Day | WT | | % diff | | % diff | | % diff | | % diff | | % diff |
| 3 | 642.4 | 608.1 | −5.34 | 615.05 | −4.26 | 627.2 | −2.37 | 497.4 | −22.57 | 281.5 | 56.18 |
| 5 | 920.75 | 827.9 | — 10.09 | 836.9 | −9.11 | 913.95 | −0.74 | 713.4 | −22.52 | 408.8 | — 55.01 |
| 7 | 1188 | 1044.5 | 12.08 | 1044 | −12.12 | 1175.5 | −1.05 | 929.2 | −21.78 | 558.15 | 53.18 |

TABLE 11

FAME/TOC ratios of ZnCys-2845 Knockdown Strains Compared to Wild Type in Batch Assay with $NO_3$-containing Culture Medium

| | WT-3730 | | BASH-3 (GE-3108) | | BASH-4 (GE-3109) | | BASH-12 (GE-13112) | | RNAi-7 (GE-13103) | | ZnCys-KO (GE-8564) | |
|---|---|---|---|---|---|---|---|---|---|---|---|---|
| Day | | s.d. | | s.d. | | s.d. | | s.d. | | s.d. | | s.d. |
| 3 | 0.25 | 0.009 | 0.46 | 0.009 | 0.42 | 0.010 | 0.36 | 0.004 | 0.47 | 0.015 | 0.86 | 0.033 |
| 5 | 0.21 | 0.001 | 0.54 | 0.006 | 0.45 | 0.003 | 0.33 | 0.011 | 0.52 | 0.023 | 0.88 | 0.040 |
| 7 | 0.23 | 0.001 | 0.57 | 0.005 | 0.41 | 0.004 | 0.29 | 0.003 | 0.50 | 0.007 | 0.85 | 0.060 |

Figure 16:
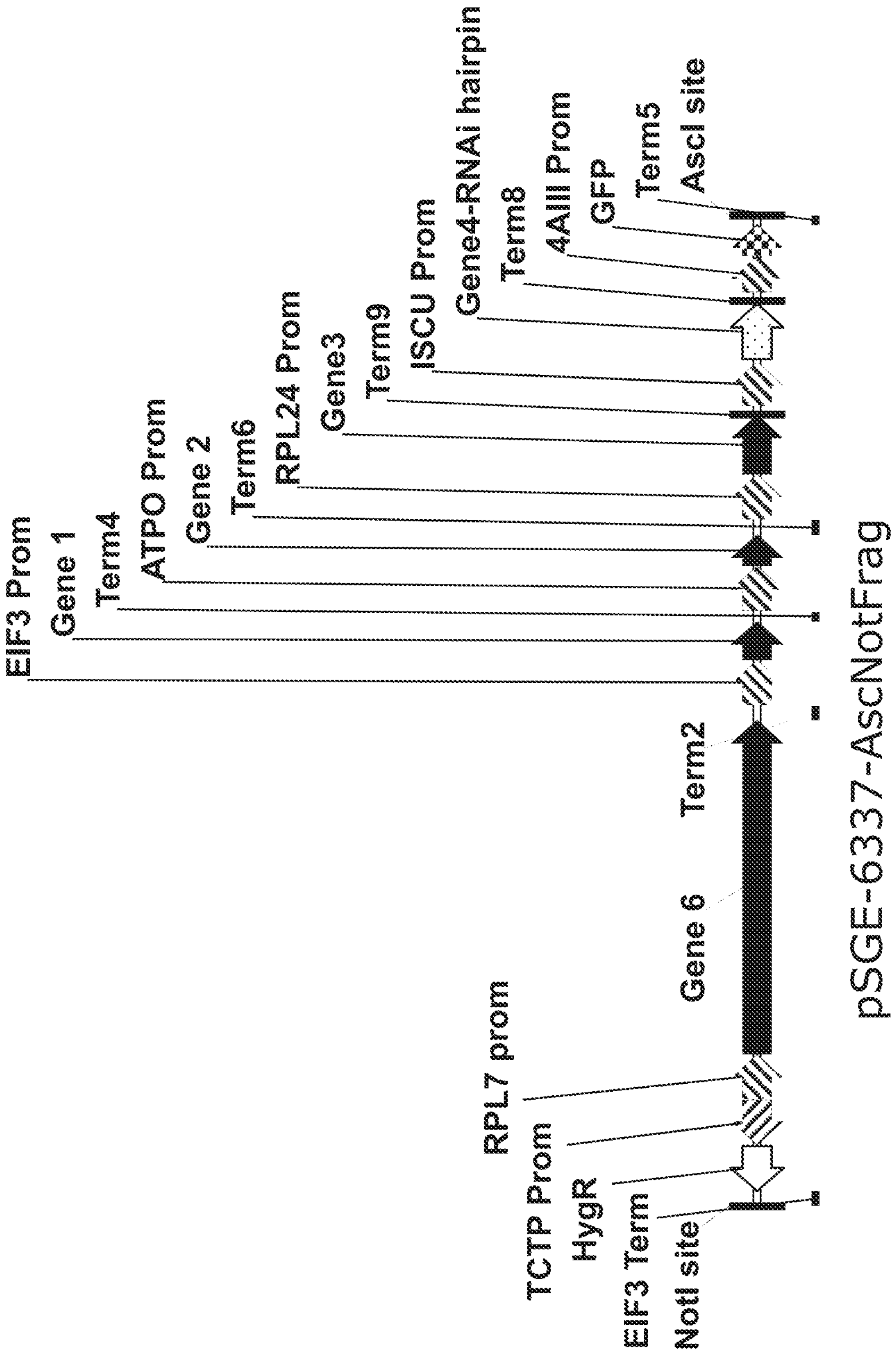
FIG. 16 provides a diagram of the 22.3 kb Donor DNA that included 6 genes, each with a separate promoter.

Example 13. Targeted Integration of Transgene(s) Using Fully Penetrant *Nannochloropsis* Cas9 Editor Line Cas9 Editor Strain GE-6791 of Example 3 was also used to assess targeted integration of a transgenic pathway to a specific locus. The aco 2 CRISPR target locus within the acyl-CoA oxidase gene was again chosen (SEQ ID NO:48) as it was successfully disrupted using the HygR cassette in Example 5 and gRNA targeting the gene (SEQ ID NO:49) was already available (see Example 5). A 22.3 kb fragment obtained by Asc/Not restriction digest and gel purification of vector pSGE-6337 (SEQ ID NO:104) was chosen for targeted integration into the aco2 site. This fragment contained 6 expression cassettes intended for metabolic engineering, and the six tandemly arranged expression cassettes were flanked by a HygR cassette on one end and a GFP cassette on the other end (FIG. 16).

Figure 17:
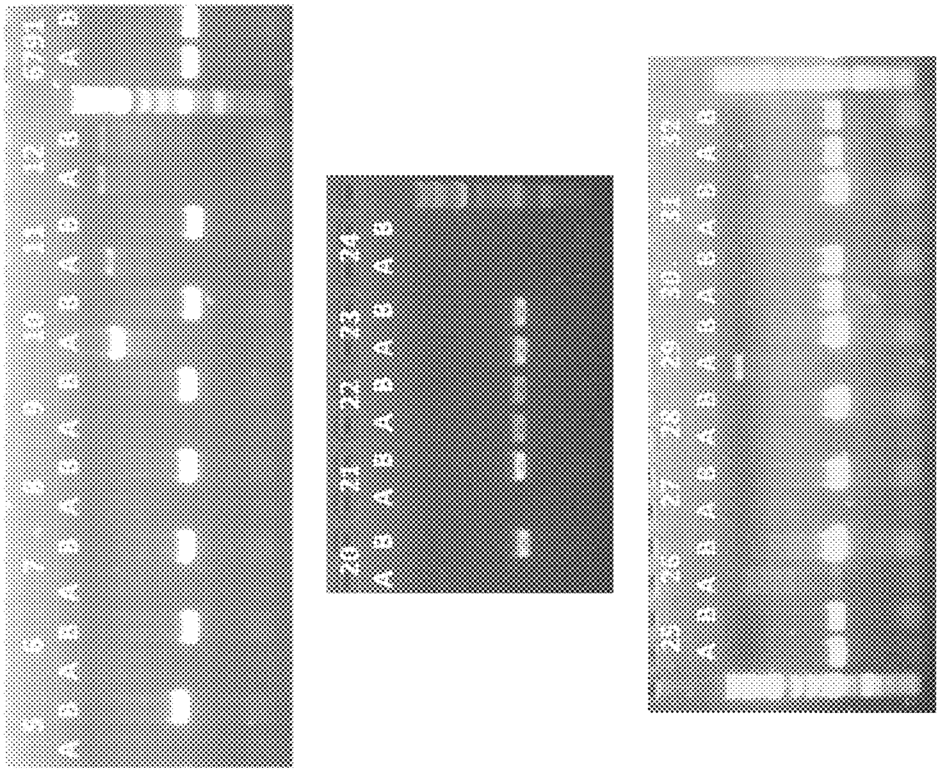
FIG. 17 provides photographs of PCR products diagnostic for the presence of the 22.3 kb integration fragment targeted to the acyl-CoA oxidase locus, with clones 5, 6, 7, 8, 9, 20, 27, 38, & 31 having directed integration events.

The GE-6791 Cas9 expression strain was transformed by electroporation using 5 μg of purified chimeric guide RNA targeting the aco2 target site, and 1 μg of one of the pSGE-6337-Asc/Not Fragment (SEQ ID NO:104). Following electroporation, cells were plated on agar media containing hygromycin to select for transformants that incorporated the 22.3 kb DNA molecule. Transformants were screened by colony PCR as described previously (see Example 2) but using primers flanking the aco2 target (SEQ ID NO:17) (SEQ ID NO:18), as well as another reaction which included a third primer that primes off of HygR gene (SEQ ID NO:105), which is near one end of the fragment and points outward. The PCR results are shown in detail (FIG. 17), in which colonies 5, 6, 7, 8, 9, 20, 27, 28, and 31 appear to have integrated the 22.3 kb donor DNA into the targeted aco2 site.

Example 14. *Nannochloropsis* Editor Strain Expressing tracrRNA

A Nannochloropsis editor strain can also be engineered by transforming wild type *Nannochloropsis* with a construct that includes: 1) a Cas9 expression cassette containing a Cas9 gene from *Streptococcus pyogenes* codon optimized for *Nannochloropsis gaditana* (SEQ ID NO:1) with an N-terminal FLAG tag (SEQ ID NO:5), nuclear localization signal (SEQ ID NO:4), and a peptide linker (SEQ ID NO:39), driven by the *N. gaditana* RPL24 promoter (SEQ ID NO:25) and terminated by *N. gaditana* bidirectional terminator 2 (SEQ ID NO:26); 2) an expression cassette designed to drive expression of a tracr RNA (SEQ ID NO:106) that includes a 20 bp sequence that hybridizes to a crRNA and a 16-22 nucleotide sequence that interacts with the Cas9 protein, driven by the *N. gaditana* putative U6 promoter (SEQ ID NO:15) and followed by the U6 terminator (SEQ ID NO:16); and 4) a selectable marker expression cassette, which contained the blast gene from *Aspergillus terreus* codon optimized for *N. gaditana* (SEQ ID NO:10), driven by the *N. gaditana* TCTP promoter (SEQ ID NO:11) and followed by the EIF3 terminator (SEQ ID NO:12); and 4) a GFP reporter expression cassette, which contained the TurboGFP gene (Evrogen, Moscow, Russia) codon-optimized for *Nannochloropsis gaditana* (SEQ ID NO:24), driven by the *N. gaditana* 4A-III promoter (SEQ ID NO:40) and followed by the *N. gaditana* bidirectional terminator 5 (SEQ ID NO:41) which occurs between the Glucosamine 6-phosphate isomerase 2 gene and the YVTN repeat like quinoprotein amine dehydrogenase gene in the *N. gaditana* genome.

Strains transformed with this construct are plated onto PM74 agar medium containing blasticidin. Colonies are patched onto selection media for analysis and archiving and optionally screened for the presence of the construct by PCR. Transformants from single colony isolates are screened by flow cytometry as described in Example 3. The resulting histograms are overlaid with histograms of wild type cells (i.e., cells not expressing a fluorescent protein) run separately. Only strains with fully penetrant expression in culture are investigated further; meaning that the flow cytometry GFP fluorescence histogram show a single peak or bell-shaped curve in which the fluorescence peak was fully shifted higher than the wild type autofluorescence (background fluorescence) peak when plotted on a log scale. These strains are designated as "fully penetrant" Cas9 and tracrRNA expressing strains, in that the expression of the physically linked GFP gene is found throughout the cells of a culture of the strain. That is, while at any given point in time the amount (and therefore fluorescence) of GFP might vary somewhat cell-to-cell, resulting in peaks or bell-shaped curves, there is no subpopulation of cells observed in these lines than exhibit a distinct distribution of GFP expression with respect to the shifted peak.

Fully GFP-penetrant Cas9 strains demonstrating a single clearly shifted fluorescence peak with respect to nontransformed cells (see for example FIGS. 5A and 5B and Table 1, in which clones are scored by 'X's' according to whether they exhibited single or double peaks) are then tested by western blotting with an anti-FLAG antibody for evidence of Cas9 expression and with a nucleic acid probe for the presence of the tracrRNA.

For genome editing, a fully penetrant Cas9 plus tracrRNA expressing strain is transformed with a crRNA targeting a particular genome locus as well as a donor DNA for insertion into the edited locus. The crRNA used includes a 20 nucleotide sequence targeting the acyl-CoA oxidase gene (SEQ ID NO:14) juxtaposed with a 20 nucleotide tracrRNA recognition or "tracr mate" sequence to provide the entire acyl-CoA oxidase gene targeting RNA (SEQ ID NO:107). The donor DNA included a hygromycin resistance (HygR) gene (SEQ ID NO:22) under the control of the *N. gaditana* EIF3 promoter (SEQ ID NO:23) terminated by *N. gaditana* bidirectional terminator 2 (SEQ ID NO:26) (the operably linked HygR gene, promoter, and terminator referred to herein as the HygR cassette).

Following transformation, HygR colonies are screened for the presence of the HygR cassette in the acyl-CoA oxidase gene locus.

Example 15. *Chlorella* Editor Strain with Tracr RNA Expressed, Cr RNA Introduced In another example, both the tracrRNA and the crRNA are transformed into fully penetrant *Parachlorella* Cas9 Editor line GE-15699 to integrate a gene cassette into a targeted locus. In this case the tracrRNA and crRNA are separate molecules. The targeting crRNA (SEQ ID NO:108) is designed to target the chloroplastic SRP54 gene whose disruption results in a reduced pigment phenotype. Both the crRNA and the transactivating RNA (SEQ ID NO:109) are chemically synthesized. The two RNAs are mixed together at a 1:1 molar ratio, at a concentration of approximately 3 μM each in 10 mM Tris, 1 mM EDTA, pH 7.5 (RNase-free). The volume can range for example, from about 20 μl to about 200 μl. The RNA solution is heated to 94-99° C. in a temperature block for approximately 2 minutes, after which the temperature block is turned off. The hybridization mixture is allowed to cool in the temperature block until the block reaches 25° C. or less. An amount of annealed RNAs ranging from about 1 to about 5 μg is then added to a cuvette containing *Parachlorella* Cas9 Editor line GE-15699 cells (approximately $5\times10^8$ cells in a 0.2 cm cuvette) that have been prepared for electroporation according to Example 7. Donor DNA (approximately 1 μg) that includes the BleR cassette optimized for expression in *Parachlorella* (SEQ ID NO:66) is then added to the cuvette and the cells are electroporated according to the methods provided in Example 7. Zeocin resistant colonies are inspected visually for reduced pigment. Pale green colonies are screened by colony PCR for the presence of the donor fragment at the cpSRP54 locus using primers designed to amplify across the native targeted locus (oligo-AE596; SEQ ID NO:67 and oligo-AE597; SEQ ID NO:68).

Example 16. Markerless Transformation Using *Nannochloropsis* Cas9 Editor Strain and Qdots The very high efficiency of genome editing in the *Nannochloropsis* cas9 Editor Strains allows for markerless transformation. In one strategy, the photosynthetic regulator gene Lar1 (disclosed in copending U.S. Patent Application Publication No. US 2014/0220638, incorporated herein by reference) was targeted for mutation because mutation of the Lar1 gene results in an easily identifiable phenotype (reduced chlorophyll) that can be visually scored to determine if there is any improvement in mutant retrieval rate over the non-enrichment method. The Cas9 Editor strain GE-6791 was transformed with a chimeric gRNA targeting Lar1 (SEQ ID NO:109) and QDot585 "Qtracker" nanoparticles (Life Tech #Q25011MP). 5 μg of gRNA was mixed with 2 μl of pre-mixed Qtracker (according to manufacturer's instructions) and transformed into *Nannochloropsis* cells by electroporation as described previously. After transformation, cells were either: 1) directly plated onto agar media, 2) FACs sorted to enrich for Qdot positive cells and then plated, or 3) incubated with Live/Dead Blue stain (Life Technologies #L-23105) according to the manufacturer's instructions, and FACs sorted to enrich for Qdot positive cells while excluding the stained "Dead" cells and then plated.

The smallest and palest colonies were patched for PCR sequencing, where they were sequence confirmed and verified to have small insertions or deletions (averaging 1 or 2 bases) from NHEJ mis-repair. An increase in the mutant retrieval rate was increased from 0.05% when directly plating them out, to 0.13% when Qdots were FACS enriched and dead cells were excluded (Table 4). Although this increase is significant, the false positive rate was quite high. It was hypothesized that some proportion of the Qdot positive cells might have had Qdots associated with the cell wall and not necessarily residing inside the cell.

TABLE 12

Markerless mutation frequency using Cas9 fully penetrant Editor line

| Condition | No. Colonies Screened | No. Mutants | % Rate |
|---|---|---|---|
| Direct plating | 2020 | 1 | 0.05 |
| FACS-Qdot enriched | 3310 | 4 | 0.12 |
| FACS-Qdot enriched + Live/Dead Exclusion | 4690 | 6 | 0.13 |

Example 17. Markerless Transformation Using *Nannochloropsis* Cas9 Editor Strain and In Vitro Transcribed mRNA for GFP In these experiments, instead of Qdots, the chimeric guide RNA is transformed into *Nannochloropsis* along with an in-vitro synthesized messenger RNA encoding a fluorescent protein such as TagGFP (Evrogen, Moscow, Russia). This would eliminate the high false positive rate seen in Example 9 because no fluorescent protein would be made unless the GFP mRNA was inside of the cell and in contact with its ribosome machinery. In this experiment, cells would be allowed to recover after transformation, for example, for a period of time that could be tested but might be from four to forty-eight hours, after which the cells would be sorted by flow cytometry. Cells displaying above-background fluorescence (where background fluorescence is determined by cells transformed without the GFP-encoding RNA) would be selected and plated without selection, and later screened by PCR using primers having homology to sequences flanking the targeted genomic locus. Furthermore, TagGFP, being a monomeric version of GFP, could also be translationally fused onto either the N-terminus or C-terminus of the Cas9 gene, and the Cas9 gene, instead of being integral to the host cell, might also be transiently expressed to perform its genome editing function. This would enable a non-GMO approach to Cas9 editing.

Figure 18:
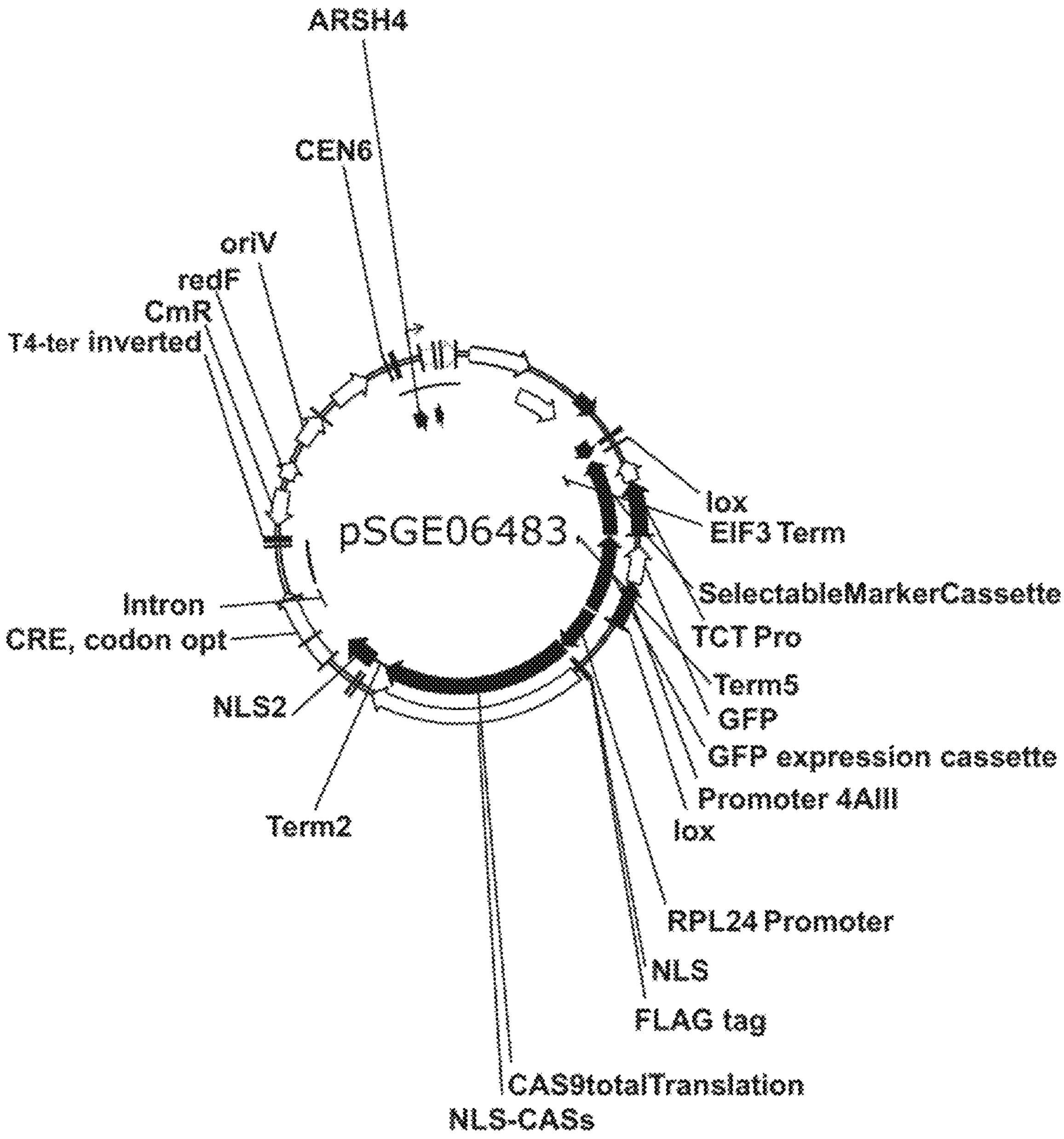
FIG. 18 is a schematic diagram of vector pSGE-6483 that includes, in addition to a Cas9 gene, GFP gene, and HygR gene, a cre recombinase gene optimized for expression in *Nannochloropsis*. Each of the Cas9, GFP, HygR, and cre genes was operably linked to a separate *Nannochloropsis* promoter. The cre recombinase gene was operably linked to the ammonia-repressible Nitrite/Sulfite Reductase promoter.

Example 18. Development of a Markerless, Reporterless *Nannochloropsis* Cas9 Editor Strain with Repressible Cre Recombinase Expression Capabilities A vector, pSG6483, was designed and engineered for constitutive expression of a Cas9 nuclease and repressible expression of Cre recombinase in *Nannochloropsis gaditana* (FIG. 18). The vector contained the following four elements: 1) the Cas9 expression cassette described in Example 3 ("Development of fully penetrant *Nannochloropsis* Cas9 Editor Lines"), 2) the selectable marker cassette ("HygR cassette") described in Example 3, 3) the same GFP reporter cassette described previously in Example 3, and 4) a repressible CRE expression cassette containing the Cre recombinase from P1 Bacteriophage codon optimized for *Nannochloropsis gaditana*, which contains the same N-terminal NLS used for the Cas9 construct and also includes an *N. gaditana* intron inserted into the Cre coding region (engineered Cre gene provided as (SEQ ID NO:111). The *Nannochloropsis*-engineered Cre gene was operably linked to the "Ammonia repressible Nitrite/Sulfite Reductase" promoter (SEQ ID NO:112) at the 5' end of the Cre gene and the "Nitrite/Sulfite Reductase" terminator (SEQ ID NO:113) at the 3' end of the Cre gene. The BlastR selectable marker and GFP reporter cassettes are arranged in tandem in the construct, and together they are flanked by identical lox sites in the same orientation. Features that are flanked by loxP sites are commonly referred to as "floxed". An ammonia-repressible promoter was to repress expression of the Cre gene as much as possible until after generating antibiotic resistant colonies and establishing full phenotypic penetrance of GFP. Additionally, cloning Cre into a vector that contains lox sites proved to be problematic, as even basal levels of Cre expression in *E. coli* looped out the floxed BlastR and GFP once Cre was cloned in. To get around this hurdle, an intron was inserted into the Cre gene disrupting the catalytic and nucleophilic domains. This resulted in the final stable vector pSGE-6483 (FIG. 18) which doesn't self-excise its floxed markers in *E. coli.* pSGE-6483 was transformed into *Nannochloropsis gaditana* and plated onto PM128 agar media that contains ammonia but not nitrate, where the medium contained 100 mg/L of blasticidin. Colonies were re-patched onto the same selective PM128 media for analysis and archiving, and screened for full phenotypic penetrance of GFP by flow cytometry as described in Example 3. Six lines were carried forward for parallel serial culturing in either media containing ammonium as the sole nitrogen source (PM128) or media containing sodium nitrate as the sole nitrogen source (PM129), with no blasticidin selection in either medium. After 2 weeks of serial culturing, the strains were examined for loss of GFP signal by flow cytometry, excision of the floxed GFP/BlastR cassettes by diagnostic PCR, Cre expression by Western Blot and qRT-PCR, and Cas9 expression by Western Blot.

Figure 19A:
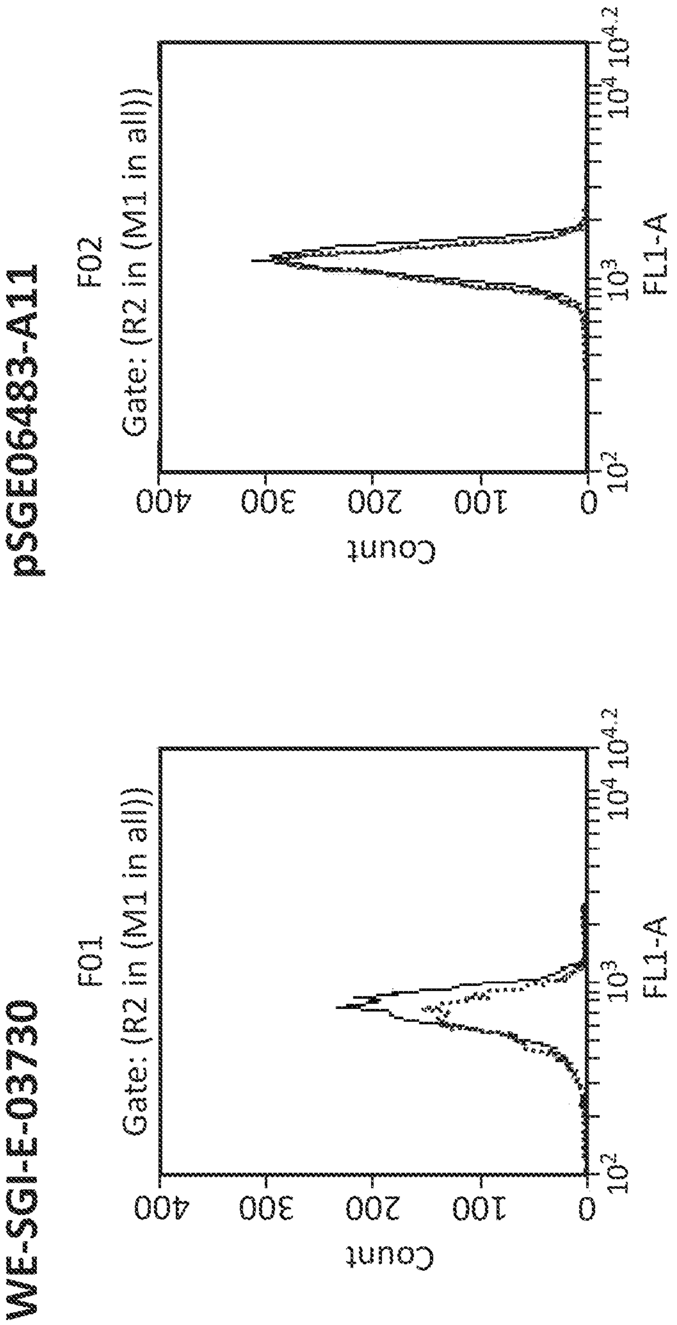
FIG. 19A-D shows the results of flow cytometry penetrance screens of cells transformed with pSGE-6483 and the difference in peak fluorescence intensity of cells grown in ammonia versus nitrate.
Figure 19B:
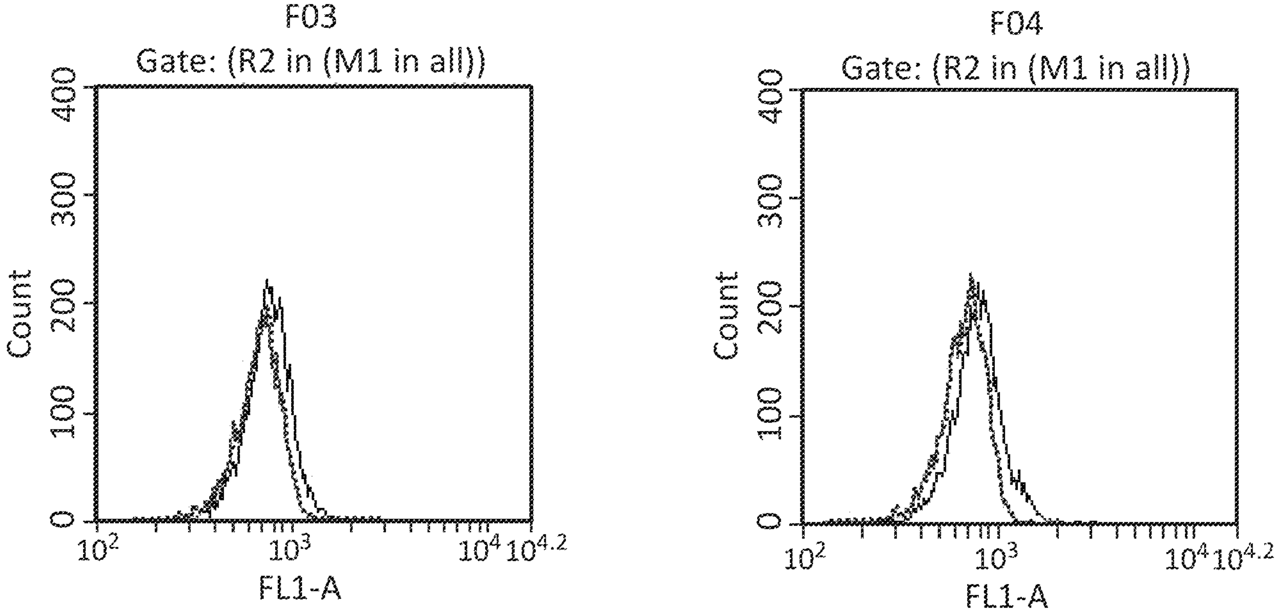
Figure 19C:
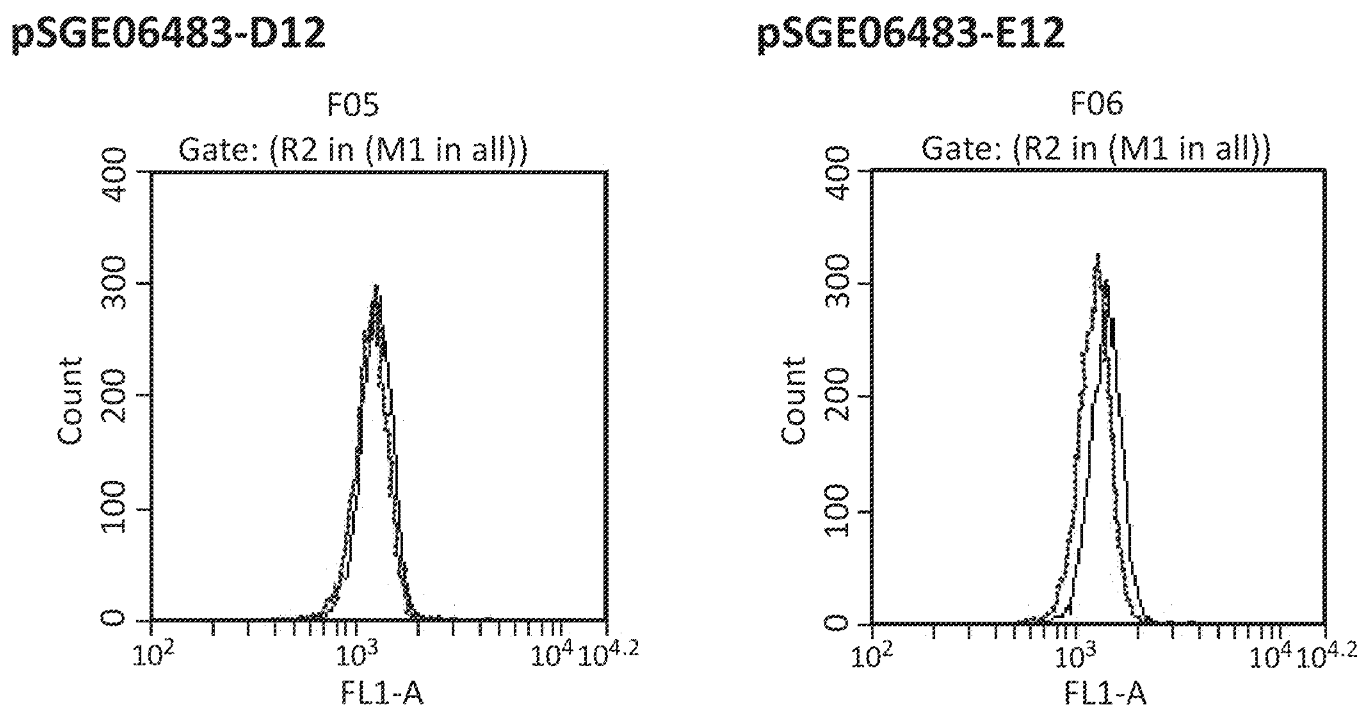
Figure 19D:
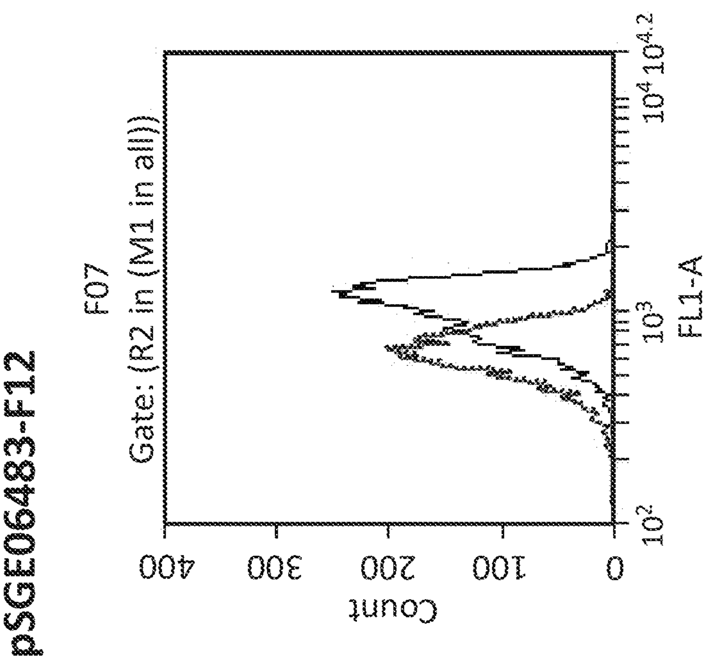
Figure 20:
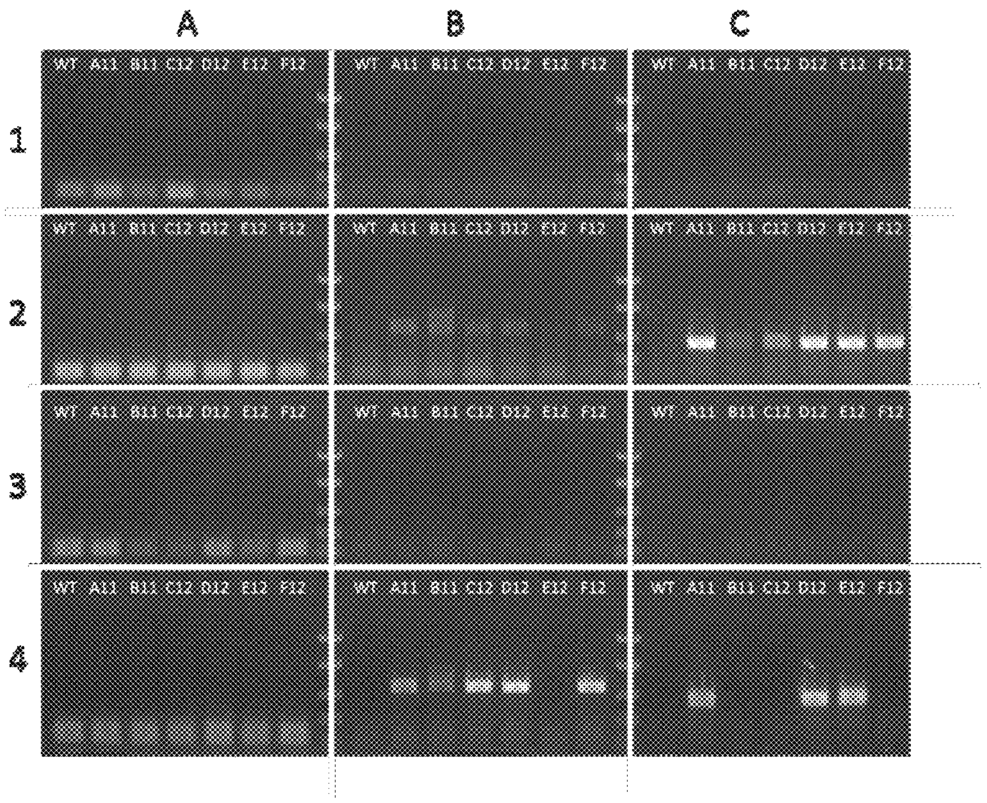
FIG. 20A-C is photographs of gels of RT/PCR products assessing levels of the GFP and cre transcripts in pSGE-6483 transformants under different nitrogen conditions.
Figure 21:
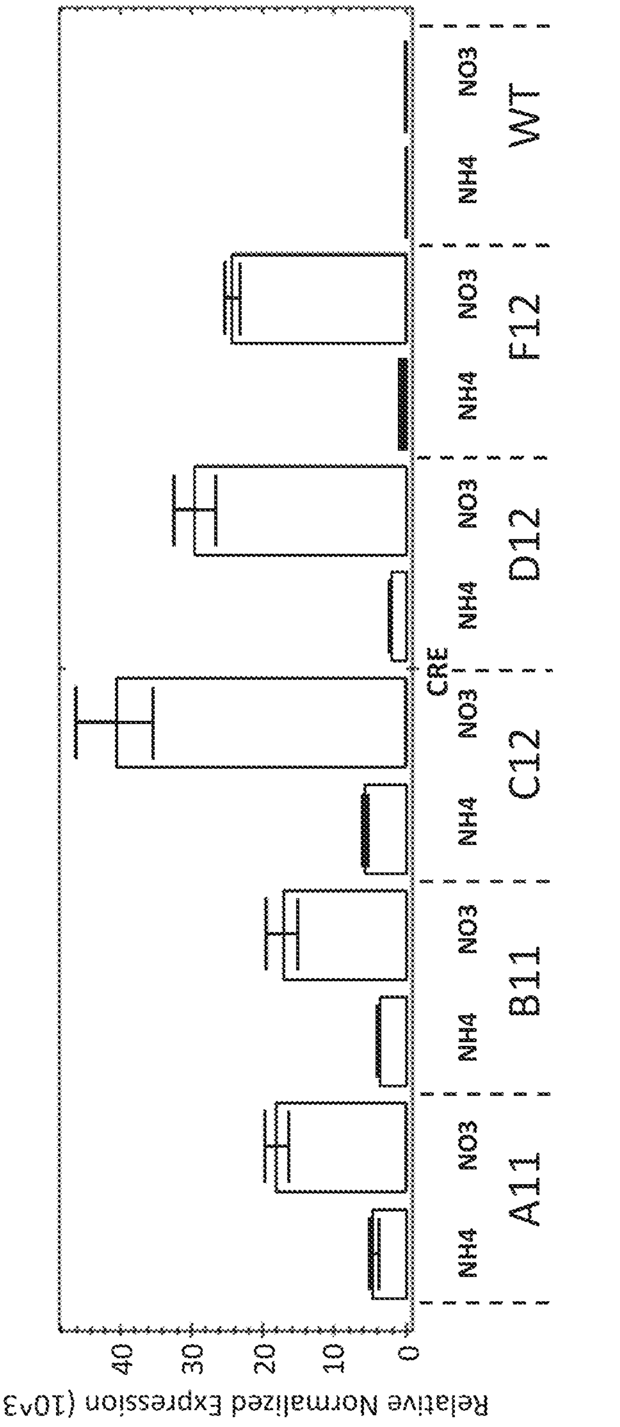
FIG. 21 provides a graphical representation of levels of the Cre transcript under different nitrogen conditions in transformants A11, B11, C12, D12, E12, and F12.

GFP histograms revealed mixed results for the different strains. Strain 6483-F12 was the only strain which showed an obvious GFP signal switch between $NH_4$ and $NO_3$ cultures (FIG. 19D). Strains B11 and C12 appeared to have lost GFP signal in both $NH_4$ and $NO_3$ (FIG. 19B), while strains A11, D12, and E12 appeared to have maintained GFP signal in both $NH_4$ and $NO_3$ (FIGS. 19A and C).

mRNA was extracted from the strains and cDNA was generated for RT-PCR and qRT-PCR experiments. RT-PCR was utilized as a fast way to detect and amplify transcripts for Cre, GFP, and a positive control gene ("1704", a gene found to have expression levels that were substantially unaffected by environmental conditions and nitrogen status of the cells) from *Nannochloropsis*. The gel image shows loss of GFP transcript in strains B11, C12, and F12 grown in $NO_3$ media (FIG. 20C), and an intensified signal for the Cre transcript grown in $NO_3$ media, except for strain E12 which had no detectable Cre transcript in either condition (FIG. 20B). qRT-PCR was used to quantify the fold changes in transcript abundance between the strains cultured in the expected repressed conditions ($NH_4$) versus non-repressed/induced conditions ($NO_3$). Varying levels of repression on $NH_4$ vs $NO_3$ was observed for all strains (FIG. 21). The basal level of Cre expression varies amongst the strains, with F12 having the least transcript for all the strains. This data aligns well with the GFP histogram data, as F12 was the only strain to still have a GFP positive histogram after the serial culturing in $NH_4$, while losing the GFP signal after serial culturing in $NO_3$. This indicates that successful repression of Cre activity is more likely to be achieved when the introduced Cre gene is relatively depressed overall (that is, even in induced conditions), but that such low-expressing strains still adequately excise floxed sequences when Cre expression was induced.

Figure 22:
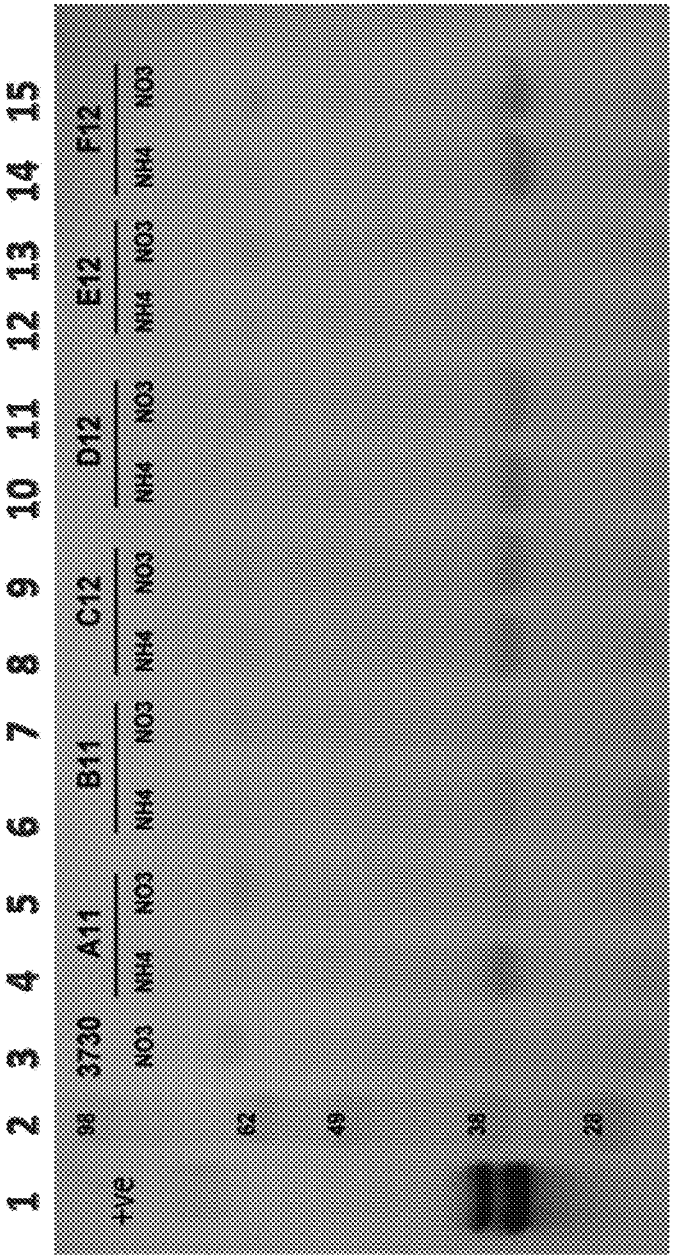
FIG. 22 provides a Western blot for detection of the Cre protein under different nitrogen conditions for transformants A11, B11, C12, D12, E12, and F12.
Figure 23:
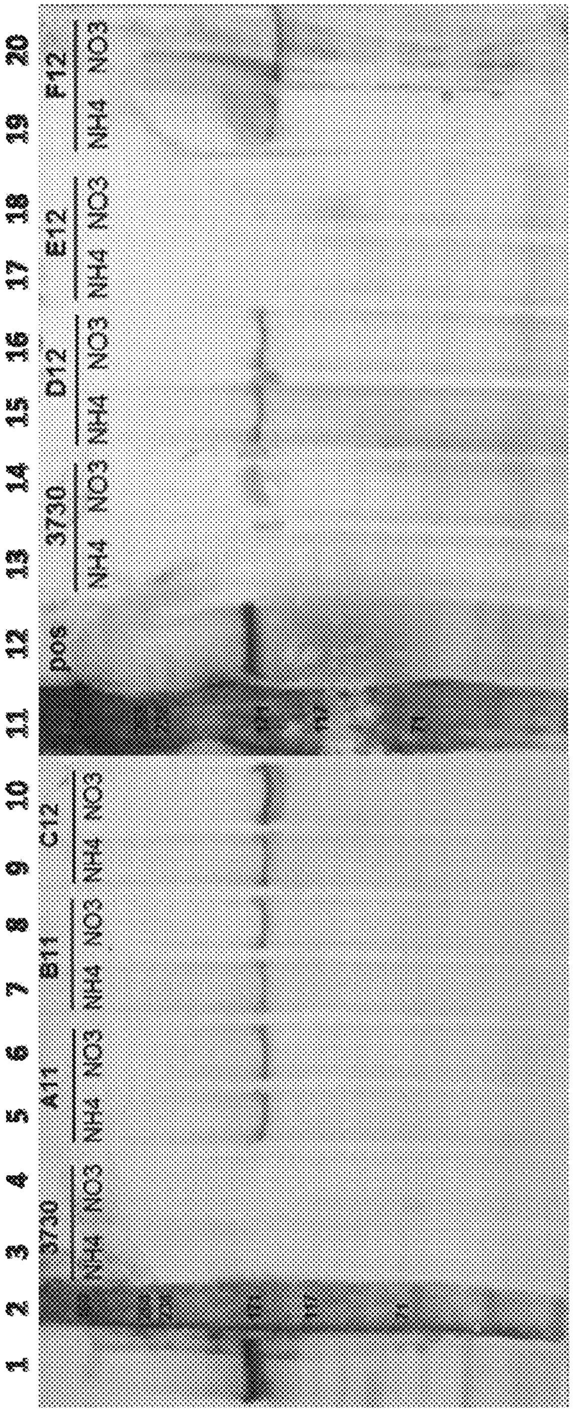
FIG. 23 provides a Western blot for detection of the Cas9 protein under different nitrogen conditions for transformants A11, B11, C12, D12, E12, and F12.

Anti-Cre western blots were done (FIG. 22), and the 38-kDa CRE protein was detected from all the cultures except E12 for which no transcript was detected by RT-PCR. Interestingly, similar amounts of Cre protein were detected in both the $NH_4$ and $NO_3$ conditions; it is possible that the differences in RNA levels detected by qRT-PCR were not reflected in the protein levels because samples were taken at different stages of growth of the cultures. Anti-Cas9 western blots were also performed, and the Cas9 enzyme was also detected in the transformed cells (FIG. 23).

Figure 24:
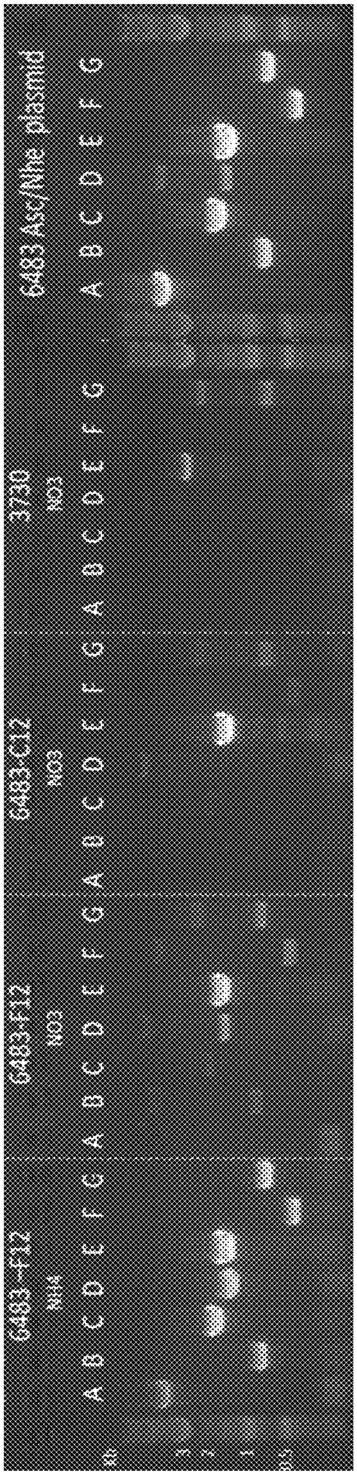
FIG. 24 is photographs of gels of PCR products of F12 and C12 cultures to determine whether the floxed GFP and BlastR gene cassettes were intact or excised by Cre-mediated recombination.
Figure 25:
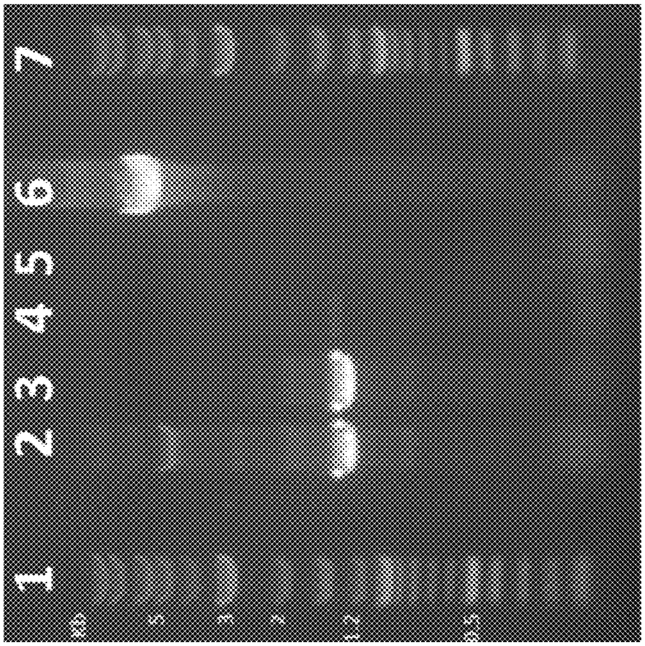
FIG. 25 is photographs of a gel of products of PCR to demonstrate in vivo excision of floxed GFP and BlastR gene cassettes.
Figure 26:
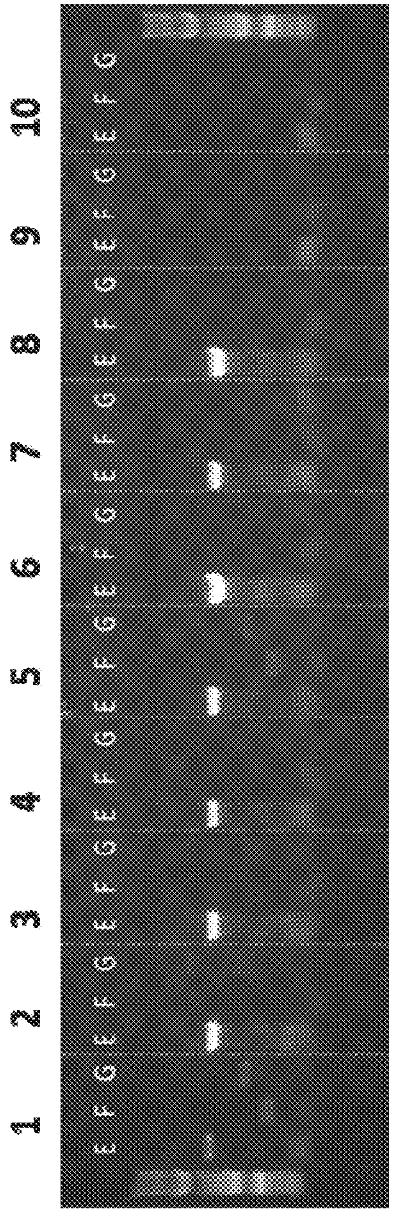
FIG. 26 is photographs of gels of PCR products of F12 and C12 cultures to determine whether the floxed GFP and BlastR gene cassettes were intact or excised by Cre-mediated recombination.

Diagnostic PCRs were performed on both F12 cultures and the induced C12 culture to determine whether the floxed GFP and BlastR gene cassettes were intact or excised by Cre-mediated recombination, to detect the presence of the circular recombination product, and to detect the presence of the GFP and BlastR genes only (FIG. 24). The F12-$NH_4$ (repressed) culture appears to be at some level of equilibrium, as both the intact floxed cassettes appear to be present (primer sets A,B,C) as well as the circular recombination product (primer set D) indicated that some level of recombination was occurring even under repressed conditions. The F12-$NO_3$ culture seems to have had the floxed genes mostly excised from the integration site, as primer set A failed to amplify across an entire intact region (no 3.7 kb band, difficult to discern whether a 185 bp band was amplified due to excision or not), and primer sets B and C yielded extremely faint bands, while primer sets D, F, and G yielded moderately faint bands. The C12-$NO_3$ culture seems to be further along in the excision process, however BlastR and GFP could still be detected on their own (primers sets F, G). In order to confidently detect if the locus is altered by excision, a new primer set was used to amplify across the floxed region (FIG. 25), in which an intact locus would yield a 4.9 kb band and the excised locus would yield a 1.3 kb band. The same equilibrium and/or heterogeneous culture was observed for the F12-$NH_4$ culture, as both the intact and excised bands are seen, while only the excised band was seen for the F12-$NO_3$ culture. Because faint GFP and BlastR signals were still observed in $NO_3$ cultures for both F12 and C12, cells from the $NO_3$ cultures for F12, C12, and B11 were diluted and plated out to single isolated colonies on agar plates containing $NO_3$ and no blasticidin to ensure strain homogeneity going forward. 3 isolated colonies from C12 and F12 were tested for the presence of the Cre, BlastR, and GFP genes by PCR (FIG. 26). The GFP and BlastR genes seem to be gone (primer sets E and F), while the CRE gene is still readily detected (primer set G).

The F12 strain was selected for further testing as anew Cre-enabled Editor strain as it demonstrated the most repressible CRE expression. This strain was named GE-13630.

Figure 27:
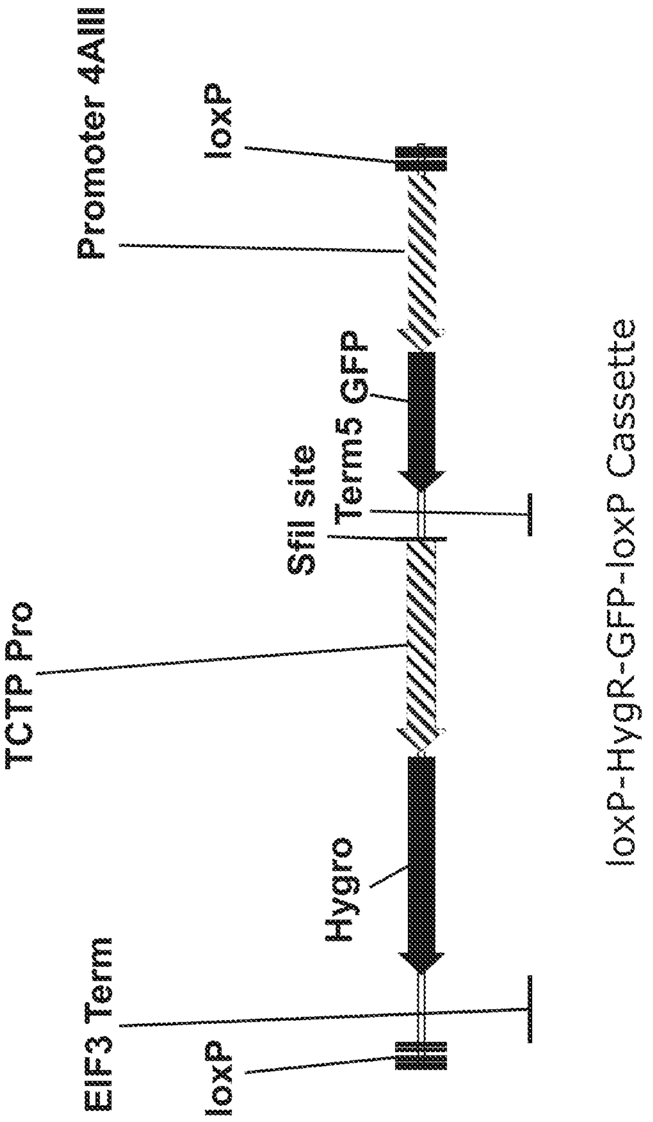
FIG. 27 is a schematic diagram of the floxed GFP and BlastR gene cassettes.
Figure 28:
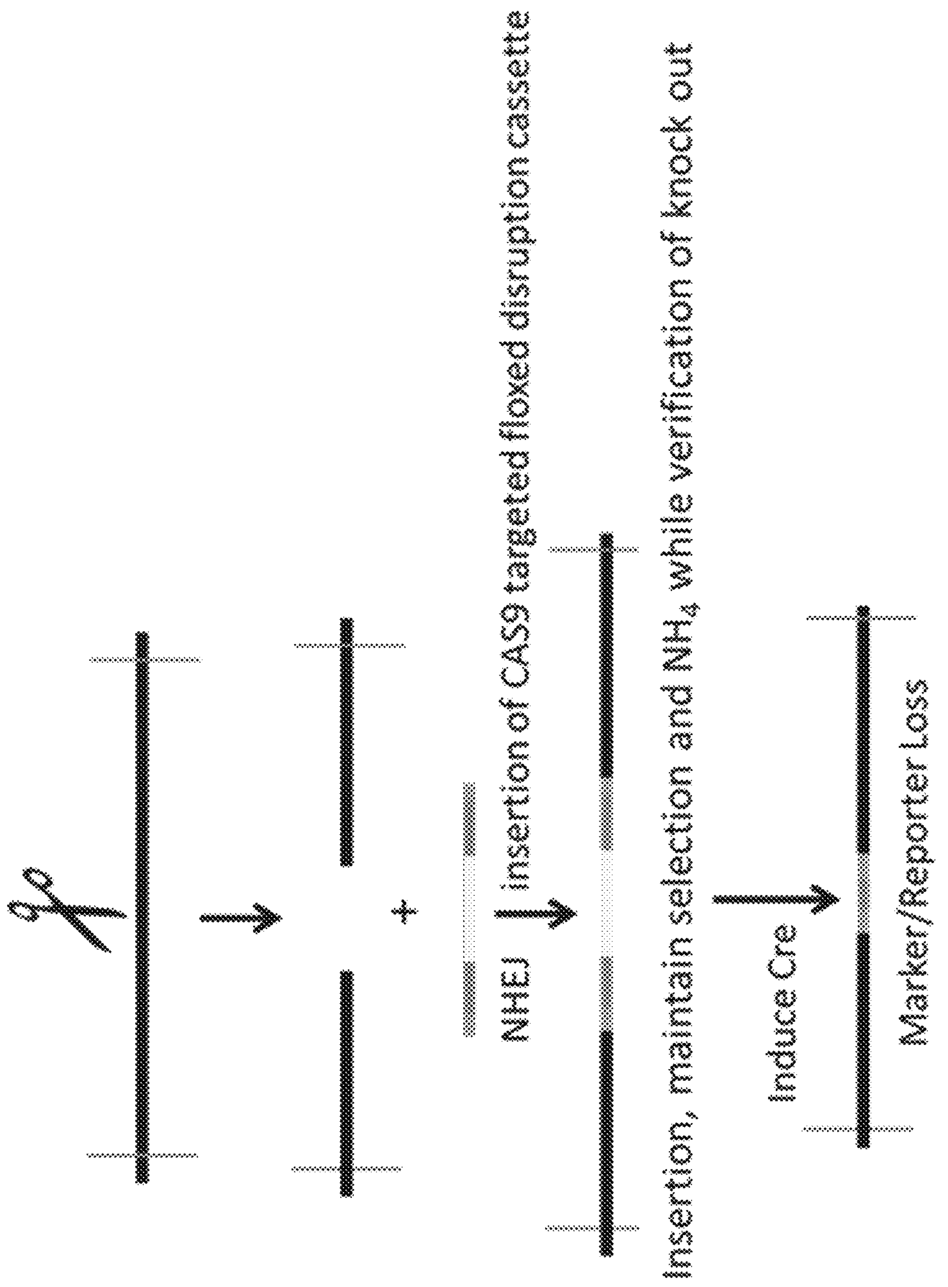
FIG. 28 is a diagram showing cas9 mediated insertion of a floxed disruption cassette which following confirmation of the insertion, is induced for cre expression resulting in excision of the reporter (fluorescent protein) and selectable marker, allowing for recycling of these components in further engineering steps.

Example 19. Markerless Knockouts by Recycling Markers in the *Nannochloropsis* Cas9 Editor Strain with Repressible Cre Recombinase Capabilities GE-13630 was transformed with gRNA targeting the acyl-CoA oxidase gene (as described earlier in Example 5) and a floxed disruption cassette (FIG. 27) (SEQ ID NO:115) as the donor fragment. This cassette included a hygromycin resistance gene and GFP gene, which were arranged in tandem and flanked by loxP sites in the same orientation. Outside of these loxP sites are three frames of stop codons. Upstream, they are in the direct orientation, and downstream they are in the reverse orientation. There are also unique "marks" on the far ends of the cassette for easy differentiation of the cassette, and also to serve as a DNA buffer to protect the stop codons and loxP sites from being damaged by the DNA end-repair mechanisms of *Nannochloropsis* during integration. The transformation was plated onto PM128 agar media containing 500 mg/L of hygromycin. This media contains ammonium to repress Cre expression so that transformants can be identified as resistant colonies and can be isolated. Colonies were patched onto the same selective media, genotyped and analyzed for GFP expression and colony PCR (as described in Example 5). A mix of DNA signals were seen, which showed the entire 4.5 kb fragment inserted as well as the 170 bp final excision product. This indicated that excision was already underway even in the presence of ammonium. To allow excision to go to completion, the strains were taken off selection and grown in media containing nitrate (PM129), which would remove the partial repression of Cre expression and promote a complete excision process throughout the culture. Strains were then genotyped and monitored for loss of GFP signal. One strain that passed these criteria (loss of HygR-GFP fragment as observed by PCR and loss of fluorescence signal) was streaked out for homogeneity on a nitrate plate with no hygromycin selection. Four isolated colonies underwent a final genotyping, and the PCR products of the acyl-CoA oxidase gene integration locus of these strains were sequenced. This clearly showed that the acyl-CoA oxidase gene was now disrupted only by the residual 170 bp scar which included translational stops to disrupt the open reading frame of the gene. This strain was verified to be sensitive to hygromycin, consistent with excision of the floxed fragment that included the HygR gene. An overview of this stacking process is shown (FIG. 28).

Example 20. Expression of Heterologous Type I FAS Genes in *Nannochloropsis gaditana*

As demonstrated in Example 11, where the penetrance screen was used to select transformed strains having culture-wide desired levels of gene attenuation achieved by RNAi expression, the penetrance screen has also proven advantageous for screening transformants expressing constructs that encode molecules other than Cas9 or other genome editing nucleases. In this example, the penetrance screen was performed on isolates resulting from transformation of *Nannochloropsis* with constructs engineered to include heterologous Type I Fatty Acid Synthase genes operably linked to *Nannochloropsis* gene regulatory elements. Nucleic acid sequences encoding the zebrafish *Danio rerio* Type I Fatty Acid Synthase (Type 1 FAS) (SEQ ID NO:116) and a Type I FAS of a proprietary isolated Thraustochytrid strain (SEQ ID NO:118) were cloned into constructs designed for expression of the genes in the Eustigmatophyte alga *Nannochloropsis gaditana*, allowing isolation of strains demonstrating the functionality of heterologous Type I FAS enzymes in the cytoplasm of an alga for the first time.

Figure 29:
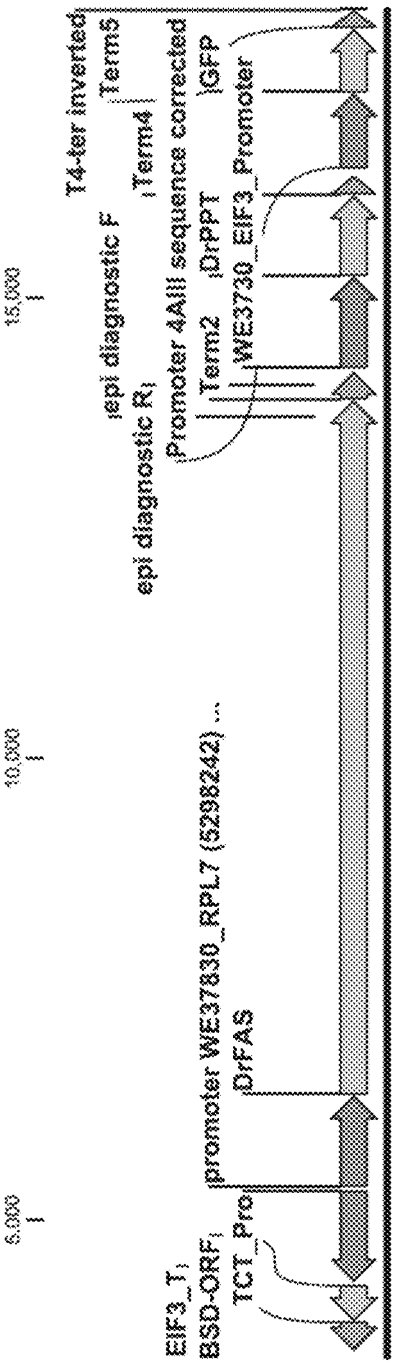
FIG. 29 provides a diagram of a construct for introduction into an algal cell that encodes a Type I FAS derived from an animal species. The construct also includes a gene encoding a pantetheine phosphotransferase (PPT). The genes are operably linked to algal promoters. The construct further includes a gene encoding a fluorescent protein for assessing culture-wide expression of the exogenous FAS and PPT genes.

The construct for expression of *C. rerio* Type I FAS, pSGE-6200 (FIG. 29), included the gene encoding the *D. rerio* Type I FAS, termed "DrFAS", which was codon optimized for *N. gaditana* (SEQ ID NO:116) and operably linked to the *N. gaditana* RPL7 promoter (SEQ ID NO:Z), positioned 5' of the DrFAS coding sequence, and the *N. gaditana* 'Terminator 2' sequence (SEQ ID NO:Q), positioned at the 3' end of the DrFAS coding sequence (SEQ ID NO:116). The expression construct also included a nucleic acid sequence (SEQ ID NO:117) encoding the *D. rerio* pantetheine phosphotransferase (PPT) which is required for activating the ACP domain of the DrFAS protein. The PPT gene (SEQ ID NO:117) used in the construct was also codon-optimized for *N. gaditana* and was operably linked at its 5' end to the *N. gaditana* 4AIII promoter, and at its 3' end to *N. gaditana* terminator 4. Upstream of the DrFAS and PPT genes was a cassette for the expression of the codon-optimized "blast" gene operably linked to the TCTP promoter (SEQ ID NO:11) at its 5' end (oriented in a direction opposite to the RPL7 promoter positioned to drive expression of the DrFAS gene), and to the EIF3 terminator at its 3' end. Downstream of the DrFAS and PPT genes was a cassette for GFP expression in which the coding sequence for TurboGFP (codon optimized for *N. gaditana*, SEQ ID NO:24) was operably linked to EIF3 promoter and *N. gaditana* terminator 5. The GFP expression cassette was oriented in the same 5' to 3' direction as the DrFAS and PPT genes.

Figure 30:
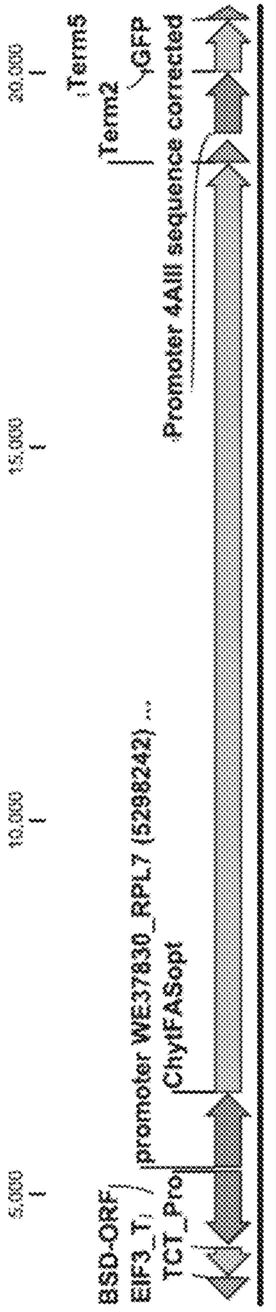
FIG. 30 provides a diagram of a construct for introduction into an algal cell that encodes a Type I FAS derived from a labyrinthulomycete species. The gene is operably linked to an algal promoter. The construct further includes a gene encoding a fluorescent protein for assessing culture-wide expression of the exogenous FAS gene.

The construct for expression of the Thraustochytrid Type I FAS, pSGE-6167 (FIG. 30), included the gene encoding the Thraustochytrid Type I FAS, termed "ChytFAS", codon optimized for *N. gaditana* (SEQ ID NO:118) operably linked to the *N. gaditana* RPL7 promoter (SEQ ID NO:Z) 5' of the ChytFAS coding sequence, and the *N. gaditana* 'Terminator 2' sequence (SEQ ID NO:Q) at the 3' end of the DrFAS coding sequence. This construct did not include a separate PPT gene, as the Chytrid FAS includes that enzymatic activity. Upstream of the ChytFAS gene was the same blast expression cassette as provided in the DrFAS construct, also oriented such that the direction of transcription was opposite that of the FAS gene, and downstream of the ChytFAS gene was the same GFP expression cassette that was employed in the DrFAS construct, again oriented in the same direction as the FAS gene.

DNA fragments that included these expression cassettes of DrFAS expression construct pSGE-6200 and ChytFAS construct pSGE-6167 were transformed, separately, as linear molecules (with the vector backbone removed by AscI and NotI digestion of the construct and isolation of the linear fragment by gel electrophoresis) into *Nannochloropsis* by electroporation essentially as described in US 2014/0220638, incorporated herein by reference. Transformants were selected on plates that contained blastocidin and screened for the presence of the construct by PCR.

Figure 31A:
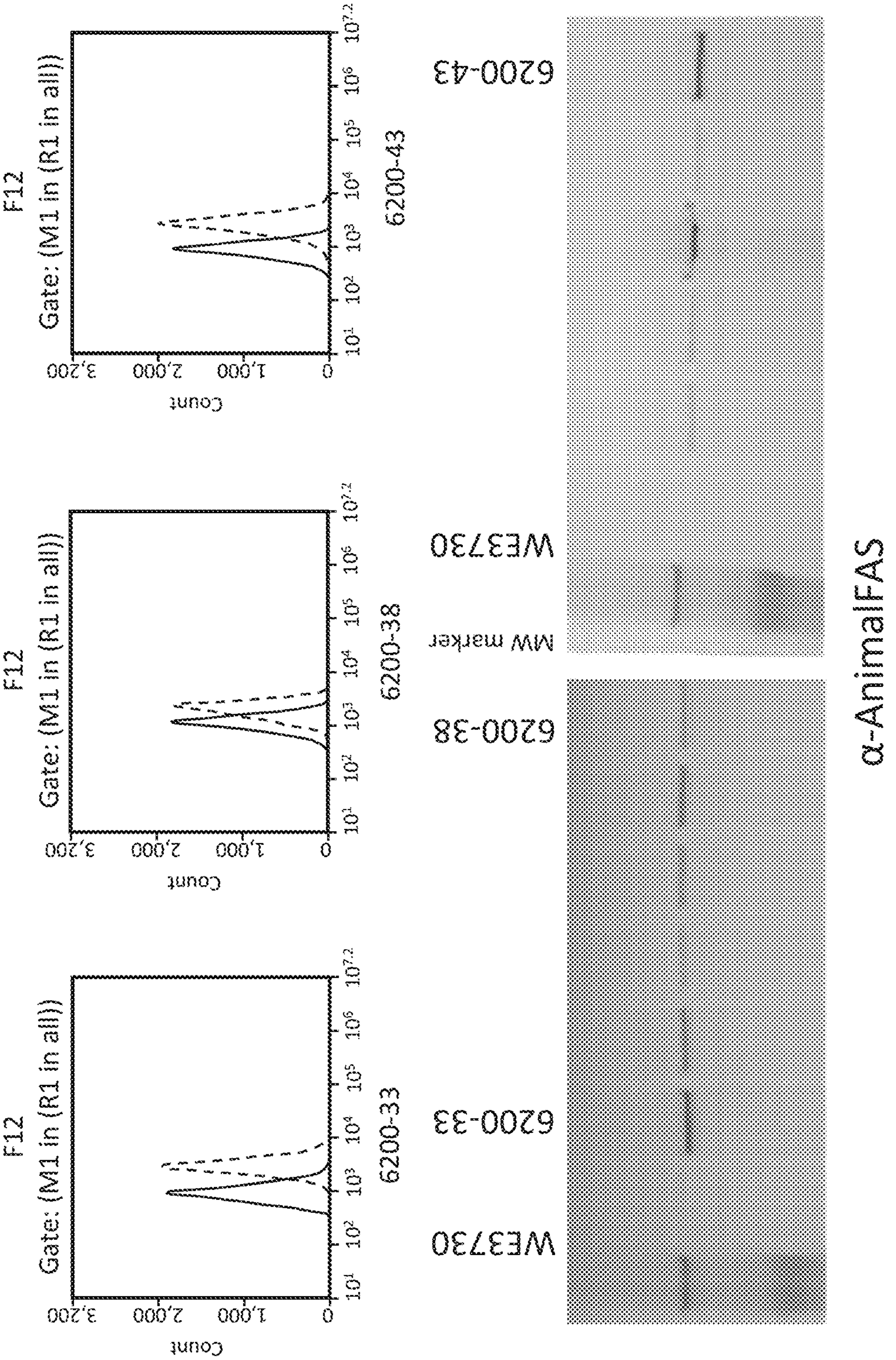
FIGS. 31 A and B provides flow cytometry traces (histograms) in which the flow cytometry profile of a *Nannochloropsis* tranformant that includes a *Danio rerio* Type I FAS gene is overlaid with the flow cytometry profile of a wild type (non-transformed) algal cell culture. The figure also provides Western blots showing levels of FAS protein expression in the profiled transformed lines. Line 6201-38 (rightmost flow cytometry trace in B) shows no difference in its fluorescence profile relative to non-transformed cells and shows no detectable FAS protein in the Western blot (third lane from the right). Other transformed lines show fully penetrant expression with fluorescence peaks that are distinct from the wild type peak. These strains also have detectable FAS protein as evidenced by the Western blots. WE3730 is the wild type strain which does not include a Type 1 FAS protein.
Figure 31B:
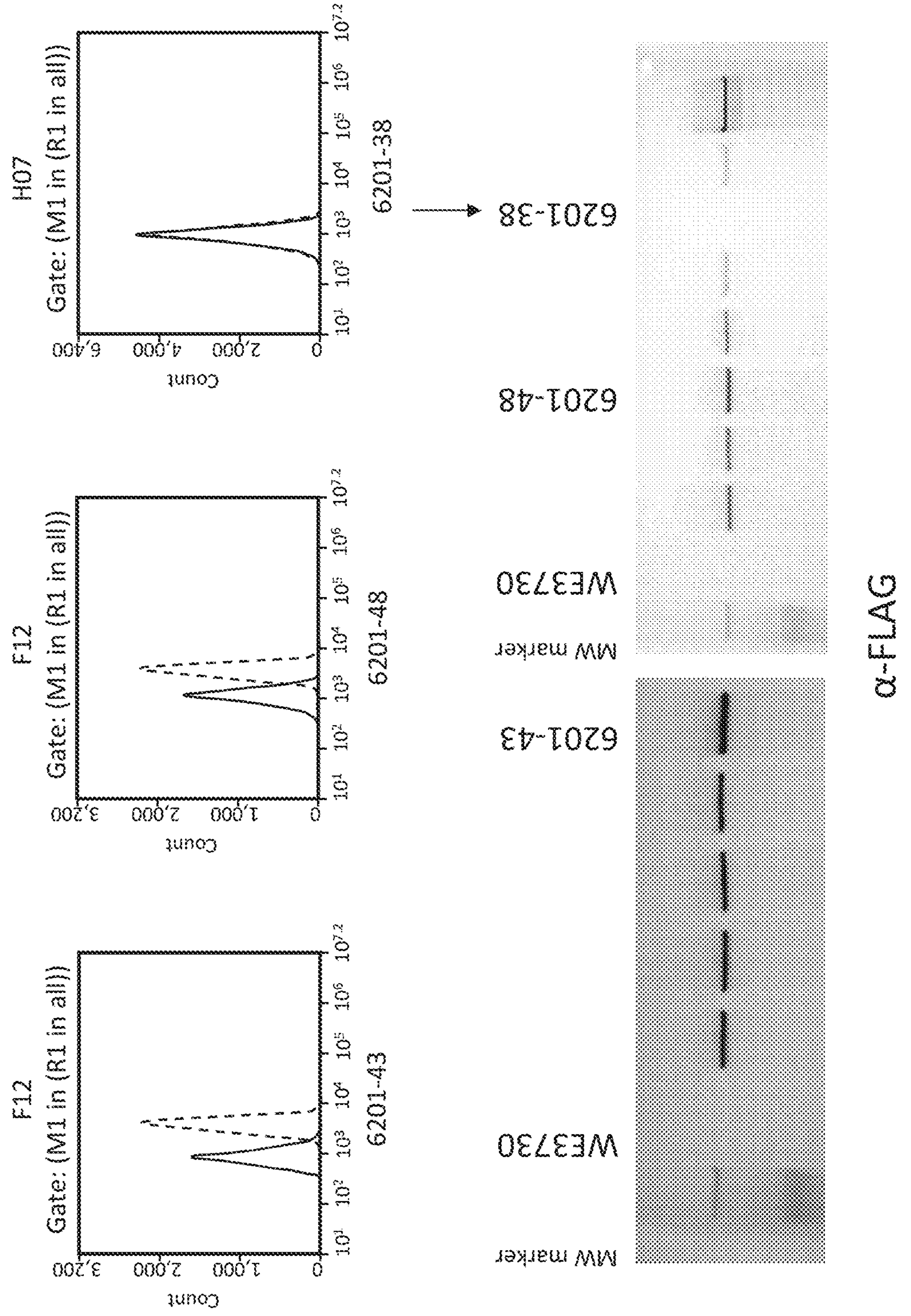
Figure 32A:
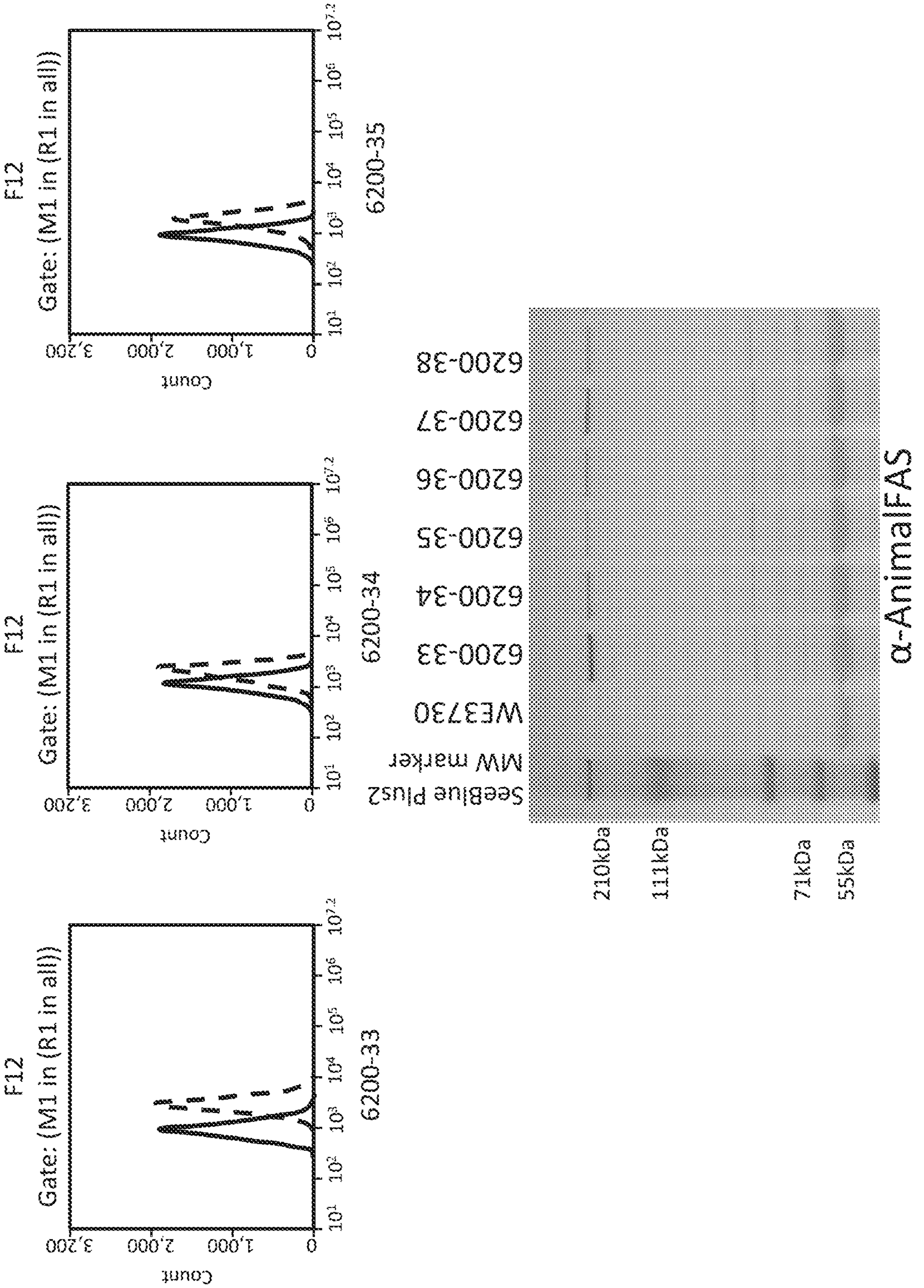
FIGS. 32 A and B provides flow cytometry traces (histograms) of *Nannochloropsis* transformants in which the flow cytometry profile of a tranformant that includes a *Danio rerio* Type I FAS gene is overlaid with the flow cytometry profile of a wild type (non-transformed) algal cell culture. The figure also provides a Western blot comparing levels of FAS protein expression in the profiled transformed lines. WE3730 is the wild type strain which does not include a Type 1 FAS protein.
Figure 32B:
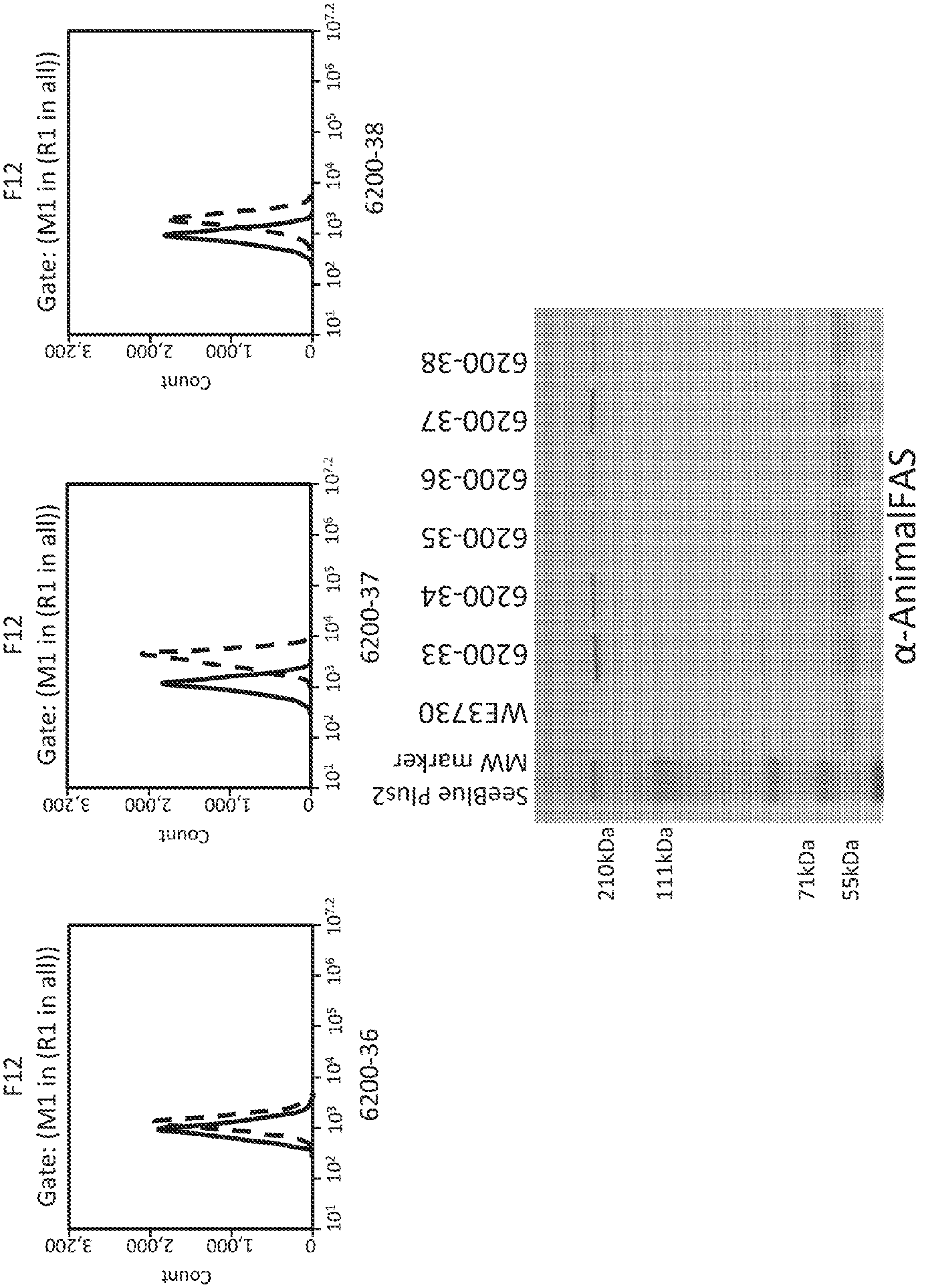

Clones that included the construct we then screened for penetrance by flow cytometry monitoring for GFP fluorescence as described in Example 3 and for FAS protein expression by Western blot using an antibody reactive against animal Type I FAS or a FLAG tag (present in some constructs) for the DrFAS transformants, or an antibody reactive against chytrid FAS for the ChytFAS transformants. FIGS. 31A and 31B show the flow cytometry traces of 6 DrFAS transformants that were found to have complete penetrance, as the transformants displayed a single fluorescence peak that was shifted with respect to the wild type fluorescence peak. In FIGS. 31A and 31B, Western blots are shown in which it can be seen that each fully penetrant clone also demonstrated protein expression. Unlabeled lanes on the gel show protein reactivity of clones that were not determined to be fully penetrant (i.e., they displayed more than one peak, one of which coincided with wild-type, or background, fluorescence, or they displayed a single peak that was coincident with the wild type or background peak). Thus, screening for protein level alone does not result in the identification of fully penetrant lines (expression throughout the culture). FIGS. 32A and 32B provide the flow cytometry traces of 6 DrFAS lines that demonstrated complete penetrance and the Western blots of these lines with anti-animal FAS antibody. Interestingly, for these fully penetrant lines, protein level as assessed by Western signal intensity does correspond to the degree of separation of the transformant peak from the background (wild type) peak; for example, strains 6200-33 and 6200-37 have the most intense Western bands and the greatest separation of their flow cytometry fluorescence peaks from the wild type fluorescence peak, demonstrating that the of GFP gene expression is reflected in the degree of expression of the linked gene.

Figure 33:
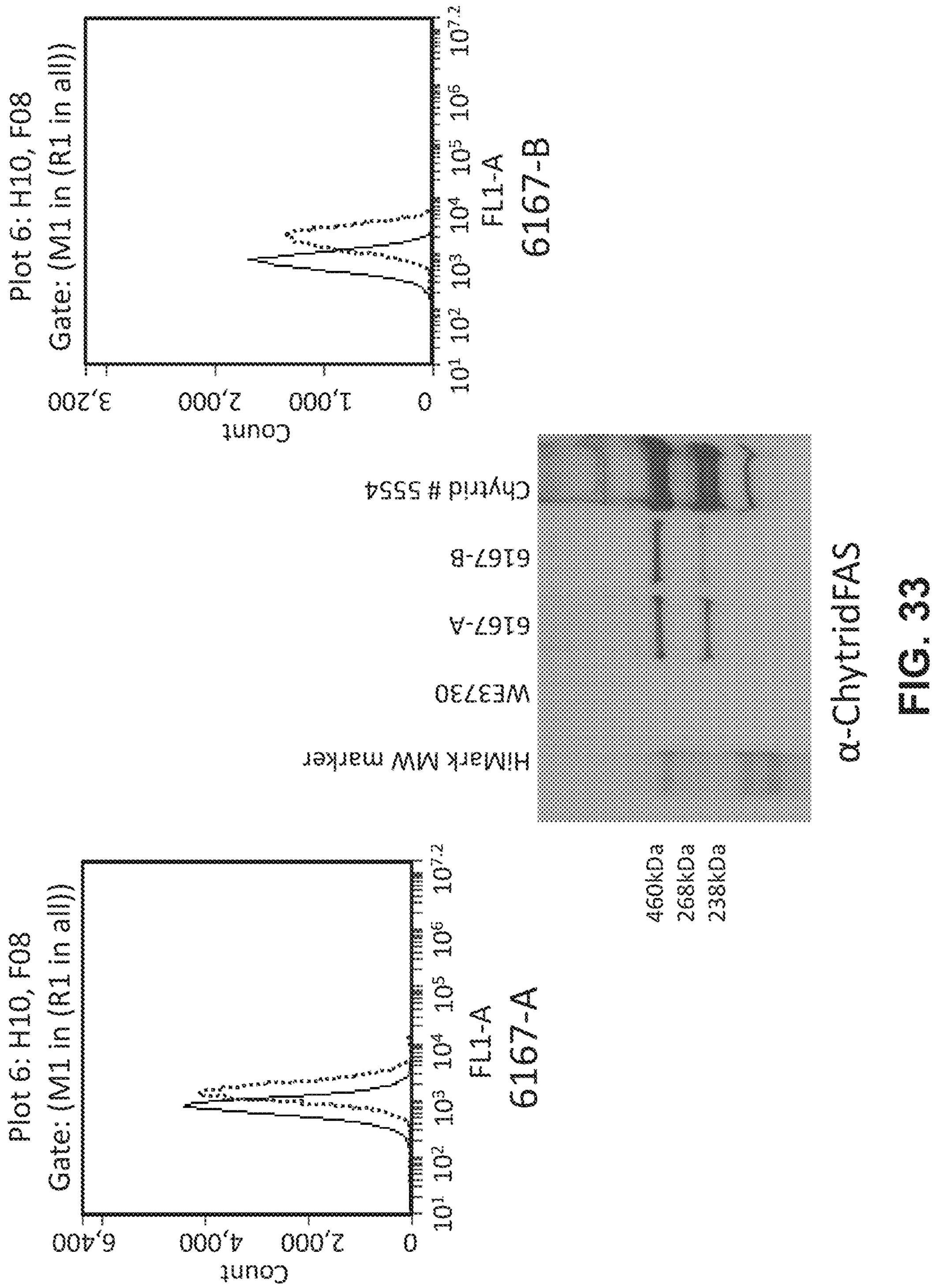
FIG. 33 provides flow cytometry traces (histograms) of *Nannochloropsis* transformants in which the flow cytometry profile of a tranformant that includes a labyrinthulomycete Type I FAS gene is overlaid with the flow cytometry profile of a wild type (non-transformed) algal cell culture. The figure also provides a Western blot comparing levels of FAS protein expression in the profiled transformed lines. WE3730 is the wild type strain which does not include a Type 1 FAS protein.

Two lines having fully penetrant ChytFAS expression were also assessed by Western for FAS protein expression (FIG. 33). Although 6167-B had a GFP fluorescence peak shifted farther to the right (at a higher fluorescence value) than the 6167-A GFP fluorescence peak was shifted (FIG. 37A), this difference was not reflected in the protein abundance as detected by Western blot. Interestingly though, strain 6167 demonstrated higher FAS activity in assays than did strain 6167A, as described below.

To analyze FAS activity in selected transformants, cell extracts of lines 6167-A and 6167-B expressing Chytrid FAS, and strains 6200-33, 6200-38, 6200-43, 6201-43, and 6201-48 expressing DrFAS, all selected as demonstrating complete penetrance (FIG. 33 and FIG. 34), were assayed. Malonyl-CoA dependent NADPH oxidation measured at ABS 340 nm was determined on clarified, desalted extracts in triplicate. Aliquots of cell cultures were pelleted and the pellets (approximately 200-400 μl packed volume) were resuspended in 2 ml of ice cold extraction buffer (50 mM HEPES pH 7.0 (or Tris pH 8.0), 100 mM KCl, 2 mM DTT (from fresh 1 M stock), 1 protease inhibitor cocktail from Roche at right concentration (e.g. 1 tablet for 10 ml). A similarly sized yeast pellet was treated the same way as a positive control extract.

Figure 34:
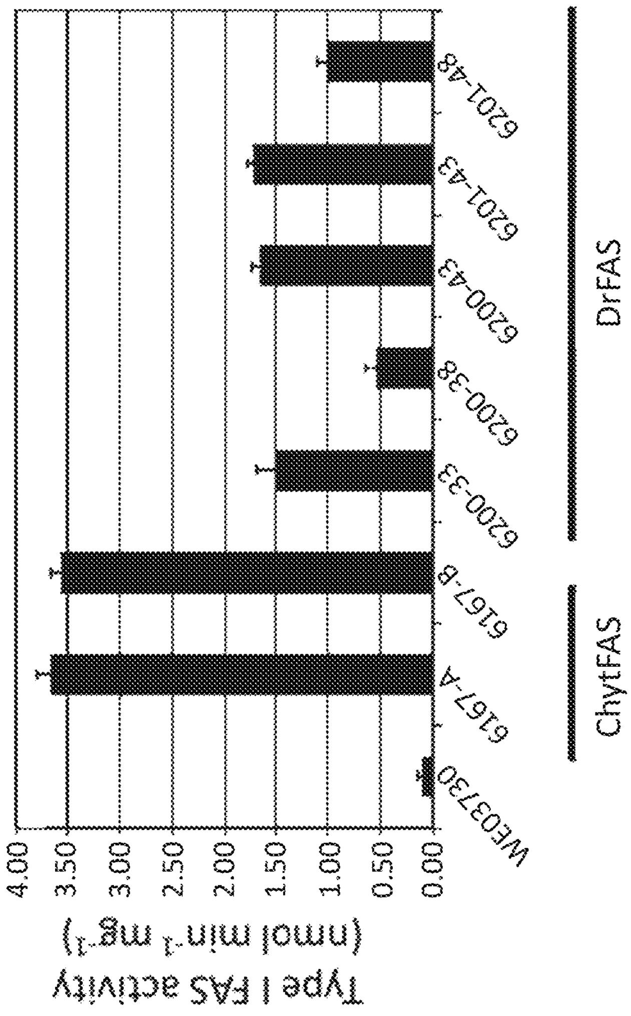
FIG. 34 provides a graph of FAS activity as assayed from cell extracts of transformants. Algal transformants having the labyrinthulomycete Type I FAS gene have the highest activity.

The resuspensions were transferred to a 2 ml screw cap vial containing approximately 500 μl bed volume of zirconium beads. The resuspensions were bead beaten in a pre-chilled block 3 times for 1 minute to disrupt the cells. The lysed cells were centrifuged at 20,000×g at 4° C. for 20 minutes, and the supernatant and de-salted on Zeba mini-columns (Pierce, product 89882) after equilibration with extraction buffer (above). Protein concentration was measured with the Pierce BCA detection kit. The fatty acid synthase (FAS) assay was essentially according to the procedure of Lynen (1969) Meth Enzymol 14:17-33: a 2× buffer stock containing 0.2 M $KH_2PO_4$ pH 6.6, 2 mM EDTA and 0.6 mg/ml BSA was used to make a working stock assay consisting of: 0.1M $KH_2PO_4$ pH 6.6, 1 mM EDTA, 1 mM DTT, 40 μM Acetyl-CoA, 110 μM Malonyl-CoA (omitted in negative control assays), 180 μM NADPH, and 1 mg/L BSA. 50 to 100 μg of total soluble protein from the extracts as prepared above were then added to each reaction mix. The change in absorbance at 340 nm per minute was measured and used to calculate the μmols oxidized NADPH per minute (FIG. 34). Interestingly, the amount of activity demonstrated in the transformed lines correlates well with the degree to which the GFP fluorescence curves are shifted to the right (FIG. 35A). Chytrid FAS transformed lines 6167-A and 6167-B were given strain named GE-6889 and GE6890, respectively, and DrFAS transformed lines 6200-33 was given the strain name GE-6947, DrFAS transformed lines 6200-33 was given the strain name GE-6947, DrFAS transformed lines 6200-38 was given the strain name GE-6948, DrFAS transformed lines 6200-43 was given the strain name GE-6949, DrFAS transformed lines 6201-43 was given the strain name GE-6950, DrFAS transformed lines 6201-48 was given the strain name GE-6951.

The lines were next analyzed for in vivo FAS rate determination under phototrophic and mixotrophic growth conditions with either $^{13}C$ bicarbonate or $^{13}C$-labeled acetate added to the medium, respectively. Cultures (duplicates were run for each culture condition) were adapted to 16:8 light/dark cycles at ~275 μE light (light limited growth) and grown to an $OD_{730}$ of approximately 3.0 in an Adaptis chamber. Prior to the onset of the photoperiod, cultures were centrifuged and resuspended (250 ml final vol.) to an $OD_{730}$ of 1.0 in PM074 medium buffered with 20 mM HEPES pH 7.4 and containing either 10 mM $^{13}C$ sodium acetate or 20 mM $^{13}C$ bicarbonate. Cultures were placed in front of an LED array supplying ~275 μE light from one direction, and FAME samples were taken at 0, 1, 2, and 4 h from a 50 ml culture volume. FAME was analyzed essentially as described in U.S. Patent Application Publication US 2015/0191515, incorporated herein by reference. FIG. 35A shows that under photoautotrophic conditions where inorganic carbon was substantially the sole source of carbon in the culture medium, strain GE-6890, demonstrating fully penetrant expression of chytrid FAS (see FIG. 35A), produced more newly synthesized fatty acids (represented as FAME) than controls. Newly synthesized fatty acids are fatty acids that show a high degree of labeling and have been synthesized de novo during the labeling experiment, where elongated fatty acids are C20:x fatty acids with one to four labeled carbons that arise from elongation of previously existing 16:x and 18:x fatty acids.

Strain GE-6890 is ChytFAS transformant line 6167-B whose penetrance profile in FIG. 33 shows a single peak shifted to the right with respect to wild type. Strain GE-6889, which is ChytFAS transformant line 6167-A, also demonstrated complete penetrance but the penetrance profile of GE-6889 (6167-A) in FIG. 33 shows a single peak that is not shifted as far to the right with respect to wild type as the fluorescence peak of GE-6890. Strain GE-6889 does not show any increase in FAME production over wild type in the radiolabeling experiment in which the strains are cultured using only an inorganic carbon source. However, when cultured under mixotrophic conditions, in which the cultures include an organic carbon source (10 mM acetate) strain GE-6889 demonstrates increased fatty acid synthesis with respect to wild type cells, demonstrating that this fully penetrant strain, while demonstrating less activity than transformant GE-6890, does have increased FAS activity in mixotrophic conditions (FIG. 35B).

With respect to transformed strains expressing DrFAS, the same culture assay for FAS activity using under photo-trophic and mixotrophic growth conditions with either $^{13}C$ bicarbonate or $^{13}C$-labeled acetate added to the medium, respectively, was performed on cultures of fully penetrant strain GE-6947 (transformed line 6200-33), fully penetrant strain GE-6949 (transformed line 6200-43), and fully penetrant strain GE-6950 (transformed line 6201-43). These assays were performed exactly as detailed above, with duplicate cultures for each strain. FIG. 36A shows that while cytoplasmically expressed Type I FAS did not increase photoautotrophic production of fatty acids, all three strains fully penetrant for expression of the heterologous Type I FAS construct produced more fatty acids (measured as FAME) than did wild type cells (FIG. 36B).

Although the invention has been described with reference to the examples herein, it will be understood that modifications and variations are encompassed within the spirit and scope of the invention. Accordingly, the invention is limited only by the following claims.

What is claimed:

1. A fully penetrant RNA-guided endonuclease expressing algal strain of the Class Trebouxiophyceae comprising:
   a Cas protein expression construct comprising:
      a Cas nuclease expression cassette;
      a repressible CRE expression cassette comprising a Cre coding region; and
      a selectable marker cassette;
      a reporter expression cassette; and
      two lox sites flanking the repressible CRE expression cassette and the selectable marker cassette.

2. The fully penetrant RNA-guided endonuclease expressing algal strain of claim 1, wherein the Cas protein is Cas9.

3. The fully penetrant RNA-guided endonuclease expressing algal strain of claim 2, further comprising an intron inserted into the Cre coding region of the Cre expression cassette.

4. The fully penetrant RNA-guided endonuclease expressing algal strain of claim 3, wherein the Cas9 expression cassette further comprises a promoter for constitutive expression of Cas9 nuclease.

5. The fully penetrant RNA-guided endonuclease expressing algal strain of claim 4, wherein the lox sites have the same orientation.

6. The fully penetrant RNA-guided endonuclease expressing algal strain of claim 2, wherein the alga is a member of the genus *Parachlorella.*

7. The fully penetrant RNA-guided endonuclease expressing algal strain of claim 2, wherein the Cas9 expression cassette comprises an N-terminal FLAG tag.

8. The fully penetrant RNA-guided endonuclease expressing algal strain of claim 2, wherein the selectable market cassette encodes blasticidin resistance.

9. The fully penetrant RNA-guided endonuclease expressing algal strain of claim 8, wherein the reporter cassette encodes a fluorescent protein.

10. The fully penetrant RNA-guided endonuclease expressing algal strain of claim 1, wherein the Cas protein is selected from the group consisting of: Cpf1, Csc2, Cas1, Cas2, Cas3, Cas4, and Cas10.

11. The fully penetrant RNA-guided endonuclease expressing algal strain of claim 10, further comprising an intron inserted into the Cre coding region of the Cre expression cassette.

12. The fully penetrant RNA-guided endonuclease expressing algal strain of claim 11, wherein the Cas protein expression cassette further comprises a promoter for constitutive expression of the Cas nuclease.

13. The fully penetrant RNA-guided endonuclease expressing algal strain of claim 12, wherein the lox sites have the same orientation.

14. The fully penetrant RNA-guided endonuclease expressing algal strain of claim 1, wherein the alga is a member of the genus *Parachlorella.*

15. The fully penetrant RNA-guided endonuclease expressing algal strain of claim 10, wherein the Cas protein expression cassette comprises an N-terminal FLAG tag.

16. The fully penetrant RNA-guided endonuclease expressing algal strain of claim 10, wherein the reporter cassette encodes a fluorescent protein.

17. The fully penetrant RNA-guided endonuclease expressing algal strain of claim 10, wherein the Cas protein is Cpf1 or Csc2.

18. The fully penetrant RNA-guided endonuclease expressing algal strain of claim 10, wherein the Cas protein is selected from the group consisting of: Cas1, Cas3, and Cas4.

* * * * *